United States Patent
Marbán et al.

(10) Patent No.: US 12,146,137 B2
(45) Date of Patent: Nov. 19, 2024

(54) METHODS FOR THERAPEUTIC USE OF EXOSOMES AND Y-RNAS

(71) Applicant: Cedars-Sinai Medical Center, Los Angeles, CA (US)

(72) Inventors: Eduardo Marbán, Los Angeles, CA (US); Linda Cambier, Los Angeles, CA (US); Geoffrey De Couto, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1012 days.

(21) Appl. No.: 16/966,840

(22) PCT Filed: Jan. 30, 2019

(86) PCT No.: PCT/US2019/015895
§ 371 (c)(1),
(2) Date: Jul. 31, 2020

(87) PCT Pub. No.: WO2019/152549
PCT Pub. Date: Aug. 8, 2019

(65) Prior Publication Data
US 2021/0207145 A1 Jul. 8, 2021

Related U.S. Application Data

(60) Provisional application No. 62/626,600, filed on Feb. 5, 2018.

(51) Int. Cl.
| | | |
|---|---|---|
| *C12N 15/113* | (2010.01) | |
| *A61K 35/34* | (2015.01) | |
| *A61K 47/69* | (2017.01) | |
| *A61P 9/00* | (2006.01) | |
| *A61P 13/12* | (2006.01) | |
| *A61P 37/02* | (2006.01) | |

(52) U.S. Cl.
CPC .......... *C12N 15/1136* (2013.01); *A61K 35/34* (2013.01); *A61K 47/6911* (2017.08); *A61P 9/00* (2018.01); *A61P 13/12* (2018.01); *A61P 37/02* (2018.01); *C12N 2310/18* (2013.01)

(58) Field of Classification Search
None
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Valkov et al. Adv Exp Med Biol 1229: 327-342 (Year: 2020).*
Cambier et al. Hypertension 72, 370-380 (Year: 2018).*
Wei et al. International Immunopharmacology 108, 108917, pp. 1-6 (Year: 2022).*
Gillis et al. Am J Physiol Renal Physiol 319: F359-F365 (Year: 2020).*
Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.
Abela et al., "A New Method for Isolation of Cardiac Myocytes by Percutaneous Endomyocardial Biopsy", Catheterization and Cardiovascular Diagnosis, 1996, vol. 37, pp. 227-230.

(Continued)

*Primary Examiner* — Brian Whiteman
(74) *Attorney, Agent, or Firm* — KNOBBE, MARTENS, OLSON & BEAR, LLP

(57) ABSTRACT

Some embodiments of the methods and compositions provided herein relate to treating a subject suffering from hypertension, a cardiac injury, or a metabolic disorder. Some embodiments include administering an exosome to a subject. Some embodiments include administering an oligonucleotide to the subject. In some embodiments, the oligonucleotide comprises a Y-RNA or Y-RNA fragment such as EV-YF1 or EV-YF1-U16. In some embodiments, the oligonucleotide or exosome also has a therapeutic effect on the subject.

25 Claims, 82 Drawing Sheets

Specification includes a Sequence Listing.

(56) References Cited

U.S. PATENT DOCUMENTS

| | | |
|---|---|---|
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,780,873 B2 | 8/2010 | Mora-Gutierrez et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 11,220,687 B2 | 1/2022 | Marbán et al. |
| 11,253,551 B2 | 2/2022 | Marbán et al. |
| 11,351,200 B2 | 6/2022 | Marbán et al. |
| 11,357,799 B2 | 6/2022 | Marbán et al. |
| 11,541,078 B2 | 1/2023 | Marbán et al. |
| 11,660,355 B2 | 5/2023 | Marbán et al. |
| 11,759,482 B2 | 9/2023 | Marban et al. |
| 11,872,251 B2 | 1/2024 | Marban et al. |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |

(56) References Cited

U.S. PATENT DOCUMENTS

| | | |
|---|---|---|
| 2005/0176620 A1 | 8/2005 | Prestwich et al. |
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0149410 A1 | 6/2009 | Elias et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1 | 11/2015 | Kaushal |
| 2015/0368618 A1 | 12/2015 | Nadal-Ginard |
| 2016/0158291 A1 | 6/2016 | Kreke et al. |
| 2016/0194631 A1 | 7/2016 | Yuan et al. |
| 2016/0237500 A1 | 8/2016 | Trabucchi et al. |
| 2016/0244723 A1 | 8/2016 | Giacomello et al. |
| 2017/0037375 A1 | 2/2017 | Palecek et al. |

(56) References Cited

U.S. PATENT DOCUMENTS

| | | |
|---|---|---|
| 2017/0049793 A1 | 2/2017 | Moon et al. |
| 2017/0087087 A1 | 3/2017 | Leonard et al. |
| 2017/0102397 A1 | 4/2017 | Zhang |
| 2017/0290860 A1 | 10/2017 | Marbán et al. |
| 2017/0304368 A1 | 10/2017 | Marbán et al. |
| 2019/0000888 A1 | 1/2019 | Marbán et al. |
| 2019/0062740 A1 | 2/2019 | Zhu |
| 2019/0160111 A1 | 5/2019 | Marbán et al. |
| 2019/0194662 A1 | 6/2019 | Dalby et al. |
| 2019/0203259 A1 | 7/2019 | Korennykh et al. |
| 2019/0255119 A1 | 8/2019 | Marbán et al. |
| 2020/0024604 A1 | 1/2020 | Marbán et al. |
| 2020/0121727 A1 | 4/2020 | Marbán et al. |
| 2020/0199555 A1 | 6/2020 | Zhang |
| 2021/0032598 A1 | 2/2021 | Ibrahim et al. |
| 2021/0071259 A1 | 3/2021 | Tahara et al. |
| 2021/0085724 A1 | 3/2021 | Marbán et al. |
| 2021/0207145 A1 | 7/2021 | Marbán et al. |
| 2021/0401896 A1 | 12/2021 | Marbán et al. |
| 2022/0072062 A1 | 3/2022 | Marbán et al. |
| 2022/0119813 A1 | 4/2022 | Marbán et al. |
| 2022/0218757 A1 | 7/2022 | Marbán et al. |
| 2022/0273729 A1 | 9/2022 | Marbán et al. |
| 2023/0141499 A1 | 5/2023 | Marbán et al. |
| 2023/0203487 A1 | 6/2023 | Marban et al. |
| 2023/0381243 A1 | 11/2023 | Marban et al. |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 679 221 | 1/2014 |
| EP | 2 687 219 | 1/2014 |
| JP | 2003-509374 | 3/2003 |
| JP | 2005-506845 | 3/2005 |
| JP | 2005-110565 | 4/2005 |
| JP | 2006-006125 | 1/2006 |
| JP | 2007-518423 | 7/2007 |
| JP | 2007-518426 | 7/2007 |
| JP | 2008-504816 | 2/2008 |
| JP | 2008-518730 | 6/2008 |
| JP | 2010-507592 | 3/2010 |
| JP | 2013-509179 | 3/2013 |
| JP | 2015-524844 | 8/2015 |
| JP | 2018-501221 | 1/2018 |
| JP | 6878274 | 5/2021 |
| JP | 2022-017178 | 1/2022 |
| JP | 7275193 | 5/2023 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/019379 | 3/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |

(56) References Cited

FOREIGN PATENT DOCUMENTS

| WO | WO 2014/013258 | 1/2014 | | |
|---|---|---|---|---|
| WO | WO 2014/028493 | 2/2014 | | |
| WO | WO 2014/114465 | 7/2014 | | |
| WO | WO 2014/152211 | 9/2014 | | |
| WO | WO 2014/160153 | 10/2014 | | |
| WO | WO 2015/022545 | 2/2015 | | |
| WO | WO 2015/055857 | 4/2015 | | |
| WO | WO 2015/085096 | 6/2015 | | |
| WO | WO 2015/092020 | 6/2015 | | |
| WO | WO 2015/120150 | 8/2015 | | |
| WO | WO 2016/054591 | 4/2016 | | |
| WO | WO 2016/057560 | 4/2016 | | |
| WO | WO 2016/065349 | 4/2016 | | |
| WO | WO-2016054569 A1 * | 4/2016 | ............ | A61K 35/28 |
| WO | WO 2016/090183 | 6/2016 | | |
| WO | WO 2016/152786 | 9/2016 | | |
| WO | WO 2017/136652 | 8/2017 | | |
| WO | WO 2017/160884 | 9/2017 | | |
| WO | WO 2017/173034 | 10/2017 | | |
| WO | WO 2019/015702 | 1/2019 | | |
| WO | WO 2019/028223 | 2/2019 | | |
| WO | WO 2019/050071 | 3/2019 | | |
| WO | WO 2019/126068 | 6/2019 | | |
| WO | WO 2019/152409 | 8/2019 | | |
| WO | WO 2019/152549 | 8/2019 | | |
| WO | WO 2020/131986 | 6/2020 | | |
| WO | WO 2020/227489 | 11/2020 | | |
| WO | WO 2021/178514 | 9/2021 | | |
| WO | WO 2021/188899 | 9/2021 | | |
| WO | WO 2021/237238 | 11/2021 | | |
| WO | WO 2023/278799 | 1/2023 | | |
| WO | WO 2023/278802 | 1/2023 | | |
| WO | WO 2023/245011 | 3/2024 | | |
| WO | WO 2024/073612 | 4/2024 | | |

OTHER PUBLICATIONS

Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.

Ajijola et al., "Ventricular Tachycardia in Ischemic Heart Disease Substrates", Indian Heart Journal, 2014, pp. S24-S34, S28 & S30, vol. 66, Supplement 1.

Albini et al., "A Rapid in Vitro Assay for Quantitating the Invasive Potential of Tumor Cells", Cancer Research, Jun. 15, 1987, pp. 3239-3245, vol. 47.

Ames et al., "Oxidants, Antioxidants, and the Degenerative Diseases of Aging", Proceedings of the National Academy of Sciences of the United States of America, Sep. 1993, vol. 90, pp. 7915-7922.

Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.

Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.

Andersen et al., "Murine 'Cardiospheres' Are Not a Source of Stem Cells with Cardiomyogenic Potential," Stem Cells, 2009, vol. 27, No. 7, pp. 1571-1581.

Anversa et al., "Primitive Cells and Tissue Regeneration", Circulation Research, 2003, vol. 92, pp. 579-582.

Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.

"ATS/ACCP Statement on Cardiopulmonary Exercise Testing", American Thoracic Society/American College of Chest Physicians, American Journal of Respiratory and Critical Care Medicine, 2003, vol. 167, pp. 211-277.

Ausma et al., "Dedifferentiation of Atrial Cardiomyocytes: From in Vivo to In Vitro", Cardiovascular Research, Jul. 2002, vol. 55, No. 1, pp. 9-12.

Baker et al. "Adaptation to Culture of Human Embryonic Stem Cells and Oncogenesis in Vivo" Nature Biotechnology, Feb. 2007, vol. 25, No. 2, pp. 207-215.

Balser et al., "Global Parameter Optimization for Cardiac Potassium Channel Gating Models", Biophysical Journal, Mar. 1990, vol. 57, pp. 433-444.

Balser et al., "Local Anesthetics as Effectors of Allosteric Gating", Journal of Clinical Investigation, Dec. 1996, vol. 98, No. 12, pp. 2874-2886.

Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.

Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.

Barile et al., "Endogenous Cardiac Stem Cells", Progress in Cardiovascular Diseases, Jul.-Aug. 2007, vol. 50, No. 1, pp. 31-48.

Barile et al., "Human Cardiospheres as a Source of Multipotent Stem and Progenitor Cells", Hindawi Publishing Corporation, Stem Cells International, 2013, vol. 2013, pp. 10.

Barr et al., "Efficient Catheter-Mediated Gene Transfer Into the Heart Using Replication-Defective Adenovirus", Gene Therapy, Jan. 1994, vol. 1, No. 1, pp. 51-58.

Barry et al., "Differential Expression of Voltage-Gated $K^+$ Channel Subunits in Adult Rat Heart", Circulation Research, 1995, vol. 77, pp. 361-369.

Barth et al., "Lentiviral Vectors Bearing the Cardiac Promoter of the $Na^+$-$Ca^{2+}$ Exchanger Report Cardiogenic Differentiation in Stem Cells", Molecular Therapy, May 2008, vol. 16, No. 5, pp. 957-964.

Bearzi et al., "Human Cardiac Stem Cells", Proceedings of the National Academy of Sciences of the United States of America (PNAS), Aug. 28, 2007, pp. 14068-14073, vol. 104, No. 35.

Beltrami et al., "Adult Cardiac Stem Cells are Multipotent and Support Myocardial Regeneration", Cell, Sep. 19, 2003, vol. 114, No. 6, pp. 763-776.

Beltrami et al., "Evidence That Human Cardiac Myocytes Divide After Myocardial Infarction", The New England Journal of Medicine, Jun. 7, 2001, vol. 344, pp. 1750-1757.

Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.

Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.

Bergmann et al., "Evidence for Cardiomyocyte Renewal in Humans", Science, Apr. 3, 2009, vol. 324, pp. 98-102.

Bernanke et al., "Effects of Hyaluronic Acid on Cardiac Cushion Tissue Cells in Collagen Matrix Cultures", Texas Reports on Biology and Medicine, 1979, pp. 271-285, vol. 39.

"Bioptome.com", Scholten Surgical Instruments, Inc., downloaded from <http://www.bioptome.com/pages.php?page=Products>, 2001, first date of publication unknown, printed on Nov. 1, 2005, pp. 2.

Bird et al., "The Human Adult Cardiomyocyte Phenotype", Cardiovascular Research, May 1, 2003, vol. 58, No. 2, pp. 423-434.

Birks et al., "Left Ventricular Assist Device and Drug Therapy for the Reversal of Heart Failure", The New England Journal of Medicine, 2006, vol. 355, No. 18, pp. 1873-1884.

Bjelakovic et al., "Mortality in Randomized Trials of Antioxidant Supplements for Primary and Secondary Prevention: Systematic Review and Meta-Analysis", JAMA, 2007, vol. 297, pp. 842-857.

Bosnali et al., "Generation of Transducible Versions of Transcription Factors Oct4 and Sox2", Biological Chemistry, Jul. 2008, vol. 389, pp. 851-861.

Bredemeyer et al., "ATM Stabilizes DNA Double-Strand-Break Complexes During V(D)J Recombination", Nature, Jul. 27, 2006, vol. 442, pp. 466-470.

(56) References Cited

OTHER PUBLICATIONS

Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.
Cai et al., "Injectable Glycosaminoglycan Hydrogels for Controlled Release of Human Basic Fibroblast Growth Factor," Biomaterials, 2005, vol. 26, pp. 6054-6067.
Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.
"CArdiosphere-Derived aUtologous Stem CElls to Reverse ventricUlar dySfunction (CADUCEUS)", ClinicalTrials.gov, Identifier NCT00893360, 2009, pp. 6.
Chambers et al., "Functional Expression Cloning of Nanog, a Pluripotency Sustaining Factor in Embryonic Stem Cells", Cell, May 30, 2003, vol. 113, No. 5, pp. 643-655.
Chen et al., "Enhanced Tumorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology—Heart and Circulatory Physiology, Oct. 2006, vol. 291, No. 4, pp. H1653-H1658.
Cheng et al., "Functional Performance of Human Cardiosphere—Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.
Chimenti et al., "Abstract 3182: Paracrine Contribution versus Direct Regeneration in Cardiosphere-Derived Cell Therapy for Acute Myocardial Infarction", Circulation, 2009, vol. 120, p. S756.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Chlopčíková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.
Cho et al., "Secondary Sphere Formation Enhances the Functionality of Cardiac Progenitor Cells", Molecular Therapy, Sep. 2012, vol. 20, No. 9, pp. 1750-1766.
Christman et al., "Biomaterials for the Treatment of Myocardial Infarction", Journal of the American College Of Cardiology, 2006, vol. 48, No. 5, pp. 907-913.
Conkright et al., "A Gene Encoding an Intestinal-Enriched Member of the Krüppel-Like Factor Family Expressed in Intestinal Epithelia Cells", Nucleic Acids Research, 1999, vol. 27, No. 5, pp. 1263-1270.

Cooper et al., "Immunobiological Barriers to Xenotransplantation", International Journal of Surgery, 2015, vol. 23, pp. 211-216.
Crisostomo et al., "Embryonic Stem Cells Attenuate Myocardial Dysfunction and Inflammation After Surgical Global Ischemia Via Paracrine Actions", American Journal of Physiology—Heart and Circulatory Physiology, 2008, vol. 295, pp. H1726-H1735.
Csete, Marie, "Oxygen in the Cultivation of Stem Cells", Annals New York Academy of Sciences, 2005, vol. 1049, pp. 1-8.
"Culture Media Database", EGM-2 (Endothelial Growth Medium 2)—ID 63, downloaded from <http://bio.lonza.com/3018.html#ext-comp-1003:tab_63:change>, printed on Jan. 14, 2013, p. 1.
Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.
Davis et al., "Validation of the Cardiosphere Method to Culture Cardiac Progenitor Cells from Myocardial Tissue", PLoS One, 2009, vol. 4, No. 9, e7195, pp. 1-8.
Davis et al., "Human Cardiospheres are a Source of Stem Cells with Cardiomyogenic Potential", Stem Cells, 2010, vol. 28, No. 5, pp. 903-904.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.
Deal et al., "Molecular Physiology of Cardiac Potassium Channels", Physiological Reviews, Jan. 1996, vol. 76, No. 1, pp. 49-67.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.
Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.
Derossi et al., "The Third Helix of the Antennapedia Homeodomain Translocates through Biological Membranes", The Journal of Biological Chemistry, Apr. 8, 1994, vol. 269, No. 14, pp. 10444-10450.
Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.
Dib et al., "Cell Therapy for Cardiovascular Disease: A Comparison of Methods of Delivery", Journal of Cardiovascular Translational Research, 2011, vol. 4, pp. 177-181.
Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.
Dispersyn et al., "Dissociation of Cardiomyocyte Apoptosis and Dedifferentiation in Infarct Border Zones", European Heart Journal, 2002, vol. 23, pp. 849-857.
Dixon et al., "Quantitative Analysis of Potassium Channel mRNA Expression in Atrial and Ventricular Muscle of Rats", Circulation Research, Aug. 1994, vol. 75, No. 2, pp. 252-260.
Dixon et al., "Role of the Kv4.3 $K^+$ Channel in Ventricular Muscle", Circulation Research, 1996, vol. 79, pp. 659-668.
Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.
Donahue et al., "Ultrarapid, Highly Efficient Viral Gene Transfer to the Heart", Proceedings of the National Academy of Sciences of the United States of America, Apr. 1997, vol. 94, pp. 4664-4668.
Dong et al., "Islet Cell and Extrapancreatic Expression of the LIM Domain Homeobox Gene isl-1", Molecular Endocrinology, 1991, vol. 5, No. 11, pp. 1633-1641.

(56) References Cited

OTHER PUBLICATIONS

Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.
Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.
Driesen et al., "Structural Remodeling of Cardiomyocytes in the Border Zone of Infarcted Rabbit Heart", Molecular and Cellular Biochemistry, 2007, pp. 225-232, vol. 302.
Duff et al., "CD105 is Important for Angiogenesis: Evidence and Potential Applications," FASEB Journal, Jun. 2003, vol. 17, No. 9, pp. 984-992.
Eguchi, Masakatsu, "Recent Advances in Selective Opioid Receptor Agonists and Antagonists", Medicinal Research Reviews, 2004, vol. 24, No. 2, pp. 182-212.
Elliott et al., "Intercellular Trafficking and Protein Delivery by a Herpesvirus Structural Protein", Cell, Jan. 24, 1997, vol. 88, pp. 223-233.
Elliott et al., "Intercellular Trafficking of VP22-GFP Fusion Proteins", Gene Therapy, 1999, vol. 6, pp. 149-151.
Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.
Engel et al. "p38 MAP Kinase Inhibition Enables Proliferation of Adult Mammalian Cardiomyocytes", Genes & Development, May 2005, vol. 19, No. 10, pp. 1175-1187.
Eppenberger-Eberhardt et al., "Reexpression of a-Smooth Muscle Acting Isoform in Cultured Adult Rat Cardiomyocytes", Developmental Biology, Jun. 1990, vol. 139, No. 2, pp. 269-278.
Eschenhagen et al., "Engineering Myocardial Tissue", Circulation Research, 2005, vol. 97, pp. 1220-1231.
Falck et al., "Conserved Modes of Recruitment of ATM, ATR and DNA-PKcs to Sites of DNA Damage", Nature, Mar. 31, 2005, vol. 434, pp. 605-611.
Fehrer et al., "Reduced Oxygen Tension Attenuates Differentiation Capacity of Human Mesenchymal Stem Cells and Prolongs their Lifespan", Aging Cell, 2007, vol. 6, pp. 745-757.
Fiset et al., Shal-Type Channels Contribute to the $Ca^{2+}$-Independent Transient Outward $K^+$ Current in Rat Ventricle, Journal of Physiology, 1997, vol. 500, No. 1, pp. 51-64.
Foreman et al., "Reactive Oxygen Species Produced by NADPH Oxidase Regulate Plant Cell Growth", Nature, Mar. 27, 2003, vol. 422, pp. 442-446.
Frankel et al., "Cellular Uptake of the Tat Protein from Human Immunodeficiency Virus", Cell, vol. 55, Dec. 23, 1988, pp. 1189-1193.
Freyman et al., "A Quantitative, Randomized Study Evaluating Three Methods of Mesenchymal Stem Cell Delivery Following Myocardial Infarction", European Heart Journal, 2006, vol. 27, pp. 1114-1122.
Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.
Gallet et al., "Cardiosphere-Derived Cells Reverse Heart Failure With Preserved Ejection Fraction in Rats by Decreasing Fibrosis and Inflammation", JACC: Basic to Translational Science, Jan. 1, 2016, vol. 1, No. 1-2, pp. 14-28.
Gallet et al., "Intracoronary Delivery of Self-Assembling Heart-Derived Microtissues (Cardiospheres) For Prevention of Adverse Remodeling In a Pig Model of Convalescent Myocardial Infarction", <http://circinterventions.ahajournals.org>, Dec. 8, 2015, pp. 21.
Galli et al., "Neural Stem Cells: An Overview", Circulation Research, 2003, vol. 92, No. 6, pp. 598-608.
Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.
George et al, "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.
Gibco, "Insulin-Transferrin-Selenium", Product Sheet, 2014.
Gibco, "Insulin-Transferrin-Selenium: 100X (For General Tissue Culture Applications)", Product Sheet, Form No. 2672, Jun. 2001, p. 1.
Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.
Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology—Heart and Circulatory Physiology, Apr. 2005, vol. 288, No. 4, pp. H1851-H1858.
Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.
Good et al., "β-Amyloid Peptide Blocks the Fast-Inactivating $K^+$ Current in Rat Hippocampal Neurons", Biophysical Journal, Jan. 1996, vol. 70, pp. 296-304.
Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.
Grayson et al. "Hypoxia Enhances Proliferation and Tissue Formation of Human Mesenchymal Stem Cells", Biochemical and Biophysical Research Communications, 2007, vol. 358, pp. 948-953.
Green et al., "Autonomous Functional Domains of Chemically Synthesized Human Immunodeficiency Virus Tat Trans-Activator Protein", Dec. 23, 1988, Cell, vol. 55, pp. 1179-1188.
Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.
Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.
Grossman et al., "Contractile State of the Left Ventricle in Man as Evaluated from End-Systolic Pressure-Volume Relations", Circulation, vol. 56, No. 5, Nov. 1977, pp. 845-852.
Gu, Yiping, "Bispecific Antibody Targeted Stem Cell Therapy for Myocardial Repair", Dissertation, University of California San Francisco and University of California Berkeley, 2008, pp. 94.
Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.
Hacein-Bey-Abina et al., "LMO2-Associated Clonal T Cell Proliferation in Two Patients after Gene Therapy for SCID-X1", Science, Oct. 17, 2003, vol. 302, pp. 415-419 with Erratum in 1 page.
Haderk et al., "Tumor-Derived Exosomes Modulate PD-L1 Expression in Monocytes", Science Immunology, Jul. 28, 2017, vol. 2, No. 13, pp. 1-11.
Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. 1108-1113.
Haider et al., "Bone Marrow Stem Cell Transplantation for Cardiac Repair", American Journal of Physiology—Heart and Circulatory Physiology, 2005, H2557-H2567, vol. 288.
Hainsworth et al., "The Nitrone Disodium 2,4-Sulphophenyl-N-Tert-Butylnitrone is Without Cytoprotective Effect on Sodium Nitroprusside-Induced Cell Death in N1E-115 Neuroblastoma Cells in vitro", Journal of Cerebral Blood Flow & Metabolism, 2008, vol. 28, pp. 24-28.

(56) References Cited

OTHER PUBLICATIONS

Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.
Harvey, "Molecular Determinants of Cardiac Development and Congenital Disease," Mouse Development, Patterning, Morphogenesis, and Organogensis, 2002, pp. 331-370, Chapter 16.
Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.
Hergenreider et al., "Atheroprotective Communication Between Endothelial Cells and Smooth Muscle Cells Through miRNAs", Nature Cell Biology, Mar. 2012, vol. 14, No. 3, pp. 249-256.
Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.
Hierlihy et al., "The Post-Natal Heart Contains a Myocardial Stem Cell Population", FEBS Letters, 2002, vol. 530, No. 1-3, pp. 239-243.
Hine et al., "NRF2 and the Phase II Response in Acute Stress Resistance Induced by Dietary Restriction", Journal of Clinical & Experimental Pathology, Jun. 19, 2012, vol. S4, No. 4, pp. 1-33.
Hochedlinger et al., "Nuclear Reprogramming and Pluripotency", Nature, Jun. 29, 2006, vol. 441, pp. 1061-1067.
Hu et al., "MicroRNA-210 as a Novel Therapy for Treatment of Ischemic Heart Disease", Circulation, Sep. 14, 2010, vol. 122, Supplement 11, S124-S131, pp. 17.
Hullinger et al., Inhibition of miR-15 Protects Against Cardiac Ischemic Injury, Circulation Research, Jan. 6, 2012, vol. 110, No. 1, pp. 71-81.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Exosomes: Fundamental Biology and Roles in Cardiovascular Physiology", Annual Review of Physiology, 2016, vol. 78, pp. 67-83.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
Ikehara et al., "Grand Challenges in Stem Cell Treatments", Frontiers in Cell and Developmental Biology, Oct. 10, 2013, vol. 1, No. 2, pp. 2.
International Search Report and Written Opinion received in PCT Application No. PCT/US2018/066072, dated May 7, 2019 in 13 pages.
Invitation to Pay Additional Fees received in PCT Application No. PCT/US2018/066072, dated Mar. 12, 2019 in 2 pages.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal of Clinical Investigation, Jun. 2001, pp. 1395-1402, vol. 107, No. 11.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.

Jutkiewicz, Emily, The Antidepressant-Like Effects of Delta-Opioid Receptor Agonists, Molecular Interventions, 2006, vol. No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.
Kamdar et al., "Dystrophin-Deficient Cardiomyopathy", Journal of the American College of Cardiology, 2016, vol. 67, No. 21, pp. 2533-2546.
Karlsson et al., "Insulin Gene Enhancer Binding Protein Isl-1 is a Member of a Novel Class of Proteins Containing Both a Homeo- and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.
Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kooijmans et al., "PEGylated and Targeted Extracellular Vesicles Display Enhanced Cell Specificity and Circulation Time", Journal of Controlled Release, 2016, vol. 224, pp. 77-85.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. 1167-1173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
Laflamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, No. 3, pp. 214-222.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Landazuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.

(56) References Cited

OTHER PUBLICATIONS

Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, MD, et al., "Transplantation of Fetal Myocardial Tissue Into the Infarcted Myocardium of Rat", Circulation, Nov. 1, 1996, vol. 94, No. 9, II-332-II-336.
Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.
Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.
Li et al., "Cardiospheres Recapitulate a Niche-Like Microenvironment Rich in Stemness and Cell-Matrix Interactions, Rationalizing Their Enhanced Functional Potency for Myocardial Repair", Stem Cells: Translational and Clinical Research, 2010, pp. 2088-2098, vol. 28.
Li et al., "Direct Comparison of Different Stem Cell Types and Subpopulations Reveals Superior Paracrine Potency and Myocardial Repair Efficacy with Cardiosphere-Derived Cells", Journal of American College of Cardiology, 2012, vol. 59, No. 10, pp. 942-953.
Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.
Li et al., "IL-6 Contributes to the Defective Osteogenesis of Bone Marrow Stromal Cells from the Vertebral Body of the Glucocorticoid-Induced Osteoporotic Mouse", PLoS ONE, Apr. 29, 2016, vol. 11, No. 4, pp. 19.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.
Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.
Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.
Liao et al., "Enhanced Efficiency of Generating Induced Pluripotent Stem (IPS) Cells from Human Somatic Cells by a Combination of Six Transcription Factors", Cell Research, 2008, vol. 18, pp. 600-603.
Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.
Lindsay, Mark A., "Peptide-Mediated Cell Delivery: Application in Protein Target Validation", Current Opinion in Pharmacology, 2002, vol. 2, pp. 587-594.
Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.
Liu et al. "Autologous Stem Cell Transplantation for Myocardial Repair", American Journal of Physiology, Heart and Circulatory Physiology, 2004, pp. H501-H511, vol. 287.
Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.
Liu et al., "The Immunogenicity and Immune Tolerance of Pluripotent Stem Cell Derivatives", Frontiers in Immunology, Jun. 2017, vol. 3, No. 645, pp. 1-6.
Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.
Lum et al., "The New Face of Bispecific Antibodies: Targeting Cancer and Much More", Experimental Hematology, 2006, pp. 1-6, vol. 34.
Lyngbaek et al., "Cardiac Regeneration by Resident Stem and Progenitor Cells in the Adult Heart", Basic Research in Cardiology, 2007, vol. 102, pp. 101-114.
Maitra et al., Genomic Alterations in Cultured Human Embryonic Stem Cells, Nature Genetics, Oct. 2005, vol. 37, No. 10, pp. 1099-1103.
Makkar et al., "Intracoronary Cardiosphere-Derived Cells for Heart Regeneration After Myocardial Infarction (CADUCEUS): A Prospective, Randomised Phase 1 Trial", Lancet, Mar. 10, 2012, vol. 379, pp. 895-904.
Maletic-Savatic et al., "Differential Spatiotemporal Expression of K+ Channel Polypeptides in Rat Hippocampal Neurons Developing In Situ and In Vitro", The Journal of Neuroscience, May 1995, vol. 15, No. 5, pp. 3840-3851.
Malliaras et al., "Intracoronary Cardiosphere-Derived Cells After Myocardial Infarction", Journal of the American College of Cardiology, 2014, vol. 63, No. 2, pp. 110-121.
Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.
Marbán, Eduardo, "Big Cells, Little Cells, Stem Cells: Agents of Cardiac Plasticity", Circulation Research, 2007, vol. 100, No. 4, pp. 445-446.
Marshall et al., "The Jellyfish Green Fluorescent Protein: A New Tool for Studying Ion Channel Express and Function", Neuron, Feb. 1995, vol. 14, pp. 211-215.
Martens et al., "Percutaneous Cell Delivery Into the Heart Using Hydrogels Polymerizing In Situ", Cell Transplantation, 2009, vol. 18, No. 3, pp. 297-304.
Matsumura, Tsuyoshi, "Cardiaphal Association in Muscular Dystrophy", Nanbyo To Zaitaku Care (Intractable Diseases and Home Care), 2013, vol. 19, No. 8, pp. 55-57.
Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.
McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.
Mehmel et al., "The Linearity of the End-Systolic Pressure-Volume Relationship in Man and its Sensitivity for Assessment of Left Ventricular Function", Circulation, 1981, vol. 63, pp. 1216-1222.
Messina et al., "Isolation and Expansion of Adult Cardiac Stem Cells from Human and Murine Heart", Oct. 29, 2004, Circulation Research, Cellular Biology, American Heart Association, vol. 95, pp. 911-921.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.

(56) References Cited

OTHER PUBLICATIONS

Miller III, et al., Meta-Analysis: High-Dosage Vitamin E Supplementation May Increase All-Cause Mortality, Annals of Internal Medicine, 2005, vol. 142, pp. 37-46.
Miltenyi et al., "High Gradient Magnetic Cell Separation With MACS¹", Cytometry, 1990, pp. 231-238, vol. 11.
Mitsui et al., "The Homeoprotein Nanog is Required for Maintenance of Pluripotency in Mouse Epiblast and ES Cells", Cell, May 30, 2003, vol. 113, No. 5, pp. 631-642.
Miyazono et al. "Latent High Molecular Weight Complex of Transforming Growth Factor β1", May 5, 1988, vol. 263, No. 13, pp. 6407-6415.
Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.
Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.
Moss et al., "Conservation of the Heterochronic Regulator Lin-28, its Developmental Expression and MicroRNA Complementary Sites", Developmental Biology, 2003, vol. 258, No. 2, pp. 432-442.
Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.
Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.
Nadal-Ginard et al., "Myocyte Death, Growth, and Regeneration in Cardiac Hypertrophy and Failure", Circulation Research, 2003, vol. 92, pp. 139-150.
Nadal-Ginard et al., "A Matter of Life and Death: Cardiac Myocyte Apoptosis and Regeneration", Journal of Clinical Investigation, May 2003, vol. 111, No. 10, pp. 1457-1459.
Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.
Naka et al., "Regulation of Reactive Oxygen Species and Genomic Stability in Hematopoietic Stem Cells", Antioxidants & Redox Signaling, 2008, vol. 10, No. 11, pp. 1883-1894.
Nakagawa et al., "Generation of Induced Pluripotent Stem Cells without Myc from Mouse and Human Fibroblasts", Nature Biotechnology, Jan. 2008, vol. 26, No. 1, pp. 101-106.
Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.
Nelson et al., "CXCR4+/FLK-1+ Biomarkers Select a Cardiopoietic Lineage from Embryonic Stem Cells", Stem Cells, 2008, vol. 26, pp. 1464-1473.
Nelson, MD, PhD et al., "Repair of Acute Myocardial Infarction with iPS Induced by Human Stemness Factors", Circulation, Aug. 4, 2009, vol. 120, No. 5, pp. 408-416.
Niethammer et al., "A Tissue-Scale Gradient of Hydrogen Peroxide Mediates Rapid Wound Detection in Zebrafish", Nature, Jun. 18, 2009, vol. 459, pp. 996-999.
Noguchi et al., "Protein Transduction Technology: A Novel Therapeutic Perspective", Acta Medica Okayama, 2006, vol. 60, No. 1, pp. 1-11.
North et al., "The Intersection Between Aging and Cardiovascular Disease", Circulation Research, Apr. 13, 2012, pp. 1097-1108.
Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.
Odelberg et al., "Dedifferentiation of Mammalian Myotubes Induced by msx1", Cell, Dec. 22, 2000, vol. 103, No. 7, pp. 1099-1109.
Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.
Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.
Oh et al., "Cardiac Muscle Plasticity in Adult and Embryo by Heart-Derived Progenitor Cells", Annals of the New York Academy of Sciences, 2004, vol. 1015, pp. 182-189.
Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, pp. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content/132/Suppl_3/A13881.short>.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Stem-Cell-Based Therapy and Lessons from the Heart", May 15, 2008, Nature, vol. 453, pp. 322-329.
Passier et al., "Origin and Use of Embryonic and Adult Stem Cells in Differentiation and Tissue Repair", Cardiovascular Research, 2003, vol. 58, No. 2, pp. 324-335.
Payne, Anthony G., "Using Immunomagnetic Technology and Other Means to Facilitate Stem Cell Homing", Medical Hypotheses, 2004, pp. 718-720, vol. 62.
Peterson, MD, MPH, et al., "Risk Stratification After Myocardial Infarction", Annals of Internal Medicine, 1997, vol. 126, No. 7, pp. 561-582.
Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.
Piper et al. "Determinants of Cardiomyocyte Development in Long-Term Primary Culture", Journal of Molecular and Cellular Cardiology, 1988, vol. 20, pp. 825-835.
Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology-Heart and Circulatory Physiology, 2008, vol. 295, pp. H2257-H2263.
Prestwich et al., "The Translational Imperative: Making Cell Therapy Simple and Effective", Acta Biomaterialia, 2012, vol. 8, pp. 4200-4207.
Prunier et al., "Delayed Erythropoietin Therapy Reduces Post-MI Cardiac Remodeling Only at a Dose that Mobilizes Endothelial Progenitor Cells", American Journal of Physiology-Heart and Circulatory Physiology, 2007, vol. 292, pp. H522-H529.
Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.
Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.
Quaini et al., "Chimerism of the Transplanted Heart", The New England Journal of Medicine, Jan. 3, 2002, vol. 346, No. 1, pp. 5-15.
Quevedo et al., "Allogeneic Mesenchymal Stem Cells Restore Cardiac Function in Chronic Ischemic Cardiomyopathy via Trilineage Differentiating Capacity", Proceedings of the National Academy of

(56) References Cited

OTHER PUBLICATIONS

Sciences of the United States of America (PNAS), Aug. 18, 2009, vol. 106, No. 33, pp. 14022-14027.
Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.
Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.
Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17.
Riazifar et al., "Stem Cell Extracellular Vesicles: Extended Messages of Regeneration", Reviews in Advance, Oct. 19, 2016, vol. 14, No. 1, pp. 1-30.
Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.
Risebro et al., "Hand1 Regulates Cardiomyocyte Proliferation Versus Differentiation in the Developing Heart", Development, Nov. 2006, vol. 133, No. 22, pp. 4595-4606.
Rossi et al., "Deficiencies in DNA Damage Repair Limit the Function of Haematopoietic Stem Cells with Age", Nature, Jun. 7, 2007, vol. 447, pp. 725-729.
Rotwein et al., "Organization and Sequence of the Human Insulin-Like Growth Factor I Gene", The Journal of Biological Chemistry, Apr. 15, 1986, vol. 261, No. 11, pp. 4828-4832.
Rubio et al., "Spontaneous Human Adult Stem Cell Transformation", Cancer Research, 2005, vol. 65, pp. 3035-3039.
Rücker-Martin et al., "Dedifferentiation of Atrial Myocytes During Atrial Fibrillation: Role of Fibroblast Proliferation in Vitro", Cardiovascular Research, 2002, vol. 55, pp. 38-52.
Rudy, B. "Diversity and Ubiquity of K Channels", Neuroscience, 1988, vol. 25, No. 3, pp. 729-749.
Saito et al., "Cell Death Caused by Selenium Deficiency and Protective Effect of Antioxidants", The Journal of Biological Chemistry, Oct. 10, 2003, vol. 278, No. 41, pp. 39428-39434.
Sareen et al., Chromosome 7 and 19 Trisomy in Cultured Human Neural Progenitor Cells, PLoS One, Oct. 2009, vol. 4, No. 10, e7630, pp. 12.
Sasano et al., "Molecular Ablation of Ventricular Tachycardia after Myocardial Infarction", Natural Medicine, 2006, vol. 12, No. 11, pp. 1256-1258.
Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.
Scaria et al., "Host-Virus Genome Interactions: Marco Roles for MicroRNAs", Cellular Microbiology, 2007, vol. 9, No. 12, pp. 2784-2794.
Seifried et al., "A Review of the Interaction Among Dietary Antioxidants and Reactive Oxygen Species", Journal of Nutritional Biochemistry, 2007, vol. 18, pp. 567-579.
Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.
Seródio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.
Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.
Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.
Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shen et al. "Isolation of an Insulin-Like Growth Factor II cDNA with a Unique 5' Untranslated Region from Human Placenta", Mar. 1988, Proceedings of the National Academy of Sciences of the United States of America (PNAS), vol. 85, pp. 1947-1951.
Shenje et al., "Lineage Tracing of Cardiac Explant Derived Cells", PLoS One, Apr. 2008, vol. 3, No. 4, e1929, pp. 10.
Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.
Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.
Sigma-Aldrich, Inc., "Nutrient Mixture F12 Ham Kaighn's Modification (F12K)", Product Description, May 2007, pp. 2.
Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.
Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.
Singh, et al. "High-Dose α-Tocopherol Therapy Does Not Affect HDL Subfractions in Patients with Coronary Artery Disease on Statin Therapy", Clinical Chemistry, 2007, vol. 53, No. 3, pp. 525-528.
Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-S39.
Smart et al., "De Novo Cardiomyocytes from Within the Activated Adult Heart After Injury", Nature, Jun. 30, 2011, vol. 474, pp. 640-646.
Smith, PhD et al., "Stem Cells in the Heart: What's the Buzz all About? Part 1: Preclinical Considerations", Heart Rhythm, May 2008, vol. 5, No. 5, pp. 749-757.
Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.
Smith et al., "Regenerative Potential of Cardiosphere-Derived Cells Expanded From Percutaneous Endomyocardial Biopsy Specimens", Circulation, Feb. 5, 2007, pp. 896-908, vol. 115.
Smith et al., "Unique Phenotype of Cardiospheres Derived from Human Endomyocardial Biopsies", Circulation, Supplement II, Oct. 25, 2005, pp. 2, vol. 112, No. 17.
Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.
Smits, Anke Maria, "Cell-Based Cardiac Repair", Thesis, Utrecht University, The Netherlands, 2009, pp. 180.
Srivastava et al., "Thymosin β4 Is Cardioprotective after Myocardial Infarction", Annals of the New York Academy of Sciences, Sep. 2007, vol. 1112, pp. 161-170. Abstract only.
Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.
Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.

(56) References Cited

OTHER PUBLICATIONS

Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.
Sussman, Mark A., "Myocardial Aging and Senescence: Where Have the Stem Cells Gone?" Annual Review of Physiology, 2004, vol. 66, pp. 29-48.
Takahashi et al., "Induction of Pluripotent Stem Cells from Adult Human Fibroblasts by Defined Factors," Cell, vol. 131, Nov. 30, 2007, pp. 861-872.
Takahashi et al., "Induction of Pluripotent Stem Cells from Fibroblast Cultures, Nature Protocols", 2007, vol. 2 No. 12, pp. 3081-3089.
Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.
Takeda et al., "Induced Pluripotant Stem(IPS) Cell-Based Cell Therapy for Duchenne Muscular Dystrophy", History of Medicine, Dec. 31, 2011, vol. 239, No. 14, pp. 1440-1444.
Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.
Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.
Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.
Ten Dijke et al. "Identification of Another Member of the Transforming Growth Factor Type β Gene Family", Proceedings of the National Academy of Sciences of the United States of America (PNAS), 1988, vol. 85, pp. 4715-4719.
Terrovitis, MD, et al., "Assessment and Optimization of Cell Engraftment after Transplantation into the Heart", Circulation Research, Feb. 19, 2010, vol. 106, No. 3, pp. 479-494.
Terrovitis, MD, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.
The Exosomes Derived from CDCs Experimental Data to Show that Unexpectedly Improved Characteristics are Exhibited, p. 1.
Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.
Torella et al., "Cardiac Stem Cell and Myocyte Aging, Heart Failure, and Insulin-Like Growth Factor-1 Overexpression", Circulation Research, 2004, vol. 95, pp. 514-524.
Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.
Trevethick et al., "Treating Lung Inflammation with Agonists from the Adenosine A2A Receptor: Promises, Problems and Potential Solutions", British Journal of Pharmacology, 2008, vol. 155, pp. 463-474.
Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Uemura et al., "Bone Marrow Stem Cells Prevent Left Ventricular Remodeling of Ischemic Heart Through Paracrine Signaling", Circulation Research, 2006, vol. 98, pp. 1414-1421.
Ueno et al., "Biphasic Role for Wnt/β-Catenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.
Ulloa-Montoya et al., "Culture Systems for Pluripotent Stem Cells", Journal of Bioscience and Bioengineering, 2005, vol. 100, No. 1, pp. 12-27.
Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.
Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.
Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.
Van Der Geest et al., "Quantification in Cardiac MRI", Journal of Magnetic Resonance Imaging, 1999, vol. 10, pp. 602-608.
Van Gent et al., "Chromosomal Stability and the DNA Double-Stranded Break Connection", Nature, Mar. 2001, vol. 2, pp. 196-206.
Van Vliet et al., "Progenitor Cells Isolated from the Human Heart: a Potential Cell Source for Regenerative Therapy", Netherlands Heart Journal, May 2008, vol. 16, No. 5, pp. 163-169.
Van Winkle et al., "Cardiogel: A Biosynthetic Extracellular Matrix for Cardiomyocyte Culture", In Vitro Cellular & Developmental Biology—Animal, Sep. 1996, vol. 21, pp. 478-485.
Vela et al., "Quest for the Cardiovascular Holy Grail: Mammalian Myocardial Regeneration", Cardiovascular Pathology, 2008, vol. 17, No. 1-5.
Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.
Von Harsdorf, R., "Can Cardiomyocytes Divide?" Heart, 2001, vol. 86, pp. 481-482.
Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Wagner, Richard, "The State of the Art in Antisense Research", Nature Medicine, Nov. 1995, vol. 1, No. 11, pp. 1116-1118.
Walder et al., "Up-Regulation of Neural Stem Cell Markers Suggests the Occurrence of Dedifferentiation in Regenerating Spinal Cord", Development Genes and Evolution, 2003, vol. 213, pp. 625-630.
Walravens et al., "Cardiosphere-Derived Cell and Mesenchymal Stem Cell Extracellular Vesicles Contain Distinct RNA Cargo", Scientific Program, ISEV2017, Dec. 2017, p. 173.
Wang et al. "The LIM Domain Homeobox Gene isl-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wang et al., "Establishment of New Mouse Embryonic Stem Cell Lines is Improved by Physiological Glucose and Oxygen", Cloning and Stem Cells, 2006, vol. 8, No. 2, pp. 108-116.
Wernig el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.

(56) References Cited

OTHER PUBLICATIONS

Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Wu et al., "Cell Delivery in Cardiac Regenerative Therapy", Ageing Research Reviews, 2012, vol. 11, pp. 32-40.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a KDR+ Embryonic-Stem-Cell-Derived Population", Nature, May 22, 2008, vol. 453, pp. 524-528.
Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLOS One, Dec. 2, 2014, pp. 1-29.
Yu et al., "Induced Pluripotent Stem Cell Lines Derived from Human Somatic cells," Science, Dec. 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1278. Abstract only.
Zhao et al., "Targeting Human CD34+ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.
Zhou et al., "Down-Regulation of microRNA-26a Promotes Mouse Hepatocyte Proliferation During Liver Regeneration", PLoS ONE, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.
Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.
Ausar et al., "Characterization of Casein Micelle Precipitation by Chitosans", Journal of Dairy Science, vol. 84, No. 2, Feb. 2001, pp. 2-4.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Bryan et al., "Implications of Protein Fold Switching", Current Comments, posted Feb. 4, 2013, printed in 4 pages. https://web.archive.org/web/20160628060217/http://www.elsevierblogs.com/currentcomments/?p=962.
Carr et al., "Cardiosphere-Derived Cells Improve Function in the Infarcted Rat Heart for at Least 16 Weeks—an MRI Study", PLoS One, Oct. 2011, vol. 6, No. 10, pp. 1-10.
Catalano, Mariadelva, "Engineering Exosomes Toward Folate Receptor Expressing Cells", Dec. 7, 2017, pp. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
Cheng et al., "Focus on Mesenchymal Stem Cell-Derived Exosomes: Opportunities and Challenges in Cell-Free Therapy", Hindawi, Stem Cells International, 2017, Article ID 6305295, pp. 10.
De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).
Declaration of Rachel Smith, PH.D., Curriculum Vitae, Exhibit A U.S. Appl. No. 13/412,051, 2018, 13 pages.
Dezawa et al., "Part 3 Toward the Realization of Autologous Cell Transplantation—Induction of Muscle Cells Using Bone Marrow Stromal Cells," Kyoto University Graduate School of Medicine Intractable, Diseases and Home Care 11 (11) 56-59, 2006.
Edelberg et al., "Platelet-Derived Growth Factor-AB Limits the Extent of Myocardial Infarction in a Rat Model: Feasibility of Restoring Impaired Angiogenic Capacity in the Aging Heart", Circulation, 2002, vol. 150, No. 5, pp. 608-613.
Fernandez-Aviles et al., "Experimental and Clinical Regenerative Capability of Human Bone Marrow Cells After Myocardial Infarction", Circulation Research, 2004, vol. 95, pp. 742-748.
Gallet et al, "Exosomes Secreted by Cardiosphere-Derived Cells Reduce Scarring, Attenuate Adverse Remodeling, and Improve Function in Acute and Chronic Porcine Myocardial Infarction", European Heart Journal, Jan. 14, 2017, vol. 38, pp. 201-211.
Genbank Accession DQ580112.1. "*Homo sapiens* piRNA piR-48224, complete sequence", Web. Dec. 2, 2008; [retrieved Sep. 7, 2021]. Retrieved from the Internet: https://www.ncbi.nlm.nih.gov/nuccore/DQ580112.1; p. 1. [This refers to a webpage and the dates apparent in the document are listed herewith. However, the webpage may have been publicly available in some form at a date earlier than those listed].
Gen Bank Accession DO592932.1. "*Homo spaiens* piRNA piR-33044, complete sequence", Web. Dec. 2, 2008; [retrieved Sep. 7, 2021]. Retrieved from the Internet: https://www.ncbi.nlm.nih.gov/nuccore/DQ592932.1; p. 1. [This refers to a webpage and the dates apparent in the document are listed herewith. However, the webpage may have been publicly available in some form at a date earlier than those listed].
Girard et al., "A Germline-Specific Class of Small RNAs Binds Mammalian Piwi Proteins", Nature, Jul. 13, 2006, vol. 442, pp. 199-202.
Heng et al., "Strategies for Directing the Differentiation of Stem Cells into the Cardiomyogenic Lineage in Vitro", Cardiovascular Research, 2004, vol. 62, pp. 34-42.
Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24, 2001, vol. 98, No. 9, pp. 5335-5340.
Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.
Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, pp. 7.

(56) References Cited

OTHER PUBLICATIONS

Kasai-Brunswick et al., "Cardiosphere-Derived Cells do not Improve Cardiac Function in Rats with Cardiac Failure," Stem Cell Research & Therapy, 2017, vol. 8, No. 36, 9 pages.

Kim, PhD et al., "Engineering Macrophage-Derived Exosomes for Targeted Paclitaxel Delivery to Pulmonary Metastases:in Vitroandin Vivoevaluations", Nanomedicine, Nanotechnology, Biology, and Medicine, vol. 14, 2018, pp. 195-204.

Kim, PhD et al., "Exosome Mediated Delivery of Paclitaxel for the Treatment of Multi Drug Resistant Pulmonary Metastases", Dissertation, Chapel Hill, Dec. 31, 2016, pp. 112.

Kim et al., "Natural Product Derivative BIO Promotes Recovery After Myocardial Infarction Bia Unique Modulation of the Cardiac Microenvironment", Scientific Reports, vol. 6:30726, 2016, pp. 13.

Kobashigawa et al., "A Randomized Active-Controlled Trial of Mycophenolate Mofetil in Heart Transplant Recipients", Transplantation, Aug. 27, 1998, vol. 66, No. 4, pp. 507-515.

Lee, et al., "Clonal Isolation of Muscle-derived Cells Capable of Enhancing Muscle Regeneration and Bone Healing," The Journal of Cell Biology, vol. 150, No. 5, Sep. 4, 2000, 1085-1099, http://www.jcb.org.

Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.

Limana et al., "Exogenous High-Mobility Group Box 1 Protein Induces Myocardial Regeneration after Infarction via Enhanced Cardiac C-Kit+ Cell Proliferation and Differentiation", Circulation Research, Oct. 14, 2005, vol. 97, No. 8, pp. 73-83.

Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.

Maqbool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.

Mason, "Techniques for Right and Left Ventricular Endomyocardial Biopsy", American Journal of Cardiology, 1978, vol. 41, No. 5, pp. 887-892.

Matsushita, Satoshi, "Treatment for Myocardial Injury Using Regenerative Medicine", 2011, vol. 57, pp. 324 to 328.

Mazer, et al., "Late-Breaking Science Abstracts From the American Heart Association's Scientific Session 2017 and Late-Breaking Abstracts in Resuscitation Science From the Resuscitation Science Symposium 2017," Scientific Sessions Nov. 11-15, 2017, Anaheim, CA, Circulation. 2017;136:e448-e467. DOI: 10.1161/CIR.0000000000000546, Dec. 12, 2017; e449-e467.

Menasché et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.

NIH: ClinicalTrials.gov, Archieve NCT02485938 on Jun. 26, 2015, Study Record (John Jefferies, investigator; Deborah Ascheim, director); retrieved from the Internet: URL, https://clinicaltrials.gov/ct2/history/NCT02485938?V_1View#StudyPageTop. [This refers to a webpage and the dates apparent in the document are listed herewith. However, the webpage may have been publicly available in some form at a date earlier than those listed].

O'Brien et al., "Human hy4 Ro RNA (associated with erythrocyte Ro RNP's)", National Library of Medicine, <https://www.ncbi.nlm.nih.gov/nucleotide/x57566>, 1991, 1 page.

Ou et al., "The Nuclear Pore Complex Protein Tpr is a Common Autoantigen in Sera that Demonstrate Nuclear Envelope Staining by Indirect Immunofluorescence", Clinical and Experimental Immunology, May 2004, vol. 136, No. 2, pp. 379-387.

Pfeffer et al., "Myocardial Infarct Size and Ventricular Function in Rats", Circulation Research, Apr. 1979, vol. 44, No. 4, pp. 503-512.

Pilia et al., "Transplantation and Perfusion of Microvascular Fragments in a Rodent Model of Volumetric Muscle Loss Injury", European Cells and Materials, vol. 28, 2014, pp. 11-24.

Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.

Schachinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.

Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, pp. 22.

Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.

Shimasaki et al., "Exosome Research and Co-culture Study", Biological and Pharmaceutical Bulletin, vol. 40, No. 9, 2018, pp. 1311-1321.

Shimomura et al., "Steroid Treatment for Duchenne Muscular Dystrophy", Brain and Development, 2011, vol. 43, pp. 24-29.

Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.

Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.

Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.

Smyth et al., "Surface Functionalization of Exosomes Using Click Chemistry", Bioconjugate Chemistry, vol. 25, No. 10, Sep. 30, 2014, pp. 1777-1784.

Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.

Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.

Tseng et al., "The GSK-3 Inhibitor BIO Promotes Proliferation in Mammalian Cardiomyocytes", Chemistry & Biology, 13, Sep. 2006, pp. 957-963.

Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.

USPTO Patent Trial and Appeal Board., "Decision on Appeal", in U.S. Appl. No. 13/412,051, dated Jun. 8, 2020, 12 pages.

USPTO Patent Trial and Appeal Board., "Decision on Appeal", in U.S. Appl. No. 14/437,812, dated Jun. 19, 2020, 22 pages.

USPTO Patent Trial and Appeal Board., "Declaration of Rachel R. Smith, PhD," in U.S. Appl. No. 13/412,051, dated Oct. 13, 2017, 16 pages.

Vella et al., "PIWI-Interacting RNA (piRNA) Signatures in Human Cardiac Progenitor Cells", The International Journal of Biochemistry & Cell Biology, 2016, vol. 76, pp. 1-11.

Wan et al., "Aptamer-Conjugated Extracellular Nanovesicles for Targeted Drug Delivery", Cancer Research, vol. 78, No. 3, Dec. 7, 2017, pp. 798-808.

Wang et al., Challenges in the Development and Establishment of Exosome-Based Drug Delivery Systems, Journal of Controlled Release, 2021, vol. 329, pp. 894-906.

(56) References Cited

OTHER PUBLICATIONS

Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.

Warsito et al., "Antibacterial Efficacy of 2-Citronellyl Benzimidazole Nanoencapsulation with Chitosan-Tripolyphosphate and Casein Micellar Coatings", IOP Conf. Series: Earth and Environmental Science, vol. 299, 2019, pp. 1-7.

Xu et al., "Generation of Induced Cardiospheres via Reprogramming of Skin Fibroblasts for Myocardial Regeneration", Stem Cells, vol. 34, No. 11, 2016, pp. 2693-2706.

Zeger et al., "Longitudinal Data Analysis for Discrete and Continuous Outcomes", Biometrics, Mar. 1986, vol. 42, No. 1, pp. 121-130.

Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.

Zhao et al., "Exosomes as Drug Carriers for Cancer Therapy and Challenges Regarding Exosome Uptake" Biomedicine & Pharmacotherapy, 2020, vol. 128, 9 pages.

Chun, et al., "Injection of Vessel-Derived Stem Cells Prevents Dilated Cardiomyopathy and Promotes Angiogenesis and Endogenous Cardiac Stem Cell Proliferation in mdx/utrn$^{-1-}$ but Not Aged mdx Mouse Models for Duchenne Muscular Dystrophy," Stem Cells Translational Medicine 2013:2:68-80 (Year: 2013).

Skoczylas, et al.: "Cellular Targets of the SV40 Small-t Antigen in Human Cell Transformation," Cell Cycle 3:5, 606-610; May 2004.

\* cited by examiner

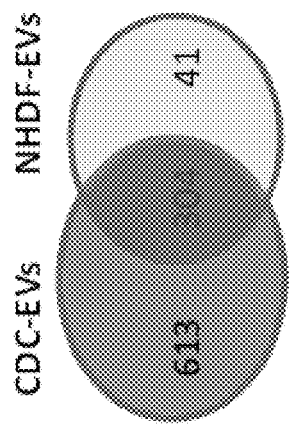
FIG. 1C
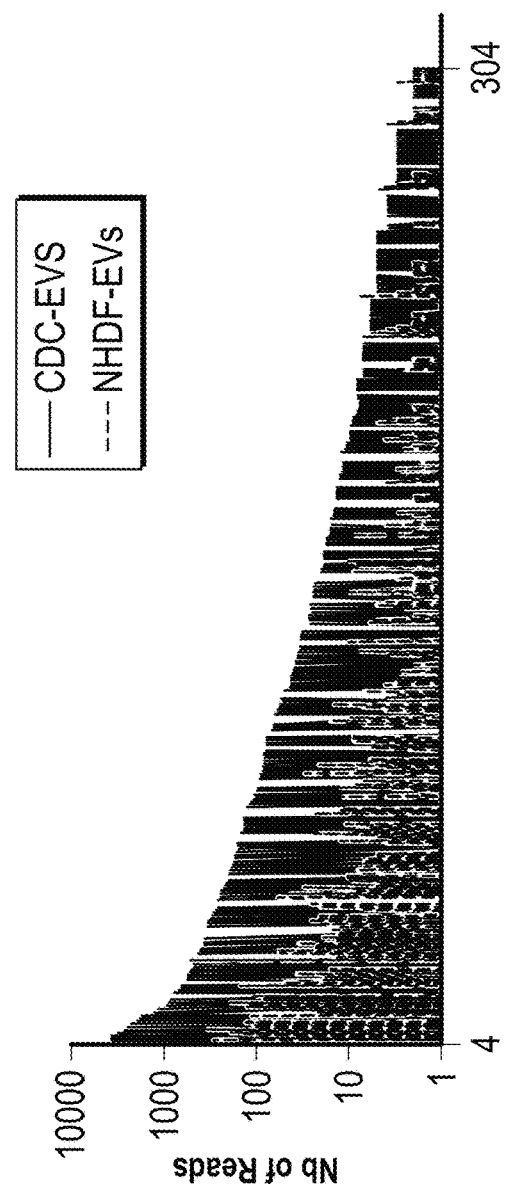
FIG. 1D
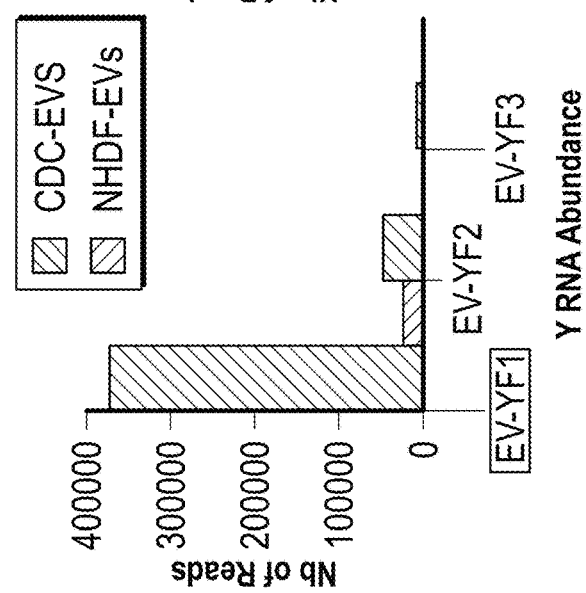

FIG. 1E

```
                   1         10        20        30        40        50        60        70        80        90       100       110    120124
                   |----|----|----|----|----|----|----|----|----|----|----|----|----|----|----|----|----|----|----|----|----|----|----|----|
hY1                GGCTGG-T---CCGAAGGT-AGTGAGTTATCTCAATTGATTGTTCACAGTAGTTACAGATCGAAGTCCTTGTTCTCCCCCTTCTACTCTTTCCCCCTTCTCACTACTGACTTGACTAGTCTTTT
hY3                GGCTGG-T---CCGAGTG--AGTG-GTGTTTACAACTAATTGATCACAGAAACCAGTACAGATT----TCTTTGTTCC-----CACTGCTTCACTTGACTAGCCTTTT
hY4                GGCTGG-T---CCGAGGT-AGTGGGTTATCAGAGATTACAGAGAACCAGTACAGATT--GTCACTAAG----TCTTTGTTCC-----ACAACCCCCACTGCTAAATTGACCGGCTTTT
hY5                AGTTGG-T---CCGAGTGT-TGTGGGTTATTGTTA--AGTTGATTAACATTGTCTC-----------CCCCCACACCGGCGTTGACTAG-CTTGCTGTGTTT

URS000072C009      GGCTGG-T---CCGAGTG--AGTG-GTGTTTACAACTAATTGATCACAGAAACCAGTTACAGATT----TCTTTG
URS000072DA11      GGCTGG-T---CCGATGGTTAGTGGGTTATCAGAGAACTATTAACTATTAACATTAGT--GTCACTAAGT
URS00006FA3EC      GGCTGGCT---CCGATGGT-AGTGGGTTATCAGAGAACTATTAACTATTAACATTAGT
URS00070E5AC       GGCTGG-T---CCGATGGT-AGTGGGTTATCAGAGATTACAGAGAACCATCATCCA
URS000072E641      GCCAAGGCGGGACGGGCTGGTCCGATGGTAG-TGAGTTATC--TCAATT
URS00006AB25C              GGCTGGTCCGATGGTAG-TGAGTTATC--TCAATTAAAAAAAA
URS00006AE197              GGCTGGTCCGATGGTAG-TGAGTTATC--TCAGGTT
URS00006CB75C              GGCTGGTCCGATGGTAG-TGAGTTATCCATCAATT
URS00006E033B              GGGCTGGTCCGATGGTAG-TGGGTTATC-TACTCT
URS00006E4C2B              GGCTGGTCCGATGGTAGGTGGGTTATC--AGAACTTATT
URS000066507               GGCTGGTCCGAAGGTAG-TGGGTTATC--AGAACTT
URS000728268               GGCGGGGCTG-TCCGATGGTAG-TGGGTTATCAGAGACC
URS000628CO5               GGCTGGCT---CCGAAGGTACGTGAGTTATC--TCAATTGA
URS00006D365A              GCTGGCT---C-GAAGGTACGTGAGTTATC--TCAATTA
URS00007205ED              AGTTGGTCCGAGTGTTGTGGGTTATTGTTAAGTTT

URS000072F137                                                                                                GC-GAACCCCCACT-GCTAA---ATTTGACTGG-CTT
URS000072DB3C                                                                                                   CCCCCACTGCTAA---ATTTGACTGG-CTTTA
URS00006E0030                                                                                                   CCCCGCACT-GCTAA---ATTTGACTGGACTTTG
URS000718090                                                                                                GTTCTACTC-TTCCCCCTTCTCACTACTGCACTGACTAGTCT

Consensus         **ggctccgaggt***tg*gttatc**a***************  ***    ********************************
```

| | |
|---|---|
| EV-YF1 | 5'-GGCUGGUCCGAUGGUAGUGGGUAUCAGAACUAUUAACAUUAGUGUCACUAAAGU-3' |
| 2 from 3' | GGCUGGUCCGAUGGUAGUGGGUAUCAGAACUAUUAACAUUAGUGUCACUAAA |
| 5 from 3' | GGCUGGUCCGAUGGUAGUGGGUAUCAGAACUAUUAACAUUAGUGUCACU |
| 10 from 3' | GGCUGGUCCGAUGGUAGUGGGUAUCAGAACUAUUAACAUUAGUG |
| 2 from 5' | CUGGUCCGAUGGUAGUGGGUAUCAGAACUAUUAACAUUAGUGUCACUAAAGU |
| 5 from 5' | GUCCGAUGGUAGUGGGUAUCAGAACUAUUAACAUUAGUGUCACUAAAGU |
| 10 from 5' | AUGGUAGUGGGUAUCAGAACUAUUAACAUUAGUGUCACUAAAGU |
| 5 from both | GUCCGAUGGUAGUGGGUAUCAGAACUAUUAACAUUAGUGUCACU |

EV-YF1    5'-GGCUGGUCCGAUGGUAGUGGGUUAUCAGAACUUAUUAACAUUAGUGUCACUAAAGU -3'

2 from 5'    CUGGUCCGAUGGUAGUGGGUUAUCAGAACUUAUUAACAUUAGUGUCACUAAAGU
3 from 5'    UGGUCCGAUGGUAGUGGGUUAUCAGAACUUAUUAACAUUAGUGUCACUAAAGU
4 from 5'    GGUCCGAUGGUAGUGGGUUAUCAGAACUUAUUAACAUUAGUGUCACUAAAGU
5 from 5'    GUCCGAUGGUAGUGGGUUAUCAGAACUUAUUAACAUUAGUGUCACUAAAGU

FIG. 34

SEQUENCE LISTING

<160> NUMBER OF SEQ ID NOS: 39

<210> SEQ ID NO 1
<211> LENGTH: 113
<212> TYPE: DNA
<213> ORGANISM: Homo sapiens

<400> SEQUENCE: 1

```
ggctggtccg aaggtagtga gttatctcaa ttgattgttc acagtcagtt acagatcgaa      60
ctccttgttc tactctttcc cccttctca ctactgcact tgactagtct ttt             113
```

<210> SEQ ID NO 2

```
<211> LENGTH: 102
<212> TYPE: DNA
<213> ORGANISM: Homo sapiens

<400> SEQUENCE: 2
ggctggtccg agtgcagtgg tgtttacaac taattgatca caaccagtta cagatttctt    60
tgttccttct ccactcccac tgcttcactt gactagcctt tt                       102

<210> SEQ ID NO 3
<211> LENGTH: 96
<212> TYPE: DNA
<213> ORGANISM: Homo sapiens

<400> SEQUENCE: 3
ggctggtccg atggtagtgg gttatcagaa cttattaaca ttagtgtcac taaagttggt    60 atacaaccccc ccactgctaa atttgactgg cttttt                             96

<210> SEQ ID NO 4
<211> LENGTH: 84
<212> TYPE: DNA
<213> ORGANISM: Homo sapiens

<400> SEQUENCE: 4
agttggtccg agtgttgtgg gttattgtta agttgattta acattgtctc ccccacaac     60 cgcgcttgac tagcttgctg tttt                                           84

<210> SEQ ID NO 5
<211> LENGTH: 56
<212> TYPE: RNA
<213> ORGANISM: Artificial Sequence
<220> FEATURE:
<223> OTHER INFORMATION: Synthesized

<400> SEQUENCE: 5
ggcugguccg augguagugg guuaucagaa cuuauuaaca uuagugucac uaaagu         56

<210> SEQ ID NO 6
<211> LENGTH: 57
<212> TYPE: RNA
<213> ORGANISM: Artificial Sequence
<220> FEATURE:
<223> OTHER INFORMATION: Synthesized

<400> SEQUENCE: 6
gauguuauua ucguaguaga ugaauaaucg gugcuacgau uaugaguguc agucgcc        57

<210> SEQ ID NO 7
<211> LENGTH: 57
<212> TYPE: RNA
<213> ORGANISM: Artificial Sequence
<220> FEATURE:
<223> OTHER INFORMATION: Synthesized

<400> SEQUENCE: 7
ggcugguccg augguuagug gguuaucaga acuuauuaac auuaguguca cuaaagu        57

<210> SEQ ID NO 8
<211> LENGTH: 20
<212> TYPE: DNA
<213> ORGANISM: Artificial Sequence
<220> FEATURE:
<223> OTHER INFORMATION: Synthesized

<400> SEQUENCE: 8
```
ggctggtccg atggttagtg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthesized

<400> SEQUENCE: 9
actttagtga cactaatgtt                                              20

<210> SEQ ID NO 10
<211> LENGTH: 18
<212> TYPE: DNA
<213> ORGANISM: Artificial Sequence
<220> FEATURE:
<223> OTHER INFORMATION: Synthesized

<400> SEQUENCE: 10
agatccattc ctatgact                                                18

<210> SEQ ID NO 11
<211> LENGTH: 20
<212> TYPE: DNA
<213> ORGANISM: Artificial Sequence
<220> FEATURE:
<223> OTHER INFORMATION: Synthesized

<400> SEQUENCE: 11
gagagatcat ctccaccaat                                              20

<210> SEQ ID NO 12
<211> LENGTH: 25
<212> TYPE: DNA
<213> ORGANISM: Artificial Sequence
<220> FEATURE:
<223> OTHER INFORMATION: Synthesized

<400> SEQUENCE: 12
gcttcggcag cacatatact aaaat                                        25

<210> SEQ ID NO 13
<211> LENGTH: 23
<212> TYPE: DNA
<213> ORGANISM: Artificial Sequence
<220> FEATURE:
<223> OTHER INFORMATION: Synthesized

<400> SEQUENCE: 13
cgcttcacga atttgcgtgt cat                                          23

<210> SEQ ID NO 14
<211> LENGTH: 19
<212> TYPE: DNA
<213> ORGANISM: Artificial Sequence
<220> FEATURE:
<223> OTHER INFORMATION: Synthesized

<400> SEQUENCE: 14
tcgtcttggc cttttggct                                               19

<210> SEQ ID NO 15
<211> LENGTH: 22
<212> TYPE: DNA

```
<213> ORGANISM: Artificial Sequence
<220> FEATURE:
<223> OTHER INFORMATION: Synthesized

<400> SEQUENCE: 15
tccaggtggt ctagcaggtt ct                                          22

<210> SEQ ID NO 16
<211> LENGTH: 22
<212> TYPE: DNA
<213> ORGANISM: Artificial Sequence
<220> FEATURE:
<223> OTHER INFORMATION: Synthesized

<400> SEQUENCE: 16
gtcggaggct taattacaca tg                                          22

<210> SEQ ID NO 17
<211> LENGTH: 25
<212> TYPE: DNA
<213> ORGANISM: Artificial Sequence
<220> FEATURE:
<223> OTHER INFORMATION: Synthesized

<400> SEQUENCE: 17
tcagaattgc cattgccatt gcaca                                       25

<210> SEQ ID NO 18
<211> LENGTH: 20
<212> TYPE: DNA
<213> ORGANISM: Artificial Sequence
<220> FEATURE:
<223> OTHER INFORMATION: Synthesized

<400> SEQUENCE: 18
acttcgggcc atgtttctct                                             20

<210> SEQ ID NO 19
<211> LENGTH: 20
<212> TYPE: DNA
<213> ORGANISM: Artificial Sequence
<220> FEATURE:
<223> OTHER INFORMATION: Synthesized

<400> SEQUENCE: 19
gctggtaggt tgattgtcgt                                             20

<210> SEQ ID NO 20
<211> LENGTH: 24
<212> TYPE: DNA
<213> ORGANISM: Artificial Sequence
<220> FEATURE:
<223> OTHER INFORMATION: Synthesized

<400> SEQUENCE: 20
aaggagaacc aagcaacgac aaaa                                        24

<210> SEQ ID NO 21
<211> LENGTH: 24
<212> TYPE: DNA
<213> ORGANISM: Artificial Sequence
<220> FEATURE:
<223> OTHER INFORMATION: Synthesized

<400> SEQUENCE: 21
tggggaactc tgcagactca aact                                        24
```

<210> SEQ ID NO 22
<211> LENGTH: 20
<212> TYPE: DNA
<213> ORGANISM: Artificial Sequence
<220> FEATURE:
<223> OTHER INFORMATION: Synthesized

<400> SEQUENCE: 22
gacaataact gcacccactt                                                   20

<210> SEQ ID NO 23
<211> LENGTH: 20
<212> TYPE: DNA
<213> ORGANISM: Artificial Sequence
<220> FEATURE:
<223> OTHER INFORMATION: Synthesized

<400> SEQUENCE: 23
cctaggaaga aaggctaggt                                                   20

<210> SEQ ID NO 24
<211> LENGTH: 20
<212> TYPE: DNA
<213> ORGANISM: Artificial Sequence
<220> FEATURE:
<223> OTHER INFORMATION: Synthesized

<400> SEQUENCE: 24
caacattagt ggcaacagtc                                                   20

<210> SEQ ID NO 25
<211> LENGTH: 20
<212> TYPE: DNA
<213> ORGANISM: Artificial Sequence
<220> FEATURE:
<223> OTHER INFORMATION: Synthesized

<400> SEQUENCE: 25
gcaacccaag taaccctaaa                                                   20

<210> SEQ ID NO 26
<211> LENGTH: 20
<212> TYPE: DNA
<213> ORGANISM: Artificial Sequence
<220> FEATURE:
<223> OTHER INFORMATION: Synthesized

<400> SEQUENCE: 26
aggaagcaga attcttaggg                                                   20

<210> SEQ ID NO 27
<211> LENGTH: 20
<212> TYPE: DNA
<213> ORGANISM: Artificial Sequence
<220> FEATURE:
<223> OTHER INFORMATION: Synthesized

<400> SEQUENCE: 27
agggttgaat aggttcacag                                                   20

<210> SEQ ID NO 28
<211> LENGTH: 20
<212> TYPE: DNA
<213> ORGANISM: Artificial Sequence
<220> FEATURE:

```
<223> OTHER INFORMATION: Synthesized

<400> SEQUENCE: 28
taagcaaaca tccatccgct                                                 20

<210> SEQ ID NO 29
<211> LENGTH: 20
<212> TYPE: DNA
<213> ORGANISM: Artificial Sequence
<220> FEATURE:
<223> OTHER INFORMATION: Synthesized

<400> SEQUENCE: 29
ctgagttcaa ggccacactg                                                 20

<210> SEQ ID NO 30
<211> LENGTH: 57
<212> TYPE: RNA
<213> ORGANISM: Artificial Sequence
<220> FEATURE:
<223> OTHER INFORMATION: Synthesized

<400> SEQUENCE: 30
ggcugguccg augguuagug gguuaucaga acuuauuaac auuaguguca cuaaagu        57

<210> SEQ ID NO 31
<211> LENGTH: 54
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 2 from 3

<400> SEQUENCE: 31
ggcugguccg augguagugg guuaucagaa cuuauuaaca uuagugucac uaaa           54

<210> SEQ ID NO 32
<211> LENGTH: 51
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 5 from 3

<400> SEQUENCE: 32
ggcugguccg augguagugg guuaucagaa cuuauuaaca uuagugucac u              51

<210> SEQ ID NO 33
<211> LENGTH: 46
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 10 from 3

<400> SEQUENCE: 33
ggcugguccg augguagugg guuaucagaa cuuauuaaca uuagug                    46

<210> SEQ ID NO 34
<211> LENGTH: 54
<212> TYPE: RNA
```

<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 2 from 5

<400> SEQUENCE: 34
cugguccgau gguagugggu uaucagaacu uauuaacauu agugucacua aagu 54

<210> SEQ ID NO 35
<211> LENGTH: 51
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 5 from 5

<400> SEQUENCE: 35
guccgauggu aguggguuau cagaacuuau uaacauuagu gucacuaaag u 51

<210> SEQ ID NO 36
<211> LENGTH: 46
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 10 from 5

<400> SEQUENCE: 36
augguagugg guuaucagaa cuuauuaaca uuagugucac uaaagu 46

<210> SEQ ID NO 37
<211> LENGTH: 46
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 5 from both

<400> SEQUENCE: 37
guccgauggu aguggguuau cagaacuuau uaacauuagu gucacu 46

<210> SEQ ID NO 38
<211> LENGTH: 53
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<223> OTHER INFORMATION: EV-YF1, truncated 3 from 5

<400> SEQUENCE: 38
ugguccgaug guaguggguu aucagaacuu auuaacauua gugucacuaa agu 53

<210> SEQ ID NO 39
<211> LENGTH: 52
<212> TYPE: RNA
<213> ORGANISM: Artificial Sequence
<220> FEATURE:
<223> OTHER INFORMATION: Synthesized
<220> FEATURE:

-continued

```
<221> NAME/KEY: misc_feature
<223> OTHER INFORMATION: EV-YF1, truncated 4 from 5

<400> SEQUENCE: 39
gguccgaugg uagugggguua ucagaacuua uuaacauuag ugucacuaaa gu        52
```

METHODS FOR THERAPEUTIC USE OF EXOSOMES AND Y-RNAS

CROSS-REFERENCE TO RELATED APPLICATIONS

This application is the U.S. National Phase of International Application PCT/US2019/015895, filed Jan. 30, 2019, which claims the benefit of priority to U.S. Provisional Application No. 62/626,600, filed Feb. 5, 2018, the disclosures of each of which are hereby incorporated by reference in their entireties.

STATEMENT REGARDING FEDERALLY SPONSORED R&D

This invention was made with government support under HL124074 awarded by the National Institutes of Health. The government has certain rights in the invention.

REFERENCE TO SEQUENCE LISTING

The present application is being filed along with a Sequence Listing in electronic format. The Sequence Listing is as a file entitled "CPRIC044WO_ST25," created on Jan. 30, 2019, which is 7.97 kilobytes in size, and is replaced by a replacement Sequence Listing provided as a file entitled "REPLACEMENT_SEQLIST_CSMC044NP_ST25.txt" created on Jun. 1, 2024, which is 13,208 bytes in size. The information in the electronic format of the Sequence Listing is incorporated herein by reference in its entirety.

FIELD

Some embodiments of the methods and compositions provided herein relate to treating a subject suffering from hypertension, a cardiac injury, or a metabolic disorder through, for example, administering one or more exosomes or one or more oligonucleotides to a subject in need of treatment.

BACKGROUND

Myocardial infarction (MI), hypertension, and metabolic disorders such as those associated with obesity affect a large portion of people in the United States and around the world. Effective therapies are needed to treat these conditions.

SUMMARY

Some embodiments of the methods provided herein include a method for treating a subject suffering from hypertension, comprising: administering an oligonucleotide to a subject with hypertension; wherein the oligonucleotide comprises EV-YF1 (SEQ ID NO: 5) or a fragment thereof; wherein the oligonucleotide increases the amount of plasma IL-10 protein, induces macrophage IL-10 gene expression, attenuates one or more of cardiac CD68 and IL1b gene expression, or attenuates one or more of renal CD68, Il6 and Il1b gene expression; and wherein the increase in the amount of plasma IL-10 protein, induction of macrophage IL-10 gene expression, attenuation of one or more of cardiac CD68 and IL1b gene expression, or attenuation of one or more of renal CD68, Il6 and Il1b gene expression, induces a therapeutic effect on the subject's heart or kidneys. In several embodiments, the administration of the oligonucleotide treats tissue damage associated with hypertension, despite the subject being asymptomatic with respect to such tissue damage (e.g., there may be cardiac or renal tissue damage, without express symptoms associated with cardiac and/or renal damage). In some embodiments, the subject's heart is hypertrophic prior to the administration of the oligonucleotide. In some embodiments, the administration of the oligonucleotide decreases cardiac hypertrophy in the subject. In some embodiments, the subject's heart is fibrotic prior to the administration of the oligonucleotide. In some embodiments, the administration of the oligonucleotide decreases cardiac fibrosis in the subject. In some embodiments, the subject's heart is inflamed prior to the administration of the oligonucleotide. In some embodiments, the administration of the oligonucleotide decreases inflammation in the subject's heart. In some embodiments, at least one of the subject's kidneys is injured or dysfunctional prior to the administration of the oligonucleotide. In some embodiments, the administration of the oligonucleotide improves the subject's kidney function. In some embodiments, at least one of the subject's kidneys is fibrotic prior to the administration of the oligonucleotide. In some embodiments, the administration of the oligonucleotide decreases fibrosis in at least one of the subject's kidneys. In some embodiments, at least one of the subject's kidneys is inflamed prior to the administration of the oligonucleotide. In some embodiments, the administration of the oligonucleotide decreases inflammation is in at least one of the subject's kidneys. In some embodiments, the therapeutic effect does not affect the subject's blood pressure.

Some embodiments of the methods provided herein include a method for treating a subject suffering from hypertension, comprising: administering a cardiosphere-derived cell (CDC)-exosome to a subject with hypertension; wherein the CDC-exosome comprises EV-YF1 (SEQ ID NO: 5) or a fragment thereof; wherein the CDC-exosome increases the amount of plasma IL-10 protein, induces macrophage IL-10 gene expression, attenuates one or more of cardiac CD68 and IL 1b gene expression, or attenuates one or more of renal CD68, Il6 and Il1b gene expression; and wherein the increase in the amount of plasma IL-10 protein, induction of macrophage IL-10 gene expression, attenuation of one or more of cardiac CD68 and IL1b gene expression, or attenuation of one or more of renal CD68, Il6 and Il1b gene expression, induces a therapeutic effect on the subject's heart or kidneys. In some embodiments, the subject's heart is hypertrophic prior to the administration of the CDC-exosome. In some embodiments, the administration of the CDC-exosome decreases cardiac hypertrophy in the subject. In some embodiments, the subject's heart is fibrotic prior to the administration of the CDC-exosome. In some embodiments, the administration of the CDC-exosome decreases cardiac fibrosis in the subject. In some embodiments, the subject's heart is inflamed prior to the administration of the CDC-exosome. In some embodiments, the CDC-exosome decreases inflammation in the subject's heart. In some embodiments, the at least one of the subject's kidneys is injured or dysfunctional prior to the administration of the CDC-exosome. In some embodiments, the administration of the CDC-exosome improves the subject's kidney function. In some embodiments, the at least one of the subject's kidneys is fibrotic prior to the administration of the CDC-exosome. In some embodiments, the administration of the CDC-exosome decreases fibrosis in at least one of the subject's kidneys. In some embodiments, one of the subject's kidneys is inflamed prior to the administration of the CDC-exosome. In some embodiments, the administration of the CDC-exosome decreases inflammation is in at least one of the subject's kidneys. In some embodiments, the therapeutic effect does not affect the subject's blood pressure.

Some embodiments of the methods provided herein include a method for treating a subject suffering from a cardiac injury, comprising: administering an oligonucleotide to a subject suffering from a cardiac injury; wherein the oligonucleotide comprises EV-YF1-U16 (SEQ ID NO: 30) or a fragment thereof; wherein the oligonucleotide increases the amount of plasma IL-10 protein, induces macrophage IL-10 gene expression, or attenuates one or more of cardiac CD68 and IL1b gene expression; and wherein the increase in the amount of plasma IL-10 protein, induction of macrophage IL-10 gene expression, or attenuation of one or more of cardiac CD68 and IL1b gene expression, induces a therapeutic effect on the subject's heart, thereby treating the cardiac injury. In some embodiments, the cardiac injury comprises an infarction. In some embodiments, the cardiac injury is caused by ischemia-reperfusion. In some embodiments, the administration of the oligonucleotide decreases an infarct's size in the subject's heart. In some embodiments, the administration of the oligonucleotide decreases inflammation in the subject's heart. In some embodiments, the administration of the oligonucleotide increases cardiomyocyte viability in the subject's heart.

Some embodiments of the methods provided herein include treating a subject suffering from a metabolic disorder, comprising: administering an oligonucleotide to a subject with a metabolic disorder; wherein the oligonucleotide comprises EV-YF1 (SEQ ID NO: 5) or a fragment thereof; wherein the oligonucleotide increases the amount of plasma IL-10 protein or induces macrophage IL-10 gene expression; and wherein the increase in the amount of plasma IL-10 protein or induction of macrophage IL-10 gene expression, induces a therapeutic effect on the subject's metabolism, thereby treating the metabolic disorder. In some embodiments, the subject is obese prior to the administration of the oligonucleotide. In some embodiments, the subject is diabetic prior to the administration of the oligonucleotide. In some embodiments, the administration of the oligonucleotide improves the subject's metabolic function. In some embodiments, the administration of the oligonucleotide improves glucose tolerance in the subject.

In some embodiments of the methods provided herein, administration of the oligonucleotide affects IL-10 gene expression in the subject's heart or spleen, in at least one of the subject's kidneys, or in splenic macrophages. In some embodiments of the methods provided herein, the oligonucleotide or exosome is administered with a pharmaceutically acceptable carrier. In some embodiments of the methods provided herein, administering the oligonucleotide or exosome comprises injecting the oligonucleotide or exosome into the subject.

Some embodiments of the methods provided herein include use of an oligonucleotide composition for treating a subject a subject suffering from hypertension, comprising: administering an oligonucleotide to a subject with hypertension; wherein the oligonucleotide comprises EV-YF1 (SEQ ID NO: 5) or a fragment thereof; wherein the oligonucleotide increases the amount of plasma IL-10 protein, induces macrophage IL-10 gene expression, attenuates one or more of cardiac CD68 and IL1b gene expression, or attenuates one or more of renal CD68, Il6 and Il1b gene expression; and wherein the increase in the amount of plasma IL-10 protein, induction of macrophage IL-10 gene expression, attenuation of one or more of cardiac CD68 and IL1b gene expression, or attenuation of one or more of renal CD68, Il6 and Il1b gene expression, induces a therapeutic effect on the subject's heart or kidneys.

Some embodiments of the methods provided herein include use of an oligonucleotide composition for treating a subject suffering from a cardiac injury, comprising: administering an oligonucleotide to a subject suffering from a cardiac injury; wherein the oligonucleotide comprises EV-YF1-U16 (SEQ ID NO: 30) or a fragment thereof; wherein the oligonucleotide increases the amount of plasma IL-10 protein, induces macrophage IL-10 gene expression, or attenuates one or more of cardiac CD68 and IL1b gene expression; and wherein the increase in the amount of plasma IL-10 protein, induction of macrophage IL-10 gene expression, or attenuation of one or more of cardiac CD68 and IL1b gene expression, induces a therapeutic effect on the subject's heart, thereby treating the cardiac injury.

Some embodiments of the methods provided herein include use of an oligonucleotide composition for treating a subject suffering from a metabolic disorder, comprising: administering an oligonucleotide to a subject with a metabolic disorder; wherein the oligonucleotide comprises EV-YF1 (SEQ ID NO: 5) or a fragment thereof; wherein the oligonucleotide increases the amount of plasma IL-10 protein or induces macrophage IL-10 gene expression; and wherein the increase in the amount of plasma IL-10 protein or induction of macrophage IL-10 gene expression, induces a therapeutic effect on the subject's metabolism, thereby treating the metabolic disorder.

Some embodiments of the methods provided herein include use of an oligonucleotide composition according to any of the preceding oligonucleotide composition claims above, wherein the oligonucleotide composition is exosome-free.

Some embodiments of the methods provided herein include treating a subject, comprising: administering an oligonucleotide to a subject; wherein the oligonucleotide comprises EV-YF1 (SEQ ID NO: 5) or a fragment thereof, or EV-YF1-U16 (SEQ ID NO: 30) or a fragment thereof; wherein the subject's heart or a kidney of the subject, is damaged, hypertrophic, fibrotic, inflamed, or dysfunctional; wherein the subject does not have hypertension; wherein the oligonucleotide increases the amount of plasma IL-10 protein, induces macrophage IL-10 gene expression, attenuates one or more of cardiac CD68 and IL1b gene expression, or attenuates one or more of renal CD68, Il6 and Il1b gene expression; and wherein the increase in the amount of plasma IL-10 protein, induction of macrophage IL-10 gene expression, attenuation of one or more of cardiac CD68 and IL1b gene expression, or attenuation of one or more of renal CD68, Il6 and Il1b gene expression, induces a therapeutic effect on the subject's heart or kidney, thereby treating the subject's damaged, hypertrophic, fibrotic, inflamed, or dysfunctional heart or kidney.

Some embodiments of the methods provided herein include treating a subject, comprising: administering a CDC-exosome to a subject; wherein the CDC-exosome comprises EV-YF1 (SEQ ID NO: 5) or a fragment thereof, or EV-YF1-U16 (SEQ ID NO: 30) or a fragment thereof; wherein the subject's heart or a kidney of the subject, is damaged, hypertrophic, fibrotic, inflamed, or dysfunctional; wherein the subject does not have hypertension; wherein the CDC-exosome increases the amount of plasma IL-10 protein, induces macrophage IL-10 gene expression, attenuates one or more of cardiac CD68 and IL 1b gene expression, or attenuates one or more of renal CD68, Il6 and Il1b gene expression; and wherein the increase in the amount of plasma IL-10 protein, induction of macrophage IL-10 gene expression, attenuation of one or more of cardiac CD68 and IL1b gene expression, or attenuation of one or more of renal CD68, Il6 and Il1b gene expression, induces a therapeutic effect on the subject's heart or kidney, thereby treating the subject's damaged, hypertrophic, fibrotic, inflamed, or dysfunctional heart or kidney.

BRIEF DESCRIPTION OF THE FIGURES

FIGS. 1A-1H. RNA content of CDC-exo (day 5). FIG. 1A is a pie chart depicting the percent distribution of small RNA species in CDC-exo. FIG. 1B is a pie chart depicting the percent distribution of small RNA species in NHDF-exo (right), collected following 5 days of serum-free culture. FIG. 1C is a Venn diagram depicting the number of unique and common Y-RNA sequences in CDC-exo and NHDF-exo. FIG. 1D includes two graphical depictions of the abundance of the common Y-RNA fragments in CDC-exo and NHDF-exo according to the number of reads obtained by RNA-seq. The left graph in FIG. 1D shows the number of counts for the top 3 most abundant Y-RNA fragments on a linear scale. The right graph in FIG. 1D shows the number of counts for the remaining 301 Y-RNA fragments on a logarithmic scale. FIG. 1E depicts a sequence alignment of each full-length human Y-RNA (hY1 (SEQ ID NO: 1), hY3 (SEQ ID NO: 2), hY4 (SEQ ID NO: 3), and hY5 (SEQ ID NO: 4) with Y-RNA fragments. The top 10 Y-RNA fragments uniquely expressed in CDC-exo are highlighted (10/613 in FIG. 1C), and Y-RNAs commonly expressed between CDC-exo and NHDF-exo are highlighted (10/304 in FIG. 1C). The most highly-expressed Y-RNA fragment (EV-YF1) is highlighte. URS000072C009 is SEQ ID NO: 40. URS000072DA11 is SEQ ID NO: 66. URS00006FA3EC is SEQ ID NO: 41. URS000070E5AC is SEQ ID NO: 42. URS000072E641 is SEQ ID NO: 43. URS00006AB25C is SEQ ID NO: 44. URS00006AE197 is SEQ ID NO: 45. URS00006CB75C is SEQ ID NO: 46. URS00006E033B is SEQ ID NO: 47. URS00006E4C2B is SEQ ID NO: 48. URS0000665607 is SEQ ID NO: 49. URS0000728268 is SEQ ID NO: 50. URS0000628C05 is SEQ ID NO: 51. URS00006D365A is SEQ ID NO: 52. URS00007205ED is SEQ ID NO: 53. URS000072F137 is SEQ ID NO: 54. URS000072DB3C is SEQ ID NO: 55. URS00006E0030 is SEQ ID NO: 56. URS0000718090 is SEQ ID NO: 57. Consensus is SEQ ID NO: 58. FIG. 1F is a graph showing the proportion of Y-RNA fragments derived from the 5'- or 3'-end of the four full-length human Y-RNA genes. FIG. 1G is a graph showing the relative expression of EV-YF1 by qPCR in CDCs and NHDFs. FIG. 1H is a graph showing the relative expression of EV-YF1 by qPCR in exosomes secreted by CDCs and NHDFs. Numerical results shown in FIGS. 1A-1H are the mean#SEM of two independent experiments, n=6. p<0.01,*p<0.001.

FIG. 2A is a graph depicting the percent distribution of small RNA species in CDC-exo from different donors. FIG. 2B is a graph representing the most abundant sequences expressed in OD220 CDC-exo. EV-YF1 (SEQ ID NO:5, annotated herein as URS000072DA11); tRNA-1: URS00006FBEE8 (RNAcentral); tRNA-2: URS000072EF3B; tRNA-3: URS0000758E15; 28S rRNA: URS00003692B6; tRNA-4: URS000072CC66; 45S pre-rRNA: URS000025EBOF; tRNA-5: URS000072F18F; tRNA-6: URS000072F2C3; Yc: URS000072E641; tRNA-7: URS000072B56D; pre-mir-23a: URS000075EDA8; 28S rRNA 5: URS000075EC78; tRNA-8: URS0000701715; pre-mir-21: URS000075E5CC; long non-coding RNA (Mir17hg gene): URS000076343C; tRNA-9: URS00006A0CFD; tRNA-10: URS0000717173; pre-mir-12: URS00007A4AA9; tRNA-11: URS0000750232; tRNA-12: URS000072345A. FIG. 2C is a graph showing a correlation between the percent change in ejection fraction (baseline 2 hrs post-MI to 21 days, ΔEF %) post-MI with CDC treatment (6 different donors, n=8 animals/donor) and EV-YF1 abundance in CDC-exo. Potent CDCs were delineated from non-potent CDCs by positive ΔEF %. FIG. 2D is a graph showing EV-YF1 abundance based on RNA-seq counts in exosomes from potent and non-potent CDCs and NHDFs.

FIG. 3A is a graph showing gene expression of IL-10 in BMDMs following transfection with EV-YF1-U16 or Ys, as determined by qPCR. FIG. 3B is a graph showing protein secretion of IL-10 from BMDMs at 24, 48, and 72 hrs following transfection with EV-YF1-U16 or Ys, by ELISA. FIG. 3C is a schematic of an in vitro protocol used in Example 1. NRVMs were cultured with or without 75 µM $H_2O_2$ (15 mins), media was replaced with serum-free media (SF) (20 mins), then Ys- or EV-YF1-U16-primed BMDMs were added in co-culture (or recombinant IL-10 [rIL-10, 10 ng/ml] was added). Six hours later, cells were analyzed for apoptosis. Mean of 2-4 independent experiments. FIG. 3D is a group of representative images taken of the cells in FIG. 3A, stained for TUNEL, α-actinin, CD45 and DAPI. FIG. 3E is a graph showing pooled analyses of TUNEL+ cardiomyocytes (CM). In FIG. 3E, "YF1" denotes EV-YF1-U16. Graphs in FIGS. 3A-3E depict mean±SEM. Tp<0.05: versus $H_2O_2$ treatment (positive control);*p<0.05: between treatment groups.

FIG. 4A is a schematic representation of an in vivo I/R protocol used in Example 1. FIG. 4B is set of photographs showing representative TTC-stained hearts from animals at 48 hrs following I/R injury. FIG. 4C is a graph of quantitative measurements of TTC-stained hearts, depicted as infarct mass (n=5-6 rats per group). The graph in FIG. 4C depicts mean±SEM. *p<0.05, p<0.01. FIG. 4D is a graph showing a pooled analysis of CD68 cells within the infarct tissue 48 hours following I/R injury. The graph in FIG. 4D depicts mean±SEM (n=3 rats per group). Groups in FIG. 4D were compared using one-way ANOVA followed by Tukey's multiple comparisons test; vehicle versus EV-YF1-U16: P=0.007; Ys versus EV-YF1-U16: *P=0.0123. FIG. 4E is a graph showing a pooled analysis of TUNEL+ cardiomyocytes (CM) within the infarct tissue 48 hours following I/R injury. The graph in FIG. 4E depicts mean±SEM (n=3 rats per group). Groups were compared using one-way ANOVA followed by Tukey's multiple comparisons test; vehicle versus EV-YF1-U16: *P=0.0377; Ys versus EV-YF1-U16: **P=0.0075.

FIG. 5A depicts information related to Biosets 1 and 2, including a Venn diagram and graph. Bioset 1 (284 genes): Total number of genes showing a new H3K27ac peak following treatment with CDC-exo. Bioset 2 (3767): Total number of genes differentially regulated following CDC-exo treatment. Common genes between biosets (105, p=1.7E-22) reveal stronger correlation between upregulated genes and H3K27ac (p=1.7E-22) than downregulated genes and H3K27ac (p=1.1E-12). Plots and p-values were generated using Next-Bio. FIG. 5B is a graphical depiction of ChIP-seq H3K27ac peaks within and around the IL-10 gene locus from untreated (K27ac control) and CDC-exo-treated (K27ac exo) BMDMs, and input chromatin without ChIP (ChIP input). Peaks 1, 3, and 4 (red): unique peaks from CDC-exo-treated BMDMs; Peak 2 (purple): induced peak between untreated and CDC-exo-treated BMDMs. FIG. 5C is a graph depicting ChIP-qPCR results from peaks 2 and 3 in FIG. 5B in untreated vs. CDC-exo-treated and EV-YF1-U16-primed vs. Ys-primed BMDMs. Data are presented as mean fold-change of % of input (n=3 independent experiments in duplicate). FIG. 5D is a graph showing Relative Light Units (RLU) measured at 8 and 24 hrs following transfection of HEK293T cells with Ys or EV-YF1-U16, where the HEK293T cells had also been transfected with an IL-10 luciferase promoter plasmid. Data in FIGS. 5A-5D are presented as mean+/– SEM, representative of 2 independent experiments (n=6).

FIG. 7A is a histogram showing a CDC-exo size distribution (CDC-exo diameter) and particle number analyzed by an LM10-HS system (NANOSIGHT). FIG. 7B is a histogram showing a NHDF-exo size distribution (NHDF-exo diameter) and particle number, also analyzed by an LM10-HS system. The data in FIGS. 7A and 7B are representative of results from a total of 6 donors.

FIG. 8A is a graph representing the nucleic acid length of the 304 common Y-RNA fragments between CDC-exo and NHDF-exo. FIG. 8B includes two graphical depictions of the abundance of the 5 most abundant unique Y-RNA fragments in CDC-exo (left graph) and in NHDF-exo (right graph) according to the number of reads obtained by RNA-seq. FIG. 8C is a graph showing the percentage of Y-RNA fragments in CDC-exo from different CDC donors derived from each full-length Y-RNA (hY1, hY3, hY4, hY5). FIG. 8D is a depiction of a sequence alignment between the DNA sequences encoding hY4 and EV-YF1-U16, and reveals a thymine insertion at position 16 in the DNA encoding EV-YF1-U16 (Score: 99.0 bits, Identities 56/57; 98%). hY4 is SEQ ID NO: 3. EV-YF1-U16 is SEQ ID NO: 66. Consensus is SEQ ID NO: 59. FIG. 8E shows secondary structures of EV-YF1-U16 that were predicted by UNAFold (dG: delta Gibbs free energy).

FIG. 9A depicts a sequence alignment of EV-YF1 from each CDC donor to hY4 (SEQ ID NO: 3). The EV-YF1 sequence expressed in OD220-exo reveals a thymine insertion at position 16 (T16) (arrow). In some embodiments of the compositions and methods described herein, EV-YF1-U16 is produced from the EV-YF1 DNA sequence of OD220-exo, which includes a T insertion at position 16. ZKN is SEQ ID NO: 60. 00220 is SEQ ID NO: 66. ZCL is SEQ ID NO: 61. YKT is SEQ ID NO: 62. LO88 is SEQ ID NO: 63. BM030 is SEQ ID NO: 64. Consensus is SEQ ID NO: 65.

FIG. 9B is a graph showing relative mRNA expression of 1110. To examine if the T16 insertion has any functional effect on EV-YF1 potency, we compared EV-YF1 to EV-YF1-U16. EV-YF1 induced IL-10 gene expression in BMDMs following transfection to a similar extent as EV-YF1-U16, as determined by qPCR. These data indicate that the T16 nucleotide insertion of EV-YF1-U16 does not impair or augment EV-YF1 function.

FIG. 10A is a schematic of the protocol for EV-YF1-fluo transfection into CDCs followed by the collection and treatment of CDC-exo into BMDMs. FIG. 10B is a graph showing the expression of EV-YF1 by qPCR in CDCs described in FIG. 10A. FIG. 10C is a graph showing the expression of EV-YF1 by qPCR in CDC-exo described in FIG. 10A. FIG. 10D is a graph showing the expression of EV-YF1 by qPCR in BMDMs described in FIG. 10A. Results in FIGS. 10B-10D depict the mean±SEM of n=3. **$p<0.01$. FIG. 10E shows representative images of EV-YF1-fluotransfected CDCs treated with CDC-exo. FIG. 10F shows representative images of EV-YF1-fluotransfected BMDMs treated with CDC-exo. In FIGS. 10E and 10F, fluorescently-conjugated EV-YF1 is EV-YF1-fluo, MitoTracker Green FM is MitoT, and nuclei are DAPI. The scale bars in FIGS. 10E and 10F are 10 µM. FIG. 10G is a schematic of the protocol for BMDMs treated with directly-transfected CDC-exo or transfected with EV-YF1-fluo. FIG. 10H is an image of immunocytochemical staining that reveals punctate, cytoplasmic localization of EV-YF1-fluo in BMDMs following treatment with directly-transfected CDC-exo. FIG. 10I is an image of BMDMs described for FIG. 10B stained with CD45 and DAPI. FIG. 10J is a schematic of the protocol for BMDMs transfected with EV-YF1-fluo. FIG. 10K is an image of immunocytochemical staining that reveals punctate, cytoplasmic localization of EV-YF1-fluo in BMDMs following transfection with EV-YF1-fluo (K). FIG. 10L is an image of BMDMs described for FIG. 10E stained with CD45 and DAPI. EV-YF1 expression in BMDMs following treatments in the conditions described for FIGS. 10G and 10J, respectively, compared to their Ys (scrambled oligoribonucleotide) control.

FIG. 11A is a graph showing a gene expression profile by qPCR of BMDMs polarized toward MI (IFNγ and LPS), M2 (IL-4 and IL-13) or treated with CDC-exo. FIG. 11B is a graph showing a gene expression profile by qPCR of BMDMs primed with EV-YF1-U16 or Ys. FIG. 11C is a graph showing IL-10 gene expression in BMDMs at 48 and 72 hours after treatment with LPS ([1 µg/ml]; positive control) or transfection with EV-YF1-U16 or Ys. FIG. 11D is a graph showing IL-10 protein secretion from conditioned media (of the BMDMs described for FIG. 11C), as determined by ELISA.

FIG. 12 is a schematic depicting how CDCs exert their beneficial effects on regeneration and cardioprotection following ischemic injury via exosomes (CDC-exo). CDC-exo transfer EV-YF1 into BMDMs (target cells), which promotes H3K27ac at the IL-10 gene locus, followed by transcriptional activation and secretion of IL-10. EV-YF1-U16-primed Mφ secrete IL-10 and reduce cardiomyocyte death.

FIG. 13 lists non-limiting examples of beneficial effects on tissues according to several embodiments disclosed herein. Also provided is a non-limiting isolation protocol for exosomes.

FIG. 14 indicates non-limiting examples of the RNA content of CDC-exosomes and a comparison of the RNA content at day 5 of CDC-exosomes to normal human dermal fibroblast (NHDF). Also shown is the overlap and abundance of Y-RNA content of CDC-exo versus NHDF-exo at day 5.

FIG. 15A depicts data that indicated that, in accordance with several embodiments disclosed herein, Y-RNA are trafficked from a donor cell to a target cell via exosomes. FIG. 15B depicts data that indicated that EV-YF1-U16 protected NRVM from cell death under oxidative stress.

FIG. 16 depicts data from experiments in which BMDM were treated with CDC-exo overnight and gene expression profile was established by qPCR.

FIG. 17 is a schematic showing two pathways of macrophage activation, including classical activation involving IFNg, LPS, and TNFa. An alternative activation pathway involves Il-4, IL-13, IL-10, and TGFb.

FIG. 18 is a graph showing gene expression. A cardioprotective phenotype that was determined not to be M1 or M2 was investigated on BMDM transfected overnight with Y-RNA fragment, Y-RNA fragment coupled to a fluorophore, Y-RNA fragment conjugated with a biotin group, or a scramble fragment. According to several embodiments, EV-YF1-U16 recapitulates some effects of CDC-exosomes on macrophage polarization.

FIG. 19A depicts a study design of Ang II infusion with EV-YF1 and CDC-exo treatment. FIG. 19B shows data related to EV-YF1 copy number by qPCR representing the distribution of EV-YF1 and CDC-exo 24 hours after retro-orbital injection. (No expression was detected in brain). Values are means±SEM; n=4 animals/group. FIG. 19C shows systolic blood pressure (SBP) recorded by tail-cuff plethysmography in mice before and after chronic subcutaneous infusion of Ang II or saline (sham) weekly for 28 days. Chronic infusion of Ang II significantly increased SBP independently of EV-YF1 or CDC-exo treatment. Values are means±SEM; n=5 animals/group. Groups were compared using 1-way ANOVA followed by Tukey's multiple comparisons test; ***P<0.001 between sham vs. all the groups at every time points except baseline.

FIG. 20E depicts heart weight-to-body weight ratio data. Values are means±SEM; n=7-10 animals/group. ~P<0.001 between sham and all the groups. FIG. 20F shows relative expression of cardiac Anp by qPCR. Values are means±SEM; n=5 animals/group. Groups were compared using 1-way ANOVA followed by Tukey's multiple comparisons test; *P<0.05, P<0.01,*P<0. 001.

FIG. 21A shows micrographs (magnification: ×20) showing representative cross-sectional area of cardiac myocytes stained with Masson's trichrome of mice that received subcutaneous infusion of saline or Ang II for 28 days treated with saline, EV-YF1 or CDC-exo. FIG. 21B shows quantitative measurements of cross-sectional area of myocytes within transverse cardiac sections. Graph depicts the mean±SEM; n=4 animals/group. Scale bars=25 µm. FIG. 21C shows micrographs (magnification: ×20) showing representative interstitial myocardial fibrosis (arrows) in myocardial sections stained with Masson's trichrome. FIG. 21D shows quantitative measurements of interstitial myocardial fibrosis within cardiac sections. Data are means±SEM; n=3 animals/group. Scale bars=50 µm. FIGS. 21E-21F depict data related to gene expression of CD68 in (21E) and Il1b in (21F) in heart tissue from mice that received subcutaneous infusion of Ang II for 2 weeks (AngII-2w) and for 28 days of saline or Ang II treated with saline, EV-YF1 or CDC-exo, as determined by qPCR. Graphs depict the mean±SEM; n=7-10 animals/group. Groups were compared using 1-way ANOVA followed by Tukey's multiple comparisons test; *P<0.05, P<0.01, *P<0.001.

FIG. 22C includes micrograph images (magnification: ×20) showing representative glomerular expansion and size in renal sections stained with Periodic acid-Schiff (PAS). Quantitative measurements of glomerular expansion are shown in FIG. 22D and size in FIG. 22E of 20 glomeruli within renal sections. Data are means±SEM; n=4 animals/group. Scale bars=50 µm. Groups were compared using 1-way ANOVA followed by Tukey's multiple comparisons test; *P<0.05, P<0.01, *P<0.001.

FIGS. 23A-C depict gene expression data of CD68 (23A), Il16 (23B) and Il1b (23C) as determined by qPCR, in kidney tissue from mice that received subcutaneous infusion for 28 days of saline or Ang II, and were treated with saline, EV-YF1 or CDC-exo. Graphs depict the mean±SEM; n=5 animals/group. FIG. 23D includes micrographs (magnification: ×20) showing representative tubulointerstitial fibrosis (arrows) in kidney sections stained with Masson's trichrome. FIG. 23E shows quantitative measurements of tubulointerstitial fibrosis within kidney sections. Data are means±SEM; n=5 animals/group. Scale bars=70 µm. Groups were compared using 1-way ANOVA followed by Tukey's multiple comparisons test; *P<0.05, P<0.01, *P<0.001.

FIG. 24A shows data relating to plasma levels of IL-10 at day 16 of the study (24 hours after the second injection of saline, EV-YF1 or CDC-exo in mice infused with Ang II), as determined by ELISA. Graph depicts the mean±SEM; n=4-5 animals/group. FIGS. 24B-24E show plasma (24B), cardiac (24C), splenic (24D) and renal (24E) levels of IL-10 at the final day (day 28) of the study in mice that received subcutaneous infusion of saline or Ang II for 28 days treated with saline, EV-YF1 or CDC-exo, as determined by ELISA. Graphs depict the mean±SEM; n=5-9 animals/group. Groups were compared using 1-way ANOVA followed by Tukey's multiple comparisons test; *P<0.05, P<0.01,*P<0.001.

FIG. 25A depicts a schematic study design. FIG. 25B shows data resulting from a glucose tolerance test on 8-week-old db/db mice administrated with EV-YF1 or Ys. Graphs depict the mean±SEM;

n=4 animals/group. FIG. 25C depicts plasma levels of IL-10 in 8-week-old db/db mice, as determined by ELISA. Graphs depict the mean±SEM; n=4 animals/group.

FIGS. 26A-26C are graphs showing cardiac function assessed by echocardiography at 2 weeks (AngII-2w) and 28 days after saline (sham) or Ang II infusion (AngII) with M-mode echocardiographic images. Additional groups of mice were treated with Ang II plus EV-YF1 (AngII-EV-YF1) or Ang II plus CDC-exo (AngII-Exo). FIG. 26D includes M-mode echocardiographic images used to generate data expressed graphically in FIGS. 26A-26C. EF: Left ventricular (LV) ejection fraction; FS: LV fractional shortening. Values are means±SEM; n=5-10 animals/group.

FIG. 27 is a graph showing gene expression of Il16 in heart tissue from mice that received subcutaneous infusion of Ang II for 2 weeks (AngII-2w) and for 28 days of saline or Ang II treated with saline, EV-YF1 or CDC-exo, as determined by qPCR. The graph depicts the mean±SEM; n=7-10 animals/group. Groups were compared using 1-way ANOVA followed by Tukey's multiple comparisons test; P<0.01, *P<0.001.

FIG. 28A is a graph showing gene expression of Anp in neonatal rat ventricular cardiomyocytes (NRVMs) cultured for 24 hours with BMDM media (control) or media conditioned during 48 hours from BMDMs overexpressing Ys scramble oligoribonucleotide (Ys-CM) or EV-YF1 (EV-YF1-CM) with or without Ang II (1 μM), as determined by qPCR. The graph depicts the mean±SEM, n=3. FIG. 28B is a graph showing gene expression of/16 in neonatal cardiac fibroblasts cultured for 16 hours with bone marrow-derived macrophages (BMDMs) media (control) or media conditioned during 72 hours from BMDMs overexpressing Ys scramble oligoribonucleotide (Ys-CM) or EV-YF1 (EV-YF1-CM) with or without Ang II (100 nM), as determined by qPCR. The graph depicts the mean±SEM of 2 independent experiments, n=3 each. Groups were compared using 1-way ANOVA followed by Tukey's multiple comparisons test; *P<0.05, ***P<0.001.

FIG. 29 is a graph showing quantitative measurements of glomeruli number within renal sections. Data are means±SEM; n=4 animals/group. Groups were compared using 1-way ANOVA followed by Tukey's multiple comparisons test; *P<0.05, P<0.01, *P<0.001.

FIG. 30 is a non-limiting depiction of EV-YF1's proposed mode of action. EV-YF1, the most abundant small RNA species in CDC-exo, induces expression and secretion of IL-10 by (splenic and/or cardiac, renal) macrophages. Upon Ang II-induced inflammation in heart and kidney, splenic macrophages migrate to these target organs. IL-10 produced by migrating and resident macrophages counteracts the inflammatory response induced by Ang II in cardiomyocytes, fibroblast and renal cells to reestablish an anti-inflammatory state leading to a decrease in cardiac hypertrophy and an improvement of kidney function. CDC-exo treatment lead to similar beneficial effects by a mechanism that might involve other target molecules, included IL-10.

FIG. 32 shows distinct nucleotide sequences of truncated EV-YF1 according to the present invention. Sequences are shown from 5' to 3'. The nomenclature denotes the number of nucleotides removed from the respective end of EV-YF1 (SEQ ID NO: 5). 2 from 3' is SEQ ID NO: 31. 5 from 3' is SEQ ID NO: 32. 10 from 3' is SEQ ID NO: 33. 2 from 5' is SEQ ID NO: 34. 5 from 5' is SEQ ID NO: 35. 10 from 5' is SEQ ID NO: 36. 5 from both is SEQ ID NO: 37.

FIG. 34 shows distinct nucleotide sequences of truncated EV-YF1 from 5' end according to the present invention. Sequences are shown from 5' to 3'. The nomenclature denotes the number of nucleotides removed from the 5' end of EV-YF1 (SEQ ID NO: 5). 2 from 5' is SEQ ID NO: 34. 3 from 5' is SEQ ID NO: 38. 4 from 5' is SEQ ID NO: 39. 5 from 5' is SEQ ID NO: 35.

FIG. 35A shows a study design for in vivo model of cardiac hypertrophy, wherein mice were implanted with osmotic minipumps to deliver continuous infusion of angiotension II (AngII) for 4 weeks (1.4 mg/kg). Animals were randomly allocated to receive infusion (tail vein or retro orbital) of Y RNA fragments at days 14, 16, 18, 20, and 22 (arrows) and sacrificed at day 28. FIG. 35B shows heart weight-to-body weight (HW/BW) measurements of animals from each group (n=4-5/group). Data presented as mean+/−SD. Statistical significance was determined using 1-way ANOVA followed by Tukey's multiple comparisons test. *p<0.05, relative to untreated.

FIGS. 37A and 37B, respectively) was assessed by echocardiography after 28 days of AngII infusion. Data presented as mean+/−SD. Statistical significance was determined using 1-way ANOVA followed by Tukey's multiple comparisons test. *p<0.05, relative to untreated.

DETAILED DESCRIPTION

Figure 1A:
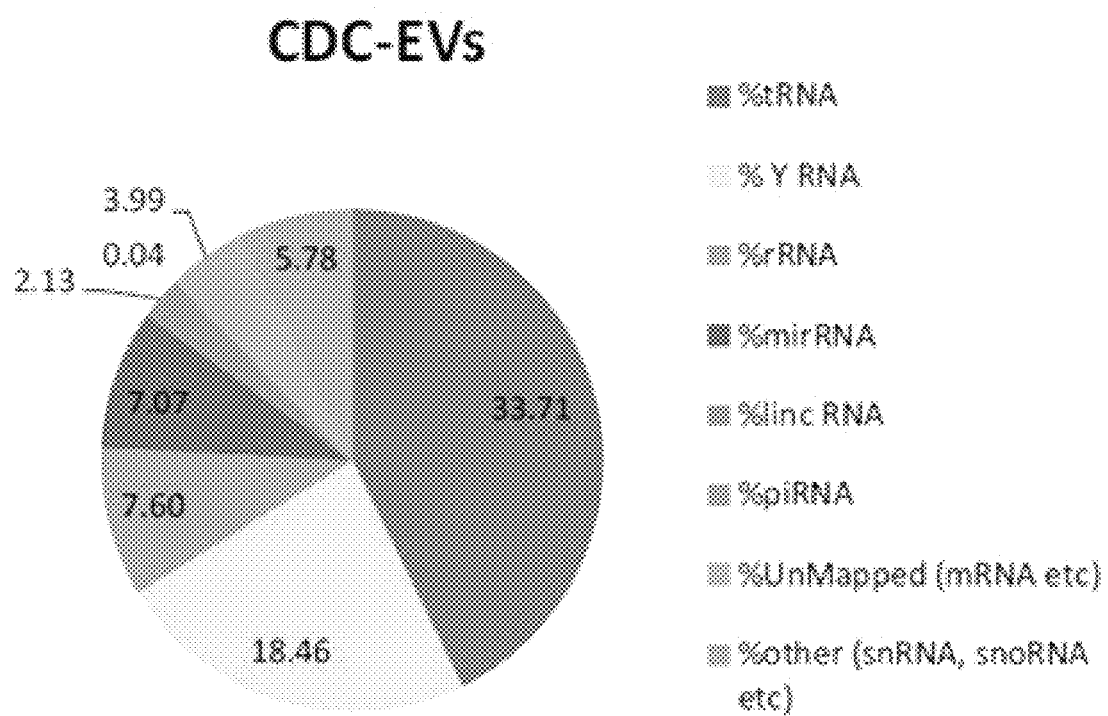

Some embodiments of the methods and compositions provided herein relate to treating a subject suffering from hypertension, a cardiac injury, or a metabolic disorder, with an oligonucleotide or with a cardiosphere-derived cell (CDC) exosome (CDC-exo). In some such embodiments, the oligonucleotide includes a Y-RNA or a fragment thereof. In some embodiments, the oligonucleotide is EV-YF1 (SEQ ID NO: 5). In some embodiments, the oligonucleotide is EV-YF1 with a uracil (U) insertion between the 15th and 16th nucleotides of the EV-YF1 sequence (denoted "EV-YF1.15_16insU" or "EV-YF1-U16") (SEQ ID NO: 30). In some embodiments, the oligonucleotide includes a truncated form of EV-YF1, e.g., a truncated EV-YF1 from which 2 nucleotides have been removed from the 3' end thereof (SEQ ID NO: 31), a truncated EV-YF1 from which 5 nucleotides have been removed from the 3' end thereof (SEQ ID NO: 32), a truncated EV-YF1 from which 10 nucleotides have been removed from the 3' end thereof (SEQ ID NO: 33), a truncated EV-YF1 from which 2 nucleotides have been removed from the 5' end thereof (SEQ ID NO: 34), a truncated EV-YF1 from which 5 nucleotides have been removed from the 5' end thereof (SEQ ID NO: 35), a truncated EV-YF1 from which 10 nucleotides have been removed from the 5' end thereof (SEQ ID NO: 36), a truncated EV-YF1 from which 5 nucleotides have been removed from both the 3' and the 5' ends thereof (SEQ ID NO: 37), a truncated EV-YF1 from which 3 nucleotides have been removed from the 5' end thereof (SEQ ID NO: 38), and a truncated EV-YF1 from which 4 nucleotides have been removed from the 5' end thereof (SEQ ID NO: 39). In some embodiments, the oligonucleotide has a therapeutic effect on the subject's heart, kidneys, or metabolism. In some embodiments, the nucleotide is at least about 80%, about 90%, about 100%, or ranges including and/or spanning the aforementioned values identical to one of SEQ ID NOs: 1-39.

In some embodiments, the oligonucleotide includes a fragment of EV-YF1 (SEQ ID NO: 5) comprising any one or a combination of SEQ ID NOS: 30-39. For example, a fragment of EV-YF1 or a truncated EV-YF1 may be used in a method of treating a subject suffering from hypertension, a cardiac injury, heart failure, or a metabolic disorder. In some embodiments, treating the subject with the fragment of EV-YF1 or truncated EV-YF1 improves heart function and/or heart morphology, and/or decreases cardiac hypertrophy, fibrosis and/or inflammation in the subject.

As used herein, the terms, "polynucleotide" and "oligonucleotide," shall be given their ordinary meaning and unless otherwise indicated, are used interchangeably herein. "Polynucleotide" and "oligonucleotide" include the term, "oligoribonucleotide." As used herein, the terms, "EV-YF1" shall be given its ordinary meaning and unless otherwise indicated, is also used interchangeably herein with "Yb."

Cardiosphere-Derived Cells and Exosomes

Some embodiments of the methods and compositions provided herein relate to exosomes. An exosome is a lipid bilayer vesicle that is exocytosed from a cell. The vesicles are of endosomal origin, and range in size between 30-200 nm, including sizes (e.g., diameter) of about 40-100 nm (including about 40 to about 50 nm, about 50 to about 60 nm, about 60 to about 70 nm, about 70 to about 80 nm, about 80 to about 90 nm, about 90 to about 100 nm, and any size therebetween, including endpoints), and, in several embodiments, possess a cup-shaped morphology as revealed by electron microscopy. Depending on the embodiment, exosomes are optionally enriched in a variety of biological factors, including cytokines, growth factors, transcription factors, lipids, and coding and non-coding nucleic acids. Exosomes are found in blood, urine, amniotic fluid, interstitial and extracellular spaces.

In several embodiments, exosomes are isolated by, for example, differential ultracentrifugation, to separate the exosomes from the supernatants of cultured cells. This approach allows for separation of exosomes from nonmembranous particles by exploiting their relatively low buoyant density. Size exclusion allows for their separation from biochemically similar, but biophysically different microvesicles that possess, for example, larger diameters of up to 1,000 nm. Differences in flotation velocity further allows for separation of differentially sized exosomes. In some embodiments, exosome sizes possess a diameter ranging from 30-200 nm, including sizes of about 40-100 nm (including about 40 to about 50 nm, about 50 to about 60 nm, about 60 to about 70 nm, about 70 to about 80 nm, about 80 to about 90 nm, about 90 to about 100 nm, and any size therebetween, including endpoints). In some embodiments, purification relies on specific properties of exosomes of interest. In some embodiments, this includes use of immunoadsorption with a protein of interest to select specific vesicles with exoplasmic or outward orientations.

Differential ultracentrifugation utilizes increasing centrifugal forces (e.g., from 2000 xg to 10,000 xg) to separate medium- and larger-sized particles and cell debris from an exosome pellet at 100,000 xg. In some embodiments, enhanced specificity of exosome purification deploys sequential centrifugation in combination with ultrafiltration, or equilibrium density gradient centrifugation in a sucrose density gradient, to provide for the greater purity of the exosome preparation (flotation density 1.1-1.2 g/ml) or application of a discrete sugar cushion in preparation.

In several embodiments, ultrafiltration is used to purify exosomes without compromising their biological activity. In some embodiments, membranes with different pore sizes-such as 100 kDa molecular weight cut-off (MWCO) and gel filtration to eliminate smaller particles—are used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. In some embodiments, HPLC is also used to purify exosomes to homogeneously sized particles and preserve their biological activity as the preparation is maintained at a physiological pH and salt concentration.

In some embodiments, other chemical methods exploit differential solubility of exosomes for precipitation techniques, such as addition to volume-excluding polymers (for example, polyethylene glycols (PEGs)), possibly combined additional rounds of centrifugation or filtration. For example, a precipitation reagent, ExoQuick®, are added to conditioned cell media to quickly and rapidly precipitate a population of exosomes, although re-suspension of pellets prepared via this technique can be difficult. Flow field-flow fractionation (FlFFF) is an elution-based technique that is used to separate and characterize macromolecules (for example, proteins) and nano to micro-sized particles (for example, organelles and cells). In some embodiments, FlFFF is applied to fractionate exosomes from culture media.

In some embodiments, additional techniques are applied to isolated specific exosomes of interest, such as relying on antibody immunoaffinity to recognizing certain exosome-associated antigens. In some embodiments, exosomes express extracellular domains of membrane-bound receptors at the surface of their membranes. In some embodiments, this surface expression profile is used for isolating and segregating exosomes in connection with their parental cellular origin, based on a shared antigenic profile. Conjugation to magnetic beads, chromatography matrices, plates or microfluidic devices allows isolating of specific exosome populations of interest. In some embodiments, the specific exosome population of interest is related to its production from a parent cell of interest or associated cellular regulatory state. Other affinity-capture methods use lectins which bind to specific saccharide residues on the exosome surface.

Some embodiments of the methods and compositions provided herein relate to a composition that includes a plurality of exosomes. In some embodiments, the plurality of exosomes is isolated from CDCs grown in serum-free media, and may include exosomes with a diameter of about 90 nm to about 200 nm and are CD81+, CD63+, or both, and further wherein administration of the composition confers protection against damage or injury, including cardioprotection, or regeneration in tissue in the subject. In some embodiments, cardioprotection includes increased myocardial viability following acute injury. In some embodiments, regeneration includes increased myocardial viability following established myocardial infarct. In some embodiments, protection against damage or injury, including cardioprotection or regeneration includes epigenetic modification or alterations in gene expression. For example, activation of epigenetic markers such as acetylated histone 3 lysine 27 (H3K27ac), a chromatin modification that denotes an active enhancer, in promoter regions of genes for anti-inflammatory growth factors or cytokines such as IL-10.

In some embodiments, the plurality of exosomes is generated by a method including providing a population of cells, and isolating a plurality of exosomes from the population of cells. In some embodiments, the cells are stem cells, progenitors or precursors. Mixtures of such cell types is used, according to several embodiments. In some embodiments, the stem cells, progenitors or precursors are CDCs. In some embodiments, the stem cells, progenitors or precursors are pluripotent stem cells (pSCs), such as embryonic stem cells (ESCs) and induced pluripotent stem cells (iPSCs) derived from any one of various somatic sources in the body such as fibroblasts, blood and hematopoietic stem cells (hSCs), immune cells, bone and bone marrow, neural tissue, among others. In some embodiments, the stem cells, progenitors or precursors include hSCs, mesenchymal stem cells (MSCs), and/or endothelial precursor cells (EPCs). In some embodiments, the cells are stem cells, progenitors and/or precursors derived from human biopsy tissue. In some embodiments, the cells are stem cells, progenitors or precursors are a primary culture. In some embodiments, the cells are stem cells, progenitors or precursors are a cell line capable of serial passaging. In some embodiments, the exosomes are synthetic.

In some embodiments, the plurality of exosomes is derived from CDCs. In some embodiments, the plurality of exosomes includes exosomes including one or more biological molecules. In some embodiments, the plurality of exosomes includes exosomes enriched for one or more biological molecules when derived from CDCs compared to exosomes derived from non-CDC sources. In some embodiments, the one or more biological molecules are proteins, growth factors, cytokines, transcription factors or morphogenic factors. In several embodiments, multiple types of such biological molecules are present in a single exosome, or across a population of exosomes as a whole. In some embodiments, the plurality of exosomes includes exosomes enriched for one or more biological molecules, such as microRNAs, and further including microRNAs that are enriched when exosomes are derived from CDCs as compared to exosomes derived from non-CDC sources. In some embodiments, the microRNAs include one or more of miR-146a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a. In some embodiments, the plurality of exosomes includes one or more exosomes enriched in at least one of miR-146a, miR-22, or miR-24.

In some embodiments, the exosomes include one or more RNA polynucleotides. In some embodiments, the RNAs include non-coding RNAs. In some embodiments, the non-coding RNAs include tRNAs, yRNAs, rTNAs, microRNAs, lncRNAs, piRNAs, snRNAs, snoRNAs, further including fragments thereof, among others. In some embodiments, the Y-RNAs include human hY1, hY3, hY4 and/or hY5 (see Table 1 for encoding sequences). In some embodiments, the RNAs include a polynucleotide sequence with 10-20, 20-30, 30-40, 40-50, 50-60, 60-70, 70-80, 80-90, 90-95, 95% or more sequence identity to hY1, hY3, hY4 and/or hY5. In some embodiments, the RNAs include a polynucleotide sequence of 30-40, 40-50, 50-60, 60-70, or 70 or more nucleotides in length. In some embodiments, the RNAs include a polynucleotide sequence of 30-40, 40-50, 50-60, 60-70, or 70 or more nucleotides in length with 10-20, 20-30, 30-40, 40-50, 50-60, 60-70, 70-80, 80-90, 90-95, 95% or more sequence identity to hY1, hY3, hY4 and/or hY5. In some embodiments, the RNAs include a polynucleotide sequence of about 50-60, 60-70, or 70 or more nucleotides in length with about 80-90, 90-95, 95% or more sequence identity to hY1, hY3, hY4 and/or hY5. This includes, for example, a polynucleotide sequence of about 90, 91, 92, 93, 94, 95, 96, 97, 98, 99 or 100% identity to hY1, hY3, hY4 and/or hY5. For example, in one embodiment, the EV-YF1-U16 RNA fragment (SEQ ID NO:30) possesses 98% identity to the 5' end of hY4. In one embodiment, the EV-YF1 RNA fragment (SEQ ID NO:5) possesses 100% identity to the 5' end of hY4. In some embodiments, the exosomes include one or more microRNAs selected from the group consisting of: microRNAs miR-146a, miR148a, miR22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a.

In some embodiments, the CDCs are mammalian. In some embodiments, the CDCs are human. In some embodiments, the exosomes are synthetic. In some embodiments, the synthetic exosomes possess substantially similar content (e.g., Y-RNAs, microRNAs, biological molecules) as exosomes derived from CDCs.

TABLE 1

Encoding Sequences of Human Y-RNAs

| SEQ ID NO: | NCBI Database No. | Name | Sequence |
|---|---|---|---|
| 1 | NR_004391 | hY1 | 5'-ggctggtccgaaggtagtgagttatctcaattgattgttcacagtcagttac agatcgaactccttgttctactctttccccccttctcactactgcacttgactag tctttt-3' |
| 2 | NR_004392 | hY3 | 5'-ggctggtccgagtgcagtggtgtttacaactaattgatcacaaccagttaca gatttctttgttccttctccactcccactgcttcacttgactagccttt-3' |
| 3 | NR_004393 | hY4 | 5'-ggctggtccgatggtagtgggttatcagaacttattaacattagtgtcacta aagttggtatacaacccccactgctaaatttgactggcttttt-3' |
| 4 | NR_001571 | hY5 | 5'-agttggtccgagtgttgtgggttattgttaagttgatttaacattgtctccc cccacaaccgcgcttgactagcttgctgtttt-3' |

Oligonucleotides

Some embodiments of the methods and compositions provided herein include administering an oligonucleotide to a subject. In some embodiments, the oligonucleotide includes an RNA polynucleotide. In some embodiments, the RNA polynucleotide includes a non-coding RNA. In some embodiments, the non-coding RNA includes one or more of: tRNAs, yRNAs (used interchangeably with "Y-RNAs"), rTNAs, microRNAs, lncRNAs, piRNAs, snRNAs, snoRNAs, and fragments thereof. In some embodiments, the RNA includes a polynucleotide sequence with 10-20, 20-30, 30-40, 40-50, 50-60, 60-70, 70-80, 80-90, 90-95, 95% or more sequence identity to hY1, hY3, hY4 and/or hY5. In some embodiments, the RNA includes a polynucleotide sequence of 30-40, 40-50, 50-60, 60-70, or 70 or more nucleotides in length. In some embodiments, the RNA includes a polynucleotide sequence of 30-40, 40-50, 50-60, 60-70, or 70 or more nucleotides in length with 10-20, 20-30, 30-40, 40-50, 50-60, 60-70, 70-80, 80-90, 90-95, 95% or more sequence identity to hY1, hY3, hY4 and/or hY5. In some embodiments, the RNA includes a polynucleotide sequence of about 50-60, 60-70, or 70 or more nucleotides in length with about 80-90, 90-95, 95% or more sequence identity to hY1, hY3, hY4 and/or hY5. In some embodiments, this includes, for example, a polynucleotide sequence of about 90, 91, 92, 93, 94, 95, 96, 97, 98, 99 or 100% sequence identity to hY1, hY3, hY4 and/or hY5. In some embodiments, the oligonucleotide is EV-YF1. In some embodiments, the oligonucleotide includes EV-YF1 or a fragment thereof. In some embodiments, the oligonucleotide is EV-YF 1-U16. In some embodiments, the oligonucleotide includes EV-YF1-U16 or a fragment thereof.

In some embodiments, the oligonucleotide is a Y-RNA or a fragment thereof. In some embodiments, the oligonucleotide includes a Y-RNA or a fragment thereof. A non-limiting example of a Y-RNA is a small noncoding RNA that is transcribed from an individual gene by RNA-polymerase III. In humans, Y-RNAs range from about 83-113 nucleotides in length. Y-RNAs are folded into conserved stem-loop-structures that include a stem formed from a double-stranded region of the Y-RNA's terminal 5'- and 3'-sequences. In some embodiments, the terminal 5'- and 3'-sequences range from about 20-30 nucleotides in length. In some embodiments, the Y-RNA is human hY1, hY3, hY4 or hY5. In some embodiments, the Y-RNA is mouse mY1 and mY3. In some embodiments, the Y-RNA is of rat origin (e.g., rY1 or rY3). In some embodiments, the Y-RNA includes EV-YF1 or a fragment thereof.

In some embodiments, the oligonucleotide is synthesized in vitro. In some embodiments, the oligonucleotide is recombinant. In some embodiments, the oligonucleotide is isolated from a biological sample. In some embodiments, the oligonucleotide includes DNA. In some embodiments, the oligonucleotide includes RNA. In some embodiments, the oligonucleotide includes DNA and RNA. In some embodiments, the oligonucleotide is a DNA molecule with a sequence encoding a Y-RNA (e.g., EV-YF1 or EV-YF1-U16), or a fragment thereof.

In some embodiments, the oligonucleotide includes one or more modified nucleotides. In some embodiments, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof. In some embodiments, the modifications are lipid or cholesterol modifications.

Administration of Compositions

Some embodiments of the methods and compositions provided herein include administering a composition to a subject. In some embodiments, the composition includes any of the oligonucleotides, CDCs, or exosomes described above. In some embodiments, the composition administered is substantially free of exosomes. In some embodiments, the subject is a mammal. In some embodiments, the subject is human. In some embodiments, the subject is a non-human animal.

In some embodiments, administering a composition includes about 1 µg/kg to about 100 mg/kg polynucleotide to body weight per administration in a single dose. For example, in several embodiments, doses range from about 1 to about 10 µg/kg, about 10 to about 20 µg/kg, about 20 to about 30 µg/kg, about 30 to about 40 µg/kg, about 40 to about 50 µg/kg, about 50 to about 60 µg/kg, about 60 to about 70 µg/kg, about 70 to about 180 µg/kg, about 80 to about 90 µg/kg, about 90 to about 100 µg/kg, about 100 to about 200 µg/kg, about 145 to about 155 µg/kg, about 100 µg/kg to about 500 µg/kg, about 500 µg/kg to about 1000 µg/kg, about 1000 µg/kg to about 10 mg/kg, about 10 mg/kg to about 50 mg/kg, about 50 mg/kg to about 100 mg/kg, or any dose between those listed. In some embodiments, administering a composition includes about 1 to about 100 mg exosome protein in a single dose (e.g., about 1 to about 5 mg, about 5 to about 10 mg, about 10 to about 20 mg, about 20 to about 40 mg, about 40 to about 50 mg, about 50 to about 70 mg, about 40 to about 80 mg, about 80 to about 90 mg, about 90 to about 100 mg, or any mass between those listed). In some embodiments, a single dose is administered multiple times to the subject (e.g., repeat administrations over a period of time). In some embodiments, administering a composition includes injecting the composition. In some embodiments, the composition is injected percutaneously, subcutaneously, intra-abdominally, retro-orbitally, intramuscularly, intracutaneously, or intraperitoneally.

In some embodiments, the quantity of polynucleotide that is administered is at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight. In some embodiments, the polynucleotide is at a unit dose less than 200 nmol of polynucleotide (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of polynucleotide per kg of bodyweight. In some embodiments, a dose of polynucleotide is in the range of 0.01 to 5.0, 0.1 to 200, 0.1 to 100, or 1.0 to 50 micrograms per kilogram body weight per day. In some embodiments, a dose of polynucleotide is in the range of 1.0 to 25 micrograms per kilogram body weight per day. In some embodiments, a dose of polynucleotide is in the range of 0.01 to 5.0, 0.1 to 200, 0.1 to 100, or 1.0 to 50 micrograms. In some embodiments, a dose of polynucleotide is in the range of 1.0 to 25 micrograms. In some embodiments, a dose of polynucleotide is in the range of 1-5 mg. In some embodiments, a dose of polynucleotide is about 10 micrograms. In some embodiments, a dose of polynucleotide is about 3 mg.

In some embodiments, the quantities of exosomes that are administered range from $1 \times 10^6$ to $1 \times 10^7$, $1 \times 10^7$ to $1 \times 10^8$, $1 \times 10^8$ to $1 \times 10^9$, $1 \times 10^9$ to $1 \times 10^{10}$, $1 \times 10^{10}$ to $1 \times 10^{11}$, $1 \times 10^{11}$ to $1 \times 10^{12}$, $1 \times 10^{12}$ or more. In some embodiments, the numbers of exosomes are relative to the number of cells used in a clinically relevant dose for a cell-therapy method. For example, in some embodiments, 3 mL/$3 \times 10^5$ CDCs, provides a therapeutic benefit in intracoronary administration. In some embodiments, administration is in repeated doses. For example, in some embodiments, the number of administered CDCs includes 25 million intracoronary CDCs per coronary artery (i.e., 75 million CDCs total) as another baseline for exosome dosage quantity. In some embodiments, the numbers of CDCs include $1 \times 10^5$, $1 \times 10^6$, $1 \times 10^7$, $1 \times 10^8$, $1 \times 10^9$ CDCs in a single dose as another baseline for exosome dosage quantity. In some instances, this is prorated to body weight (range 100,000-1M CDCs/kg body weight total CDC dose). In some embodiments, exosome quantity is defined by protein quantity, such as dosages including 1-10, 10-25, 25-50, 50-75, 75-100, or 100 or more mg exosome protein.

In some embodiments, the oligonucleotides and/or extracellular vesicles ("EVs") (e.g., exosomes) as described herein are treated, administered, or co-administered with an agent that enhances efficacy by preventing premature degradation of the oligonucleotide or exosome. In some embodiments, the oligonucleotides and/or exosomes are administered with a transfection or transduction reagent. For example, an oligonucleotide as described herein (such as, but not limited to EV-YF1, or a fragment thereof) is administered with lipofectamine and/or a cationic liposome formulation. In some embodiments, the oligonucleotides are reconstituted into lipid vesicles and/or nanoparticles. In some embodiments, the oligonucleotides are administered with a lipoprotein or an RNA-binding protein. In some embodiments, the oligonucleotides are coupled or administered with a protease inhibitor or a nuclease inhibitor such as an RNase inhibitor or a DNase inhibitor.

In some embodiments, defining an effective dose range, dosing regimen and route of administration, is guided by studies using fluorescently labeled exosomes, and measuring target tissue retention, which in some embodiments is >10×, >50×, or >100× background, as measured 5, 10, 15, 30, or 30 or more min as a screening criterion. In some embodiments, >100× background measured at 30 mins is a baseline measurement for a low and high dose that is then assess for safety and bioactivity (e.g., using MRI endpoints: scar size, global and regional function). In some embodiments, single doses are compared to two, three, four, four or more sequentially-applied doses. In some embodiments, the repeated or sequentially-applied doses are provided for treatment of an acute disease or condition. In some embodiments, the repeated or sequentially-applied doses are provided for treatment of a chronic disease or condition.

In some embodiments, administration of polynucleotides to the subject occurs through any technique known in the art. In some embodiments, administration of exosomes to the subject occurs through any technique known in the art. In some embodiments, administration includes percutaneous delivery. In some embodiments, additional delivery sites are used, including any one or more compartments of the heart, such as arterial, venous, intracoronary or ventricular locations. In some embodiments, administration includes delivery to a tissue or organ site that is different from the site or diseased or dysfunctional tissue. In some embodiments, the delivery is via inhalation or oral administration. Systemic administration is used in several embodiments. However, in several embodiments, local delivery is employed.

In some embodiments, the composition to be administered is a pharmaceutical composition including one or more of the oligonucleotides described above, and a pharmaceutically acceptable carrier. Examples of pharmaceutically acceptable carriers include solvents, dispersion media, coatings, antibacterial and antifungal agents, isotonic and absorption delaying agents, and the like, compatible with pharmaceutical administration. In some embodiments, such carriers include, but are not limited to, saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include, but are not limited to sodium and calcium carbonate, sodium and calcium phosphate, and lactose. Suitable disintegrating agents include, but are not limited to corn starch and alginic acid. Binding agents include, but are not limited to starch and gelatin. In some embodiments, a lubricating agent is present. In some embodiments, the lubricating agent is magnesium stearate, stearic acid or talc. In some embodiments, the tablets are coated with a material such as glyceryl monostearate or glyceryl distearate, e.g., to delay absorption in the gastrointestinal tract. In some embodiments, supplementary active compounds are incorporated into the compositions. In some embodiments, an oligonucleotide is administered with a pharmaceutically acceptable carrier.

In some embodiments, the pharmaceutical compositions include conventional pharmaceutical excipients or additive. In some embodiments, the pharmaceutical excipients include stabilizers, antioxidants, osmolality adjusting agents, buffers, and pH adjusting agents. Suitable additives include physiologically biocompatible buffers (such as tromethamine hydrochloride), chelants (such as DTPA or DTPA-bisamide) or calcium chelate complexes (such as calcium DTPA, CaNaDTPA-bisamide). Suitable additives also include additions of calcium or sodium salts (for example, calcium chloride, calcium ascorbate, calcium gluconate or calcium lactate). In some embodiments, pharmaceutical compositions are packaged for use in liquid form, or lyophilized. In some embodiments, for solid compositions, conventional non-toxic solid carriers are used: for example, pharmaceutical grades of mannitol, lactose, starch, magnesium stearate, sodium saccharin, talcum, cellulose, glucose, sucrose, magnesium carbonate, and the like.

In some embodiments, the composition includes a solid pharmaceutical composition for oral administration with any of the carriers and excipients listed above and 10-95% or 25%-75%, of one or more polynucleotide agents described herein. In some embodiments, the composition includes a therapeutically effective amount of polynucleotide.

Therapeutic Effects

Some embodiments of the methods and compositions provided herein relate to conferring beneficial therapeutic effects on a subject, such as protection, cardioprotection, preventing or retarding progression of inflammation, or regenerating tissue. In some embodiments, the composition includes an oligonucleotide, CDC, and/or exosome described above. In some embodiments, administering an oligonucleotide, CDC, and/or exosome described above regenerates tissue, or modulates apoptosis, inflammation hypertrophy, cardiac function, or fibrosis.

In some embodiments, the therapeutic benefits are derived through indirect mechanisms involving regenerated tissue arising from endogenous origin. For example, in some embodiments, cellular exosomes produced by CDCs allow for production and delivery of growth factors, transcription factors, cytokines and nucleic acids for new therapeutic approaches in a manner that not only ameliorates progression of the disease, but repairs and regenerates disease or dysfunctional tissue. In some embodiments, CDC-derived exosomes recruit synergistic mechanisms to attract endogenous stem cells to sites of tissue degeneration and injury, promote cellular differentiation, and reverse chronic disease pathophysiology.

Some embodiments relate to a method for treatment including, administering a composition including a plurality of exosomes to the individual, wherein the administration of the composition treats the subject. In some embodiments, the subject is in need of treatment for an inflammatory disease or condition. In some embodiments, the inflammatory related disease or condition is acute. In some embodiments, the inflammatory related disease or condition is chronic. In some embodiments, the inflammatory related disease or condition is a heart related disease or condition. In some embodiments, the heart related disease or condition is a myocardial infarction. In some embodiments, the heart related disease or condition is an ischemia reperfusion injury. In some embodiments, the heart related disease or condition is atherosclerosis or heart failure. In several embodiments, the disease or condition results in damage or dysfunction in the kidney. In some embodiments, the subject is in need of treatment for a disease or condition involving tissue damage or dysfunction.

In some embodiments, treatment of the subject results in decreased fibrosis, decreased inflammation, and/or increased mitochondrial function. In some embodiments, decreased fibrosis includes a reduction in collagen accumulation. In some embodiments, collagen includes collagen I or collagen III. In some embodiments, decreased inflammation includes an increase in cytoplasmic nuclear factor (erythroid-derived 2)-like 2 (Nrf2), a reduction in fatty acid peroxidation end products, reduced numbers of inflammatory cells, and/or upregulated expression of antioxidants. In some embodiments, antioxidants include, but are not limited to, heme oxygenase-1 (HO-1), catalase, superoxide dismutase-2 (SOD-2), or a glutamate-cysteine ligase catalytic (GCLC) subunit. In some embodiments, inflammatory cells include CD68+ macrophages and CD3+ T-cells. In some embodiments, increased mitochondrial function includes increased mitochondrial ultrastructure or increased mitochondrial biogenesis. In some embodiments, increased mitochondrial function includes increased nuclear PPAR-γ co-activator-1 (PGC-1) expression.

In some embodiments, administration of polynucleotides or a plurality of exosomes alters gene expression in inflamed, damaged or dysfunctional tissue, modulates or reduces inflammation in a tissue, improves viability of the damaged tissue, or enhances regeneration or production of new tissue in the individual. In some embodiments, administration of the exosomes or polynucleotides results in functional improvement in the tissue. In several embodiments, exosomes comprising polynucleotides (e.g., biological factors) are administered in conjunction with polynucleotides that are "free" (e.g., not housed within or on an exosome).

In some embodiments, the damaged or dysfunctional tissue is in need of repair, regeneration, or improved function due to an acute event. In some embodiments, an acute event includes trauma such as laceration, crush or impact injury, shock, loss of blood or oxygen flow, infection, chemical or heat exposure, poison or venom exposure, or drug overuse or overexposure. In some embodiments, tissue is also subject to damage due to chronic disease. In some embodiments, the administration is in repeated doses, such as two, three, four, four or more sequentially-applied doses. In some embodiments, the repeated or sequentially-applied doses are provided for treatment of an acute disease or condition. In some embodiments, the repeated or sequentially-applied doses are provided for treatment of a chronic disease or condition.

Some embodiments of the methods and compositions provided herein relate to treating a subject suffering from hypertension, comprising: administering an oligonucleotide to a subject with hypertension; wherein the oligonucleotide comprises EV-YF 1 or a fragment thereof; and wherein the oligonucleotide has a therapeutic effect on the subject's heart or kidneys.

Some embodiments herein relate to a method for treating a subject suffering from hypertension. In some embodiments, the subject has high blood pressure. In some embodiments, the subject has a resting blood pressure of over 130/90 mmHg. In some embodiments, the subject has a resting blood pressure of over 140/90 mmHg. In some embodiments, the hypertension is associated with activation of the renin-angiotensin system (RAS). In some embodiments, an oligonucleotide is administered to a subject with hypertension. In some embodiments, the oligonucleotide is an oligonucleotide described above. In some embodiments, the oligonucleotide comprises EV-YF1 or a fragment thereof. In some embodiments, the oligonucleotide comprises EV-YF1-U16 or a fragment thereof. In some embodiments, the oligonucleotide has a therapeutic effect on the subject's heart or kidneys. In several embodiments, the composition ameliorates one or more symptoms of hypertension. In several embodiments, the compositions do not reduce blood pressure, though other beneficial effects are seen.

In some embodiments, the subject's heart is hypertrophic. In some embodiments, cardiac hypertrophy is determined by increased or excessive septal or ventricular wall thickness in the heart, such as an increase in left ventricular (LV) posterior wall thickness at end-diastole (LVPWd), LV internal diastolic diameter (LVIDd), or interventricular septal thickness at end-diastole (IVSd). In some embodiments, cardiac hypertrophy is determined by increased or excessive heart mass, heart mass/body weight ratio, heart mass/tibia length ratio, LV mass, right ventricular (RV) mass, Atrial natriuretic peptide (ANP) levels, Anp gene expression, Brain natriuretic peptide (BNP) levels, Bnp gene expression, cardiomyocyte length, or cardiomyocyte width. In some embodiments, administration of the oligonucleotide decreases cardiac hypertrophy (or a marker thereof) in the subject. In some embodiments, the decrease in cardiac hypertrophy is indicated by a decrease in an index of cardiac hypertrophy. In some embodiments, the subject's heart is damaged, hypertrophic, fibrotic, inflamed, or dysfunctional due to hypertension. In some embodiments, the subject's heart is damaged, hypertrophic, fibrotic, inflamed, or dysfunctional due to a cause other than hypertension. In some embodiments, the subject's heart is damaged, hypertrophic, fibrotic, inflamed, or dysfunctional, and the subject does not have hypertension.

In some embodiments, the subject's heart is fibrotic. In some embodiments, the fibrosis in the heart includes interstitial myocardial fibrosis. In some embodiments, fibrosis is determined by Masson's trichrome staining, or by increased or excessive expression of collagen genes or proteins. In some embodiments, administration of the oligonucleotide decreases cardiac fibrosis in the subject.

In some embodiments, the subject's heart (or other organ) is inflamed. Markers of inflammation include markers of infiltrating inflammatory cells, such as CD68, and pro-inflammatory cytokines such as Il6 and Il1b. In some embodiments, tissue inflammation is determined by increased or excessive expression of genes such as CD68, Il6, or Il1b. In some embodiments, administration of the oligonucleotide decreases inflammation or gene expression of a marker of inflammation in the subject's heart.

In some embodiments, at least one of the subject's kidneys is injured or dysfunctional. In some embodiments, kidney dysfunction is determined by increased or excessive protein levels in the subject's urine (proteinuria). In some embodiments, kidney dysfunction is determined by increased or excessive creatinine levels in the subject's blood, plasma, or serum. In some embodiments, administration of the oligonucleotide improves one or more aspects of the subject's kidney function. In some embodiments, an injury to the kidney is determined by increased or excessive neutrophil gelatinase associated lipocalin (NGAL), or by structural changes in the kidney. In some embodiments, the structural changes are determined after periodic acid-Schiff staining. In some embodiments, the structural changes include mesangial expansion or decreased glomerular size. In some embodiments, administration of the oligonucleotide (whether housed in or on an exosome or "free") decreases the extent of the injury to the kidney.

In some embodiments, at least one of the subject's kidneys is fibrotic or inflamed. In some embodiments, the fibrosis includes tubulointerstitial fibrosis in at least one of the subject's kidneys. In some embodiments, administration of the oligonucleotide decreases fibrosis or inflammation in at least one of the subject's kidneys. In some embodiments, a kidney of the subject is damaged, hypertrophic, fibrotic, inflamed, or dysfunctional due to hypertension. In some embodiments, a kidney of the subject is damaged, hypertrophic, fibrotic, inflamed, or dysfunctional due to a cause other than hypertension. In some embodiments, a kidney of the subject is damaged, hypertrophic, fibrotic, inflamed, or dysfunctional, and the subject does not have hypertension.

Some embodiments of the methods and compositions provided herein relate to treating a subject suffering from a cardiac injury, comprising: administering an oligonucleotide to a subject suffering from a cardiac injury; wherein the oligonucleotide comprises EV-YF1-U16 or a fragment thereof; and wherein the oligonucleotide has a therapeutic effect on the subject's heart.

Some embodiments herein relate to a method for treating a subject suffering from a cardiac injury. In some embodiments, the cardiac injury includes a myocardial infarction or heart attack. In some embodiments, the cardiac injury is caused by ischemia or ischemia-reperfusion. In some embodiments, an oligonucleotide is administered to a subject suffering from a cardiac injury. In some embodiments, the oligonucleotide is an oligonucleotide described above. In some embodiments, the oligonucleotide comprises EV-YF1 or a fragment thereof. In some embodiments, the oligonucleotide comprises EV-YF1-U16 or a fragment thereof. In some embodiments, the oligonucleotide has a therapeutic effect on the subject's heart. In some embodiments, administration of the oligonucleotide decreases the extent of the injury. In some embodiments, administration of the oligonucleotide decreases an infarct's size in the subject's heart.

In some embodiments, administration of the oligonucleotide decreases inflammation, or gene expression of a marker of inflammation in the injured heart of the subject.

In some embodiments, the injury decreases cardiomyocyte viability in the subject's heart. In some embodiments, the heart (or other organ), as a result of the injury, contains excessive or increased numbers of necrotic or apoptotic cells or cardiomyocytes. In some embodiments, apoptosis is determined by the number of TUNEL-positive cells or cardiomyocytes. In some embodiments, the injury causes oxidative stress, such as increased $H2O_2$ or superoxide production, in the subject's heart. In some embodiments, administration of the oligonucleotide increases cardiomyocyte viability in the subject's heart. In some embodiments, administration of the oligonucleotide decreases the numbers of necrotic or apoptotic cells or cardiomyocytes in the subject. In some embodiments, administration of the oligonucleotide decreases the number of TUNEL-positive cells or cardiomyocytes in the subject. In some embodiments, administration of the oligonucleotide decreases oxidative stress in the subject's heart.

Some embodiments of the methods and compositions provided herein relate to treating a subject suffering from a metabolic disorder, comprising: administering an oligonucleotide to a subject with a metabolic disorder; wherein the oligonucleotide comprises EV-YF1 or a fragment thereof, or EV-YF1-U16 or a fragment thereof; and wherein the oligonucleotide has a therapeutic effect on the subject's metabolism.

Some embodiments herein relate to a method for treating a subject suffering from a metabolic disorder. In some embodiments, the subject is obese. In some embodiments, the subject is diabetic. In some embodiments, the subject has excessive or increased blood glucose levels. In some embodiments, the subject exhibits glucose intolerance, or excessive or increased blood glucose levels in response to a glucose challenge. In some embodiments, an oligonucleotide is administered to a subject with a metabolic disorder. In some embodiments, the oligonucleotide is an oligonucleotide described above. In some embodiments, the oligonucleotide comprises EV-YF1 or a fragment thereof. In some embodiments, the oligonucleotide comprises EV-YF1-U16 or a fragment thereof. In some embodiments, the oligonucleotide has a therapeutic effect on the subject's metabolism. In some embodiments, administration of the oligonucleotide improves the subject's metabolic function or decreases the extent of the subject's diabetes. In some embodiments, administration of the oligonucleotide decreases blood glucose levels or improves glucose tolerance in the subject.

In some embodiments, administration of the oligonucleotide increases IL-10 gene expression in the subject's heart or spleen, or in at least one of the subject's kidneys. In some embodiments, administration of the oligonucleotide increases circulating IL-10 in the subject. In some embodiments, administration of the oligonucleotide increases IL-10 in the subject's blood, serum, or plasma.

Some embodiments herein relate to use of an oligonucleotide composition for treating a subject a subject suffering from hypertension, comprising: administering an oligonucleotide to a subject with hypertension; wherein the oligonucleotide comprises EV-YF 1 or a fragment thereof; and wherein the oligonucleotide has a therapeutic effect on the subject's heart or kidneys.

Some embodiments herein relate to use of an oligonucleotide composition for treating a subject suffering from a cardiac injury, comprising: administering an oligonucleotide to a subject suffering from a cardiac injury; wherein the oligonucleotide comprises EV-YF1-U16 or a fragment thereof; and wherein the oligonucleotide has a therapeutic effect on the subject's heart.

Some embodiments herein relate to use of an oligonucleotide composition for treating a subject suffering from a metabolic disorder, comprising: administering an oligonucleotide to a subject with a metabolic disorder; wherein the oligonucleotide comprises EV-YF1 or a fragment thereof, or EV-YF1-U16 or a fragment thereof; and wherein the oligonucleotide has a therapeutic effect on the subject's metabolism.

Some embodiments herein relate to method for treating a subject by administering an oligonucleotide as described herein, or a CDC-EV (e.g., CDC-exosome) comprising the oligonucleotide, to the subject. In some embodiments, the subject's heart or kidneys are damaged, hypertrophic, fibrotic, inflamed, or dysfunctional. For example, the subject may suffer from heart failure or cardiomyopathy. Examples of heart failure include heart failure with reduced ejection fraction (such as reduced left or right ventricular ejection fraction), and heart failure with preserved ejection fraction. In some embodiments, the cardiomyopathy includes heart failure, cardiac hypertrophy or fibrosis.

In some embodiments, the oligonucleotide or CDC-EV (e.g., CDC-exosome) increases the amount of plasma IL-10 protein, induces macrophage IL-10 gene expression, attenuates one or more of cardiac CD68 and IL1b gene expression, and/or attenuates one or more of renal CD68, Il6 and Il1b gene expression. In some embodiments, the oligonucleotide, CDC-EV (e.g., CDC-exosome), increase in the amount of plasma IL-10 protein, induction of macrophage IL-10 gene expression, attenuation of one or more of cardiac CD68 and IL1b gene expression, and/or attenuation of one or more of renal CD68, Il6 and Il1b gene expression, induces a therapeutic effect on the subject's heart or kidney, thereby treating the subject's damaged, hypertrophic, fibrotic, inflamed, or dysfunctional heart or kidney. For example, treatment with or use of the oligonucleotide or CDC-EV (e.g., CDC-exosome) leads to an improvement in heart function, fibrosis, and/or another condition of the heart in a subject with heart failure (such as heart failure with reduced or preserved ejection fraction) and/or cardiomyopathy (such as inheritable, heritable, or sporadic hypertrophic cardiomyopathy).

EXAMPLES

Example 1

Methods Used in Example 1

Figure 6:
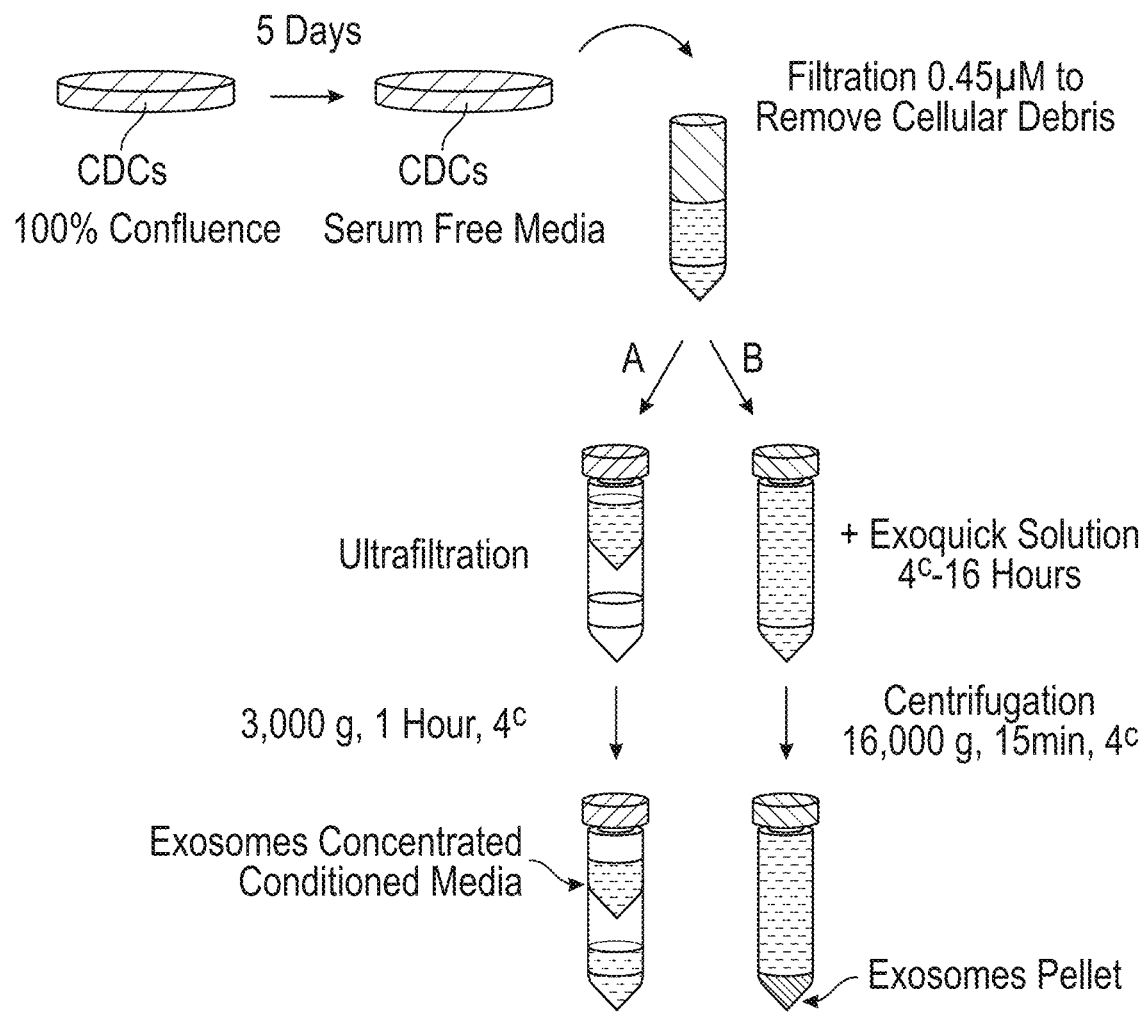
FIG. 6 depicts an exosome isolation protocol used in Example 1. After Step A, exosomes concentrated from conditioned media are used to treat cells directly or after transfection of exosomes. After Step B, the exosome pellet is submitted to RNA-seq.

Exosome Generation, Purification, and Transfection. For all experimental procedures in Example 1, CDC exosomes (CDC-exo) were generated from CDCs at passage 4. Normal human dermal fibroblast (NHDF) exosomes (NHDF-exo) served as a control. More specifically, CDCs and NHDFs were grown to confluence then washed with PBS prior to the addition of serum-free media. Cells were then cultured for 5 days before media collection. The resulting conditioned media was purified with a 0.45 µm-filter to remove cellular debris then concentrated with an Amicon 3 kDa centrifugation filter (Millipore). The resulting suspension was utilized for in vitro studies. For RNA-seq, this exosome suspension was precipitated with ExoQuick (System Biosciences) to isolate exosomal RNA (FIG. 6).

Transfection. CDC-exo were transfected with EV-YF1-U16, with EV-YF 1-fluo (5'-linked Rhodamine Red™-X [NHS Ester], IDT) (linked as follows:/5RhoR-XN/[SEQ ID NO: 7]), or with a truncated EV-YF1, using Exo-Fect (System Biosciences) (Table 2).

TABLE 2

Oligoribonucleotide sequences

| SEQ ID NO: | Oligo Name | Sequence |
|---|---|---|
| 5 | EV-YF1 | 5'-GGCUGGUCCGAUGGUAGUGGGUUAUCAGAACUUAUUAACAUUAGUGUCACUAAAGU-3' |
| 6 | Ys | 5'-GAUGUUAUUAUCGUAGUAGAUGAAUAAUCGGUGCUACGAUUAUGAGUGUCAGUCGCC-3' |
| 7 | EV-YF1-fluo | 5'-GGCUGGUCCGAUGGUAGUGGGUUAUCAGAACUUAUUAACAUUAGUGUCACUAAAGU-3' |
| 30 | EV-YF1-U16 | 5'-GGCUGGUCCGAUGGUAGUGGGUUAUCAGAACUUAUUAACAUUAGUGUCACUAAAGU-3' |
| 31 | EV-YF1, truncated 2 from 3' | 5'-GGCUGGUCCGAUGGUAGUGGGUUAUCAGAACUUAUUAACAUUAGUGUCACUAAA-3' |
| 32 | EV-YF1, truncated 5 from 3' | 5'-GGCUGGUCCGAUGGUAGUGGGUUAUCAGAACUUAUUAACAUUAGUGUCACU-3' |
| 33 | EV-YF1, truncated 10 from 3' | 5'-GGCUGGUCCGAUGGUAGUGGGUUAUCAGAACUUAUUAACAUUAGUG-3' |
| 34 | EV-YF1, truncated 2 from 5' | 5'-CUGGUCCGAUGGUAGUGGGUUAUCAGAACUUAUUAACAUUAGUGUCACUAAAGU-3' |
| 35 | EV-YF1, truncated 5 from 5' | 5'-GUCCGAUGGUAGUGGGUUAUCAGAACUUAUUAACAUUAGUGUCACUAAAGU-3' |
| 36 | EV-YF1, truncated 10 from 5' | 5'-AUGGUAGUGGGUUAUCAGAACUUAUUAACAUUAGUGUCACUAAAGU-3' |

TABLE 2-continued

Oligoribonucleotide sequences

| SEQ ID NO: | Oligo Name | Sequence |
|---|---|---|
| 37 | EV-YF1, truncated 5 from both | 5'-GUCCGAUGGUAGUGGGUUAUCAGAACUUAU UAACAUUAGUGUCACU-3' |
| 38 | EV-YF1, truncated 3 from 5' | 5'-UGGUCCGAUGGUAGUGGGUUAUCAGAACUU AUUAACAUUAGUGUCACUAAAGU-3' |
| 39 | EV-YF1, truncated 4 from 5' | 5'-GGUCCGAUGGUAGUGGGUUAUCAGAACUA UUAACAUUAGUGUCACUAAAGU-3' |

Generation of Human Cardiosphere-Derived Cells (CDCs). CDCs were derived as follows. Heart tissue from 6 human donors (Table 3) was minced into small pieces and digested with collagenase. Tissue was then plated and cultured on fibronectin (BD Biosciences)-coated dishes, where stromal-like cells and phase-bright round cells grew out spontaneously from the tissue fragments and reached confluence. These cells were then harvested with 0.25% trypsin (GIBCO) and cultured in suspension on Ultra-Low attachment dishes (Corning) to form cardiospheres. CDCs were obtained by seeding cardiospheres onto fibronectin-coated dishes and passaged. All cultures were maintained at 5% CO2 at 37° C., using IMDM (GIBCO; supplemented with 20% FBS (Hyclone), 1% penicillin/streptomycin, and 0.1 ml 2-mercaptoethanol). The medical history was unremarkable in all donors except ZCI who had hydrocephalus due to craniometaphyseal dysplasia.

TABLE 3

Demographic properties of human CDC donors

| Donor | Age | Sex | Ethnicity | Cause of death |
|---|---|---|---|---|
| YKT | 56 | M | Hispanic | Head trauma |
| BM030 | 27 | F | Caucasian | Anoxia |
| L088 | 64 | M | Caucasian | Stroke |
| ZCI | 9 | F | Chinese | Anoxia |
| ZKN | 26 | F | Hispanic | Head trauma/Motor Vehicle Accident/Blunt injury |
| OD220 | 3 | M | Caucasian | Motor Vehicle Accident |

Exosome RNA-sequencing (RNA-seq). Sequencing was performed by the Cedars-Sinai Genomics Core (Los Angeles, CA). Library construction was performed according to the manufacturers' protocols using the Ion Total RNASeq Kit v2 (Life Technologies). One microgram of total RNA was assessed for quality using the Agilent Bioanalyzer 2100, enriched with magnetic beads, fragmented, ligated with adapters, and reversed transcribed to make cDNA. The resulting cDNA was barcoded using Ion Xpress™ RNA-Seq Barcode 1-16 Kit and then amplified. RNA-seq libraries were assessed for concentration (Qubit dsDNA HS Assay Kit, Invitrogen) and size (DNA 1000 Kit, Agilent). Samples were multiplexed and amplified (pooled libraries) onto Ion Sphere™ particles using Ion PI™ Template OT2 200 Kit. Ion Sphere™ particles were then purified and prepared (Ion PI™ Sequencing 200 Kit) for sequencing on an Ion Proton sequencer. The raw sequencing signal was processed (FASTQ) and the adaptor was trimmed (Torrent Suite software) to obtain 10 million reads per sample.

All reads <15 nucleotides (nt) after adapter removal were excluded from further analysis. To obtain an integrated view of all types of non-coding RNAs, the filtered reads were aligned to a comprehensive non-coding RNA database (RNACentral Release v1.0) (3) downloaded from http://rnacentral.org/, using blast+ toolkit v2.2.30) with "blastn-short" mode. An alignment score >75% (High-scoring Segment Pair) of the query coverage was used to annotate each read. Reads annotated as "Y-RNA" were further aligned to sequences encoding full-length human genomic Y-RNAs (Table 1).

Bone Marrow-Derived Macrophages (BMDM) Chromatin Immunoprecipitation-sequencing (ChIP-seq). Cells were washed in PBS, pelleted, snap-frozen and samples were sent to Active Motif (Carlsbad, CA) for ChIP-Seq. In brief, cells were fixed with 1% formaldehyde for 15 min and quenched with 0.125 M glycine. Chromatin was isolated by adding lysis buffer, followed by disruption with a Dounce homogenizer. Lysates were sonicated and the DNA sheared to an average length of 300-500 bp with Active Motif's EpiShear probe sonicator (53051) and cooled sonication platform (53080). Genomic DNA (Input) was prepared by treating aliquots of chromatin with RNase, proteinase K and heat for de-crosslinking, followed by ethanol precipitation. Pellets were resuspended and the resulting DNA was quantified on a NANODROP spectrophotometer. Extrapolation to the original chromatin volume allowed quantitation of the total chromatin yield.

An aliquot of rat macrophage chromatin (25 µg) along with 750 ng of Drosophila S2 chromatin was precleared with protein A agarose beads (Invitrogen). Genomic DNA regions of interest were isolated using 4 µg antibody against H3K27Ac (Active Motif 39133) and 0.4 µg of Drosophila specific H2Av antibody (Active Motif 53083). Complexes were washed, eluted from the beads with SDS buffer, and subjected to RNase and proteinase K treatment. Crosslinks were reversed by incubation overnight at 65° C., and ChIP DNA was purified by phenolchloroform extraction and ethanol precipitation.

Quantitative PCR (qPCR) reactions were carried out in triplicate on specific genomic regions using SYBR Green Supermix (Bio-Rad). The resulting signals were normalized for primer efficiency by carrying out QPCR for each primer pair using Input DNA.

ChIP-Seq and ChIP-seq data analysis. Illumina sequencing libraries were prepared from the ChIP and Input DNAs by the standard consecutive enzymatic steps of end-polishing, dA-addition, and adaptor ligation. After a final PCR amplification step, the resulting DNA libraries were quantified and sequenced on Illumina's NextSeq 500 (75nt reads, single end).

Raw ChIP-seq files were processed using the BioWardrobe pipeline, as follows. Fastq files from Illumina pipeline were aligned by bowtie (version 1.0.0) with maximum one allowed error in a sequence and number of hits was not more than one. MACS2 (version 2.0.10.20130712 was used to estimate fragment size (198 bp and 206 bp for CDC-exo treated and untreated BMDMs, respectively) and to find islands of enrichment. MACS2 were used with q-value threshold less than 0.2 and with PCR duplicates removed. To produce list of differentially enriched regions MANORM was used. For peaks that were specific to CDC-exo treated cells, the peaks were ranked in order of normalized read count (FPKM), and found that a strong inflection point was reached at the top ~500 peaks. The same inflection point was observed when ranking by log 10(p-value) values reported by MANORM. Thus, the top 500 peaks were used for subsequent analyses.

RNA-seq data analysis. The USC Norris Cancer Center Next-generation sequencing core performed mRNA-seq. Macrophages from control (n=2) and CDC-exo-treated (n=2) groups were lysed with QIAzol and total RNA extracted using miRNeasy mini isolation kit (QIAGEN).

manufacturer's protocol. The resulting cDNA was standardized across samples prior to qPCR analysis with iQ™ SYBR® Green Supermix (BioRad) on a LightCycler 7900 Fast Real-Time PCR System (Roche Applied Science). Relative gene expression was determined by the ΔΔCt method. Primers were ordered from Integrated DNA Technologies (IDT) (Table 4).

TABLE 4

Primer sequences

| SEQ ID NOS: | Name | Primer 1 | Primer 2 |
|---|---|---|---|
| qPCR | | | |
| 8-9 | EV-YF1 | 5'-GGCTGGTCCGATGGTTAGTG-3' | 5'-ACTTTAGTGACACTAATGTT-3' |
| 10-11 | Hprt | 5'-AGATCCATTCCTATGACT-3' | 5'-GAGAGATCATCTCCACCAAT-3' |
| 12-13 | U6 | 5'-GCTTCGGCAGCACATATACTAAAAT-3' | 5'-CGCTTCACGAATTTGCGTGTCAT-3' |
| 14-15 | Anp | 5'-TCGTCTTGGCCTTTTGGCT-3' | 5'-TCCAGGTGGTCTAGCAGGTTCT-3' |
| 16-17 | Il6 | 5'-GTCGGAGGCTTAATTACACATG-3' | 5'-TCAGAATTGCCATTGCCATTGCACA-3' |
| 18-19 | CD68 | 5'-ACTTCGGGCCATGTTTCTCT-3' | 5'-GCTGGTAGGTTGATTGTCGT-3' |
| 20-21 | Il1b | 5'-AAGGAGAACCAAGCAACGACAAAA-3' | 5'-TGGGGAACTCTGCAGACTCAAACT-3' |
| ChIP-qPCR | | | |
| 22-23 | Peak 1 | 5'-GACAATAACTGCACCCACTT-3' | 5'-CCTAGGAAGAAAGGCTAGGT-3' |
| 24-25 | Peak 2 | 5'-CAACATTAGTGGCAACAGTC-3' | 5'-GCAACCCAAGTAACCCTAAA-3' |
| 26-27 | Peak 3 | 5'-AGGAAGCAGAATTCTTAGGG-3' | 5'-AGGGTTGAATAGGTTCACAG-3' |
| 28-29 | Peak 4 | 5'-TAAGCAAACATCCATCCGCT-3' | 5'-CTGAGTTCAAGGCCACACTG-3' |

Prior to library construction, RNA integrity was verified by Experion analysis (BioRad). RNA was then enriched using the Illumina TruSeq V2 polyA beads for library preparation (Kapa Biosystems) according to the manufacturer's protocol. Libraries were visualized (Bioanalyzer Analysis, Agilent) and quantified (Library Quantification Kit, Kapa Biosystems) prior to sequencing with V2 chemistry (NextSeq 500, Illumina). Raw RNA-seq (fastq) files were processed using the BioWardrobe pipeline, as follows. Fastq files from Illumina pipeline were aligned by STAR (version STAR 2.4.0c with "-outFilterMultimapNmax 1-outFilterMismatchNmax 2." RefSeq annotation from UCSC genome browser for rn5 genome was used. The outFilterMultimapNmax parameter is used to allow unique alignment only and -outFilterMismatchNmax parameter is used to allow at max 2 errors. All reads from produced .bam files were split for related isoform with respect to RefSeq annotation. Then EM algorithm was used to estimate appropriate number of reads for each isoform (see STAR documentation for details). To identify differentially regulated transcripts, DESeq2 v.1.8.2 was used to determine significant read count differences between 2 control replicates and 2 CDC-exotreated replicates. Raw p-values were adjusted for multiple hypotheses testing using the Benjamini-Hochberg method, and all genes with FDR-adjusted p-values <0.05 were considered significant for subsequent analyses.

Quantitative RT-PCR (qPCR). To assess IL-10 and EV-YF1 expression, cDNA was synthesized from mRNA using iScript™ cDNA Synthesis Kit (Bio-Rad) according to the Association between ChIP-seq peaks and differentially expressed genes. Differentially expressed genes (FDR-adjusted p-value <0.05) were intersected with the top 500 H3K27ac peaks gained in CDC-exo treated cells, as follows. Both lists were uploaded to the NextBio functional database (Illumina Inc.), which associated each H3K27ac peak to the nearest gene promoter, yielding 284 genes. NextBio was used to calculate intersections using a statistical model based on Fisher's test.

ChIP-qPCR. DNA samples were purified and used as templates for qPCR. The primer sequences designed for peak analysis are described in Table 4. Quantitative PCR was performed and data expressed as the percentage of input according to the formula $100*2^{\wedge}(\text{Adjusted input-Ct (IP)})$.

NRVM isolation and in vitro assay. Neonatal rat ventricular myocytes (NRVMs) were cultured. Briefly, hearts were harvested from 2-day-old Sprague-Dawley rats then ventricles were isolated, minced, and enzymatically digested in a solution of trypsin and collagenase overnight. Cells were resuspended in M199 media (10% FBS, glucose, penicillin, vitamin B12, HEPES, and MEM nonessential amino acids; GIBCO) and pre-plated to allow non-cardiomyocyte cell attachment.

The resulting NRVM suspension was collected and counted prior to plating for experimental use. To induce oxidative stress in NRVMs, cells were incubated with 75 μM $H_2O_2$ (Sigma-Aldrich) for 15 min at 37° C. prior to media exchange for 20 min, then Ys- or EV-YF1-U16-primed BMDMs were added to the NRVM culture dishes. Control NRVMs were treated with or without recombinant rat IL-10 (10 ng/ml) (rIL-10; R&D systems). NRVM-BMDM co-cultures and IL-10 treated NRVMs were cultured in the presence or absence of rat IL-10 neutralizing antibody (αIL-10; R&D systems). Cardiomyocyte apoptosis was determined 6 hrs later with a TdT dUDP Nick-End Labeling (TUNEL, Roche) kit according to the manufacturer's protocol. All samples were co-stained with rabbit α-actinin (Abcam), CD11b (BD Biosciences), and DAPI (Sigma).

Ischemia/Reperfusion rat model. Twelve-week-old female Wistar-Kyoto rats (Charles River Labs) were used for in vivo experimental protocols. To induce I/R injury, rats were provided general anesthesia and then a thoracotomy was performed at the fourth intercostal space to expose the heart and left anterior descending coronary artery (LAD). A 7-0 silk suture was then used to ligate the LAD, which was subsequently removed after 45 minutes to allow for reperfusion. Ten minutes later, 100 µl of EV-YF1-U16 (sequence in Table 2), Ys or vehicle was injected into the LV cavity over a period of 20 seconds with aortic crossclamp. Briefly, 10 µg of EV-YF1-U16 or Ys were incubated in IMDM basal media (Thermo Scientific) with DHARMAFECT_transfection reagent (DHARMACON) for 10 minutes at room temperature then resuspended in 100 µL IMDM for injection.

Histology. Two days following I/R injury, 10% KCL was injected into the LV to arrest hearts in diastole. Then, hearts were harvested, washed in PBS, and then cut into 1 mm sections from apex to base, above the infarct zone. Sections were incubated with 1% solution 2,3,5-triphenyl-2Htetrazolium chloride (TTC) for 20 minutes in the dark and washed with PBS. Then sections were imaged and weighed. The infarcted zones (white) were delineated from viable tissue (red) and analyzed (ImageJ software). Infarct mass was calculated according the LV area on both sides of the tissue sections according to the following formula: (infarct area/LV area)× weight (mg).

Bone marrow cell isolation and Mφ differentiation. Femurs were isolated from 7 to 10-week-old Wistar-Kyoto rats. Bone marrow was isolated by flushing with PBS (containing 1% FBS, 2 mM EDTA) then filtering through a 70 µm mesh. Red blood cells were lysed with ACK buffer (INVITROGEN) then resuspended in IMDM (GIBCO) containing 10 ng/ml M-CSF (eBioscience) for plating. The media was exchanged every 2-3 days until day 7, at which point bone marrow-derived macrophages (BMDMs) were obtained. BMDMs were transfected with Ys (50 nM) or EV-YF1-U16 (50 nM) using DHARMAFECT 4 reagent (DHARMACON), treated with LPS (1 µg/ml), or primed toward M1 (100 ng/ml LPS and 50 ng/ml IFN-γ; Sigma-Aldrich and R&D Systems, respectively) or M2 (10 ng/ml IL-4 and IL-13; R&D Systems), the night between days 7 and 8 (~18 hours).

RNA isolation. Cells were washed and collected for RNA isolation using a miRNeasy Mini Kit (QIAGEN) according to the manufacturer's protocol. Exosomal RNA was isolated using the miRNeasy Serum/Plasma Kit (QIAGEN) according to the manufacturer's protocol. RNA concentration and purity were determined using a NanoDrop Spectrophotometer (Thermo Scientific).

Enzyme-Linked Immunosorbent Assay (ELISA). Protein levels of secreted IL-10 were determined using an IL-10 ELISA kit (R&D systems) according to the manufacturer's protocol. Conditioned media collected from Ys- and EV-YF1-U16-primed BMDMs at 24, 48, and 72 hours following transfection were utilized to determine secreted levels of IL-10.

Cellular Transfection. To overexpress EV-YF1-U16, Ys, or EV-YF1-fluo, cells (BMDMs or CDCs) were transfected with EV-YF1-U16, Ys, or EV-YF1-fluo at a final concentration of 50 nM using DHARMAFECT 4 reagent (DHARMACON), according to the manufacturer's protocol.

DUAL-LUCIFERASE Reporter Assay. HEK293T cells were plated in a 48-well plate then transfected with 250 ng of a firefly luciferase IL-10 promoter reporter plasmid (pGL2B 1538/+64, gift from Stephen Smale (Addgene plasmid #24942)) and 25 ng Renilla luciferase reporter using Lipofectamine 2000 (Thermo-Fisher).

Following overnight transfection (16 hours), cells were treated with LPS (1 µg/ml) or transfected with EV-YF1-U16 or Ys (50 nM) using DHARMAFECT 1 reagent (DHARMACON). After 8 and 24 hours, luciferase activity was determined using the DUAL-LUCIFERASE_Reporter Assay kit (Promega) according to the manufacturer's instructions. To control for transfection efficiency, firefly luciferase was normalized to Renilla luciferase. Data are represented as Relative Light Units (RLU).

Y-RNA Fragments are Enriched in CDC-exo

Figure 1B:
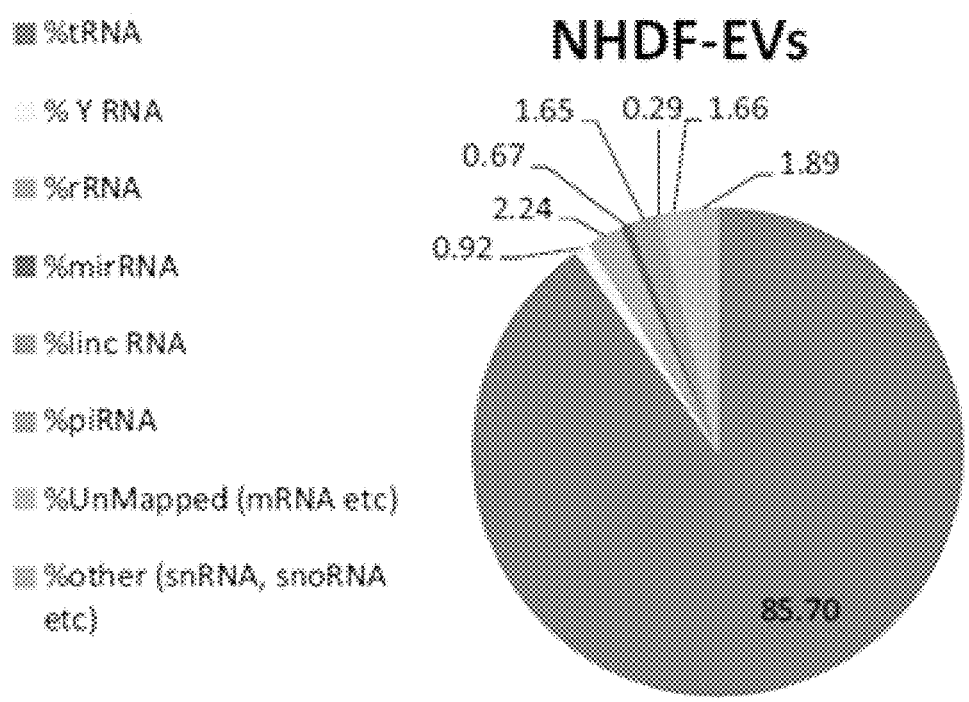
Figure 2A:
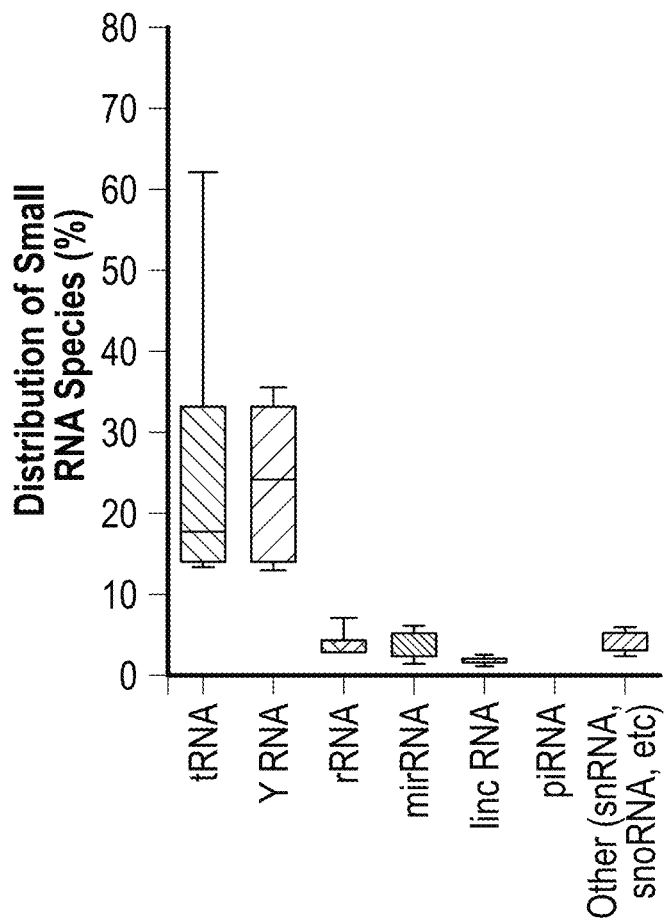
FIGS. 2A-2D. CDC-derived exosomes (CDC-exo) EV-YF1 content correlates with CDC potency in vivo.
Figure 7A:
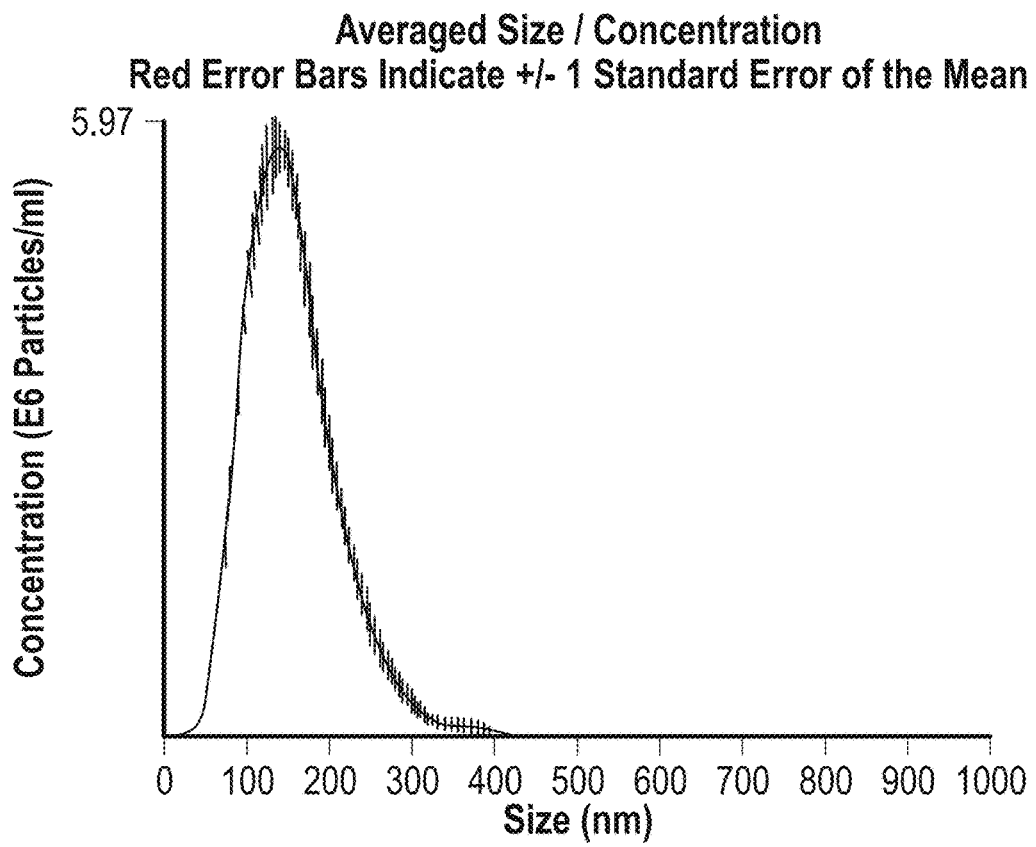
FIGS. 7A-7B. CDC-exo and NHDF-exo size/concentration.
Figure 7B:
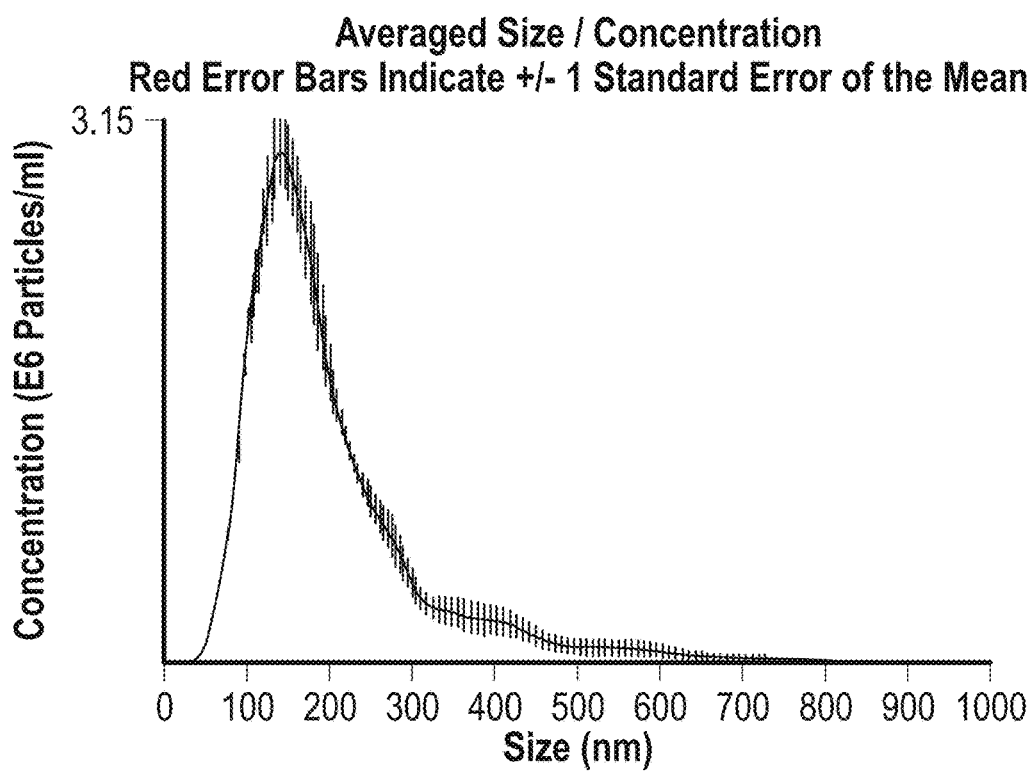

Exosomes from 6 human CDC donors exhibited typical particle numbers and size distributions, as exemplified in FIG. 7A. RNA sequencing (RNA-seq) revealed that CDC-exo contain many small RNA species: FIG. 1A shows a representative pie chart from one donor (OD220), and FIG. 2A shows pooled data from all 6 CDC donors. For comparison, FIG. 1B shows the ncRNA distribution in NHDF exosomes (NHDF-exo). Exosomes from the two cell types differed markedly in their RNA profiles, with a much greater dominance of tRNA in NHDF-exo. The most abundant RNA species in CDC-exo after tRNA was Y-RNA (~20% of total RNA). Indeed, Y-RNAs were much more plentiful than miRNAs, which represented only ~5% of the total RNA (FIGS. 1A and 2A).

Figure 2B:
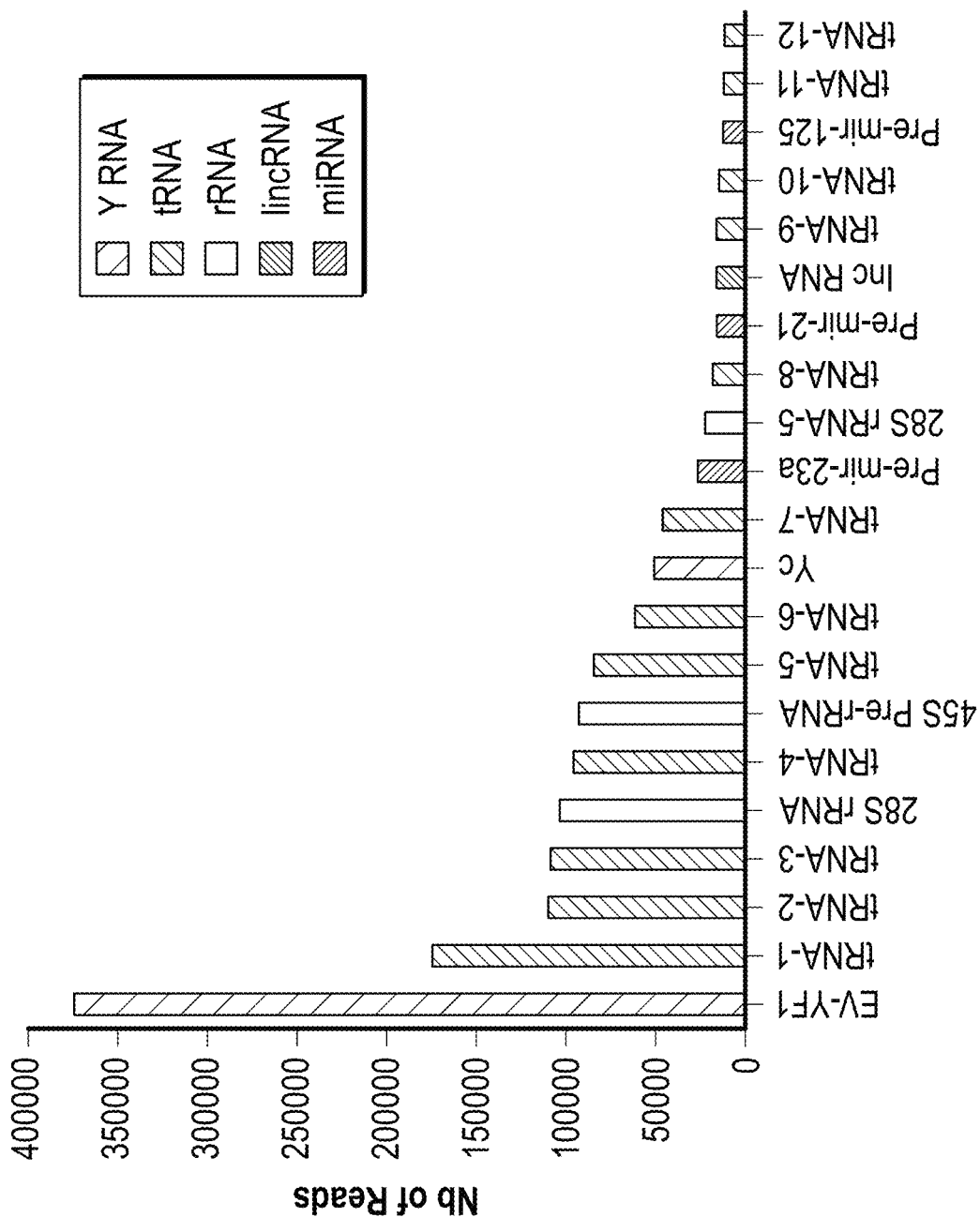
Figure 8A:
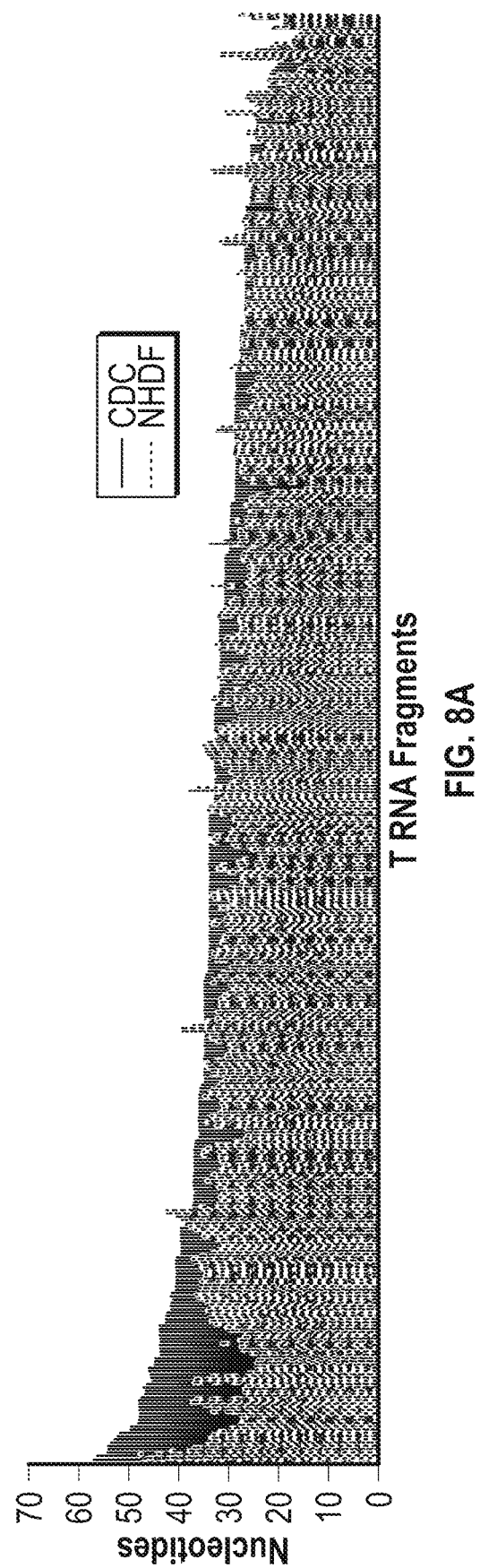
FIGS. 8A-8E. Exosomal Y-RNA fragment length, distribution, and alignment.
Figure 8B:
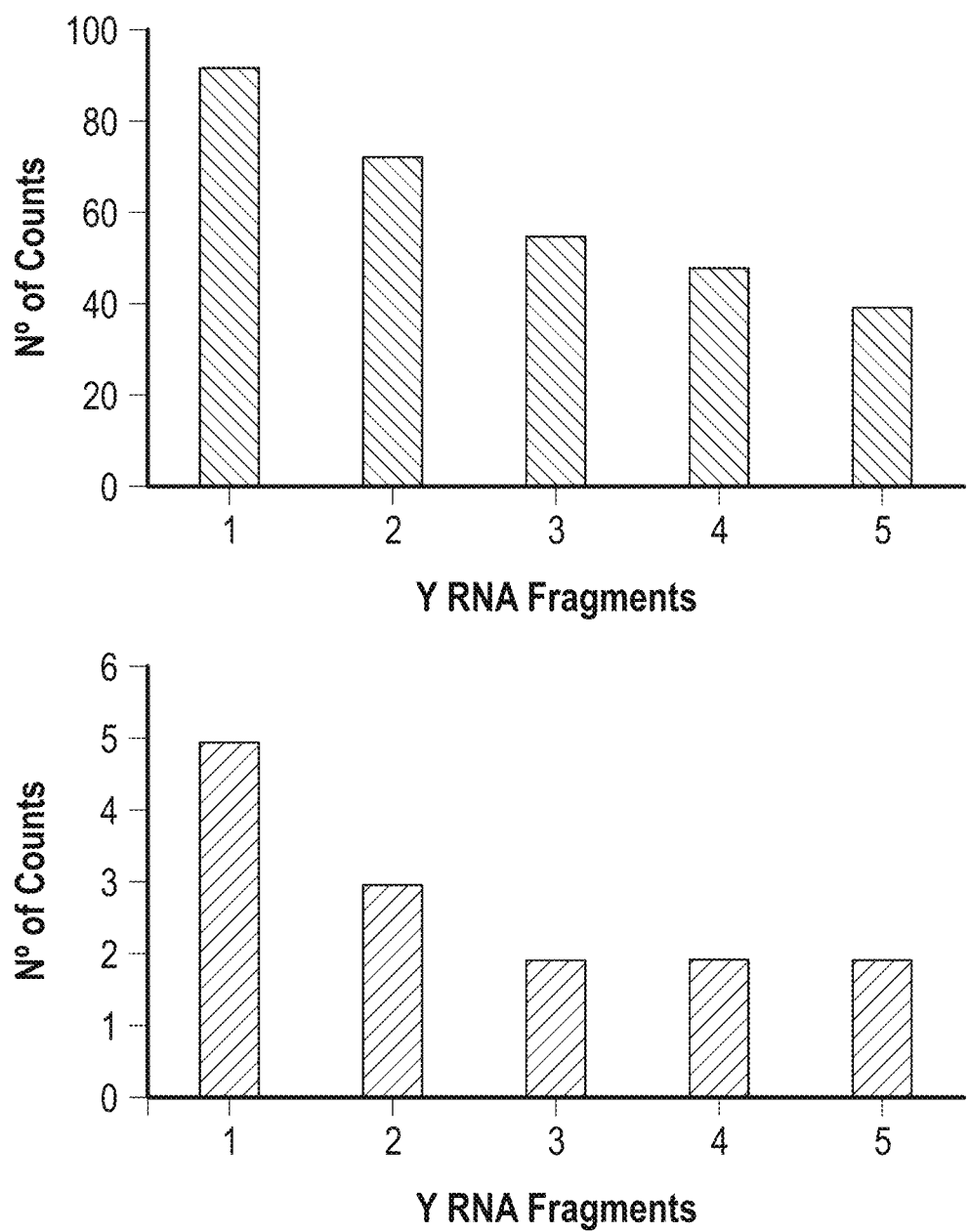

To determine if Y-RNAs play a role in mediating the effects of CDCs and CDC-exo, the RNA content of CDC-exo was determined. RNA-seq revealed 917 Y-RNA sequences in CDC-exo and 345 in NHDF-exo. The Y-RNA sequences in both groups were fragments of Y-RNA that varied in length (15-62 nt) (FIG. 8A). Among those sequences, 613 were unique to CDC-exo, 41 were unique to NHDF-exo, and 304 were common to CDC-exo and NHDF-exo (FIG. 1C); unique Y-RNA species were, however, very low in abundance in both types of exosomes (<1000-fold the number of reads as for the shared species; cf. FIG. 8B). The Y-RNA fragments present in both CDC-exo and NHDF-exo were generally more abundant in CDC-exo (FIG. 1D). For example, the most plentiful Y-RNA fragment in CDC-exo (annotated herein as URS000072DA11, SEQ ID NO:5; denoted EV-YF1) was 15.7-fold more abundant in CDC-exo than NHDF-exo (FIG. 1D). Indeed, according to several embodiments, EV-YF1 is the single most abundantly expressed ncRNA species in CDC-exo (FIG. 2B).

Figure 1F:
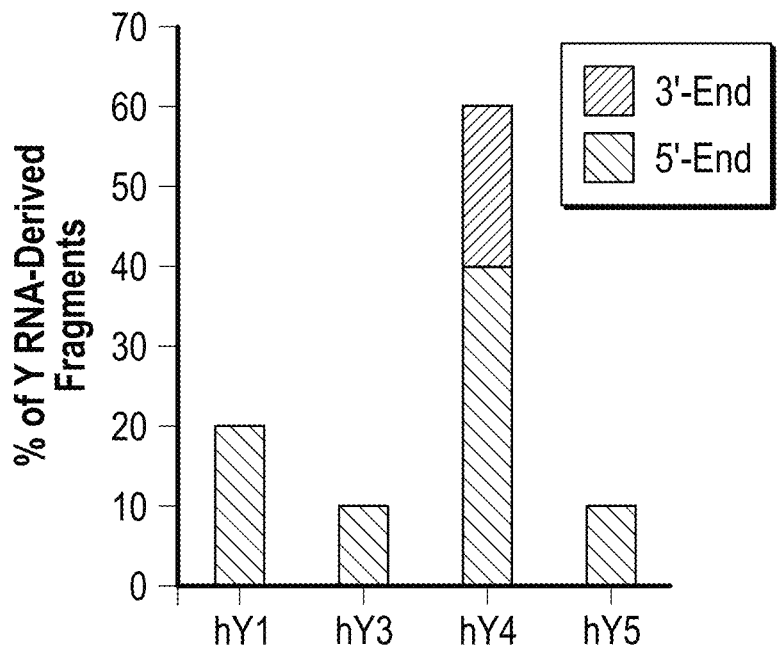
Figure 1G:
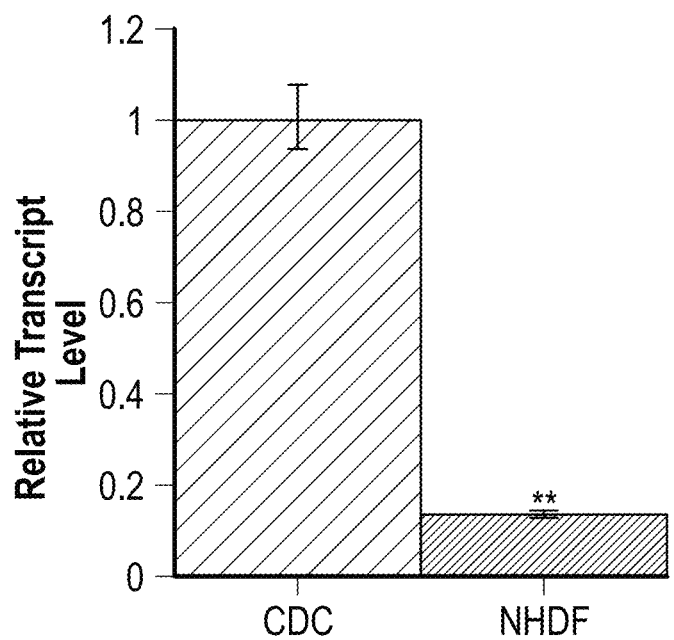
Figure 1H:
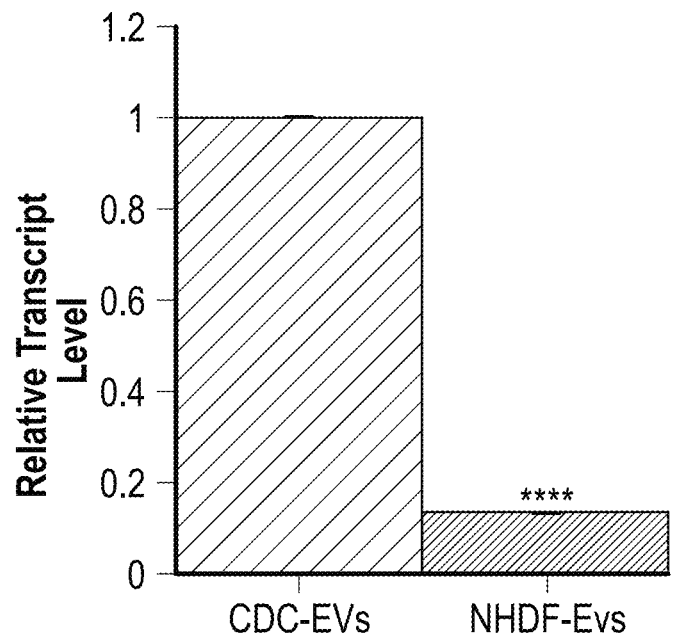
Figures 8C, 8D:
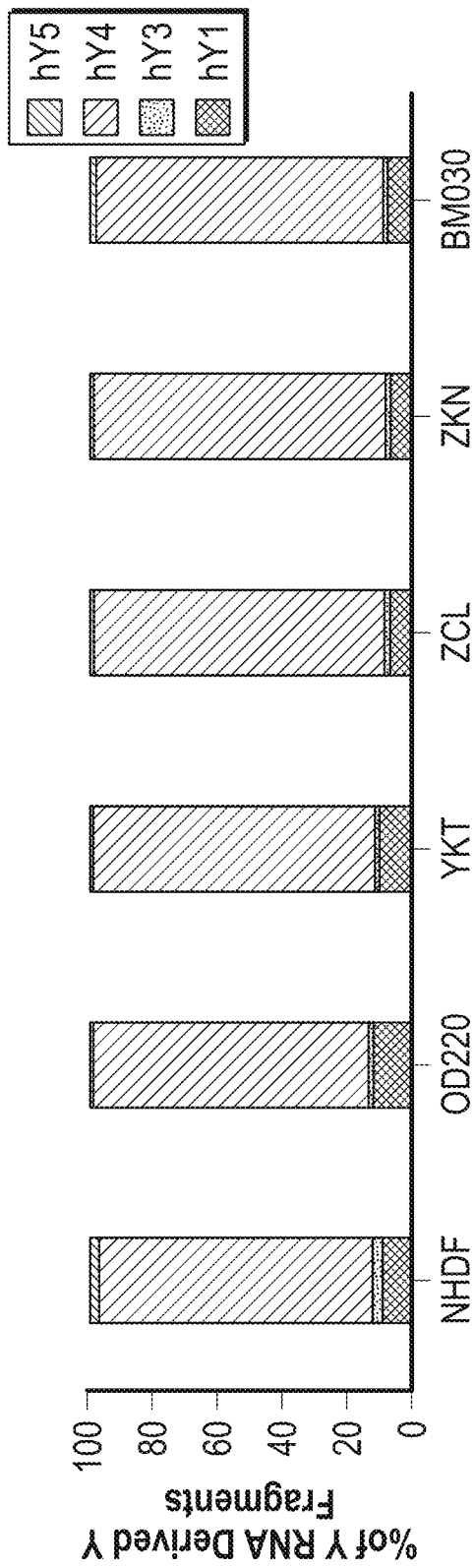
Figure 8E:
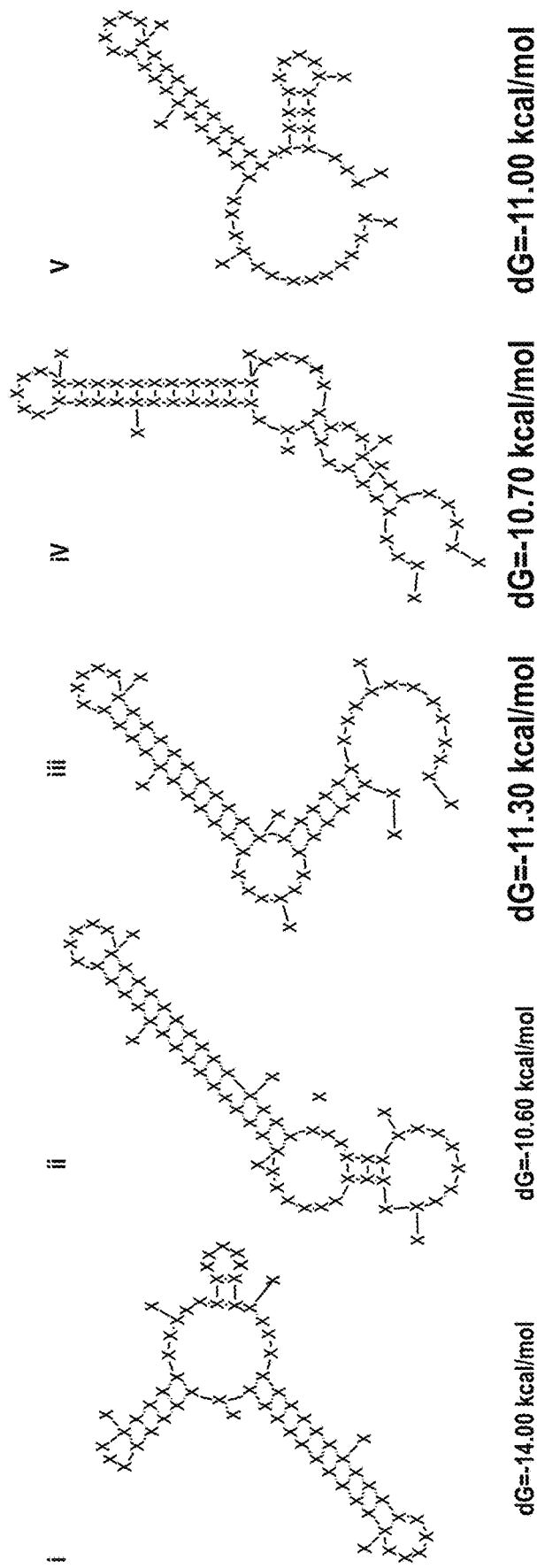

Full length human Y-RNAs (hY) exhibit extensive sequence and structural conservation among members. FIG. 1E shows BLAST sequence alignments of the four hY family members, the top 10 most abundant Y-RNA fragments found only in CDC-exo (FIG. 1E), and the top 10 most abundant Y-RNA fragments found both in CDC-exo and NHDF-exo (FIG. 1E). Sixteen of the 20 Y-RNA fragments aligned to or near the 5' end of the four hY family members (FIGS. 1E and 1F); however, there was a particular enrichment in those homologous to hY4 (FIG. 1F). To validate these findings, all of the Y-RNA fragments within CDC-exo and NHDF-exo were examined, and it was found that ~85% of all Y-RNA fragments appeared to be derived from hY4 (FIG. 8C). Based on these results, EV-YF1 was focused on further because of its abundance. To confirm the RNA-seq data, primers were designed for EV-YF1 and analyzed its expression by qPCR in cells (CDCs and NHDFs; FIG. 1G) and exosomes (CDC-exo and NHDF-exo; FIG. 1H). EV-YF1 expression was much greater in CDCs and CDC-exo than in the respective NHDF controls (~10-fold, FIGS. 1G and 1H). The EV-YF1-U16 fragment aligns well with the 5' end of hY4 (98% homology, with the exception of an additional thymine [T] at position 16 in EV-YF1; FIG. 8D). The EV-YF1 fragment also aligns well with the 5' end of hY4 (100% homology; data not shown). Thermodynamics-based UNAFold software yielded 5 energetically-probable secondary structures for EV-YF1-U16 (FIG. 8E). While details of predicted structures differ, all share stem-loop motifs common in Y-RNA species.

Figure 9A:
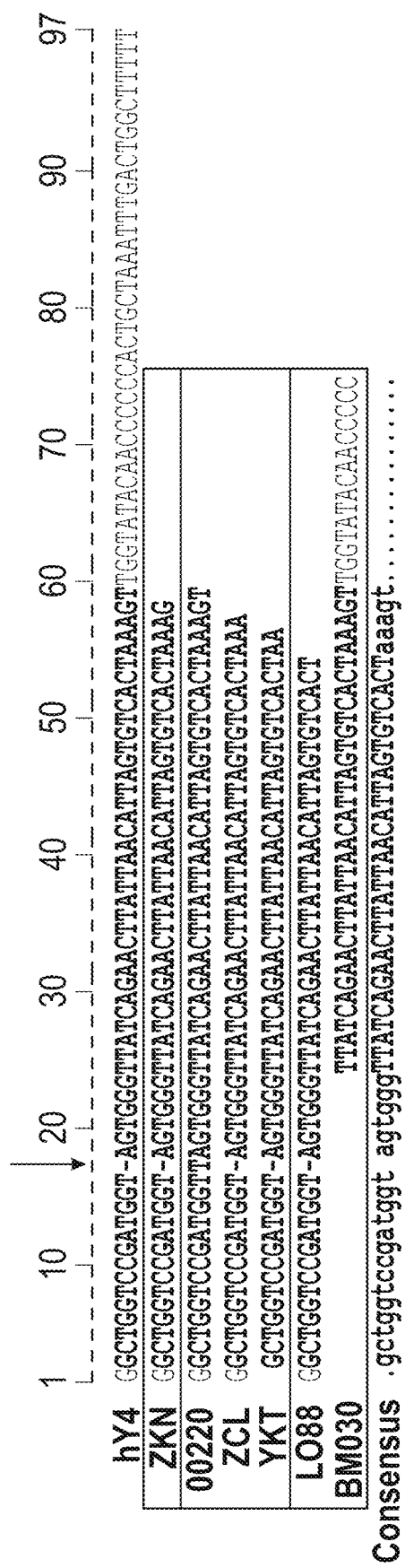
FIGS. 9A-9B. CDC donor exosomal EV-YF1 sequence variation.
Figure 9B:
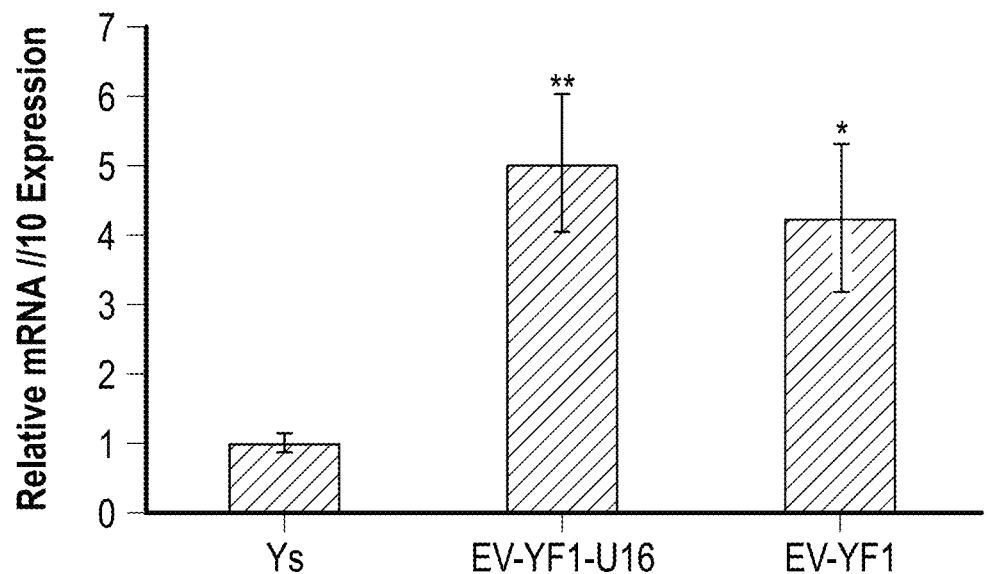

Next, the similarity of the exosomal EV-YF1 sequence from OD220 among the 6 CDC donors was examined. When the EV-YF1 sequence (annotated herein as URS000072DA11 in all sequencing reads) from each CDC donor and hY4 were aligned, perfect homology between nucleotides 23-52 was observed (FIG. 9A). While the flanking 5' and 3' regions outside the 23-52 nt homologous sequence were similar in exosomes from human CDC cell lines ZKN, OD220, ZCL, YKT, and L088, they were different in BM030 (i.e., lack of the 5' region and an extended 3' region). A single nucleotide difference (T16 in EV-YF1) did not appear consequential (see FIG. 9B and the associated brief description for details). Thus, according to several embodiments, those effects observed for EV-YF1-U16 are also observed with EV-YF1, and vice versa.

Elevated EV-YF1 Content within CDC-Exo Correlates with In Vivo CDC Potency

Figure 2C:
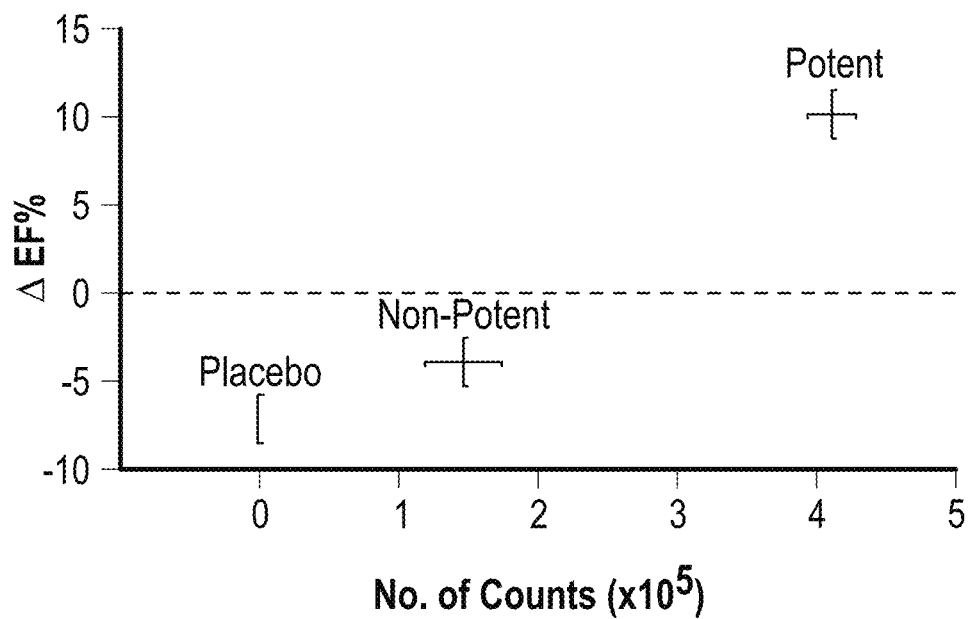
Figure 2D:
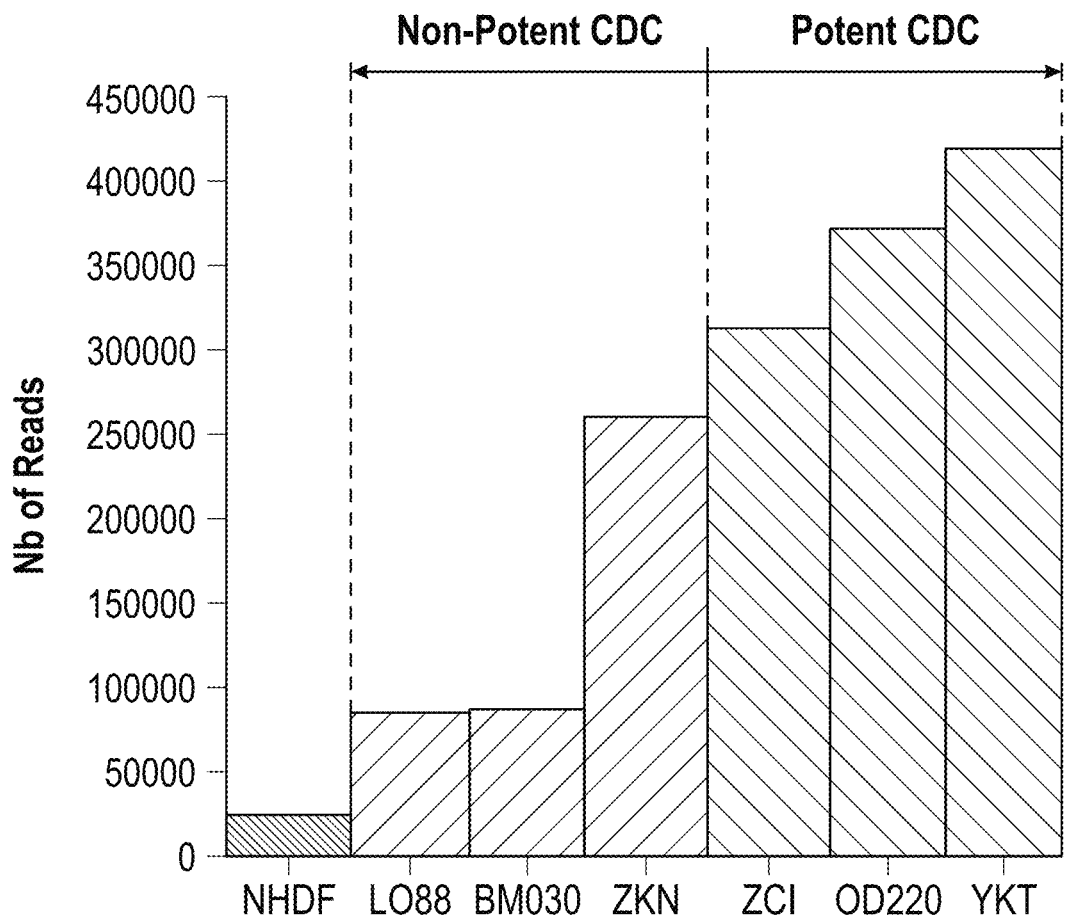

To test whether the abundance of EV-YF1 within CDC-exo correlates with in vivo functional benefit of the parent CDCs, an established mouse model of MI was utilized. Potent CDC lines (i.e., those which increased post-MI ejection fraction after intramyocardial injection) produced exosomes with a higher average abundance of EV-YF1 than non-potent CDCs (FIG. 2C). While the CDC lines varied considerably in EV-YF1 abundance, the negative control NHDFs yielded exosomes with the lowest expression of EV-YF 1 (FIG. 2D).

Packaging and Exosome-Mediated Transfer of EV-YF1

Figure 3A:
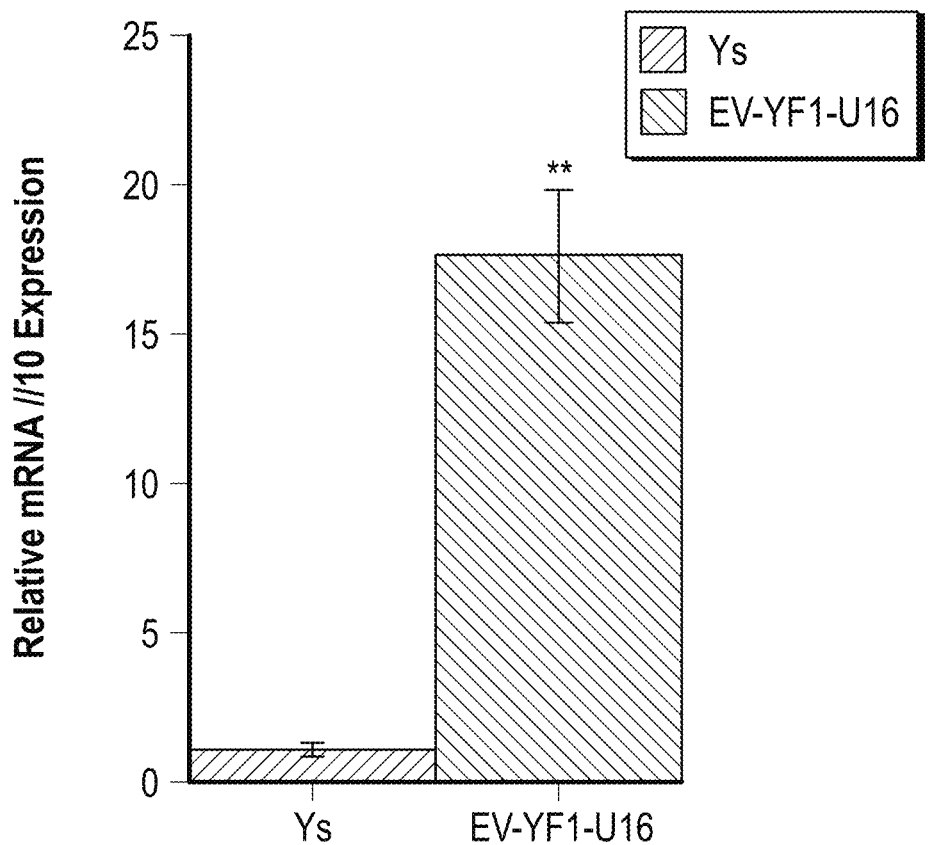
FIGS. 3A-3E. EV-YF1-U16-primed BMDMs induce IL-10 and protect cardiomyocytes from oxidative stress.
Figure 3B:
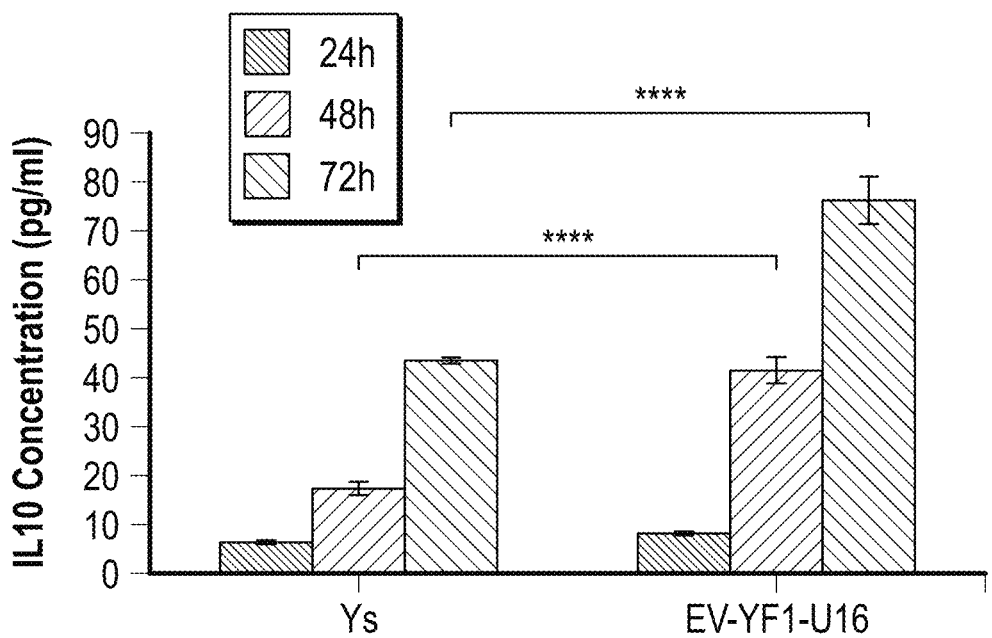
Figure 3C:
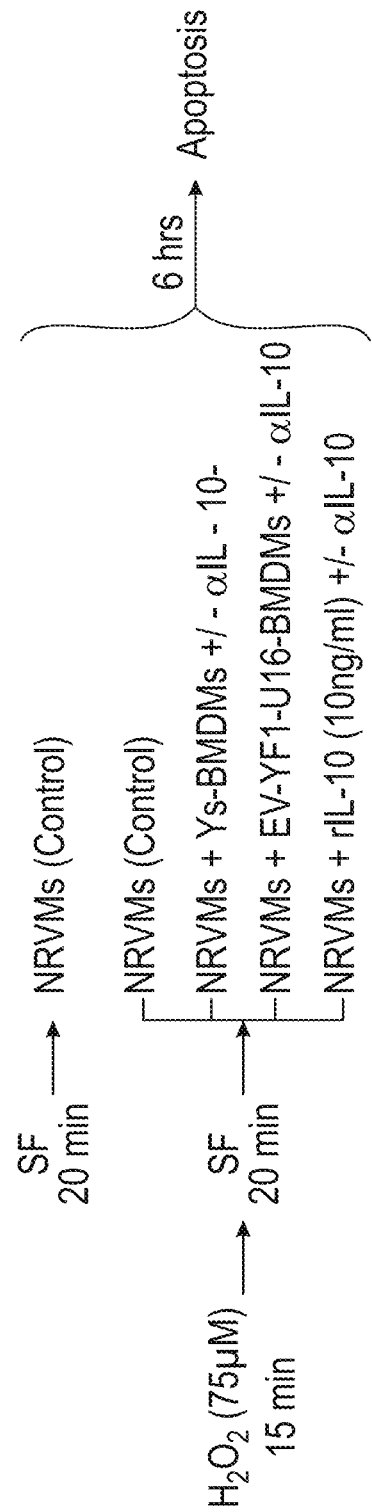
Figure 10A:
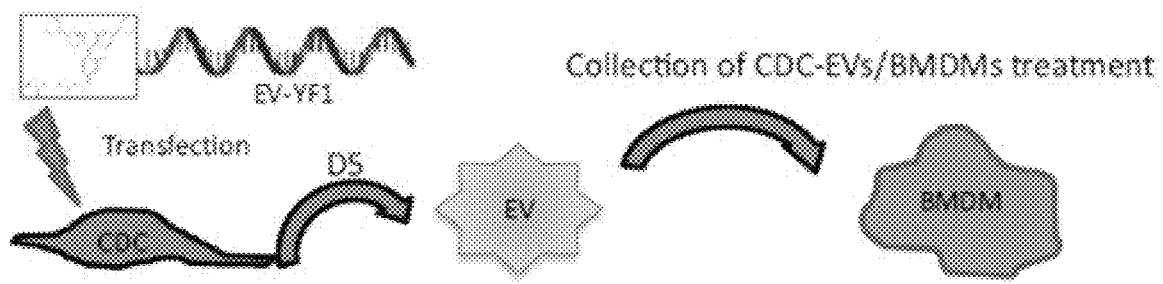
FIGS. 10A-10L. Cytoplasmic localization and expression of EV-YF1-fluo.
Figure 10B:
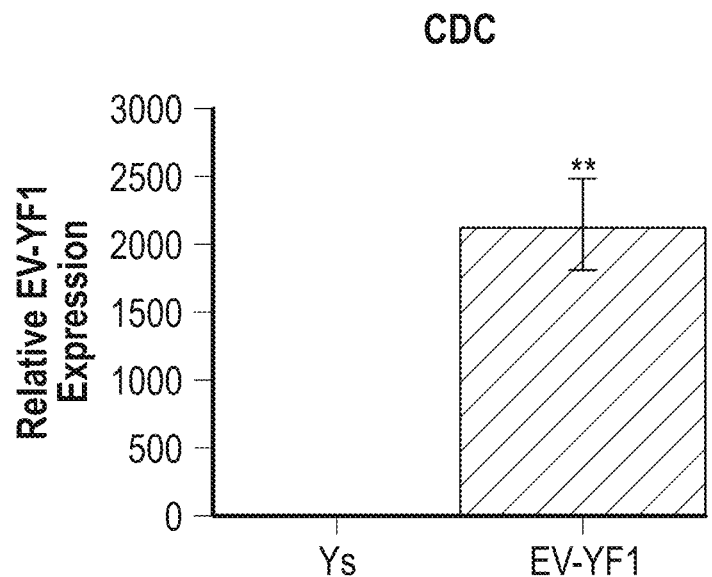
Figure 10C:
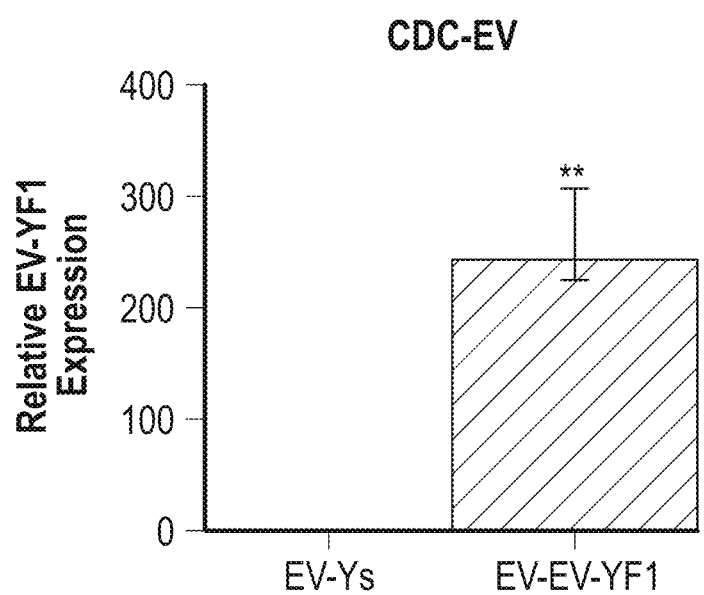
Figure 10D:
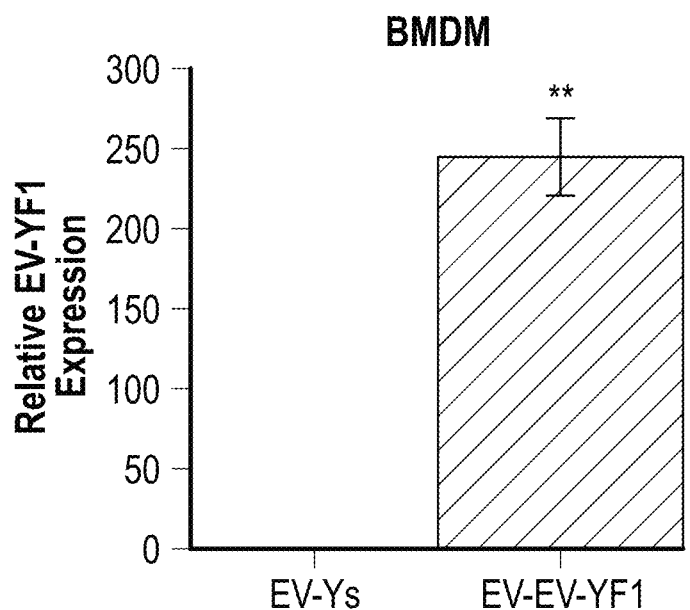
Figure 10E:
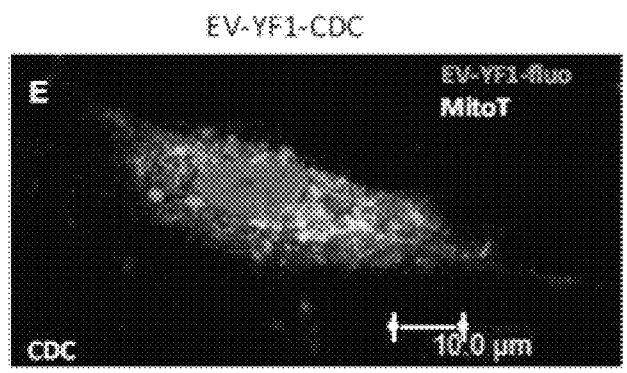
Figure 10F:
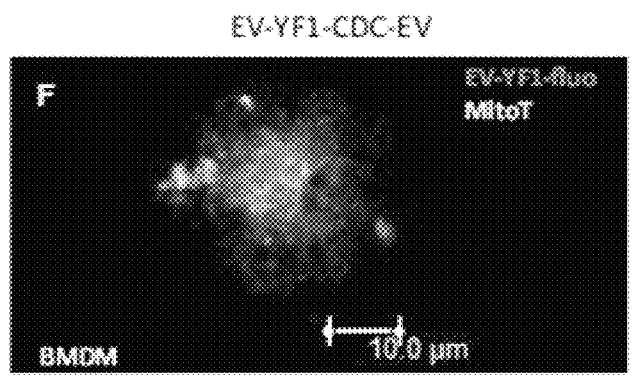
Figure 10G:
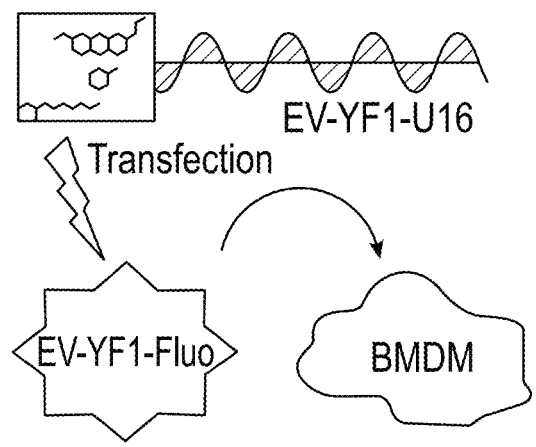
Figure 10H:
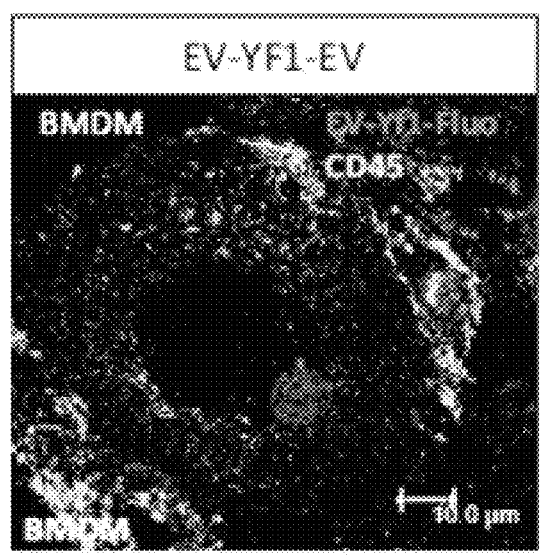
Figure 10I:
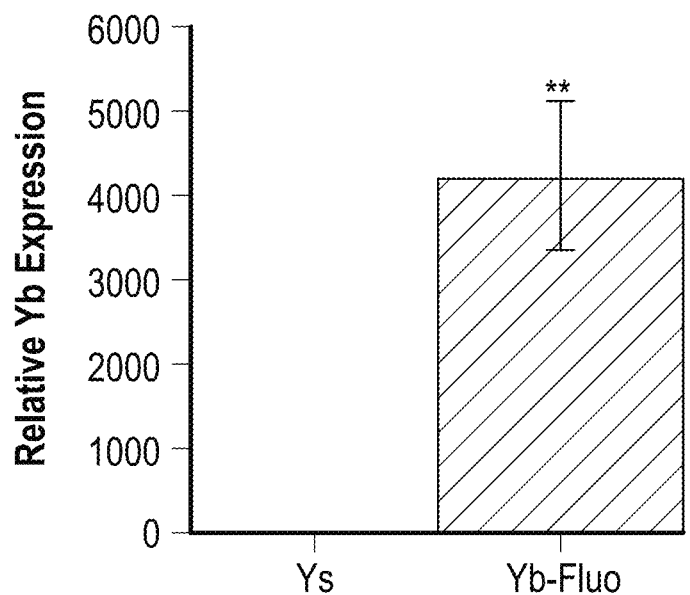
Figure 10J:
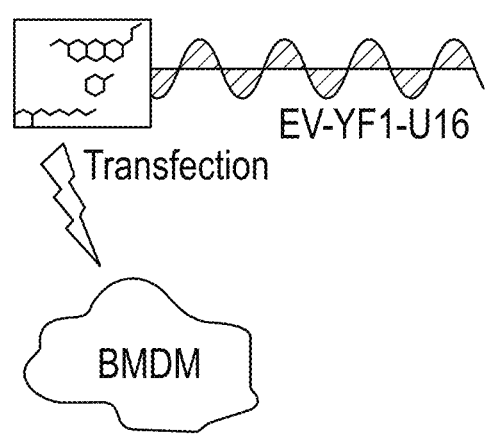
Figure 10K:
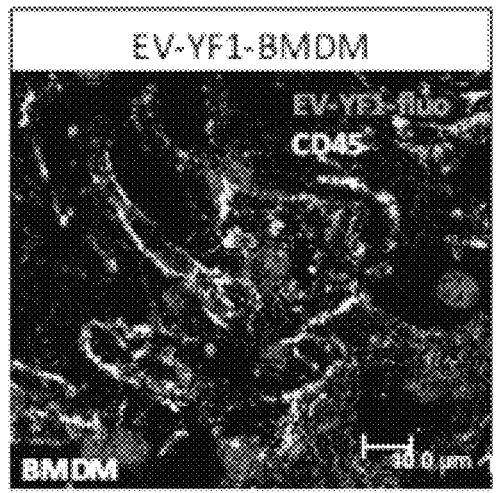
Figure 10L:
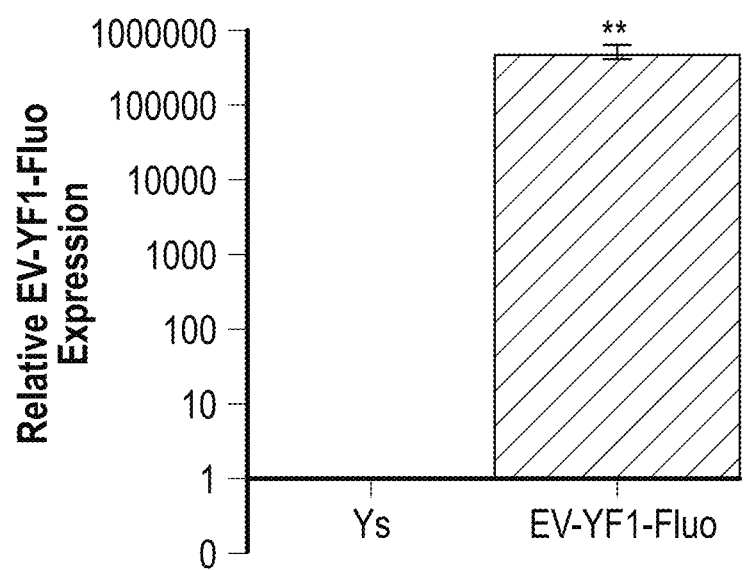

To assess the transfer of EV-YF1 via CDC-exo to target cells (BMDMs), a fluorescently-conjugated EV-YF1 (EV-YF1-fluo) was transfected into CDCs, and CDC-exo were isolated after 5 days in SF culture (FIG. 10A). By immunocytochemistry (ICC), EV-YF 1-fluo showed punctate signals within the cytoplasm of CDCs (FIG. 10E); by qPCR, both CDCs and CDC-exo revealed enhanced expression of EV-YF1 (FIGS. 10B and 3C). Together these data demonstrated successful EV-YF1-fluo transfection into CDCs and packaging of EV-YF1-fluo into CDC-exo (CDC-exo[EV-YF1-fluo]). Next, to determine if EV-YF1-fluo could be transferred to target cells via CDC-exo, BMDMs were exposed to CDC-exo[EV-YF1-fluo]) (FIG. 10A). Two hours later, punctate signals within the cytoplasm of BMDM (FIG. 10F) and enhanced EV-YF1 expression (FIG. 10D) were observed. Following exposure to CDC-exo directly transfected with EV-YF1-fluo, BMDMs took up EV-YF1-fluo (FIGS. 10G-10I); this could also be achieved by direct EV-YF1-fluo transfection (FIGS. 10J-10L). Based on ICC, EV-YF1 did not overlap with the mitochondrial network within CDC or BMDM (FIGS. 10E and 10F). Although EV-YF1-fluo was not detected in the nuclei of CDCs or BMDMs, the possibility that dispersed molecules of EV-YF 1-fluo, not forming visible clumps, might still be present within the nucleus with a weak fluorescent intensity undetectable by ICC, was not excluded.

IL-10 Expression is Induced by EV-YF1-U16

Figure 11A:
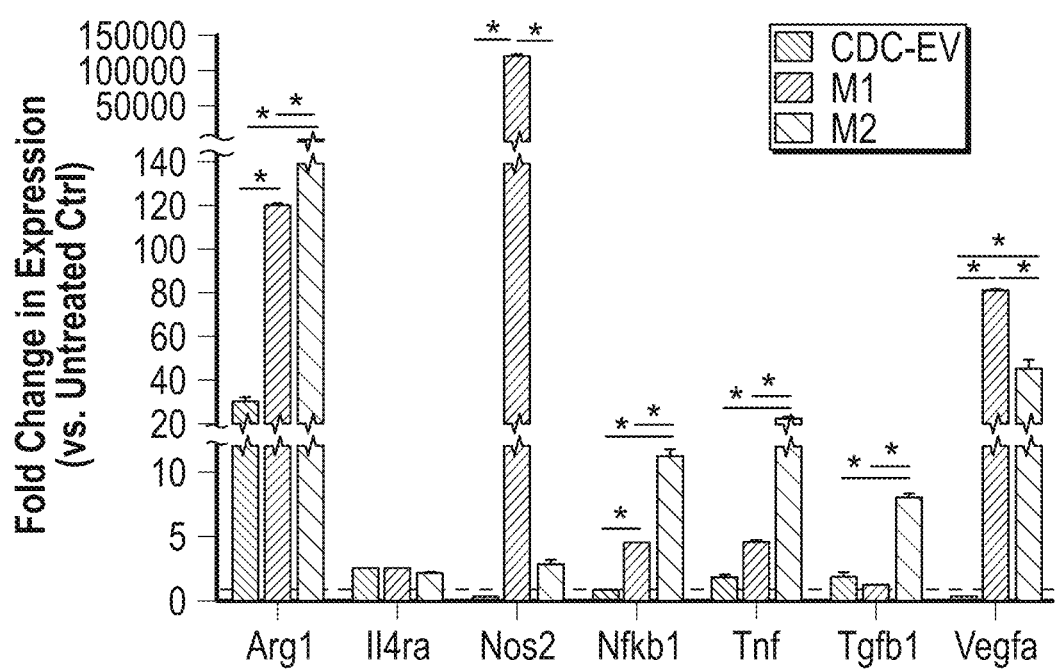
FIG. 11A-11D. EV-YF1-U16 modulates IL-10 expression.
Figure 11B:
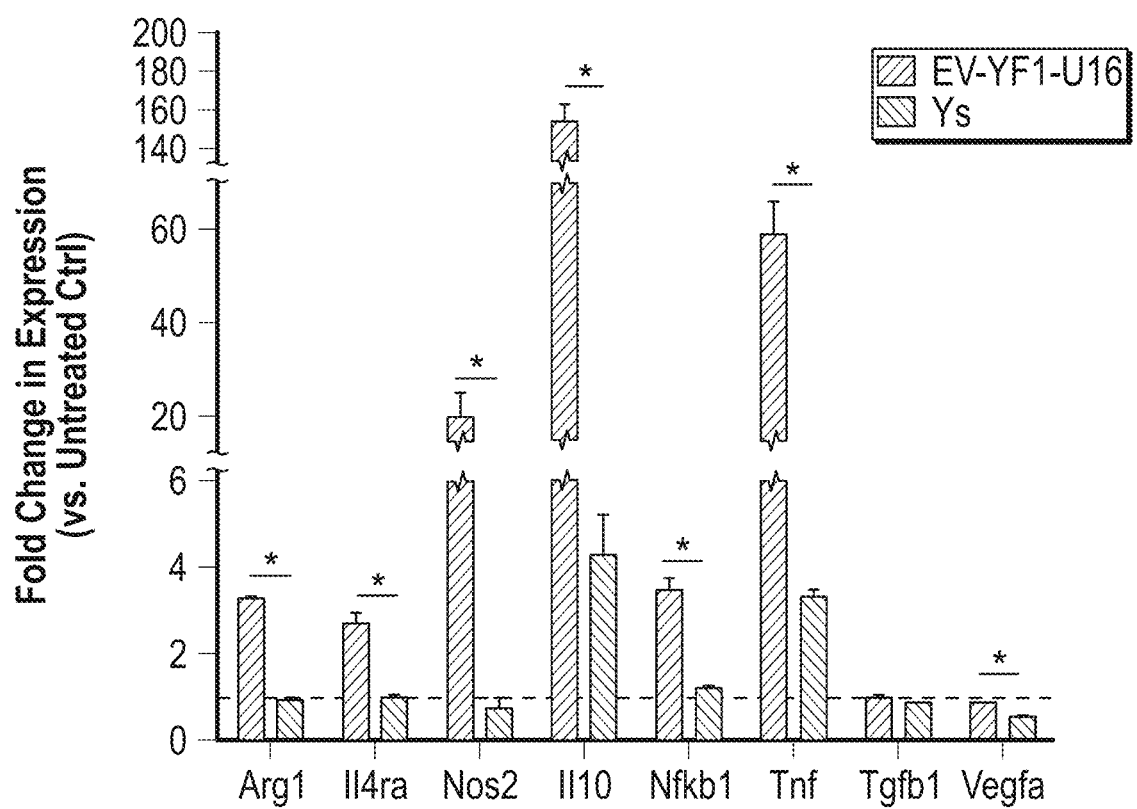
Figure 11C:
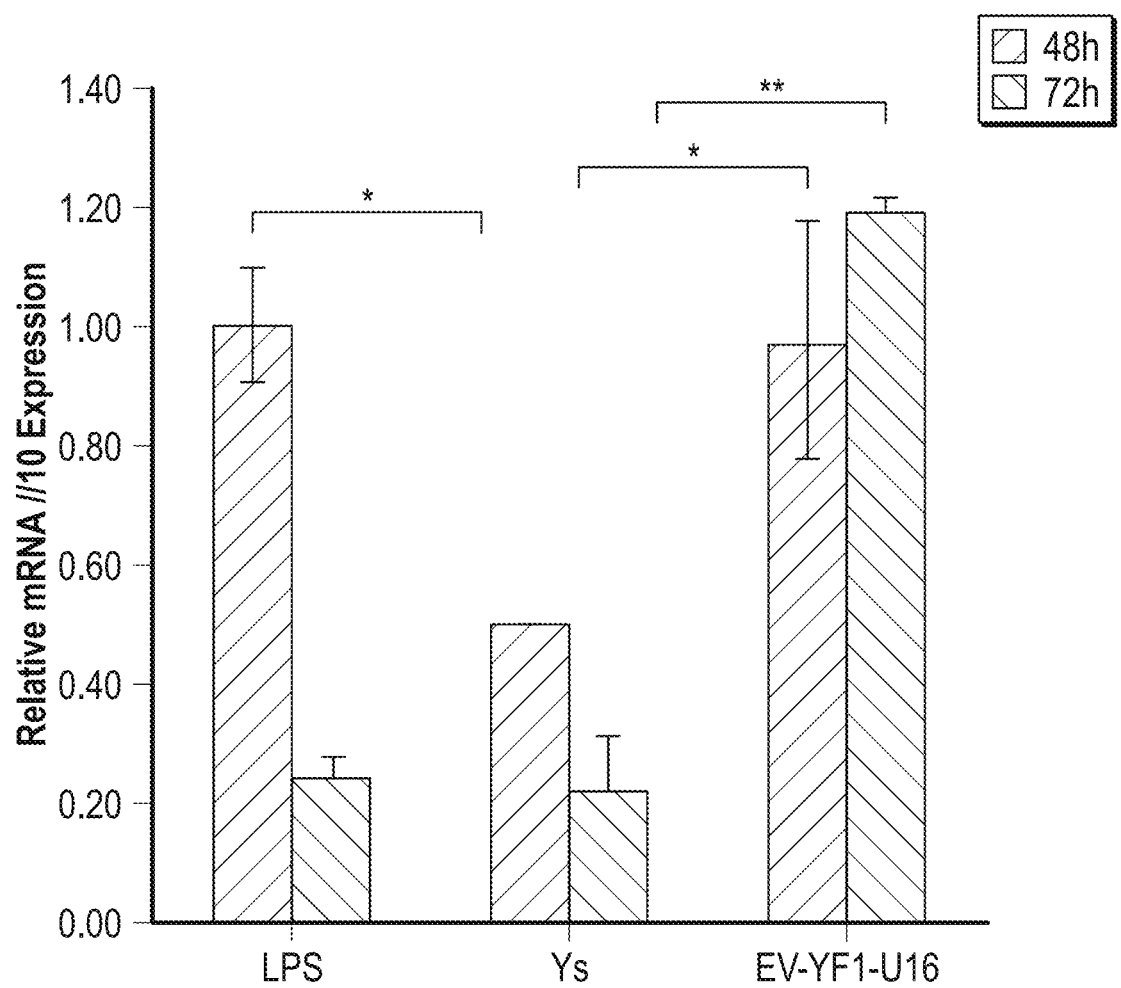
Figure 11D:
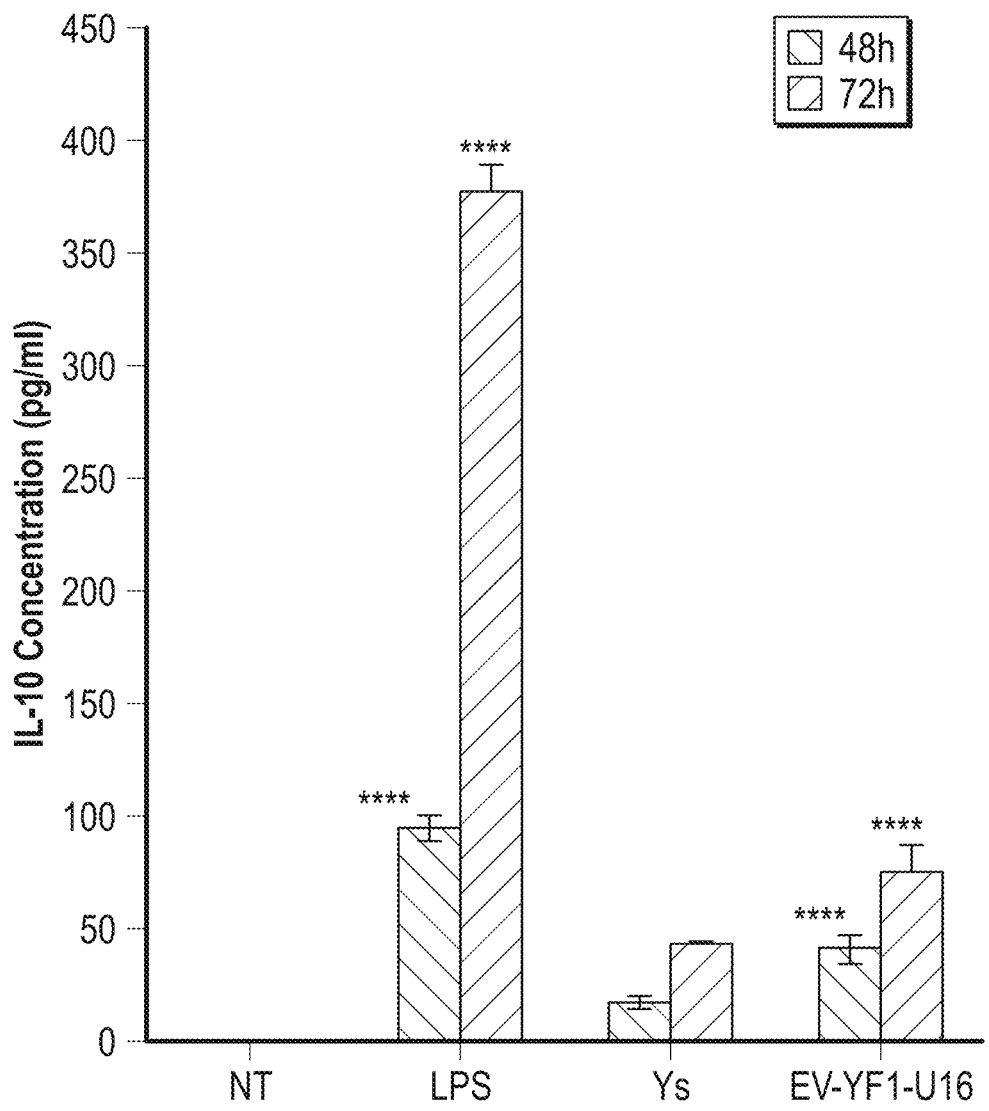
Figure 12:
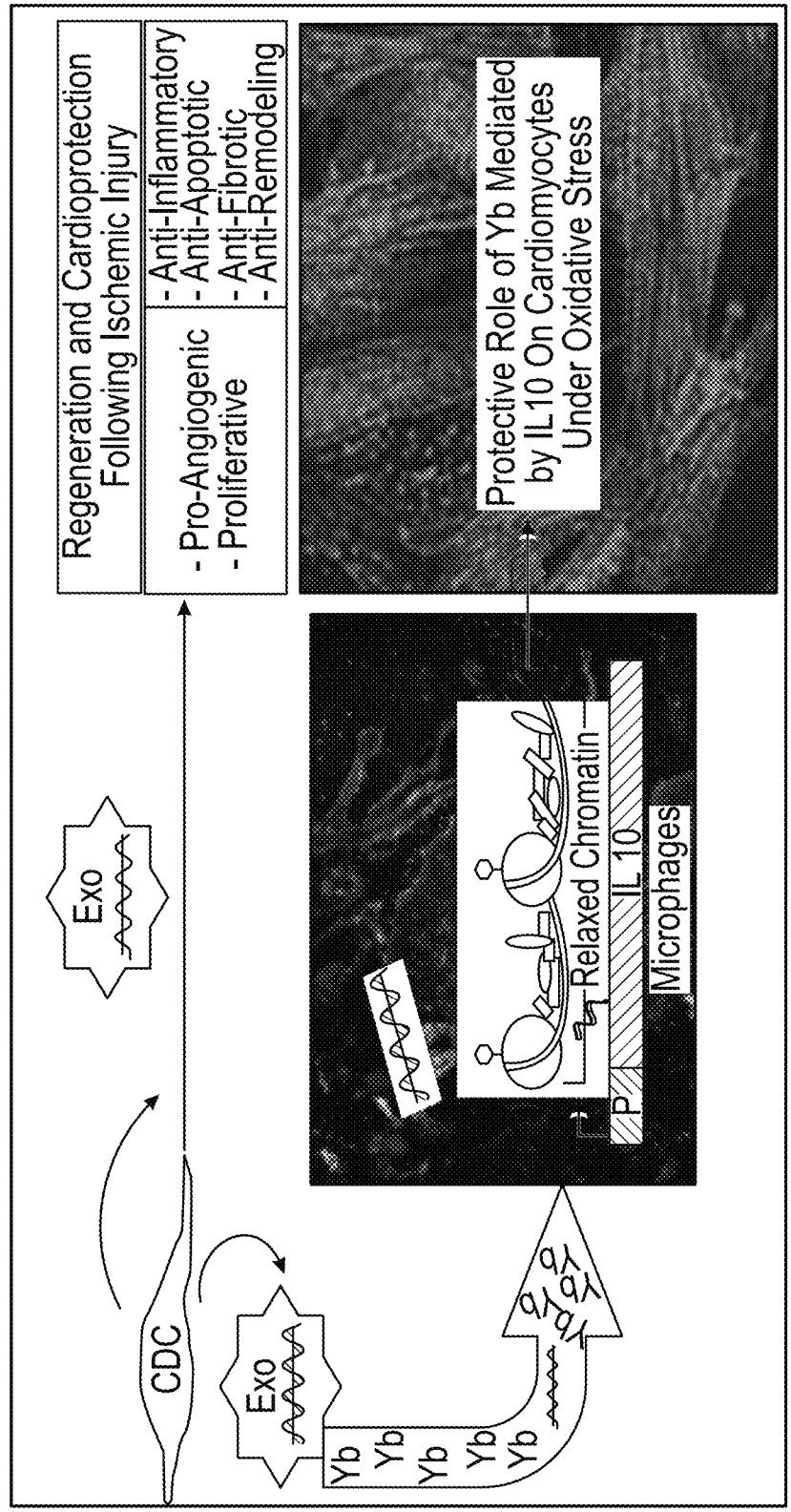
FIG. 12. EV-YF1 (depicted here as "Yb,") (and EV-YF1-U16, not depicted) packaged in CDC-exo, elicits IL-10 expression in BMDMs.
Figure 13:
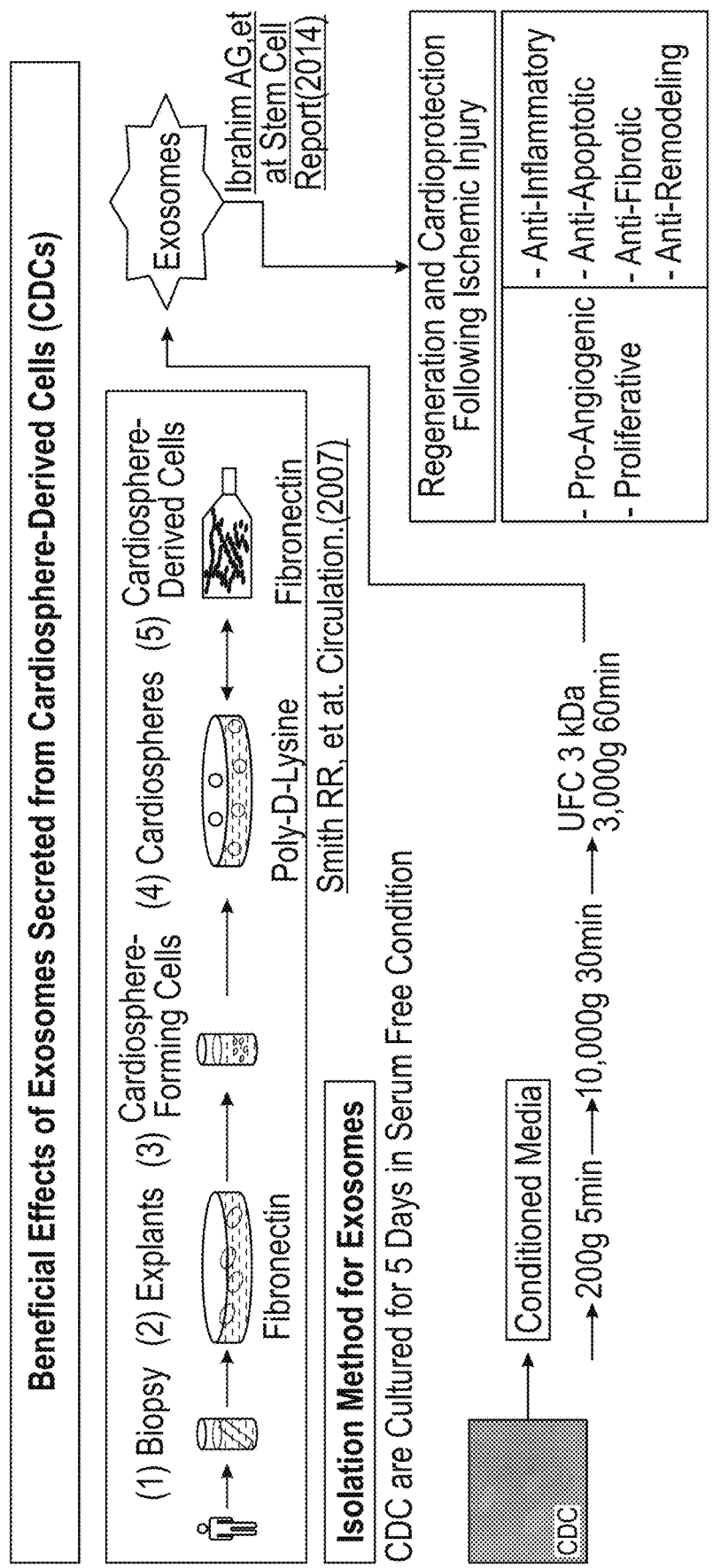
FIG. 13. Effects of CDC-exo and isolation method for exosomes.
Figure 14:
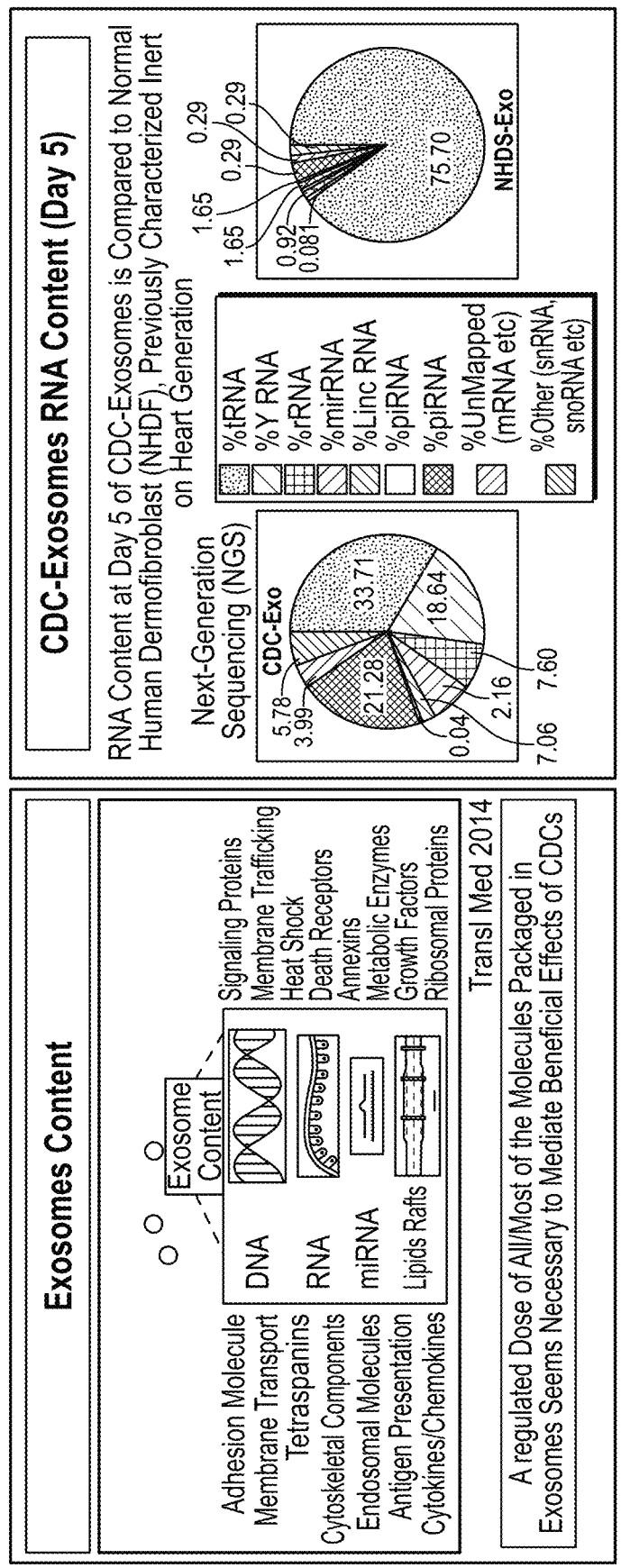
FIG. 14. Exosomes content.
Figure 14:
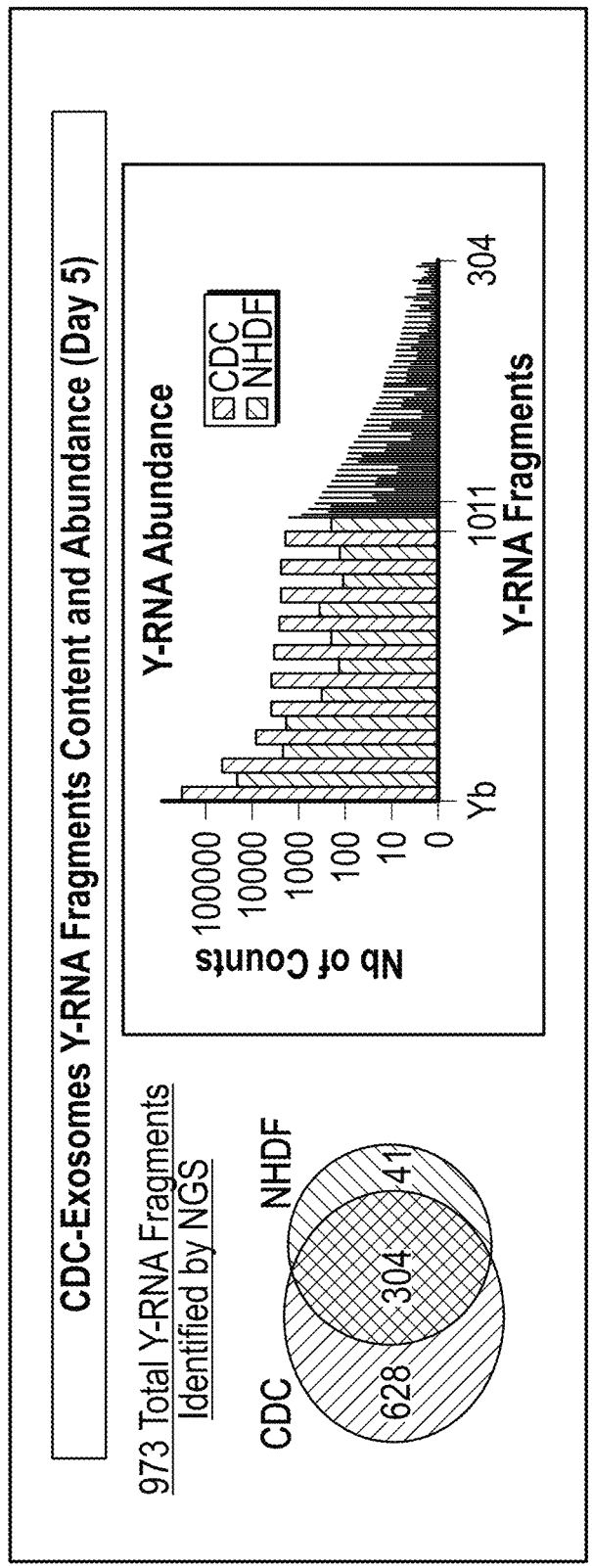
Figure 15A:
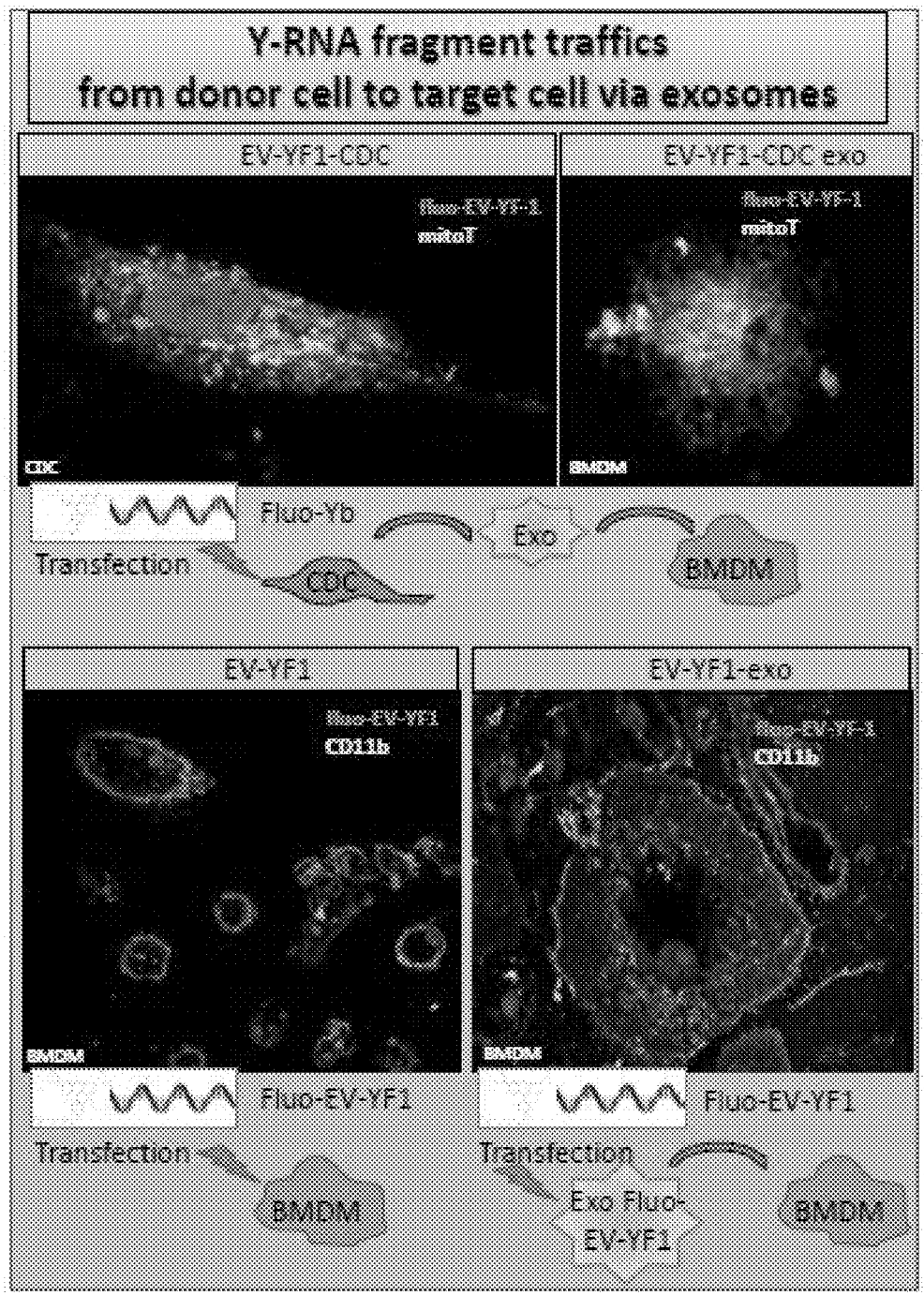
FIGS. 15A-15B. Y-RNA fragment traffics from donor cell to target cell via exosomes, and has a cardioprotective effect in NRVM.
Figure 15B:
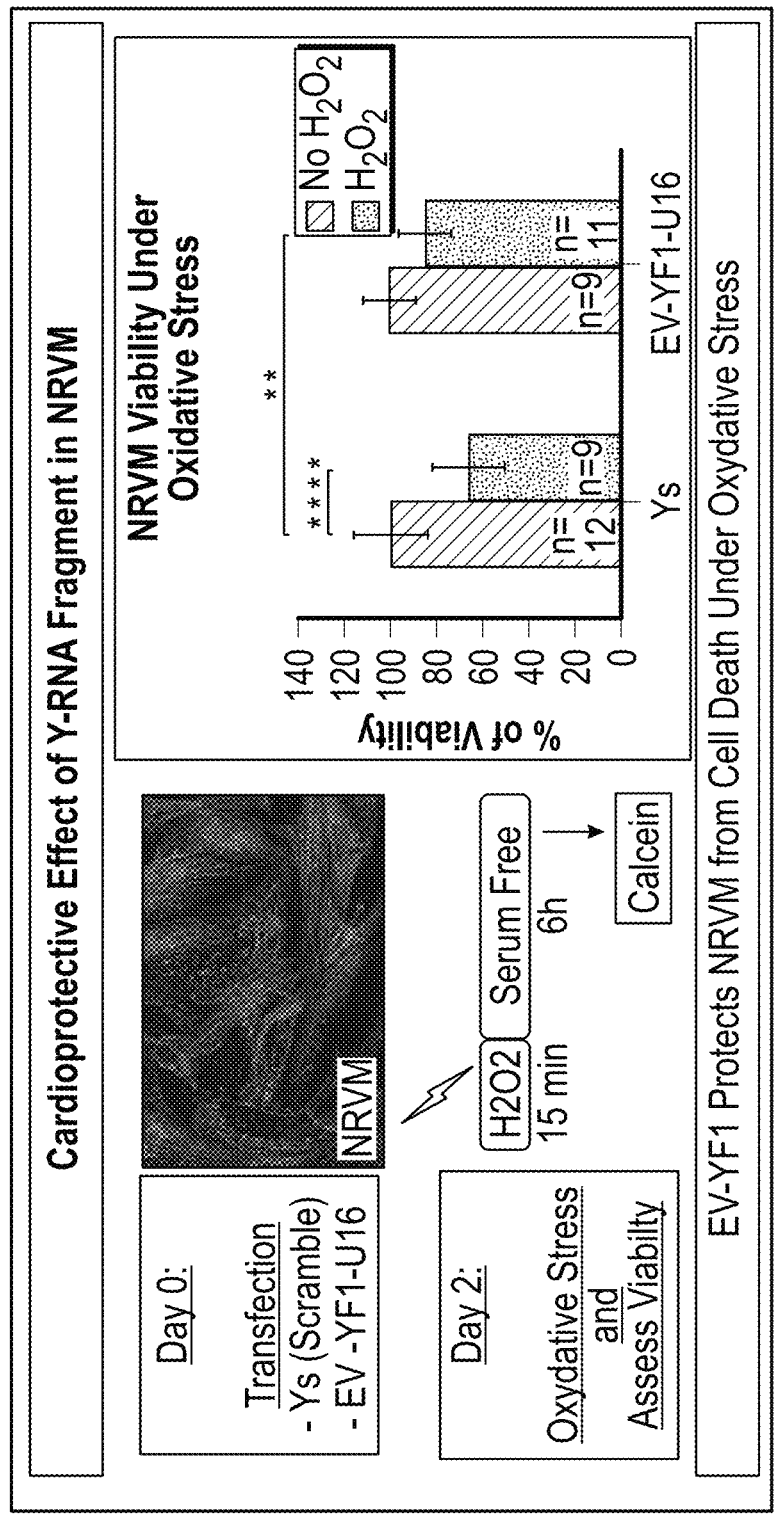
Figure 16:
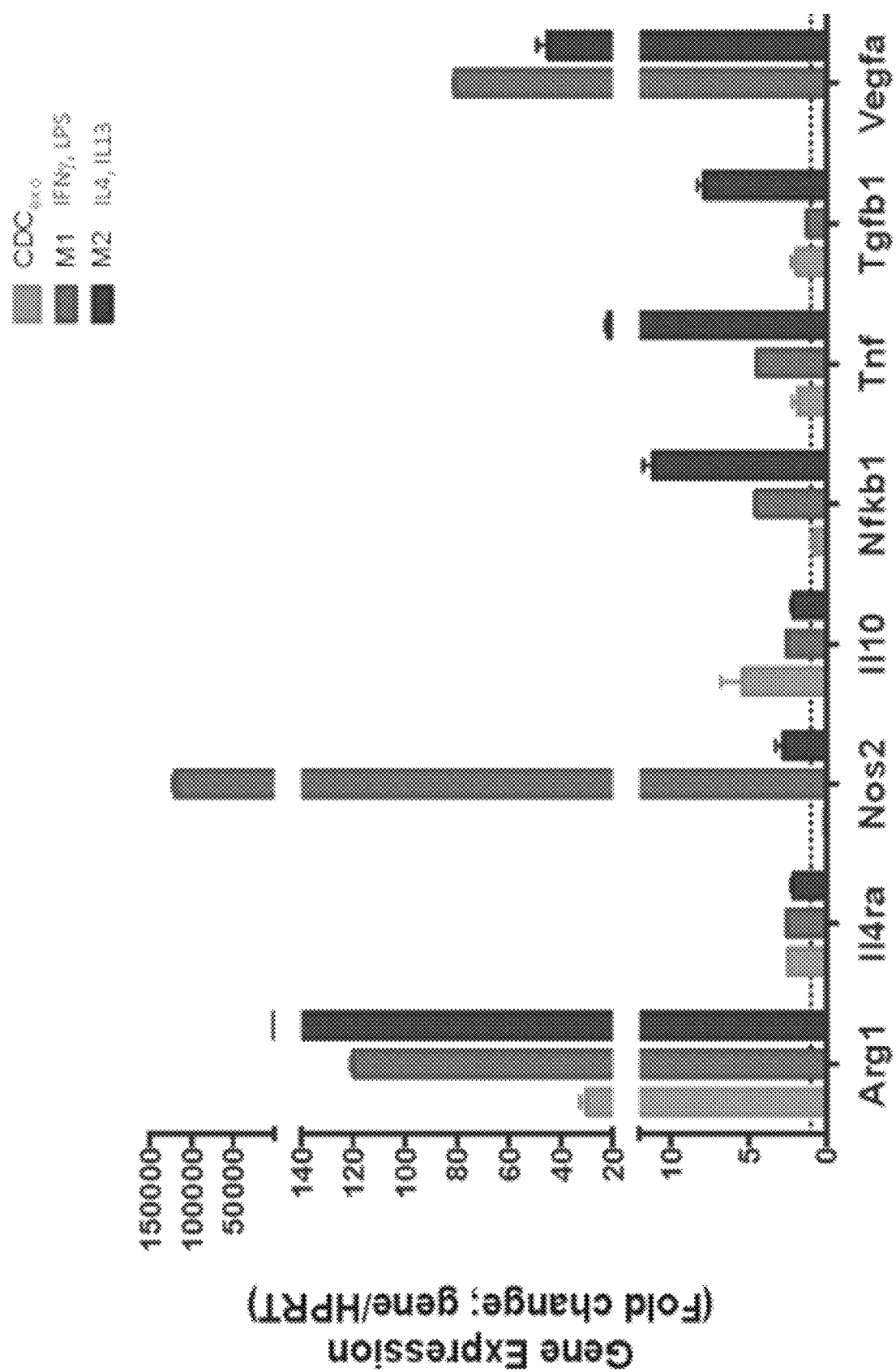
FIG. 16. Effect of CDC-exosomes on macrophage polarization.
Figure 17:
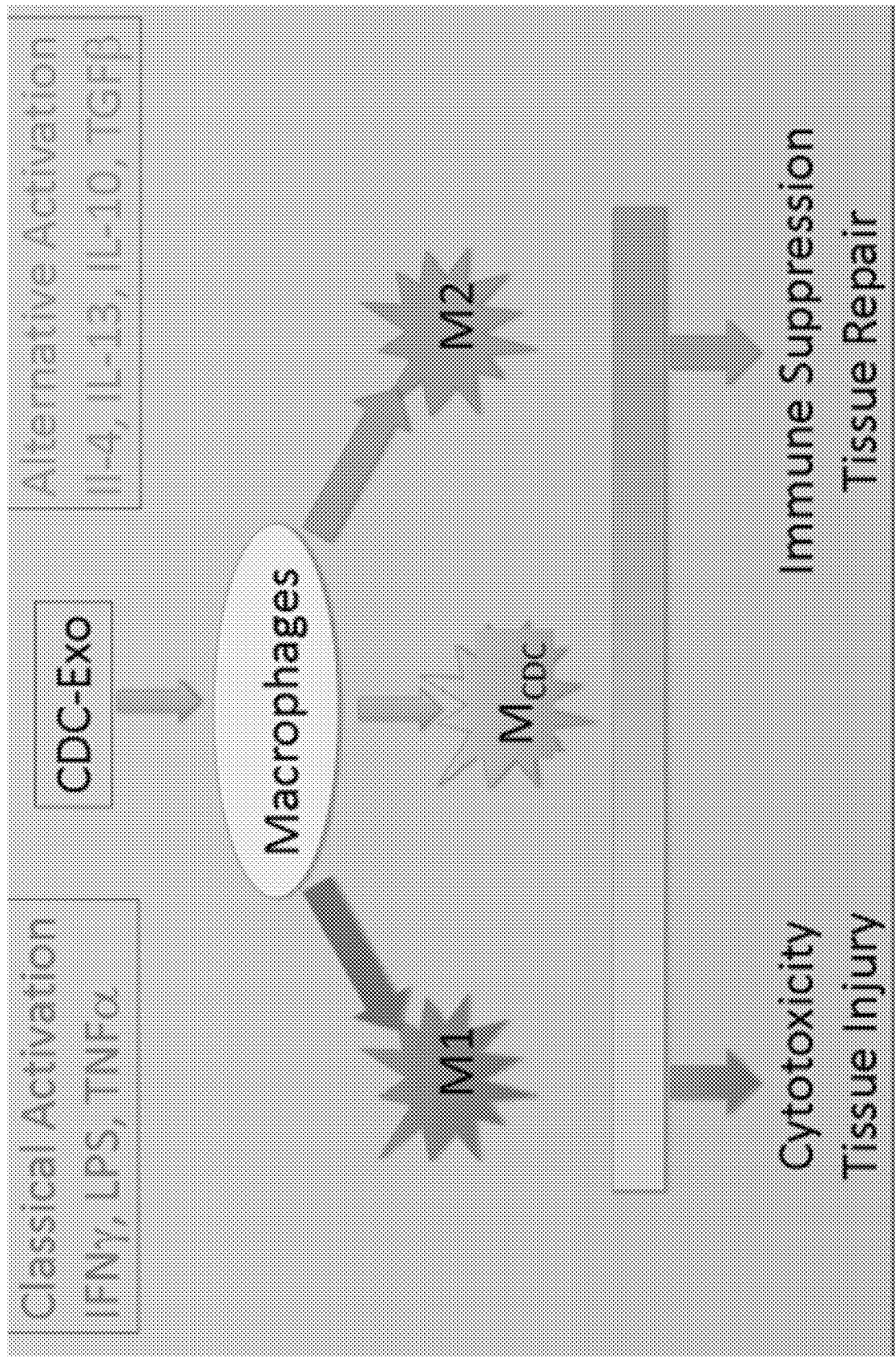
FIG. 17. Effect of CDC-exosomes on macrophage polarization.
Figure 18:
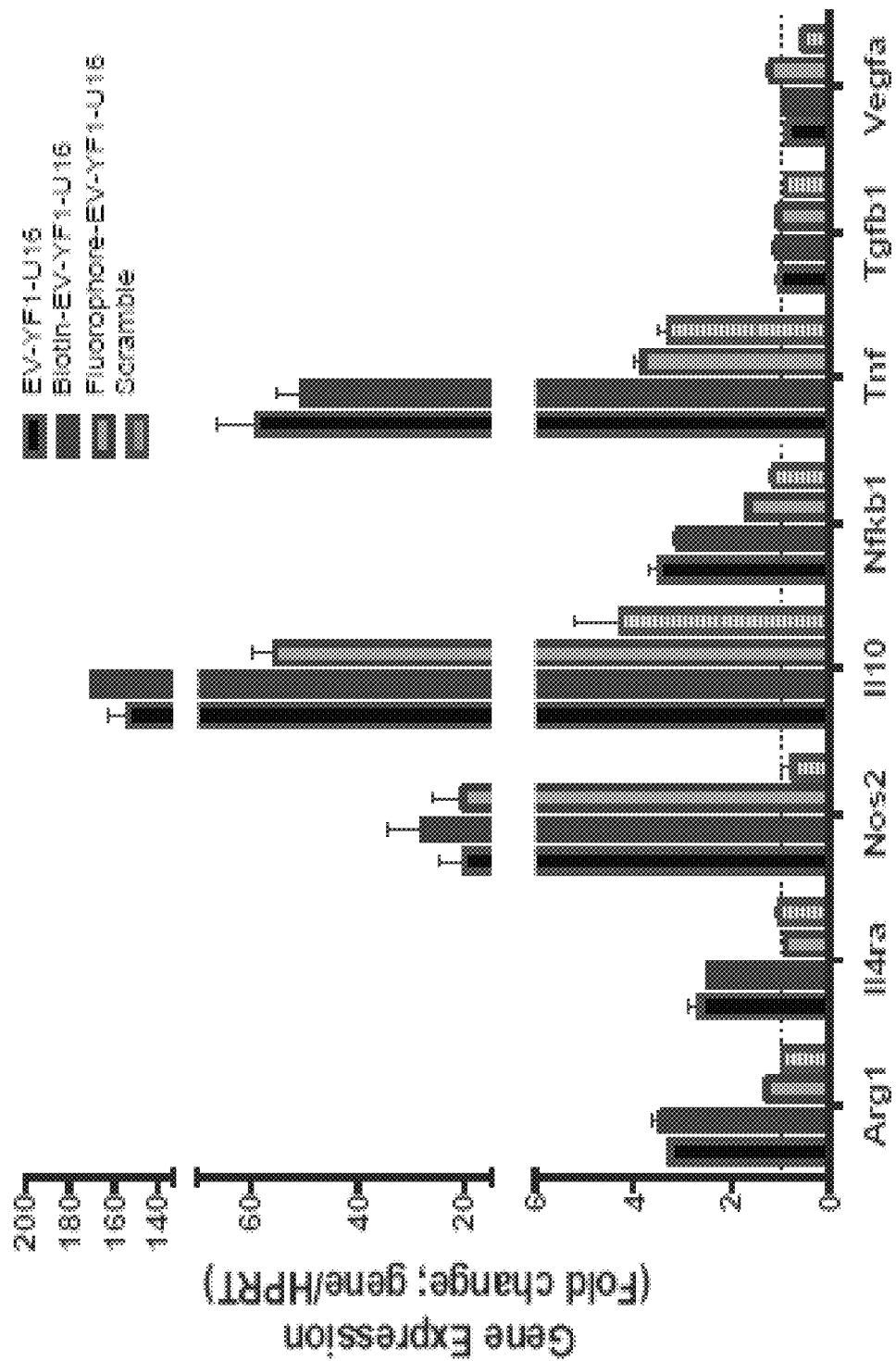
FIG. 18. Effect of Y-RNA on macrophage polarization CDC-exo treatment polarizes macrophages toward a distinctive cardioprotective phenotype that is not M1 or M2.

Exposure of BMDMs to CDC-exo yielded changes in gene expression similar to those described after transwell culture with CDCs (FIG. 11A). To determine if EV-YF 1-U16 (and, by extrapolation, EV-YF1) modulates gene expression, EV-YF1-U16 or a scrambled oligoribonucleotide control (Ys) was transfected into BMDMs. EV-YF1-U16 recapitulated some, but not all, of the effects of CDC-exo (FIG. 11B). Strikingly, EV-YF1-U16 induced an 18-fold increase in IL-10 gene expression relative to Ys within 18 hrs of transfection (FIG. 3A), an effect sustained for at least 72 hours (FIG. 11C). These findings were in contrast to those observed when BMDMs were treated with LPS, where IL-10 gene expression rapidly decreased after 72 hours (FIG. 11C). Consistent with the increased Il-10 transcript levels (FIG. 3A), the secretion of IL-10 protein was enhanced in EV-YF1-U16-primed (compared to Ys-primed) BMDMs 48 and 72 hours post-transduction (FIG. 3B). While LPS also induced secretion of IL-10 in BMDMs (FIG. 11D), Nos2 increased much less in EV-YF1-U16-primed BMDMs than in M1 Mϕ (LPS-treatment) (FIGS. 11A and 11B).

Cardioprotective Role of EV-YF1-U16

Figure 3D:
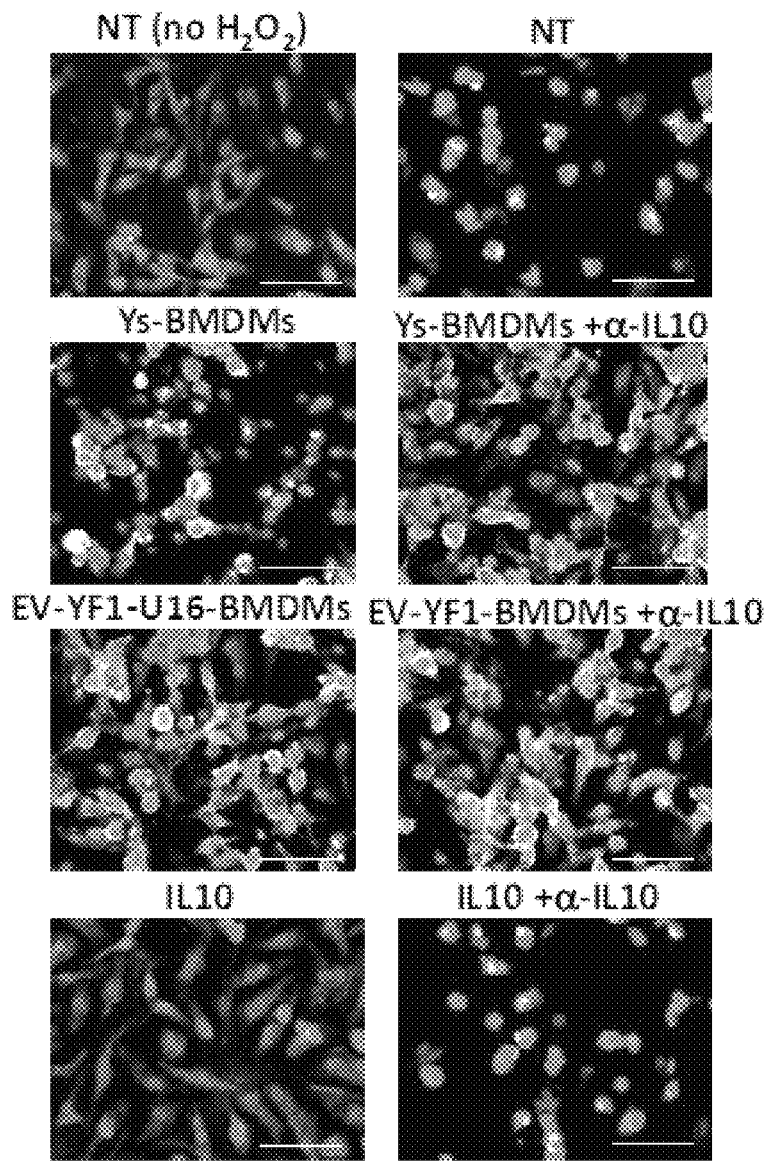
Figure 3E:
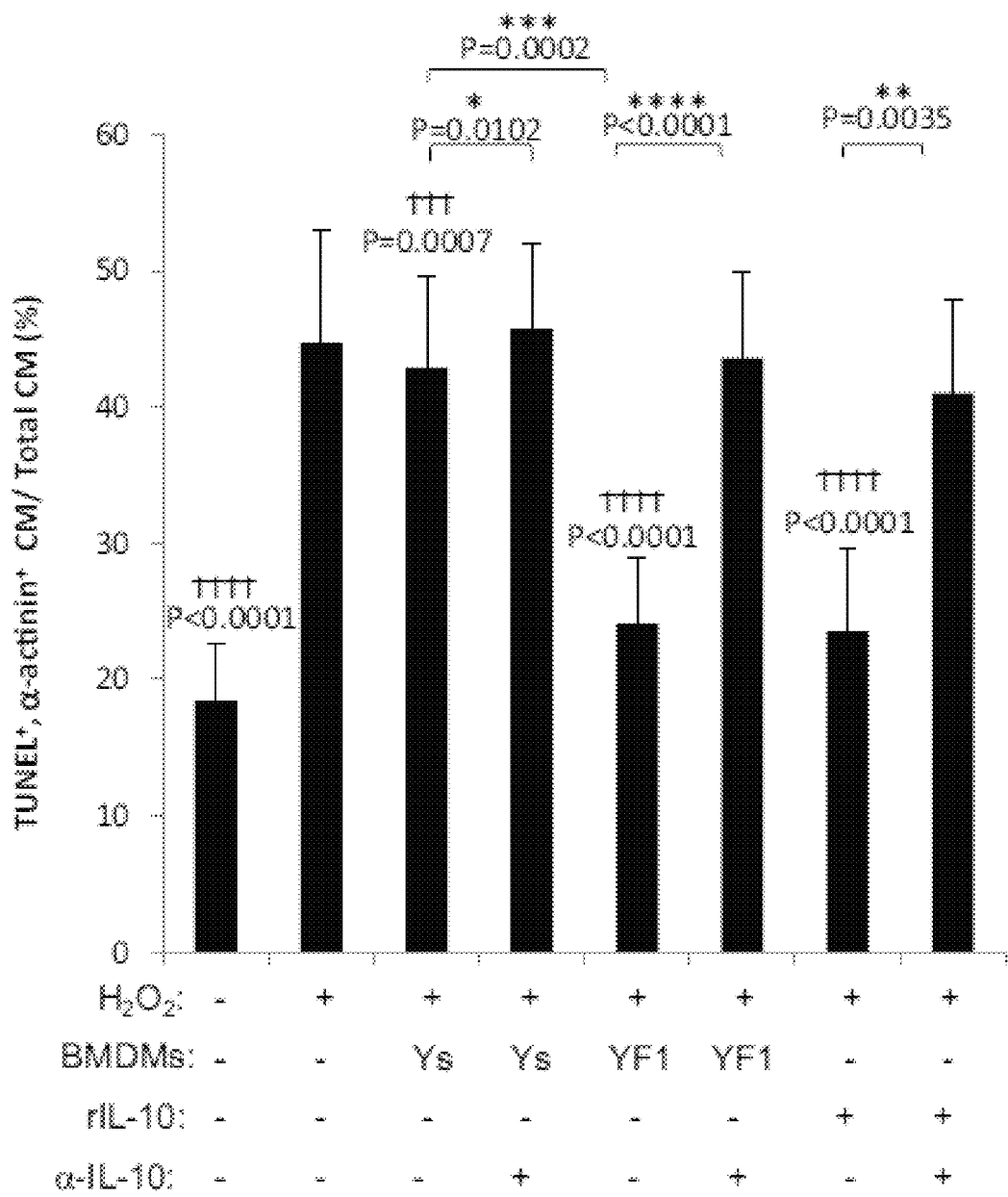

To determine the functional consequence of increased IL-10 secretion in EV-YF1-U16-primed BMDMs, I/R was mimicked in vitro. Neonatal rat ventricular myocytes (NRVMs) were stressed with 75 µM $H_2O_2$ for 15 min (simulating an ischemic phase), then washed with SF media for 20 min (simulating reperfusion), prior to the addition of EV-YF1-U16- or Ys-primed BMDMs in the presence or absence of anti-IL-10 neutralizing antibody (αIL-10). Stressed ($H_2O_2$) and unstressed NRVMs served as comparators (FIG. 3C). NRVM apoptosis was reduced in co-culture with EV-YF1-U16-primed BMDMs (TUNEL$^+$α-actinin$^+$: 24%, versus Ys-primed BMDMs or NRVMs alone: TUNEL$^+$α-actinin$^+$~45%) (FIGS. 3D and 3E). The protective effects of EV-YF1-U16-primed BMDMs were strong, as the apoptotic percentage decreased to a level comparable to that in unstressed NRVMs (TUNEL$^+$α-actinin$^+$20%). The addition of recombinant IL-10 (rIL-10) to stressed NRVMs (without BMDM) mimicked the benefits of co-culture with EV-YF 1-U16-primed BMDMs (TUNEL$^+$α-actinin$^+$24%) (FIGS. 3D and 3E). The protective effects of either EV-YF1-U16-primed BMDMs or rIL-10 were abrogated by αIL-10 neutralizing antibody (FIGS. 3D and 3E).

Figure 4A:
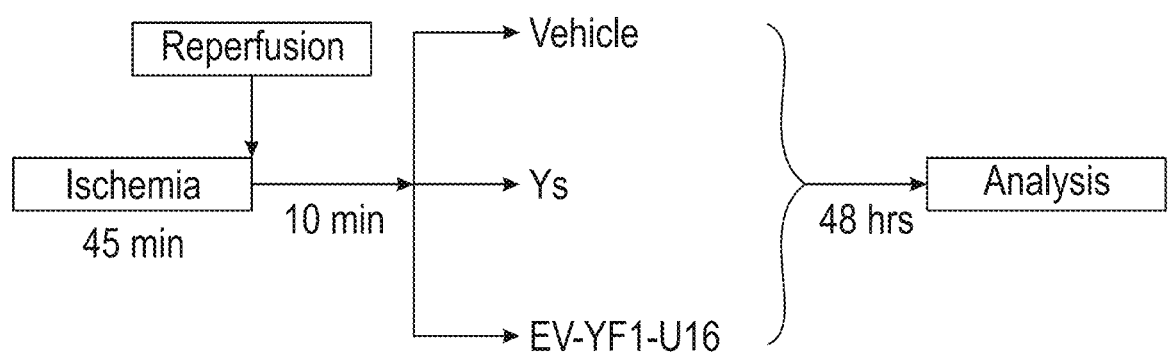
FIGS. 4A-4E. EV-YF1-U16 is cardioprotective against I/R injury in rats.
Figure 4B:
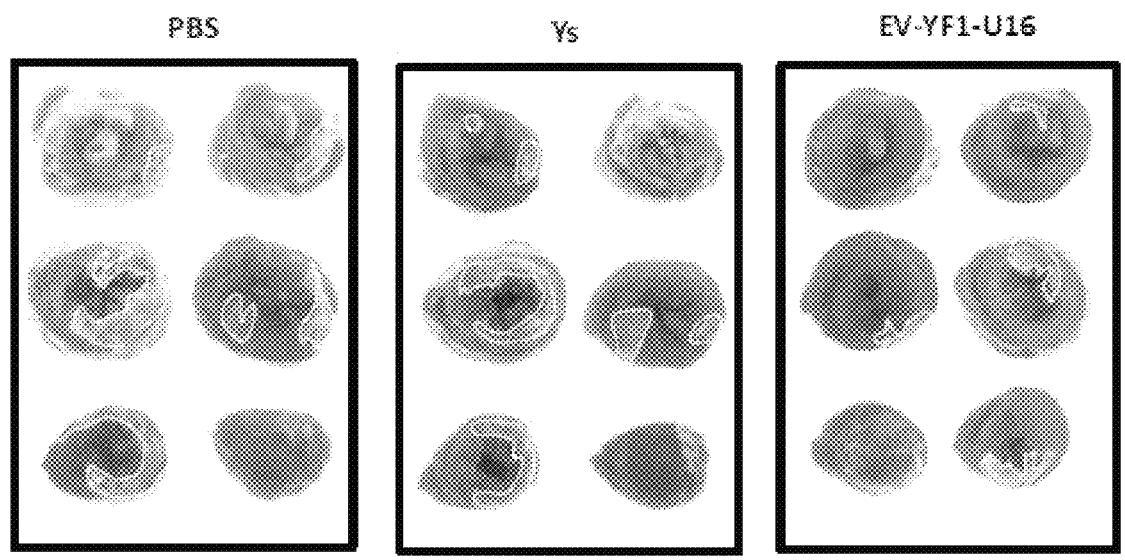
Figure 4C:
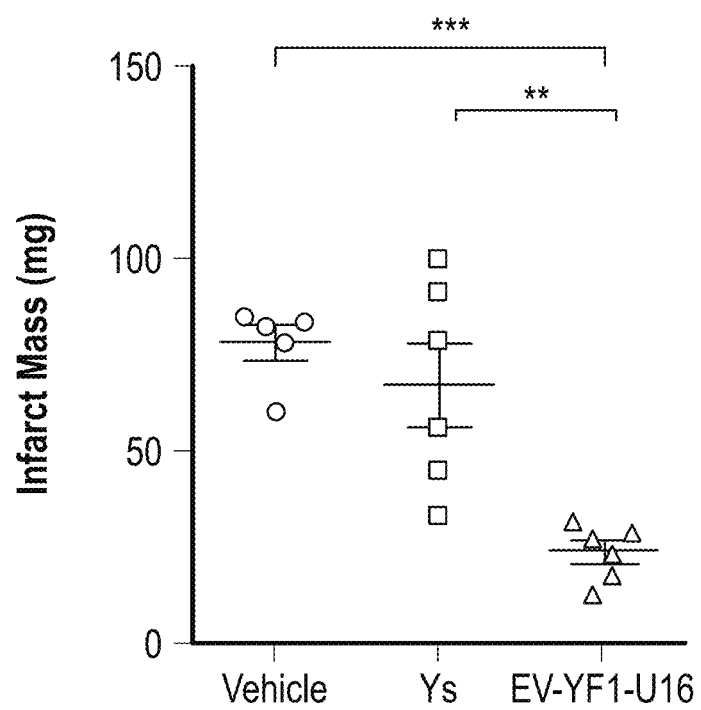
Figure 4D:
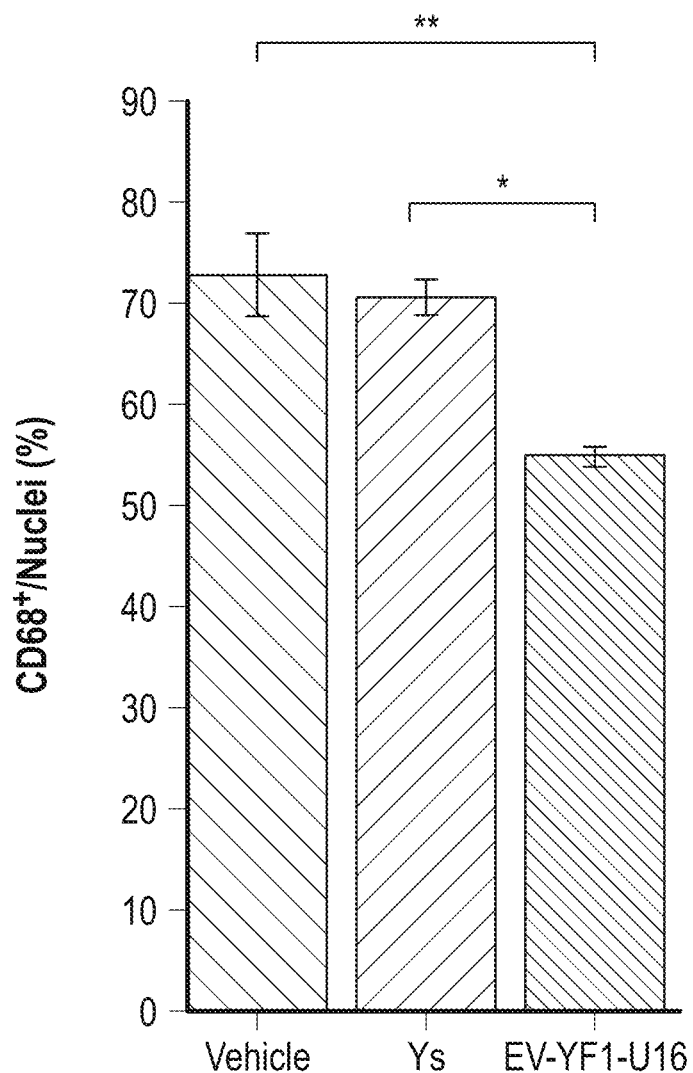
Figure 4E:
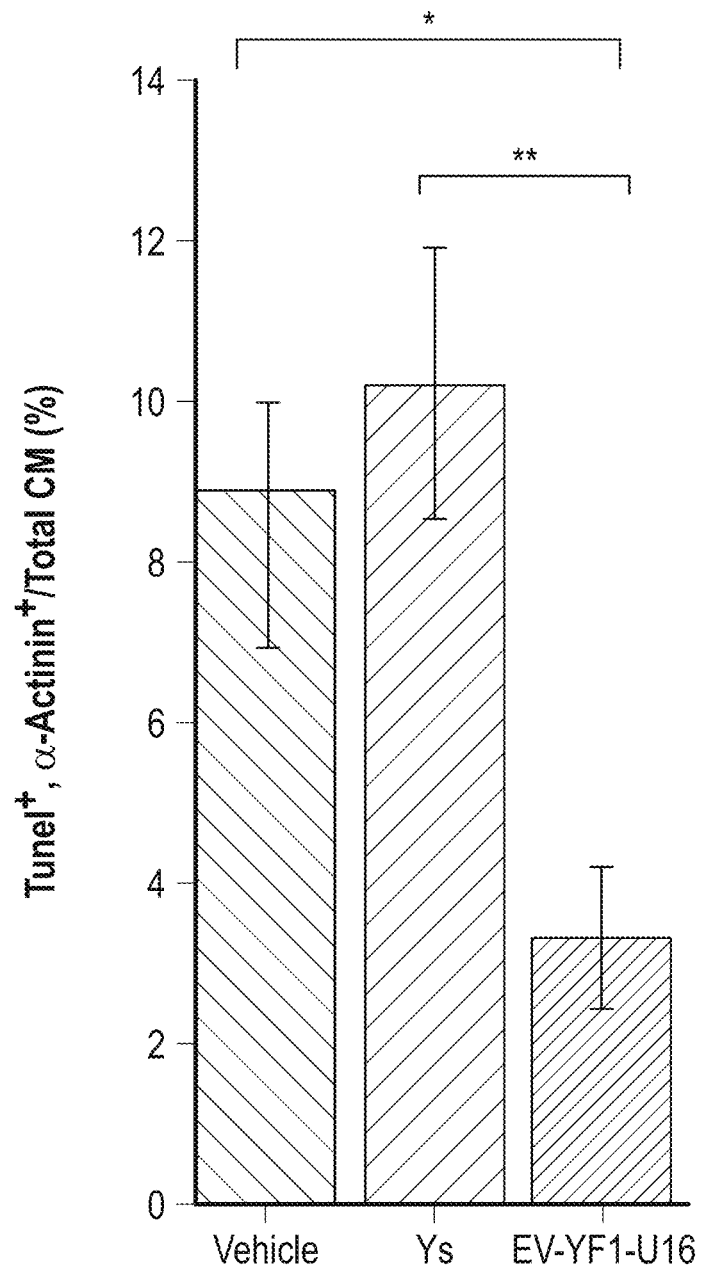

A test was performed to see whether EV-YF1-U16 could mediate cardioprotection in rats subjected to 45 min of ischemia and 10 min of reperfusion. By random allocation, hearts were then infused with 10 µg of EV-YF1-U16, Ys or vehicle, with infarct size quantification two days later (FIG. 4A). Animals treated with EV-YF1-U16 exhibited reduced infarct mass compared to animals treated with Ys or vehicle (EV-YF1-U16: 24.30±2.85 mg, Ys: 67.41±10.9 mg, vehicle:

78.33±4.43 mg) (FIGS. 4B and 4C). EV-YF1-U16-treated animals also exhibited a decrease in CD68 nuclei and TUNEL nuclei (FIGS. 4D and 4E). Thus, the cytoprotective effects of EV-YF1-U16 seen in vitro (FIG. 3) are also manifested in vivo in a genuine MI model. Thus, according to several embodiments, those effects observed for EV-YF1-U16 are also observed with EV-YF1, and vice versa.

Epigenetic Modulation

Figure 5A:
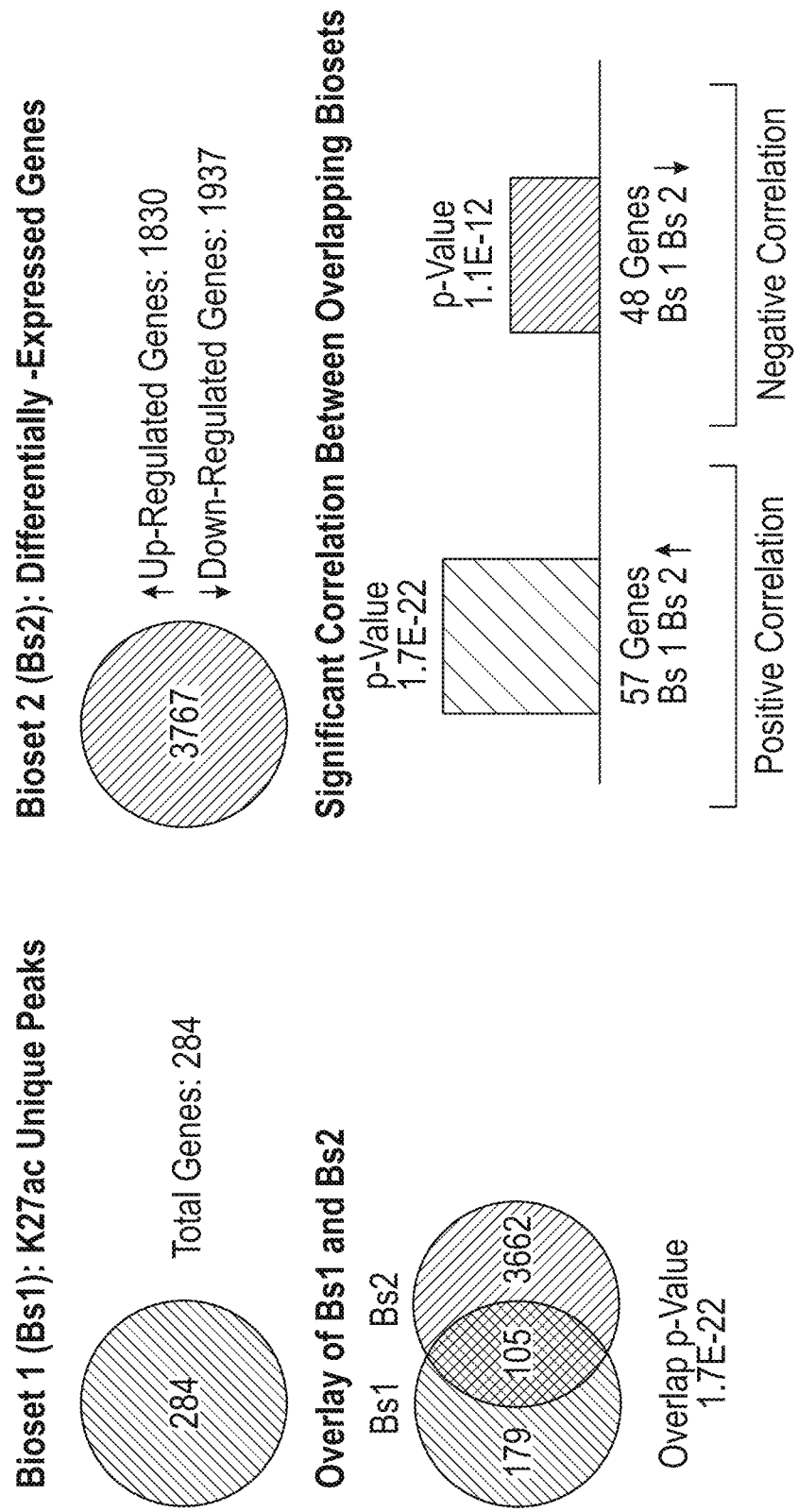
FIGS. 5A-5D. CDC-exo and EV-YF1 induce epigenetic modification of the IL-10 gene in BMDMs.
Figure 5B:
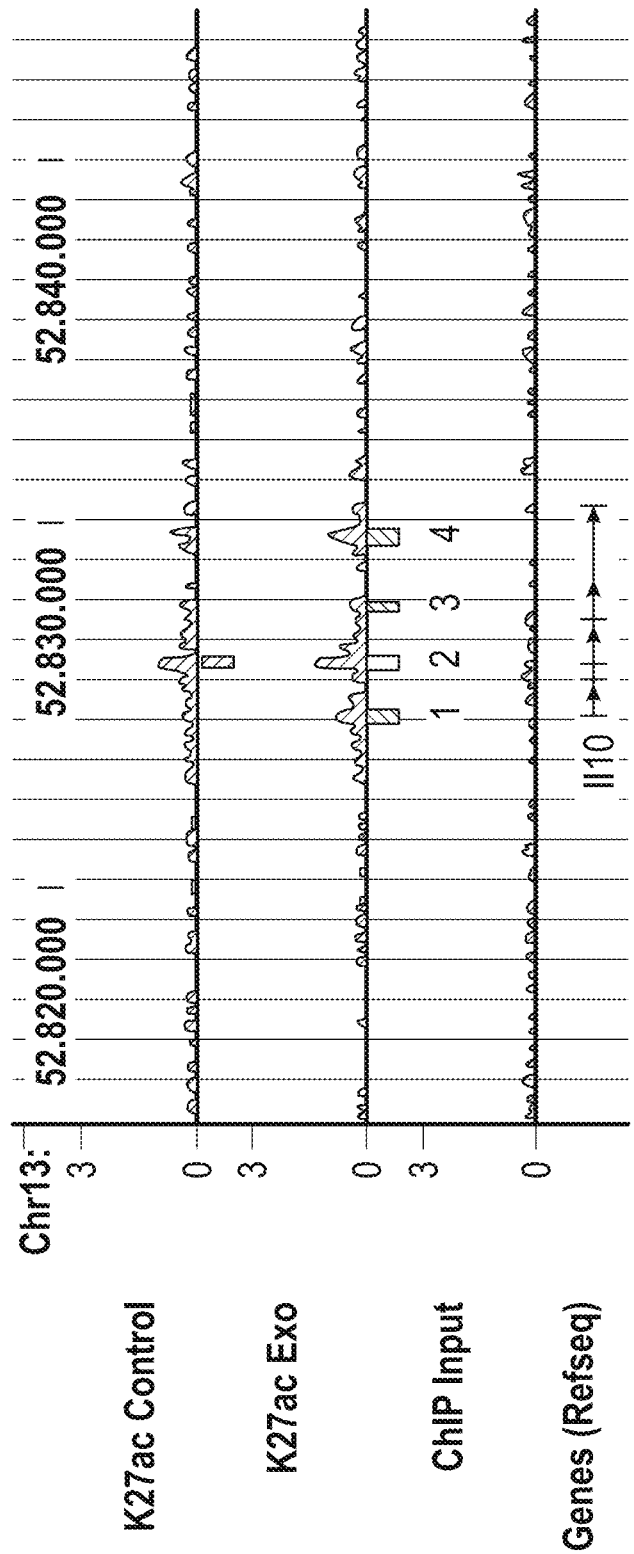
Figure 5C:
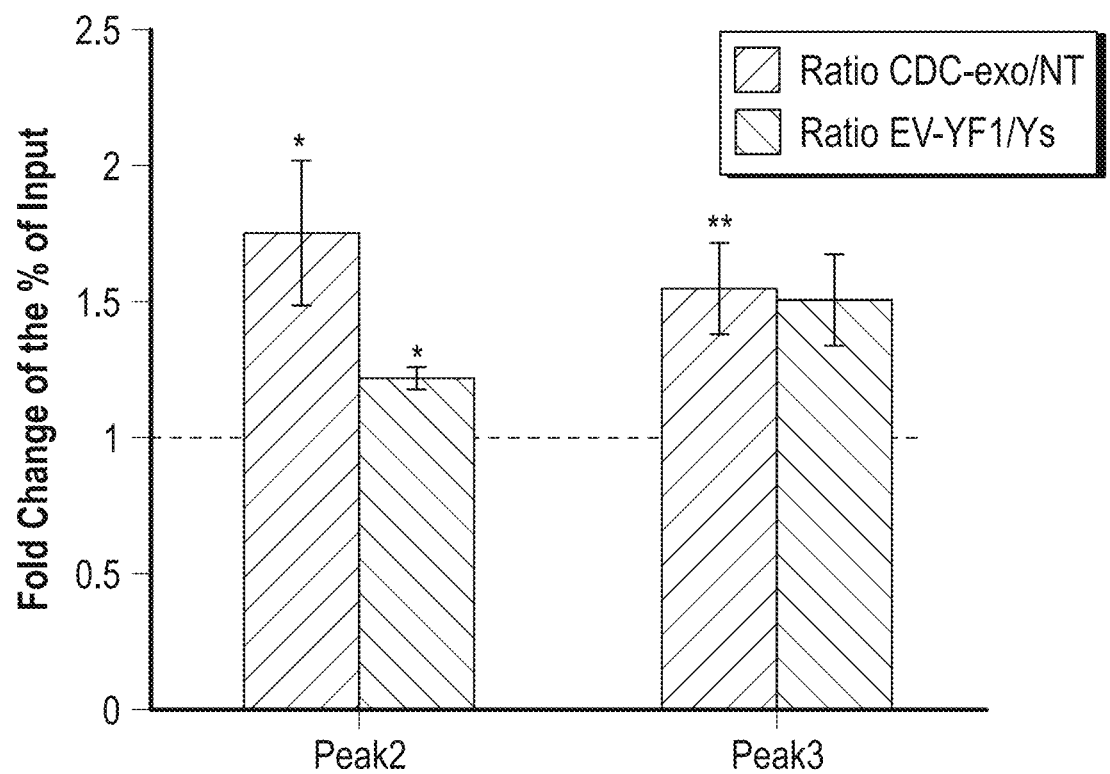
Figure 5D:
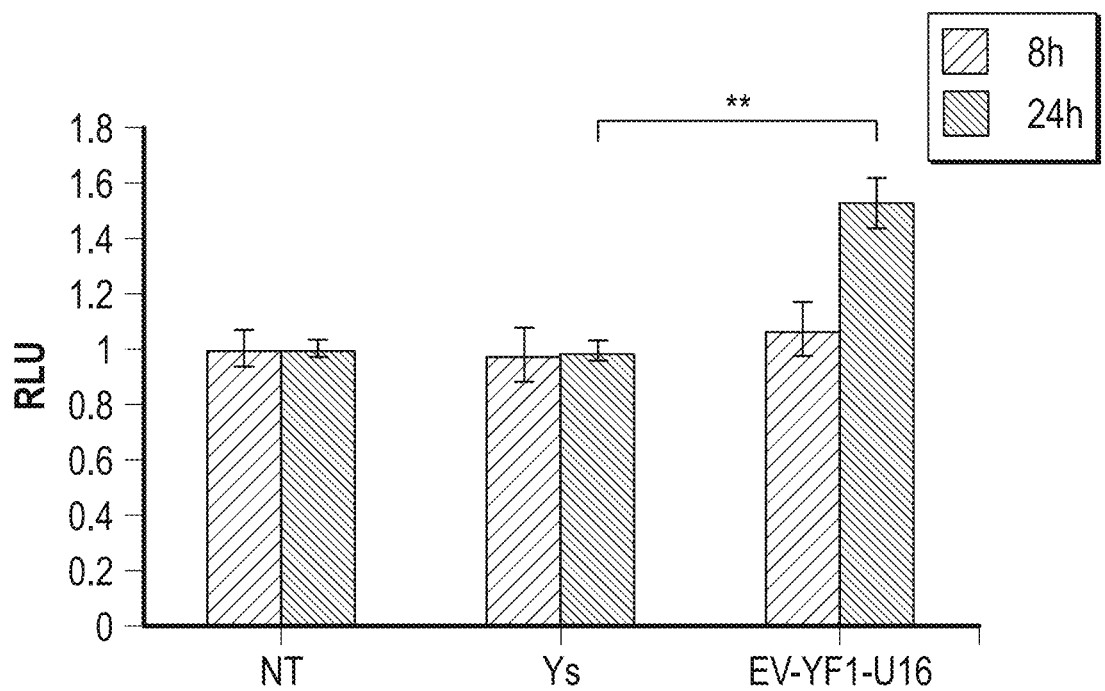

To determine whether CDCs and their exosomes modulate epigenetic features of target cells, ChIP-seq was performed on acetylated histone 3 lysine 27 (H3K27ac), an epigenetic marker that distinguishes active enhancers and promoters from inactive/poised elements, on CDC-exo-treated and non-treated BMDMs. 1,751 genomic elements were identified that gained new H3K27ac peaks in the CDC-exo-treated BMDMs, and the top 500 most significantly enriched peaks were investigated. Each of these was associated to the nearest gene, resulting in 284 genes gaining H3K27ac peaks. To correlate transcriptional effects with the observed epigenetic changes, RNA-seq was performed on CDC-exo-treated vs. non-treated BMDMs, and found 3,767 differentially regulated genes (up-regulated: 1,830; down-regulated: 1,937). CDC-exo specific H3K27ac peaks were significantly associated with altered expression of the nearest gene (FIG. 5A): 57 of the peaks (~20%) correlated with a gene up-regulated in CDC-exo treated cells, while 48 peaks (~17%) correlated with gene down-regulation, consistent with complex epigenetic regulation as seen in other systems (FIG. 5A, right). CDC-exo induced H3K27ac at the Il-10 locus with 4 distinct acetylation patterns at the promoter (peak 1), exonic (peak 2), intronic (peak 3), and intergenic (peak 4) regions (FIG. 5B). ChIP-qPCR confirmed enhanced H3K27ac in BMDMs at peaks 2 and 3 following CDC-exo and EV-YF1-U16-treatment (compared to untreated and Ys controls, respectively) (FIG. 5C), but peaks 1 and 4 were not confirmed by ChIP-qPCR. To determine if the EV-YF1-U16-induced increase in IL-10 gene expression was not only associated with opened chromatin, but also increased promoter activity, a luciferase IL-10 promoter reporter plasmid (pGL2B 1538/+64) was transfected into HEK293T cells. Cells overexpressing EV-YF1-U16, in contrast to Ys or non-treated (NT) cells, had enhanced IL-10 promoter activity (FIG. 5D). Thus, EV-YF1-U16 (and likely EV-YF 1) regulates IL-10 gene expression in BMDMs dually through promoter transactivation and epigenetic mechanisms.

Example 2

Tests were performed to see whether EV-YF1 and CDC-exo could attenuate cardiorenal syndromes (and to see the likelihood of whether EV-YF1-U16 could likewise attenuate cardiorenal syndromes). In particular, whether EV-YF1 and CDC-exo exert beneficial effects on fibrosis, cardiac hypertrophy, and kidney injury induced by chronic infusion of angiotensin (Ang) II and hypertension. It was demonstrated that EV-YF1 largely recapitulates the effects of CDC-exo by attenuating maladaptive cardiac hypertrophy and improving kidney function, without altering blood pressure. These benefits were associated with enhanced IL-10 secretion.

Methods Used in Example 2

Animals. Eight to ten-week-old male C57BL/6J mice were obtained from Jackson Laboratories. Mice were housed under controlled conditions with a 12:12-h light-dark cycle. Food and water were available to animals ad libitum. Hypertension was induced with subcutaneous Ang II infusion (1.4 mg/kg/day) (Sigma-Aldrich, St. Louis, MO, USA) using osmotic mini-pumps (Alzet, Cupertino model 1004, CA, USA) for 28 days. Sham animals were infused with saline solution. At day 14, 15, 18, 20 and 22 of Ang II-infusion, animals were treated with EV-YF1 synthetic oligoribonucleotide (0.15 mg/kg body weight), CDC-exo (350 µg) or placebo by retro-orbital injection (FIG. 1A). Injections were performed on alternate eyes (no more than 3 injections per eye) and no sign of ocular injury was observed. Blood samples were collected from the retro-orbital plexus. Blood pressure was monitored weekly by tail-cuff plethysmography using a Visitech BP2000 system (Visitech Systems Inc., Apex, NC) in previously trained mice. After 14 and 28 days of Ang II-infusion, mice were euthanized and heart, spleen and kidneys were collected. The Institutional Animal Care and Use Committee approved all animal care and related procedures before study commencement.

CDCs, exosomes and EV-YF1. Human CDCs were isolated and cultured, and exosomes isolated, as described in Example 1. EV-YF1 was synthesized commercially from Integrated DNA Technologies (IDT) (Coralville, IA) (sequence in Table 2).

Cardiac echocardiography. Cardiac function and morphology were assessed under general anesthesia by transthoracic two-dimensional echocardiography using VEVO 770 (VisualSonics Toronto, Canada) equipped with a 30 MHz transducer. Echocardiographic studies were performed at baseline before pump implantation (day 0), day 14 and day 28.

Assessment of cardiac and renal morphology. The heart and kidneys were collected, washed with cold saline solution, weighed and fixed in 10% formalin-PBS solution. Five µm-thick paraffin-embedded sections were stained with Masson's trichrome solutions. Images were captured using Pathscan Enabler IV scanner (Meyer Instruments, Houston, Tx), and cross-sectional area of cardiomyocytes was determined in the LV wall by tracing the boundaries of cells using Image J software. 100 myocytes/heart were measured and averaged. Cardiac fibrosis was determined in the LV using Image J software as a percentage of LV area and renal fibrosis was determined in the whole histology section as a percentage of total section area. Glomerular number, size and mesangial expansion were analyzed on 5 µm-thick paraffin-embedded kidney sections stained with periodic acid-Schiff (PAS). Images were captured using the Slide scanner Aperio (Leica Biosystems Imaging, Vista, CA) and analyses were performed using ImageScope software (Aperio Technologies, Inc., Vista, CA). Glomeruli number was determined on the entire section, glomerular size and expansion were measured on 20 glomeruli.

Neonatal Rat Ventricular Myocytes (NRVMs) and neonatal Cardiac Fibroblasts (neoCFs) in vitro assay. NRVMs, neoCFs and bone marrow-derived macrophages (BMDMs) were isolated. NRVMs were cultured for 24 hours with BMDMs media (control) or media conditioned during 48 hours from BMDMs overexpressing Ys scrambled oligoribonucleotide (Ys-CM) or EV-YF1 (EV-YF1-CM) with or without Ang II (1 µM). NeoCFs were cultured for 16 hours with BMDMs media (control) or media conditioned during 72 hours from BMDMs overexpressing Ys (Ys-CM) or EV-YF1 (EV-YF 1-CM) with or without Ang II (100 nM). BMDMs were transfected with Ys or EV-YF1 synthetic oligoribonucleotides (Integrated DNA Technologies, IDT), at a final concentration of 50 nM using DHARMAFECT 4 reagent (DHARMACON), according the manufacturer's protocol.

RNA isolation and quantitative RT-PCR (qPCR). Cells or tissues were washed and collected for RNA isolation using a miRNeasy Mini Kit (QIAGEN) according to the manufacturer's protocol. RNA concentration and purity were determined using a NanoDrop Spectrophotometer (Thermo Scientific). cDNA was synthesized from mRNA using iScript™ cDNA Synthesis Kit (Bio-Rad) according to the manufacturer's protocol. The resulting cDNA was standardized across samples prior to qPCR analysis with iQ™ SYBR® Green Supermix (Bio-Rad) on a LIGHTCYCLER 7900 Standard Real-Time PCR System (Roche Applied Science). Relative gene expression was determined by the ΔΔCt method. Primers were ordered from Integrated DNA Technologies (IDT) (sequences in Table 4).

Enzyme-linked immunosorbent assay (ELISA). Heart, spleen, kidney tissues and plasma levels of IL-10 were measured using a Mouse IL-10 QUANTIKINE ELISA Kit (R&D Systems, Minneapolis, MN, USA) according to manufacturer's instructions.

Proteinuria. Mice were individually housed in metabolic cages for urine sampling. To avoid urine contamination with food, mice were fed a gelled diet containing all necessary nutrients (NUTRA-GEL; Bio-Serv; Frenchtown, NJ; Cat: S4798). Animals had free access to food and water at all times. Urinary protein excretion was measured using the micro BCA method.

Statistics. Results are expressed as mean±SEM. Groups were compared using 1-way ANOVA followed by Tukey's multiple comparisons test. *$p<0.05$, $p<0.01$, *$p<0.001$. All analyses were performed using Prism 5 software (GraphPad).

Figure 19A:
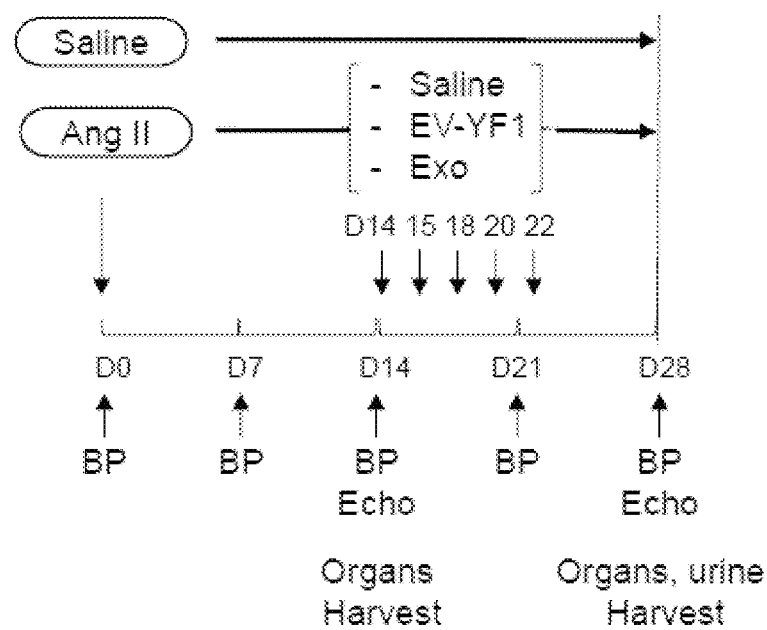
FIGS. 19A-19C. EV-YF1 and CDC-exo biodistribution after retro-orbital injection in an Ang II-infused mouse.
Figure 19B:
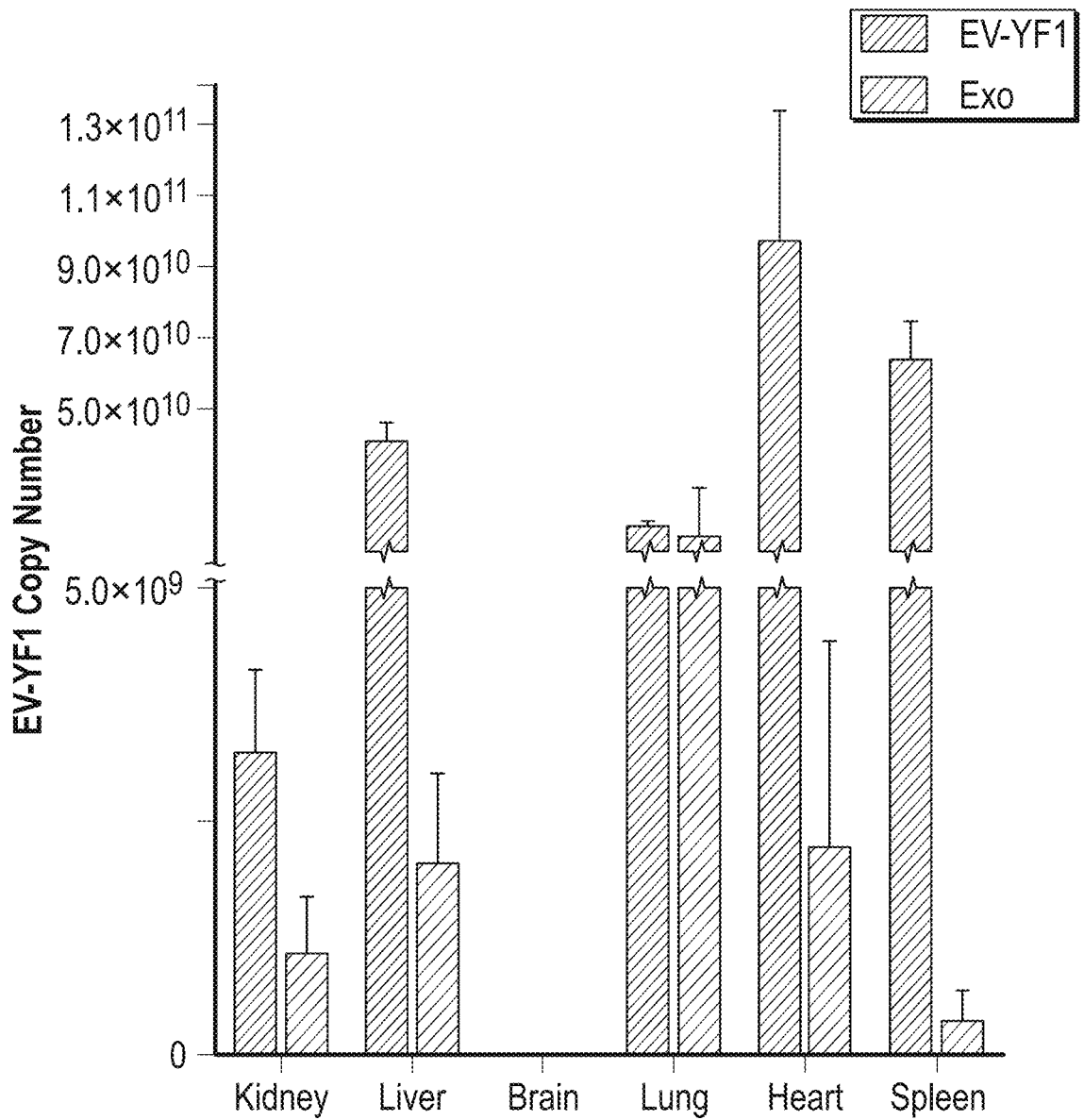
Figure 19C:
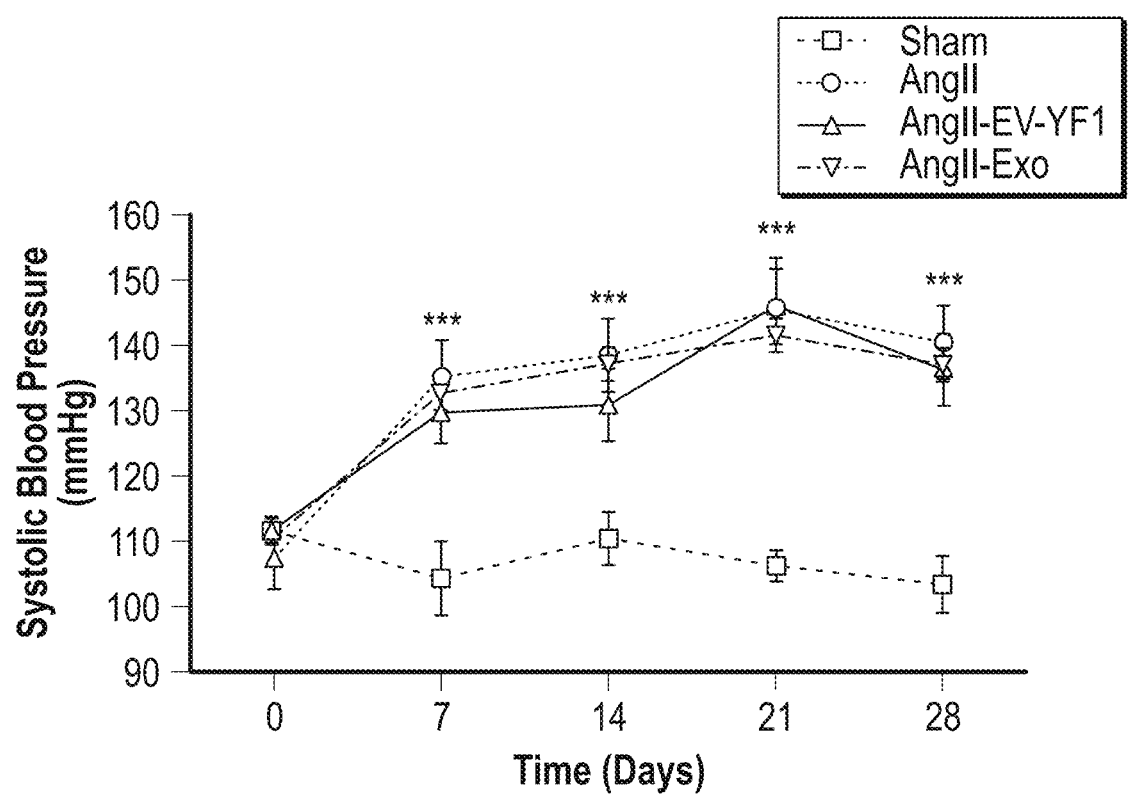

EV-YF1 and CDC-Exo Biodistribution after Retro-Orbital Injection in Ang II-Infused Mice To investigate the role of EV-YF1 and CDC-exo during cardiac hypertrophy and renal injury, the Ang II-induced hypertension model was used. LV hypertrophy was induced in C57BL/6J mice by subcutaneous infusion of Ang II (1.4 mg/kg/day) using osmotic mini-pumps for 28 days. Sham animals were infused with saline solution. On days 14, 15, 18, 20 and 22 of Ang II infusion, animals were treated with consecutive doses of EV-YF1 synthetic oligoribonucleotide, CDC-exo or saline by retro-orbital injection (FIG. 19A). To determine the efficacy of retro-orbital injection, expression of EV-YF1 was analyzed 24 hours after a single injection of the EV-YF1 synthetic oligoribonucleotide or CDC-exo. Even though EV-YF1 is highly abundant in CDC-exo, the dose of synthetic oligoribonucleotide (4.79E+14 copies) injected likely exceeds the abundance of EV-YF1 delivered in CDC-exo. Indeed, more expression of EV-YF1 after EV-YF 1 injection than CDC-exo injection was observed in all tested organs with higher copy numbers in heart, spleen and liver. Similar expression levels of EV-YF1 were observed in lung and kidneys, but no expression was detected in brain (FIG. 19B). To confirm the hypertensive effect of Ang II, systolic blood pressure (SBP) was measured before (day 0) and weekly during Ang II infusion. After one week of Ang II, SBP increased significantly compared to the sham group infused with saline (135±6 vs. 107±5 mmHg, n=5). This increase persisted during the 4 weeks of infusion. Neither the administration of EV-YF1 nor CDC-exo altered blood pressure levels (FIG. 19C).

Effects of EV-YF1 and CDC-Exo on Cardiac Function and Hypertrophy

Figure 20A:
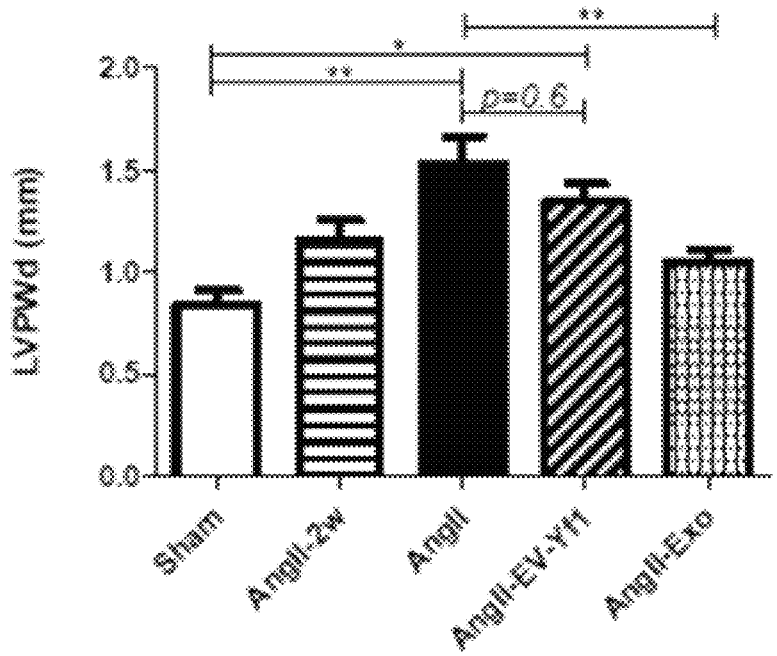
FIGS. 20A-20F. Effect of EV-YF1 and CDC-exo treatment on cardiac function and hypertrophy. Various endpoints of cardiac morphology (shown in FIGS. 20A-20D) were assessed by echocardiography at 2 weeks (AngII-2w) and 28 days after saline (sham) or Ang II infusion (AngII). Additional groups of mice were treated with Ang II plus EV-YF1 (AngII-EV-YF1) or Ang II plus CDC-exo (AngII-Exo). LVPWd: LV posterior wall thickness, end-diastole; LVIDd: LV internal diastolic diameter; IVSd: interventricular septal thickness, end-diastole. Values are means±SEM; n=5-10 animals/group.
Figure 20B:
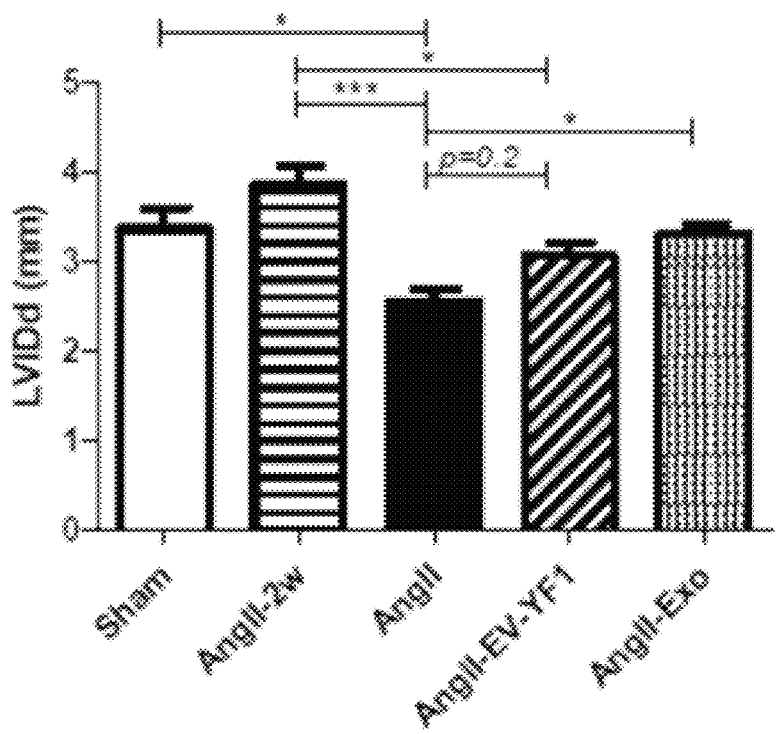
Figure 20C:
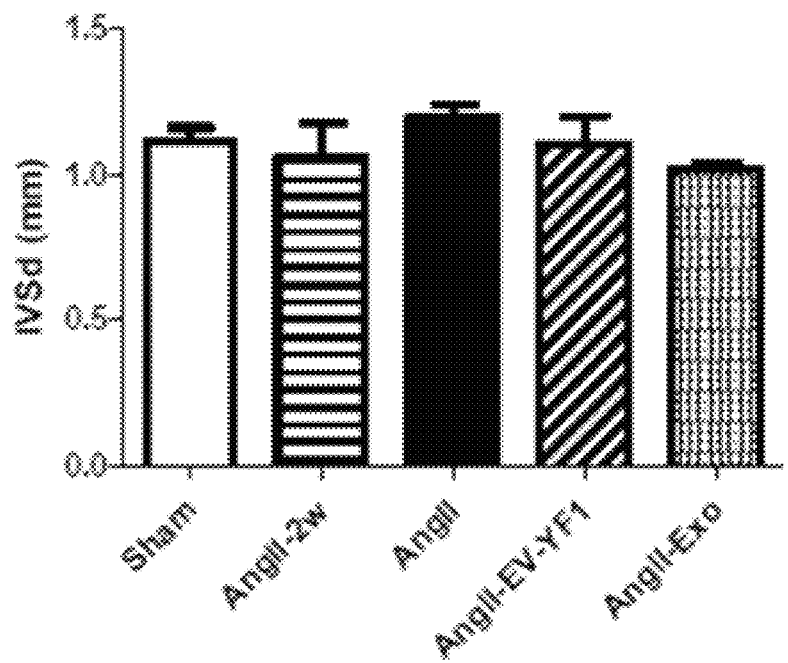
Figure 20D:
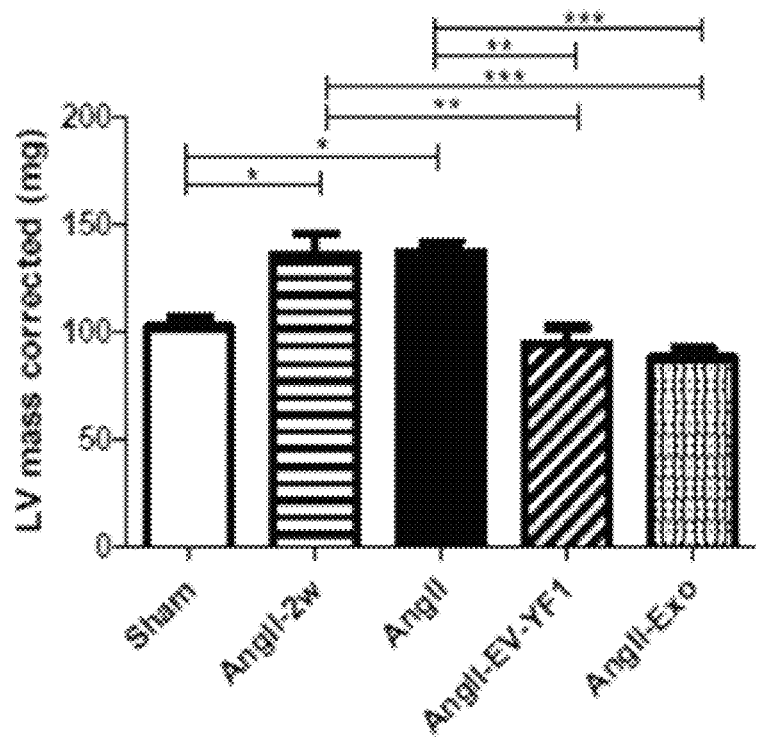
Figure 20E:
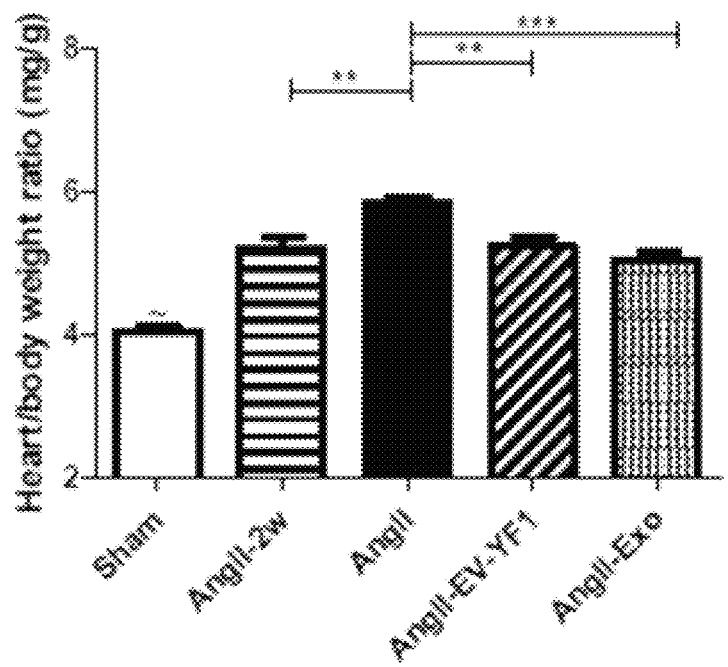
Figure 20F:
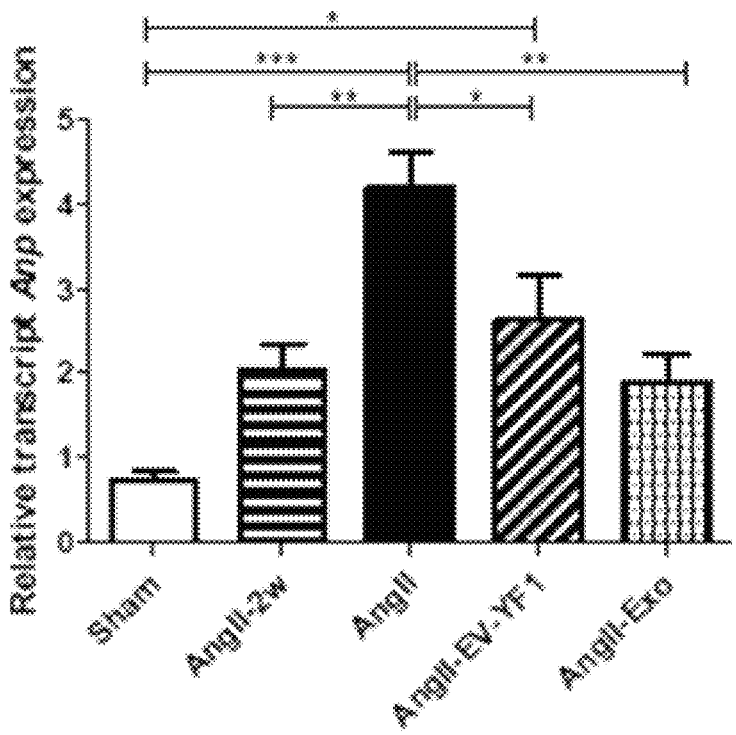
Figure 26A:
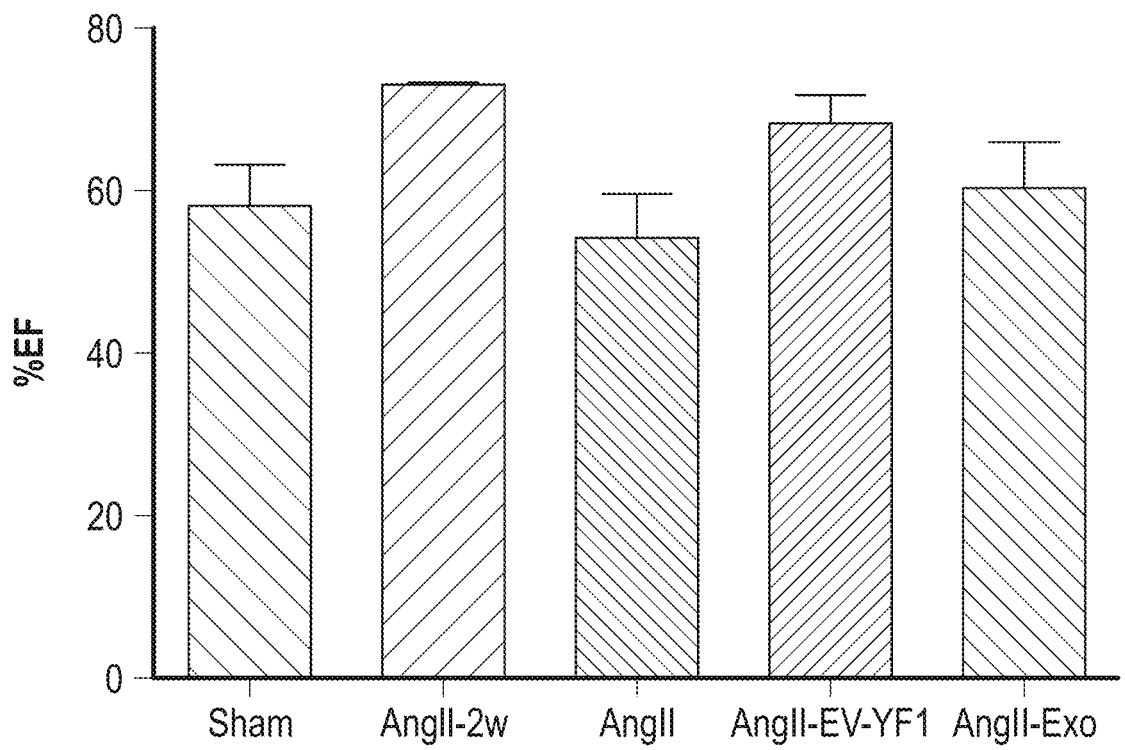
FIGS. 26A-26D. Effect of EV-YF1 and CDC-exo treatment on cardiac function and hypertrophy.
Figure 26B:
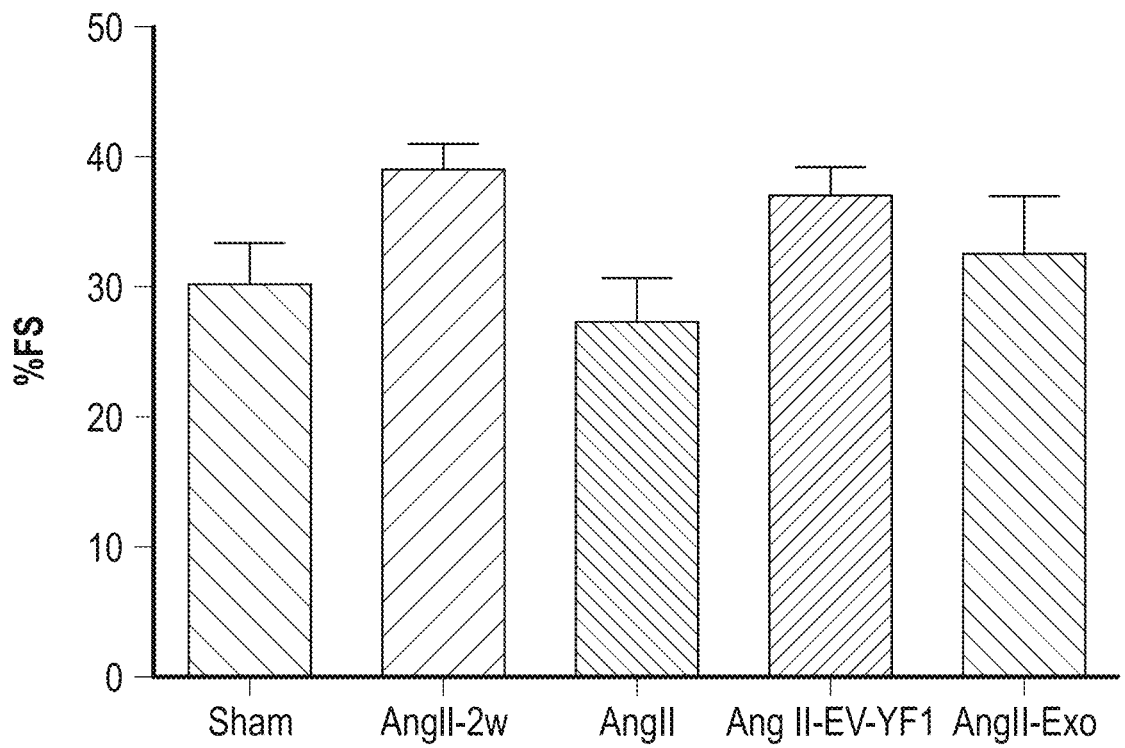
Figure 26C:
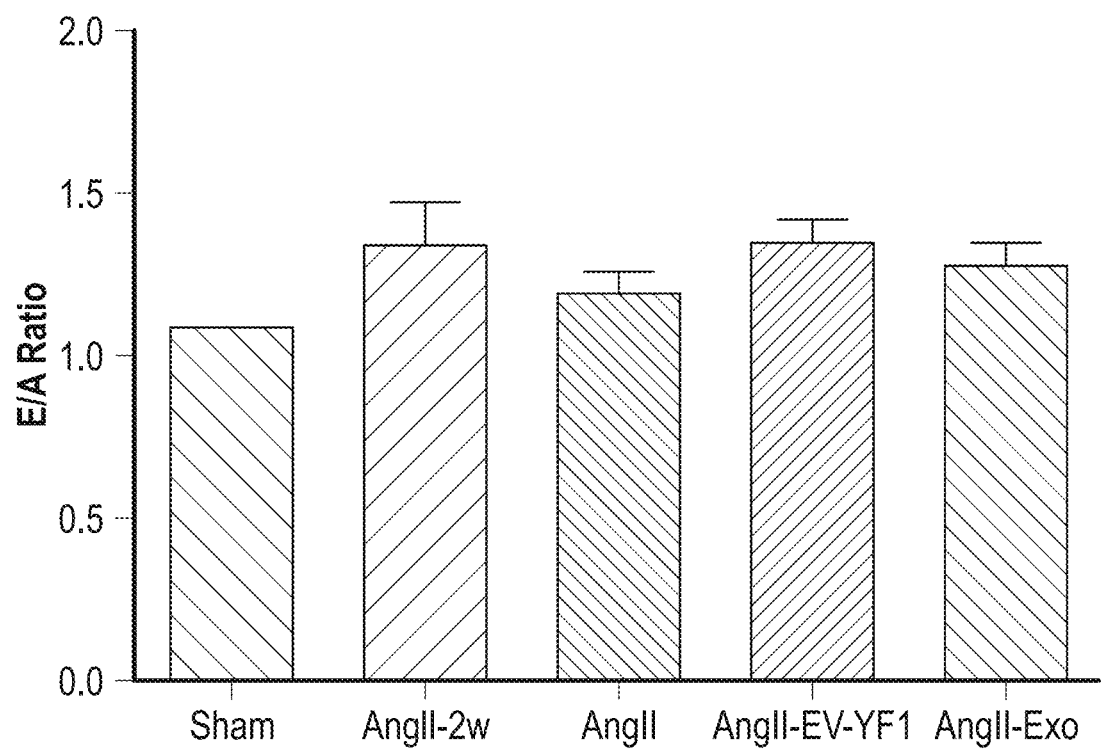
Figure 26D:
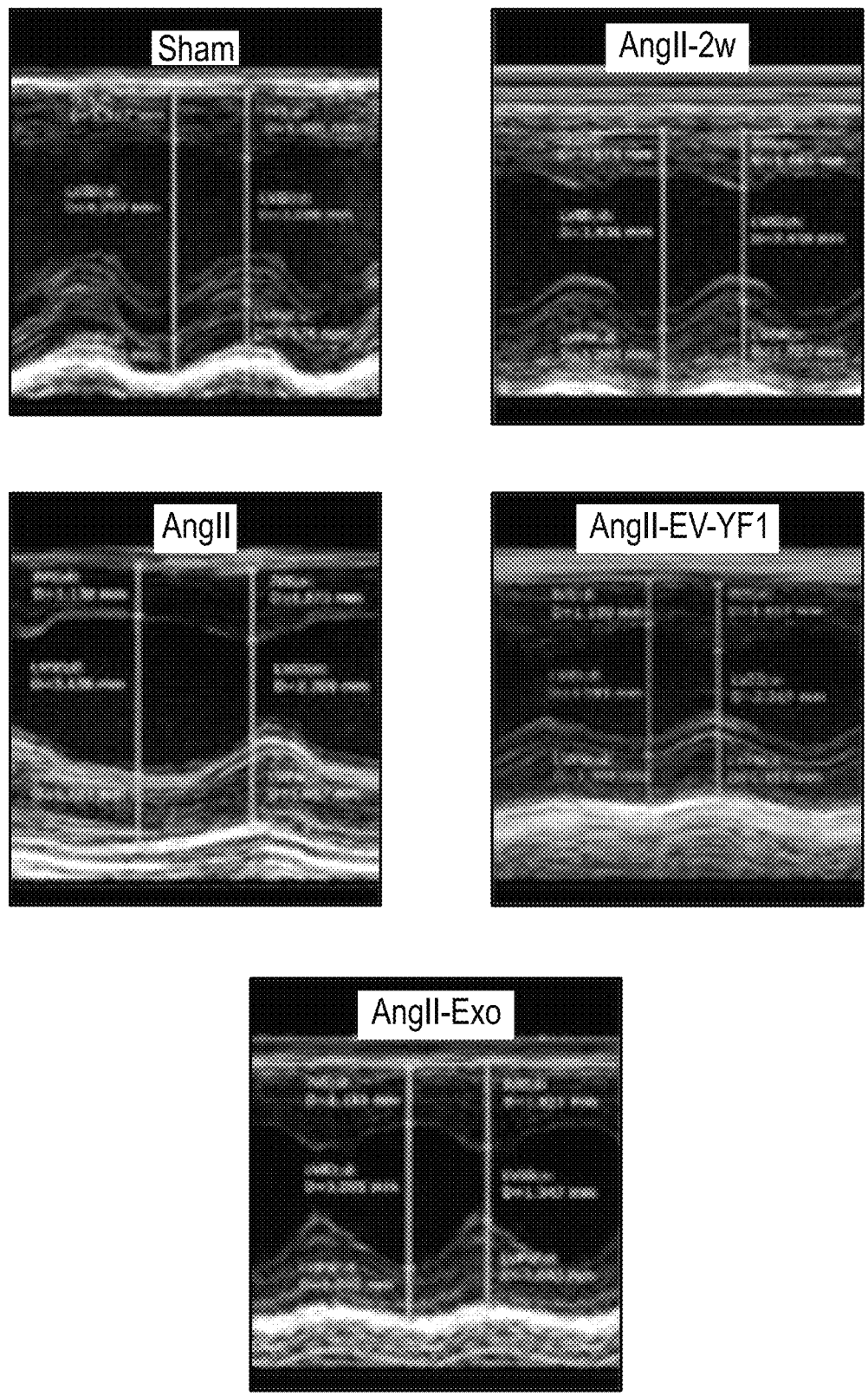

Echocardiography revealed no differences in LV systolic (FIGS. 26A-26B) or diastolic (FIG. 26C) function after Ang II infusion with or without EV-YF1 or CDC-exo. However, LV posterior wall dimension in end-diastole was greater after 4 weeks of Ang II infusion compared to sham (1.5±0.1 vs. 0.84±0.06 mm, $p<0.01$, n=3-6). The augmented thickness was significantly blunted in the CDC-exo group (1.05±0.07 mm; $p<0.01$, n=6). No improvement of LV posterior wall thickness was observed in the EV-YF1 group (1.34±0.09 mm, p=0.6, n=6) (FIGS. 20A and 26D). The decrease in LV internal diastolic diameter induced by Ang II-infusion (Sham: 3.4±0.2; Ang II: 2.5±0.1 mm, $p<0.05$, n=4-5) was less pronounced in CDC-exo group (3.2±0.11 mm, $p<0.05$ vs. Ang II, n=6). EV-YF1 also blunted the decrease in LV internal diameter induced by Ang II, albeit not significantly (3.0±0.1 mm vs. Ang II, p=0.2) (FIGS. 20B and 26D). No differences in interventricular septal thickness in end-diastole were observed between groups (FIGS. 20C and 26D), but LV mass showed a significant increase in the Ang II-infused group (137±5 mg vs sham 102±6 mg, $p<0.05$, n=5). This augmentation in mass was reduced in both EV-YF 1 (94±8 mg, $p<0.01$, n=8) and CDC-exo (87.7±4.6 mg, $p<0.001$, n=8) groups (FIG. 20D). The heart/body weight ratio, indicative of cardiac hypertrophy, mimicked the profile obtained for corrected LV mass (FIG. 20E). Another characteristic of cardiac hypertrophy is the re-expression of fetal genes such as Anp. Indeed, Anp expression was 5.7-fold greater in Ang II-infused compared to sham group ($p<0.001$, n=6) while the induction was only 3.6 and 2.6-fold in EV-YF1 and CDC-exo groups; ($p<0.01$ and $p<0.001$ vs. Ang II-infused group; respectively, n=6-5) (FIG. 20F). Taken together, these data indicate that both EV-YF1 and CDC-exo attenuated cardiac hypertrophy induced by Ang II infusion for 4 weeks.

Figure 21A:
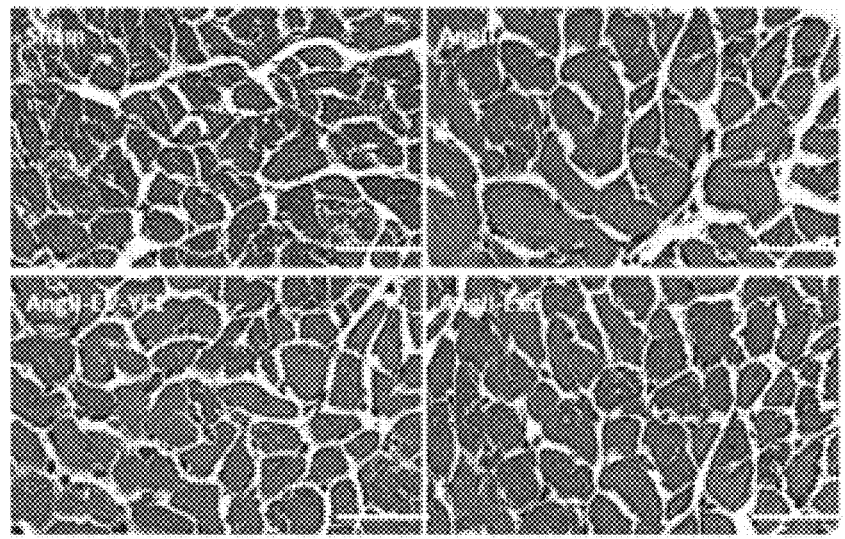
FIGS. 21A-21F. EV-YF1 and CDC-exo treatment decrease Ang II-induced cardiac hypertrophy, fibrosis and inflammation.
Figure 21B:
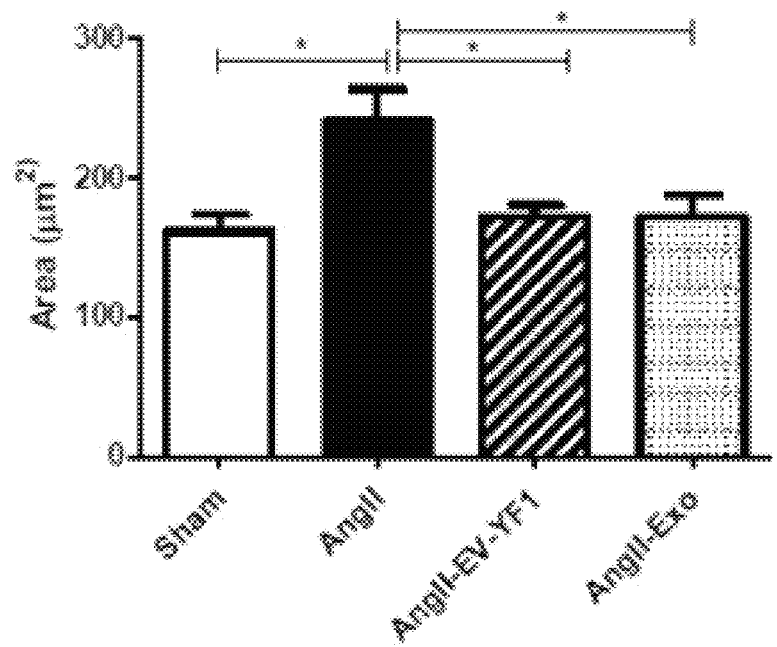
Figure 21C:
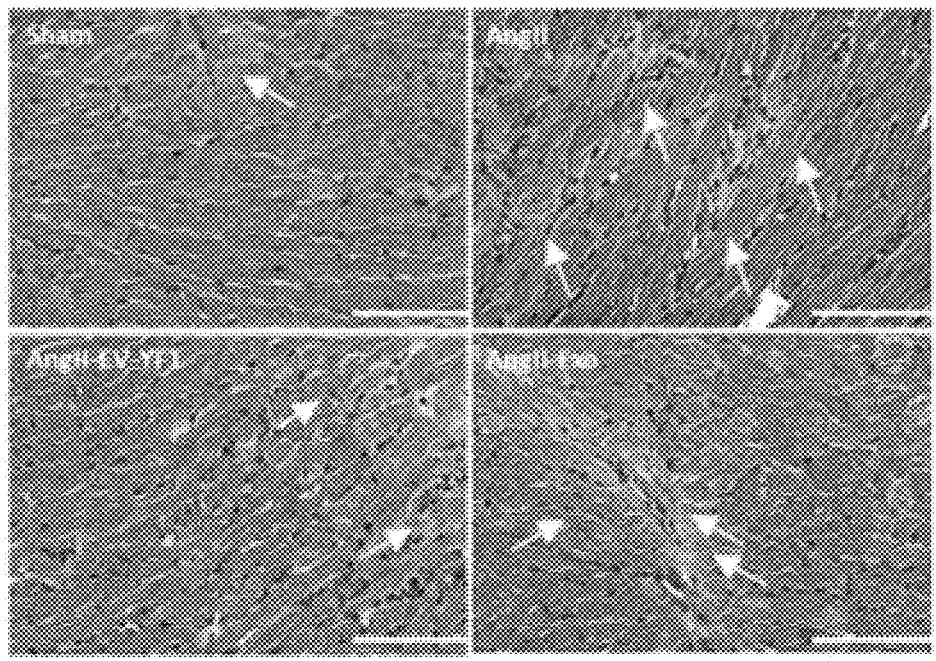
Figure 21D:
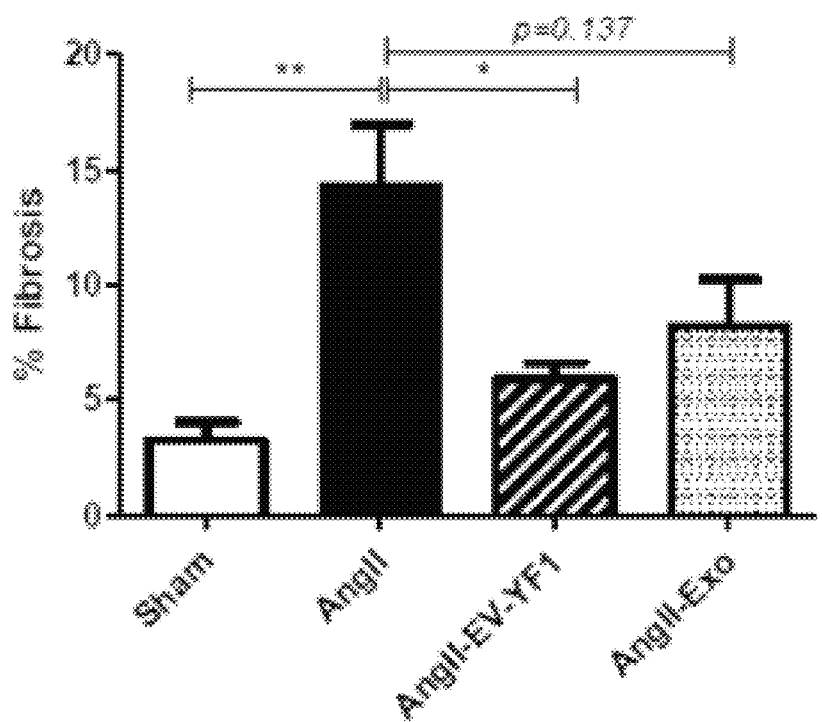
Figure 21E:
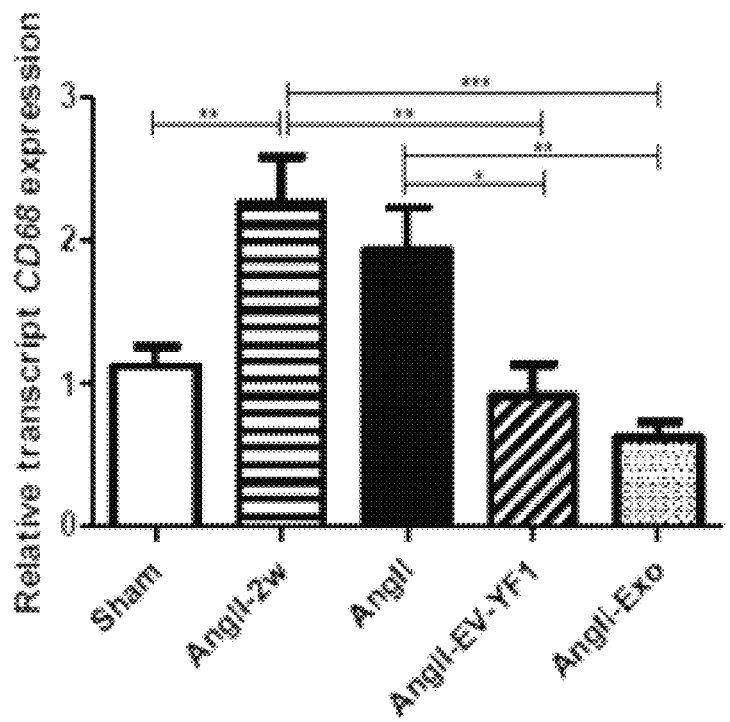
Figure 21F:
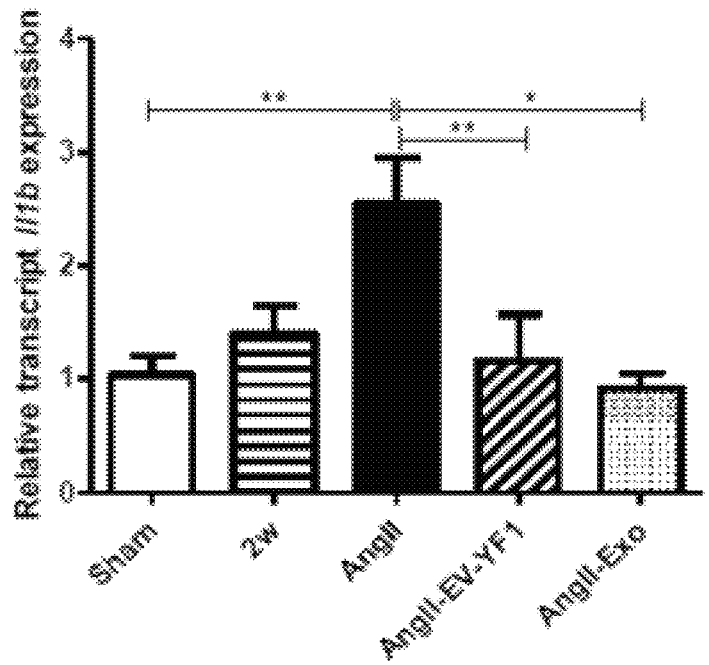
Figure 27:
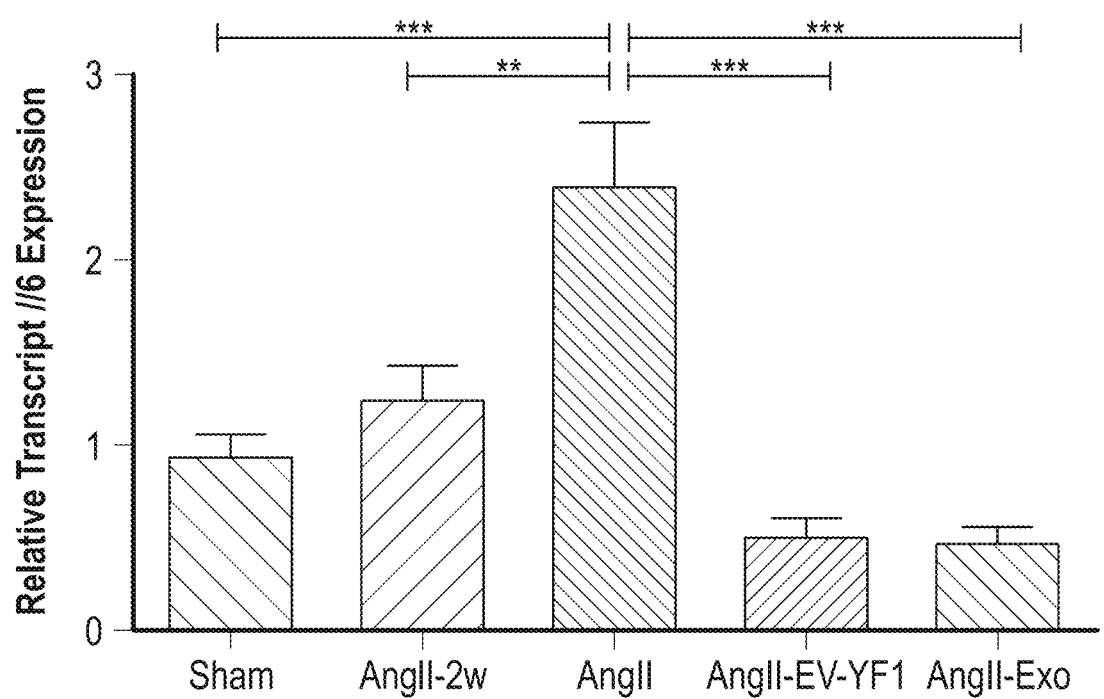
FIG. 27. EV-YF1 and CDC-exo treatment decrease Ang II-induced cardiac hypertrophy, fibrosis, and inflammation.

EV-YF1 and CDC-Exo Decrease Ang II-Induced Cardiac Hypertrophy, Fibrosis and Inflammation Examples of indicators of LV remodeling during cardiac hypertrophy are increases in cardiomyocyte size, cardiac fibrosis and inflammation. Cardiomyocyte cross-sectional area was increased in Ang II-infused group (240±23 µm$^2$) compared to sham (161+12 µm$^2$, $p<0.05$, n=4); this increase was significantly attenuated in EV-YF1 and CDC-exo groups (171±9 and 171±15 µm$^2$, $p<0.05$ vs. Ang II group; respectively, n=4) (FIGS. 21A and 3B). Interstitial cardiac fibrosis was also increased by Ang II infusion (Ang II: 14±3% vs. Sham: 3.2±0.8% of area, $p<0.01$, n=3) while EV-YF1 and CDC-exo groups showed attenuated fibrosis (EV-YF1: 5.9±0.7%, $p<0.05$, n=3 and CDC-exo: 8.24±2%, p=0.137 vs. Ang II mice, n=3) (FIGS. 21C and 21D). Inflammation was determined by analyzing the expression of CD68, a marker of infiltrating inflammatory cells, as well as expression of pro-inflammatory cytokine genes Il6 and Il1b, in heart tissue. EV-YF1 and CDC-exo significantly reduced the expression of those markers in Ang II infused animals, providing further evidence of an anti-inflammatory effect (FIGS. 21E, 21F and 27).

These results show that EV-YF1 and CDC-exo attenuated the progression of cardiac hypertrophy. Cardiac mass assessed by echocardiography, heart-to-body weight ratio and expression of the fetal gene Anp were significantly decreased in EV-YF1 or CDC-exo groups compared to Ang II-infused mice. In most cases, these parameters reached values comparable to those in the sham group. These data are concordant with the observation of reduced cardiomyocyte size in mice exposed to EV-YF1 or CDC-exo, as well as attenuated Ang II-induced fibrosis.

EV-YF1 Inhibits Ang II Effects on Cardiomyocytes and Cardiac Fibroblasts

Figure 28A:
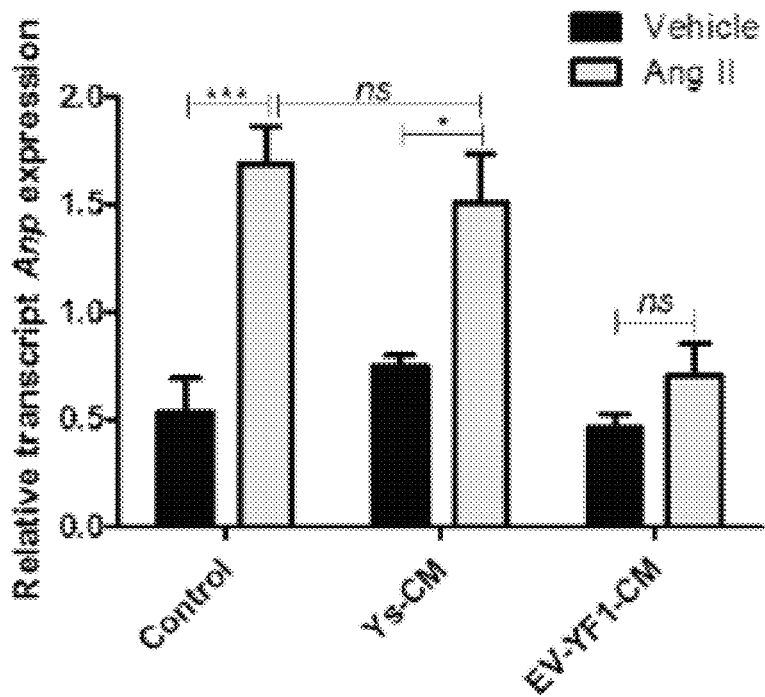
FIGS. 28A-28B. EV-YF1 and CDC-exo treatment inhibit Ang II effects on cardiomyocytes and cardiac fibroblasts.
Figure 28B:
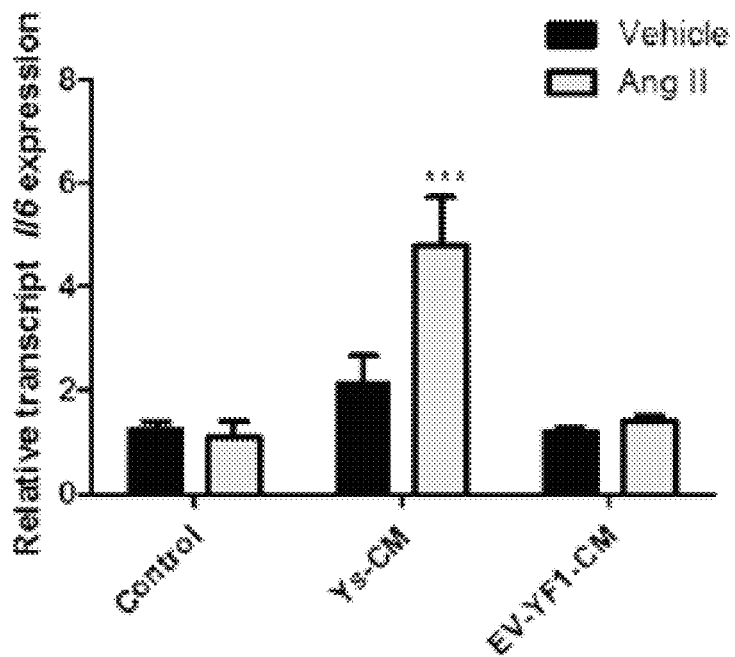

Tests were performed to see if EV-YF1 inhibits the effects of Ang II by modulating macrophage activity. Neonatal rat ventricular cardiomyocytes (NRVMs) were cultured for 24 hours with non-conditioned media (control) or media conditioned for 48 hours by bone marrow-derived macrophages (BMDMs) overexpressing Ys scrambled oligoribonucleotide (Ys-CM) or EV-YF1 (EV-YF1-CM) with or without Ang II (1 µM). In the presence of Ang II, Anp expression increased 3-fold ($p<0.001$) in NRVMs cultured with control media vs. no Ang II. A similar increase (2-fold, $p<0.05$) was observed in NRVMs cultured in Ys-CM in the presence of Ang II. On the contrary, the increase in Anp expression induced by Ang II was significantly blunted in NRVMs cultured in EV-YF1-CM (FIG. 28A). These data are consistent with the notion that, upon overexpression of EV-YF1, BMDMs secrete cytokines, including IL-10, that inhibit the effect of Ang II on NRVM Anp expression. The role of EV-YF1 on Ang II inhibitory effect via macrophages was also tested in neonatal cardiac fibroblasts (neoCFs). NeoCFs were cultured for 16 hours with BMDM media (control) or media conditioned over 72 hours by BMDMs overexpressing Ys (Ys-CM) or EV-YF1 (EV-YF1-CM) with or without Ang II (100 nM). Adult cardiac fibroblasts (CFs) produce low levels of IL-6, which increase in the presence of Ang II or in co-culture with macrophages. In this experiment, Il6 expression was not increased in the presence of Ys-CM, EV-YF1-CM or Ang II alone, possibly due to the use of neonatal vs adult CFs. However, a significant increase (2.2-fold, $p<0.001$) in Il6 expression was observed when neoCFs were cultured with conditioned media from BMDMs overexpressing Ys (Ys-CM) with Ang II. In contrast, when neoCFs were cultured with media from BMDMs overexpressing EV-YF1 (EV-YF1-CM) with Ang II, Il6 expression was not different from the conditioned media without Ang II (FIG. 28B). Direct overexpression of EV-YF1 in neoCFs exposed to Ang II did not change 16 expression. Thus, EV-YF1 acts on BMDMs to inhibit Il6 induction by Ang II in neoCFs.

EV-YF1 and CDC-Exo Decrease Ang II-Induced Kidney Injury

Figure 22A:
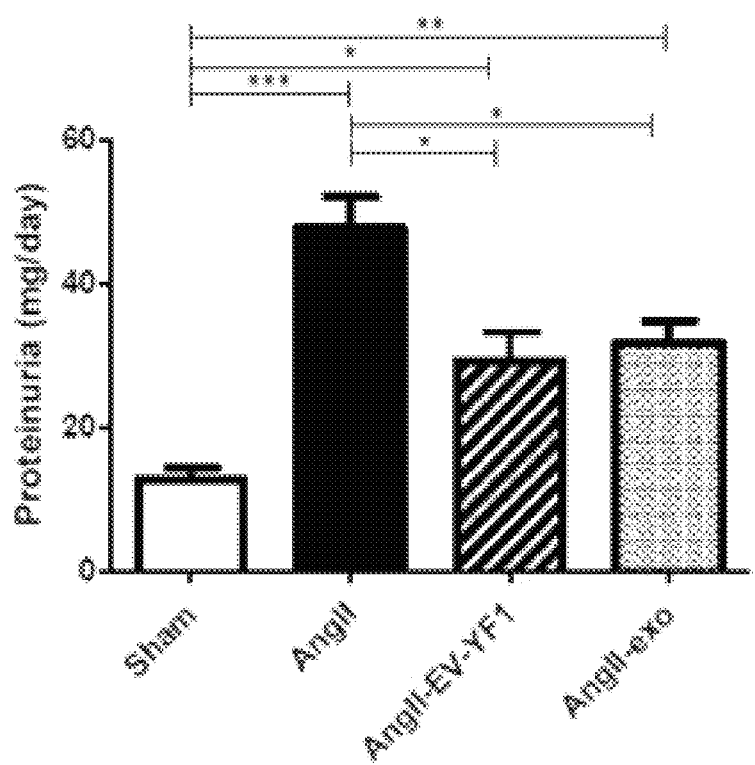
FIGS. 22A-22E. EV-YF1 and CDC-exo treatment decrease Ang II-induced kidney dysfunction. Proteinuria in FIG. 22A and NGAL levels in kidney in FIG. 22B as determined by ELISA. Graphs depict the mean±SEM; n=4 animals/group.
Figure 22B:
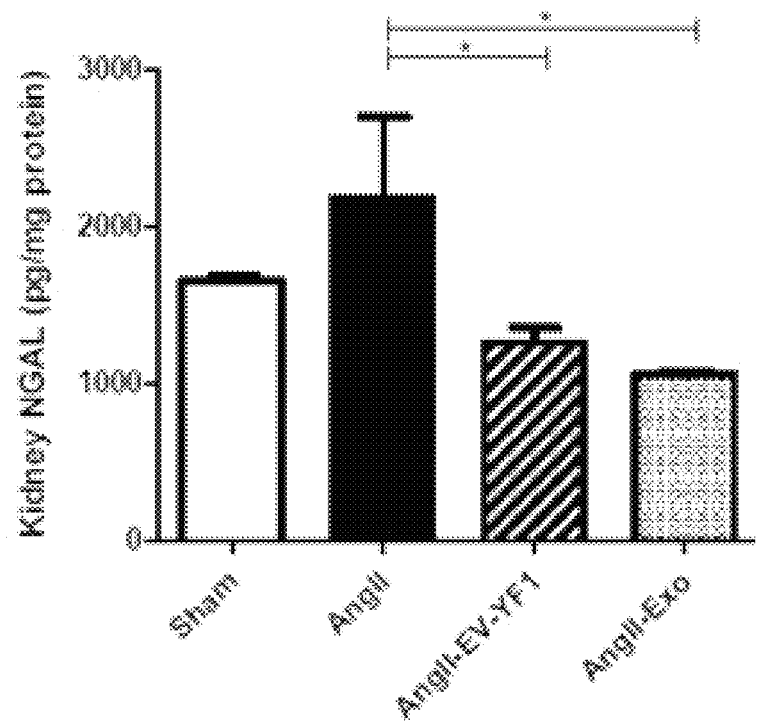

Chronic activation of the renin-angiotensin system (RAS) increases blood pressure, and leads to progressive kidney injury and proteinuria. Accordingly, an analysis was performed to see whether EV-YF1 or CDC-exo exert renoprotective effects. Proteinuria was significantly increased after 4 weeks of Ang II infusion compared to saline infusion (Sham: 13±1 vs. Ang II: 48±4 mg/day, $p<0.001$, n=4). In EV-YF1 and CDC-exo groups, proteinuria was decreased compared to Ang II group (29±4 and 31±3 mg/day, $p<0.05$, n=4; respectively; FIG. 22A). Kidney levels of neutrophil gelatinase associated lipocalin (NGAL), a biomarker of renal injury, tended to increase after 4 weeks of Ang II infusion compared to sham, while EV-YF1 and CDC-exo groups showed significant decreases compared to Ang II-infused group (Ang II: 2184±518 vs. EV-YF1: 1261±94 and CDC-exo: 1058±25 pg/mg total kidney protein, $p<0.05$, n=4). These data reveal that EV-YF1 and CDC-exo ameliorate the renal injury induced by Ang II infusion (FIG. 22B).

Figure 22C:
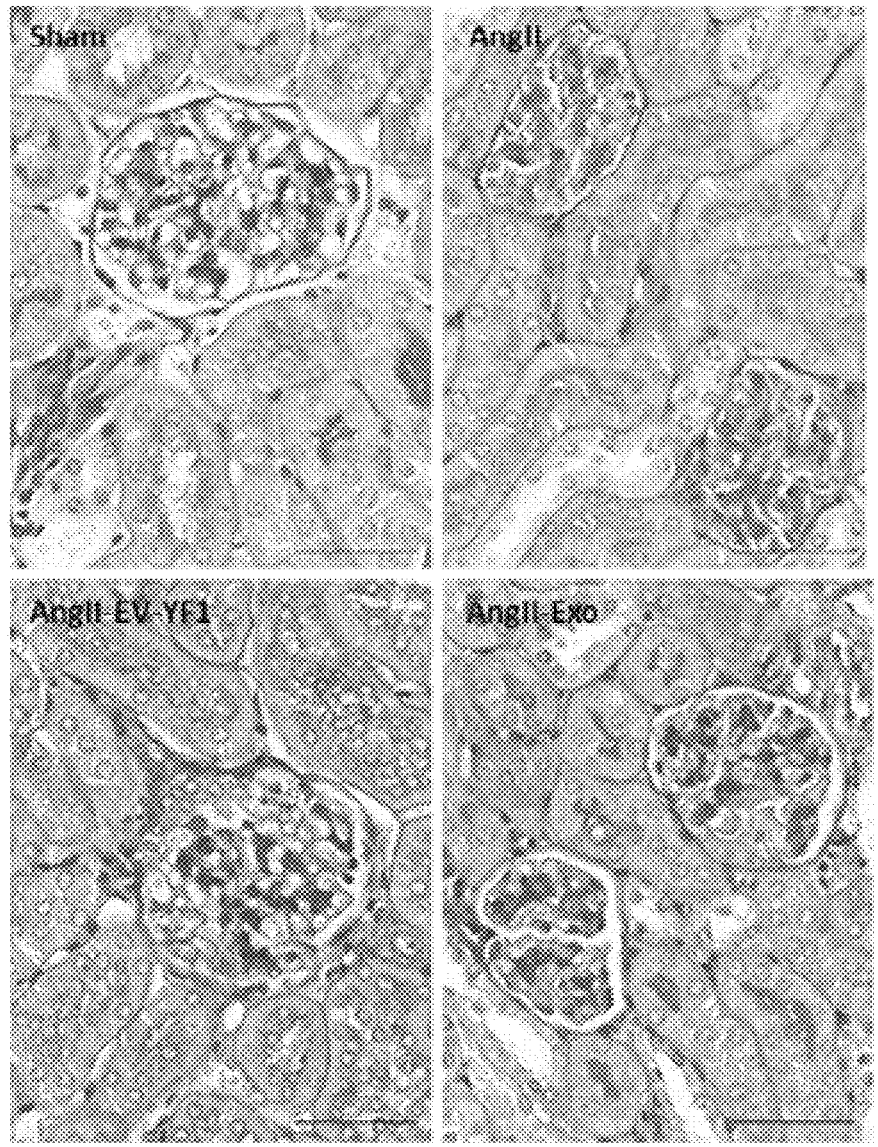
Figure 22D:
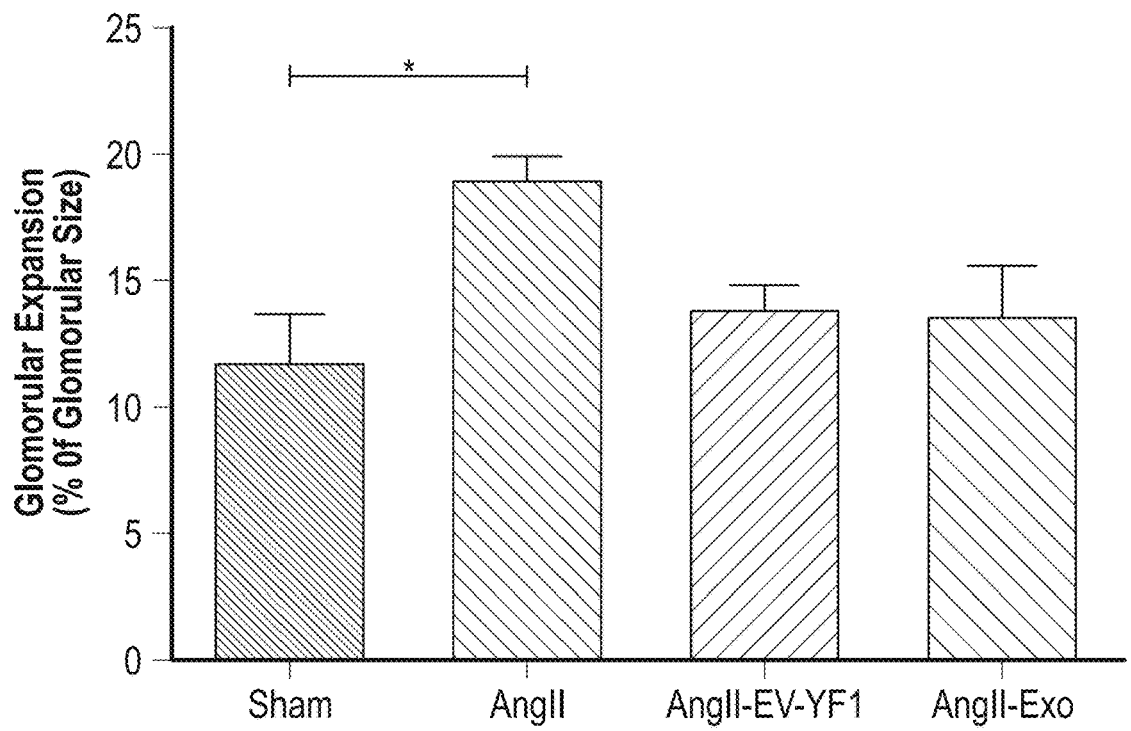
Figure 22E:
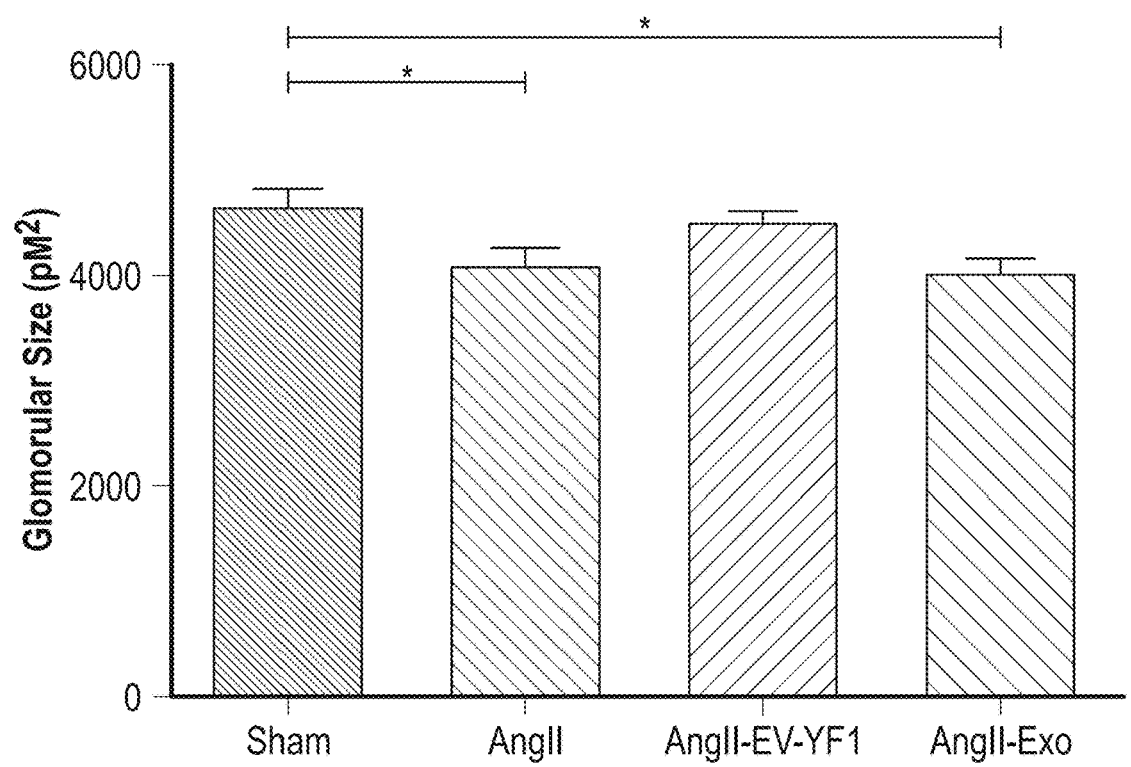
Figure 29:
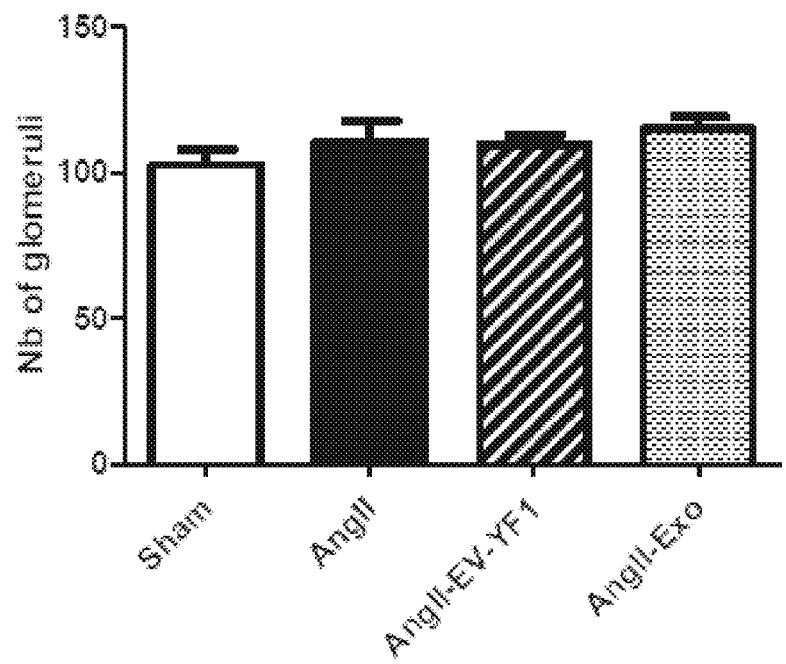
FIG. 29. Glomeruli number within renal sections.

To quantify glomerular injury, structural changes were evaluated histologically using periodic acid-Schiff staining. Mesangial expansion was significantly higher in Ang II-infused mice compared to control mice (Sham: 12±2 vs. Ang II: 19±1% of total glomerular area, $p<0.05$; n=5; FIGS. 22C and 22D). On the other hand, both EV-YF1 and CDC-exo groups showed mesangial areas that were indistinguishable from those in control mice. Glomerular size was significantly decreased in Ang II-infused mice compared to control mice (Sham: 4692±151 vs. Ang II: 4111±176 µm², $p<0.05$, n=5, FIG. 22E). In EV-YF1 group, glomerular size was increased, reaching values comparable to sham (4540±93 µm²). No restoration of glomerular size was observed in CDC-exo group, and no change in the number of glomeruli was observed in any experimental group (FIG. 29).

These data show that EV-YF1 or CDC-exo decrease tubulointerstitial fibrosis, mesangial expansion and proteinuria. In addition, EV-YF1 or CDC-exo decreased expression levels of NGAL, a biomarker of renal injury used in patients with HF to estimate the risk of worsening renal function.

EV-YF1 and CDC-Exo Decrease Ang II-Induced Renal Inflammation and Fibrosis

Figure 23A:
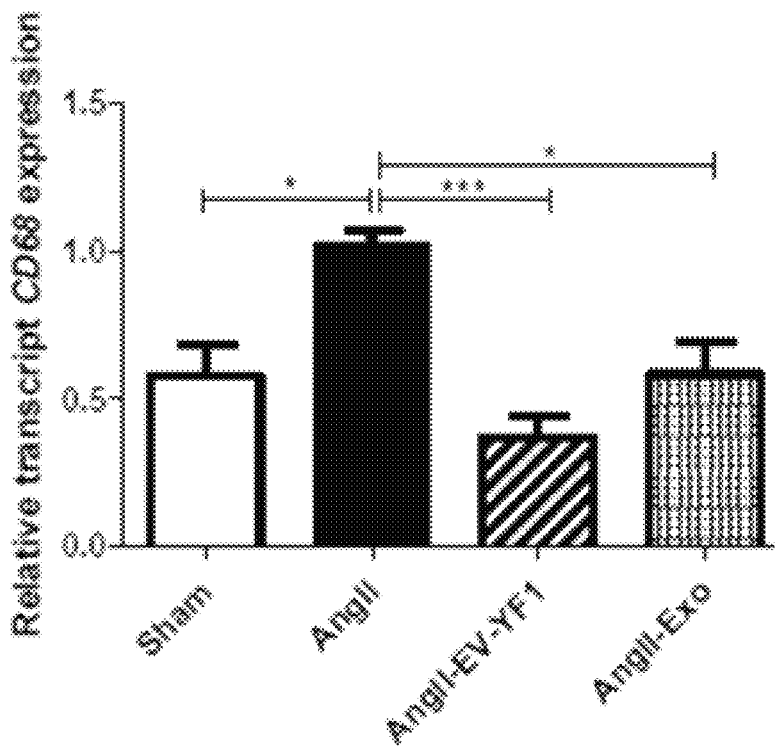
FIGS. 23A-23E. EV-YF1 and CDC-exo treatment decrease Ang II-induced kidney inflammation and fibrosis.

Ang II-induced hypertension is associated with an increase of infiltrating macrophages in the kidney and a consequent elevation of intrarenal cytokines, which facilitates the progression of hypertension and kidney injury. To test whether EV-YF1 or CDC-exo could attenuate Ang II-induced inflammation, expression of CD68, a marker of infiltrating cells, was analyzed in renal tissue. CD68 expression was decreased in EV-YF1 and CDC-exo groups compared to Ang II group (FIG. 23A).

Figure 23B:
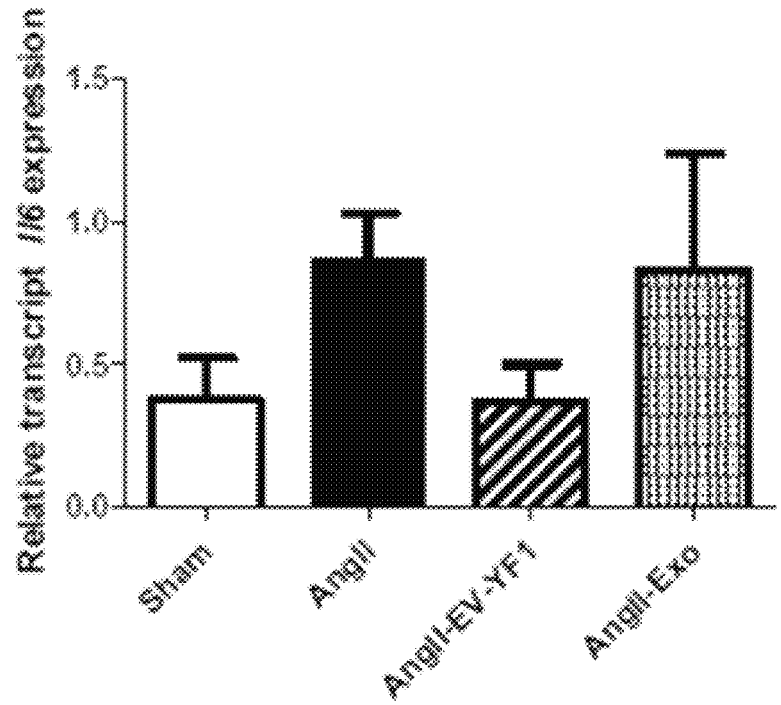
Figure 23C:
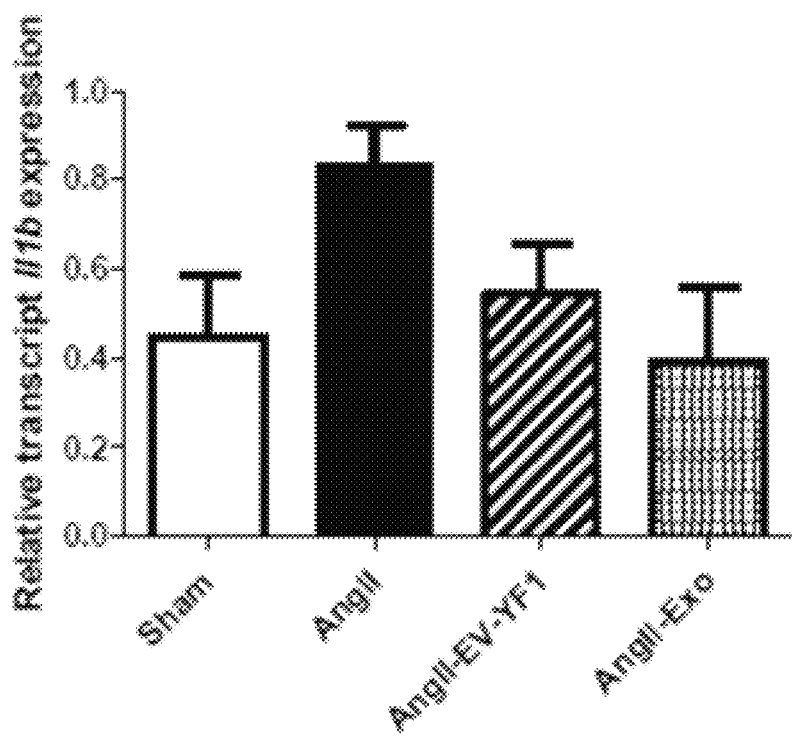

Expression levels of pro-inflammatory cytokines Il6 and Il1b were also analyzed. Here, the differences were not significant, but a trend was observed in favor of a decrease in Il1b expression in both intervention groups compared to Ang II alone, along with a tendency for EV-YF1 to decrease/ 16 expression (FIGS. 23B and 23C).

Figure 23D:
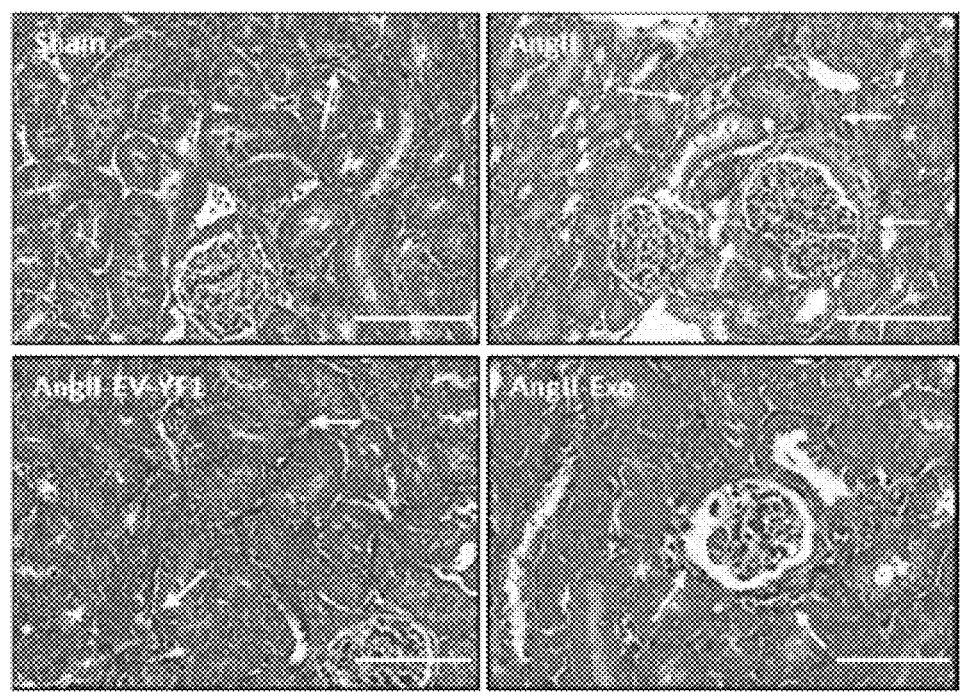
Figure 23E:
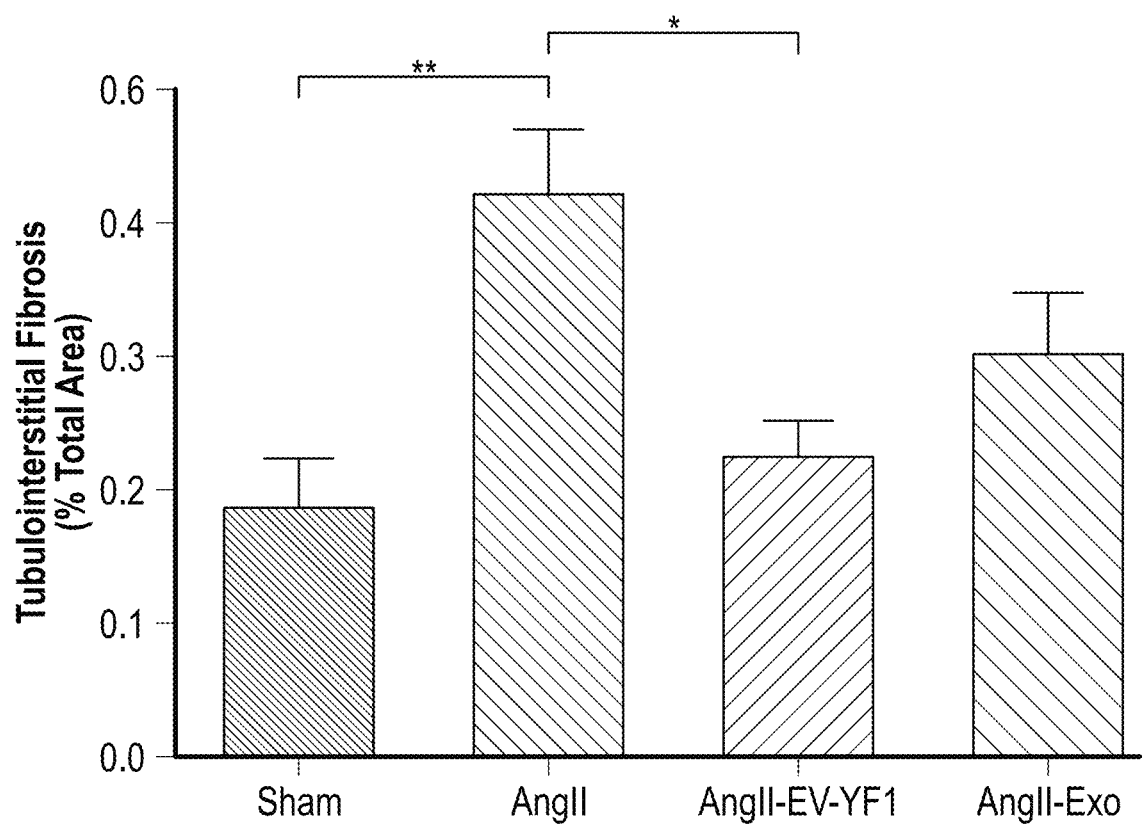

Further assessment of renal injury was performed by Masson's trichrome staining to evaluate fibrosis. Renal cortices revealed increased tubulointerstitial fibrosis in Ang II-infused mice compared to controls (Sham: 0.19±0.03% vs. Ang II: 0.4±0.1% of total cortical area; $p<0.01$; n=5; FIGS. 23D and 23E). EV-YF1 significantly decreased renal interstitial fibrosis (0.23±0.03%, $p<0.05$ compared to Ang II group). CDC-exo also decreased renal fibrosis (0.30±0.04%, $p<0.09$), albeit not significantly (FIGS. 23D and 23E).

EV-YF1 and CDC-Exo Modulate IL-10 Expression

Figure 24A:
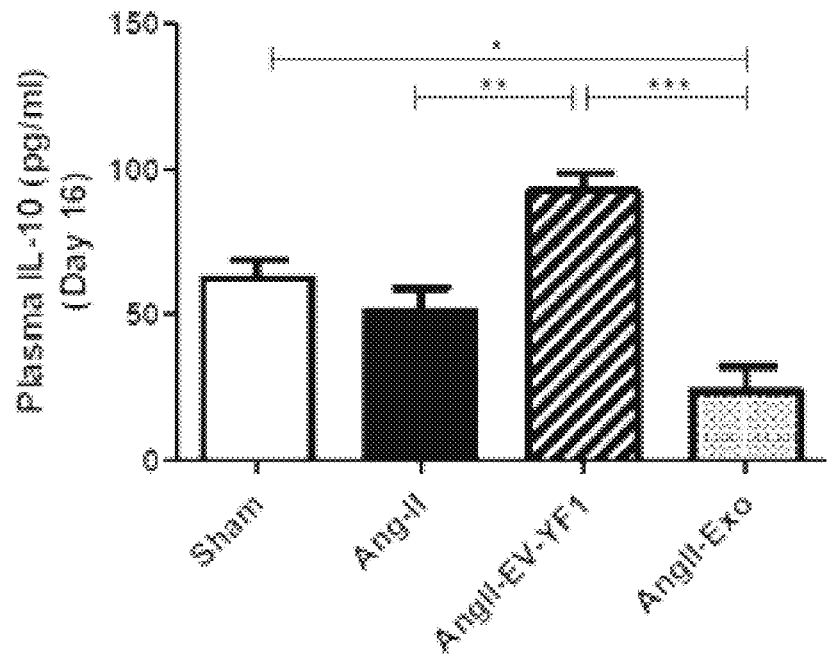
FIGS. 24A-24E. EV-YF1 and CDC-exo modulate IL-10 expression.

To determine whether EV-YF1 attenuates the effect of Ang II on cardiac hypertrophy by modulating IL-10 secretion, IL-10 levels were measured in plasma of mice infused with Ang II 24 hours after the second injection of EV-YF1 or CDC-exo (day 16). At this time point, no differences in IL-10 levels were observed between mice infused with Ang II or saline. However, EV-YF1 did increase IL-10 levels relative to saline injection (1.8-fold, $p<0.01$, n=4) (FIG. 24A).

Figure 24B:
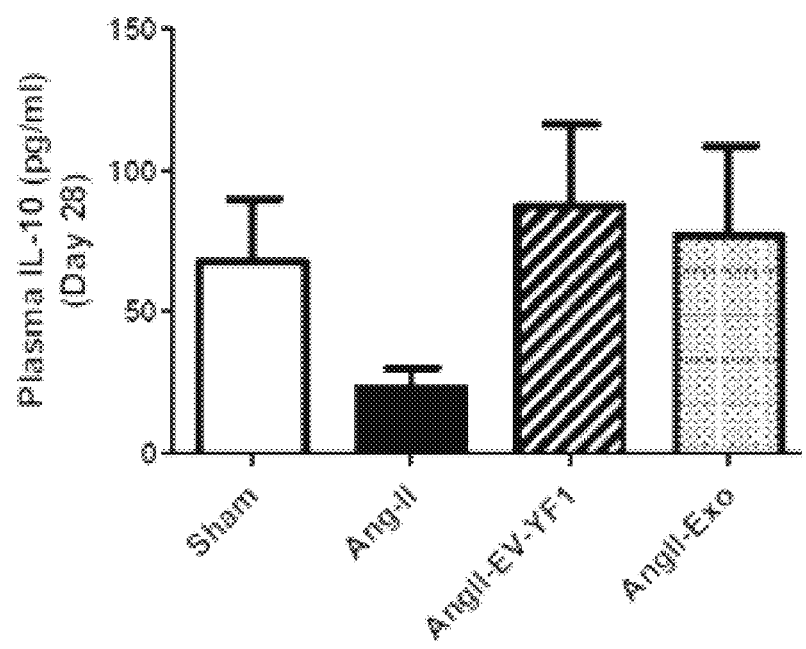

On the contrary, the second injection of CDC-exo seemed to lower plasma IL-10 levels compared to sham group (2.3-fold, $p<0.05$, n=4). At the end of the Ang II infusion (day 28), the profile of plasma IL-10 changed: IL-10 levels in the Ang II-infused group decreased modestly compared to sham, while those in EV-YF1 and CDC-exo groups were comparable to sham group (FIG. 24B).

Figure 24C:
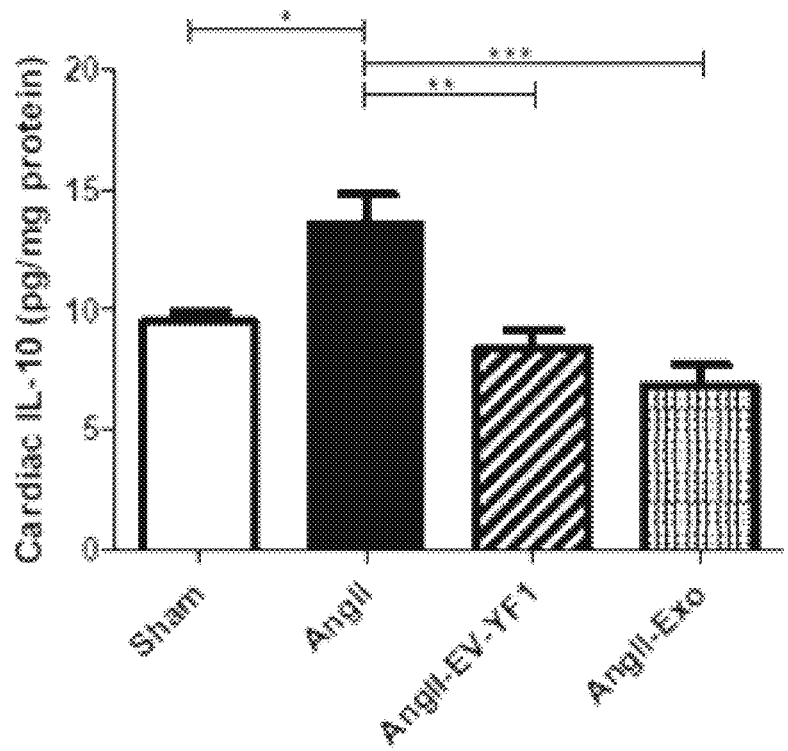
Figure 24D:
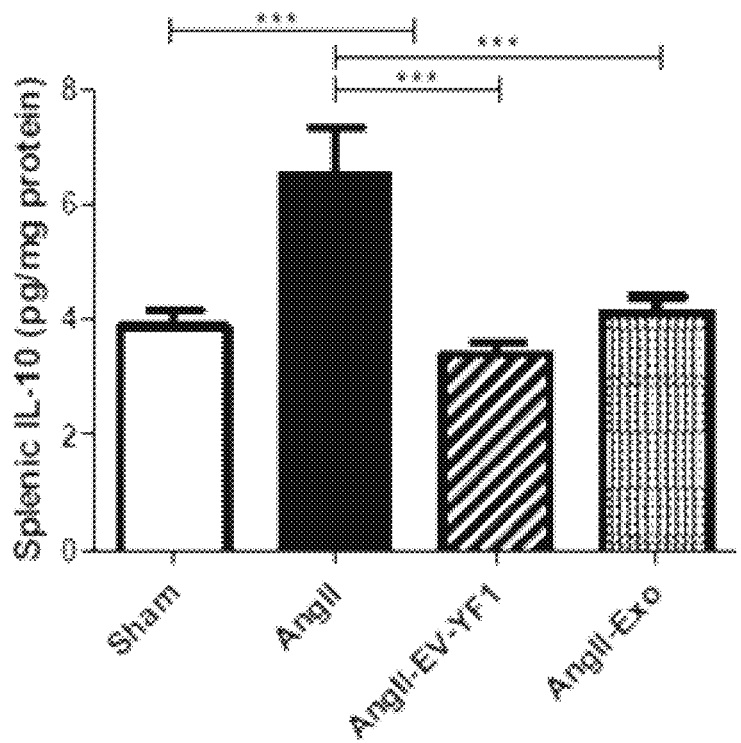

At the end of the study (day 28), tissue IL-10 levels in heart, spleen and kidney were analyzed (FIG. 24CE). Cardiac IL-10 levels were significantly higher in Ang II-infused group than in sham (13.54±1.285 (Ang II) vs. 9.496±0.457 pg/mg protein (Sham), p<0.05, n=6-8). In contrast, levels of cardiac IL-10 in EV-YF1 and CDC-exo groups were similar to those in the sham group (FIG. 24C). The same profile was observed for IL-10 levels in spleen (FIG. 24D).

Figure 24E:
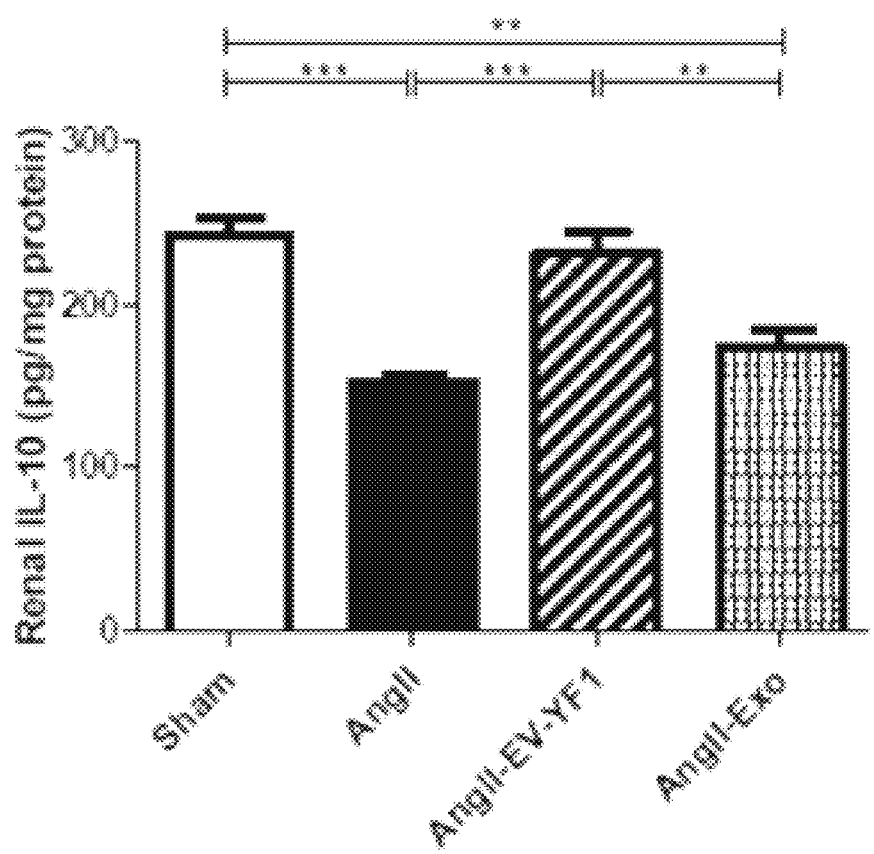

To establish whether the improved renal function was associated with higher levels of IL-10 in the kidney, IL-10 levels were measured in all experimental groups. A substantial decrease in IL-10 was observed in Ang II-infused group compared to sham (152±3 (Ang II) vs. 243±10 pg/mg protein (Sham), p<0.001, n=4). The EV-YF1 group showed similar levels to those in the sham group, significantly different from Ang II group (232±12 pg/mg protein, p<0.001, n=4), while the CDC-exo group showed no difference with Ang II-infused group (FIG. 24E).

Figure 30:
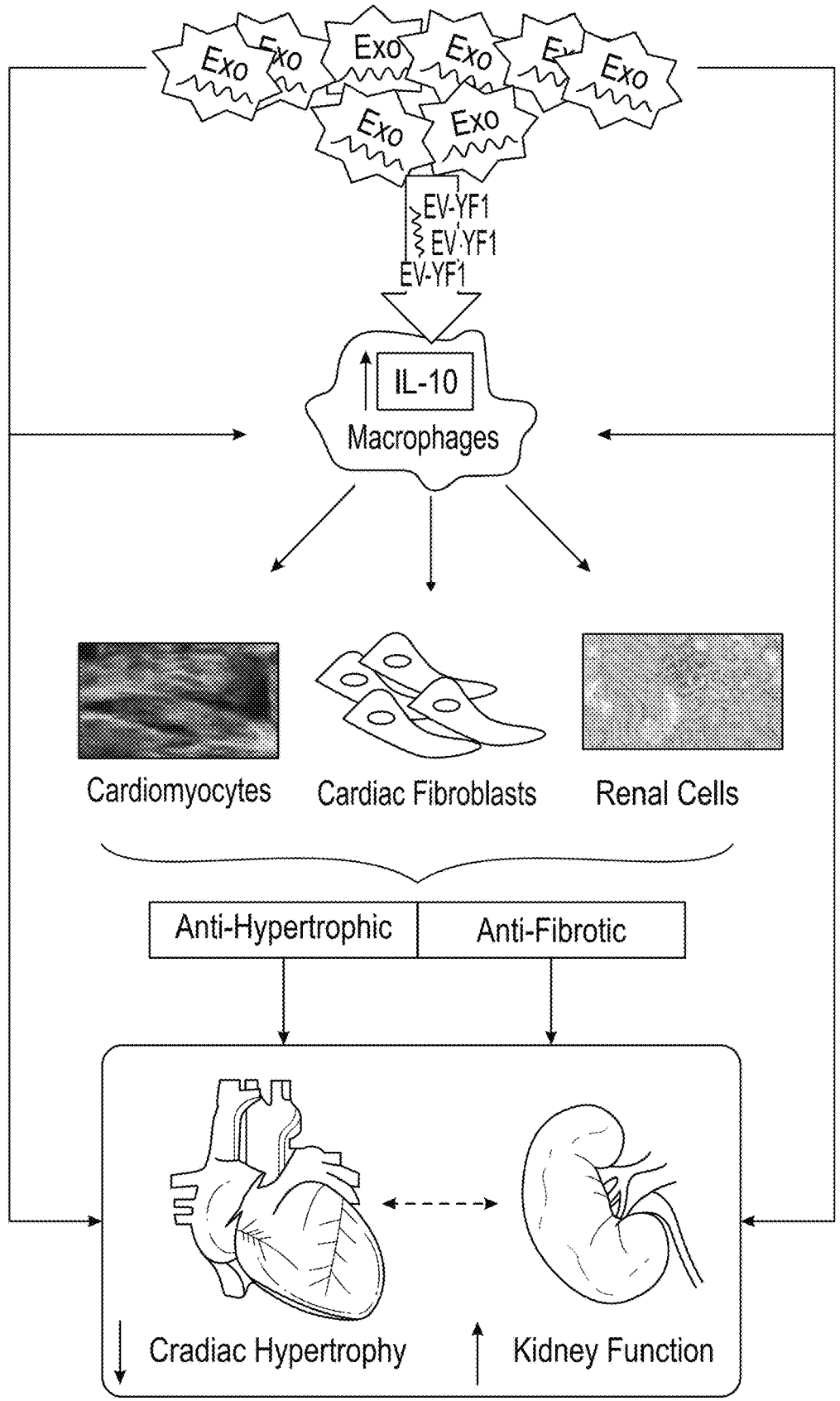
FIG. 30. EV-YF1, via modulation of IL-10, mediates beneficial effects of CDC-exo on cardiac hypertrophy and kidney function.
Figure 31:
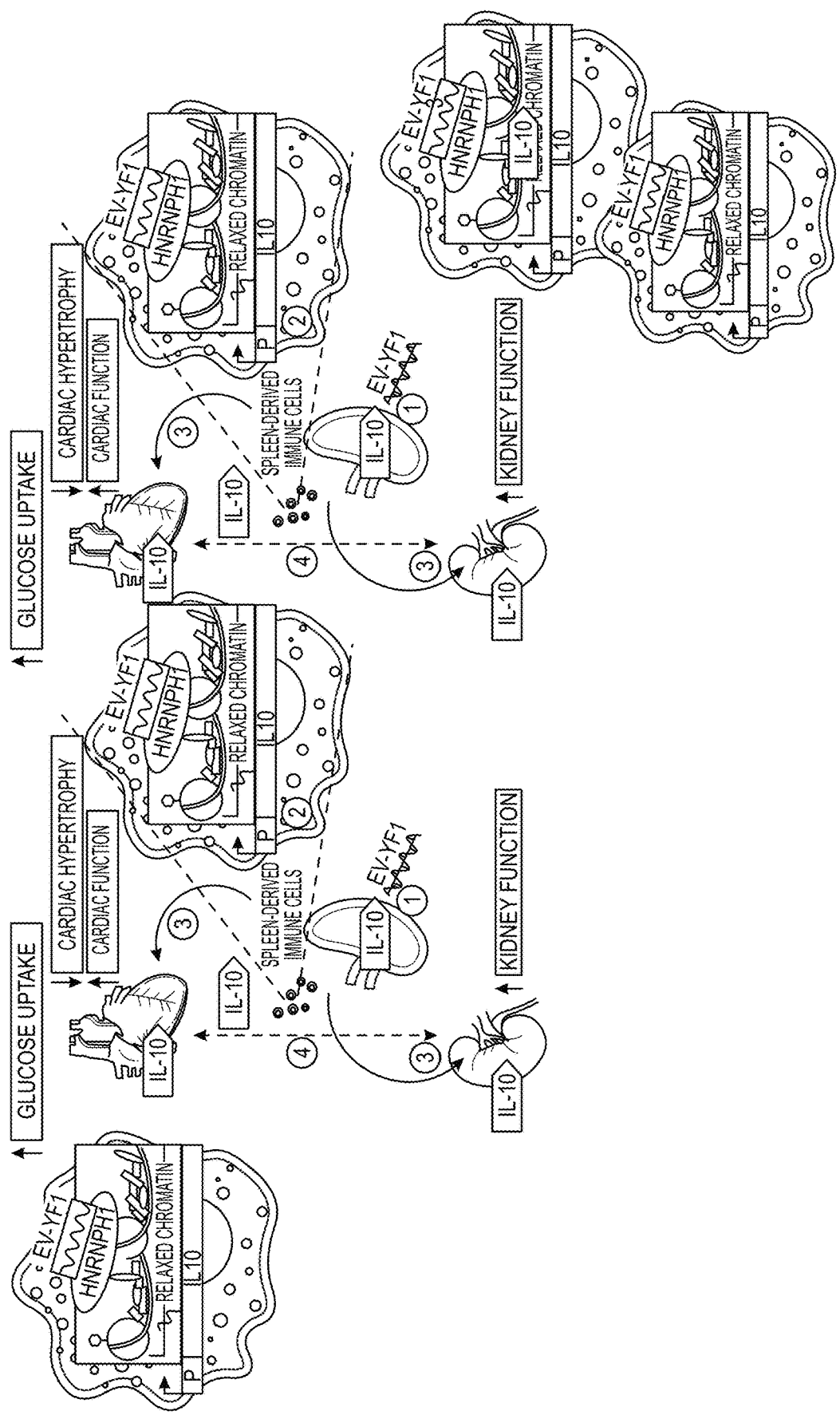
FIG. 31. Hypothesis of EV-YF1 mechanism of action in diabetic model. Without being bound by theory, several embodiments disclosed herein may activate one or more of the following biochemical pathways (1) EV-YF1 induces IL-10 expression in splenic immune cells (2) via an epigenetic mechanism by interaction with hnRNPH1. (3) Under diabetic conditions, splenic immune cells home to injured organs like heart and kidney to counteract the pro-inflammatory balance detrimental to these organs. Consequently, myocardium structure and function as well as kidney function are ameliorated. Beneficial effects on these 2 organs attenuate cardiorenal syndromes.
Figure 33A:
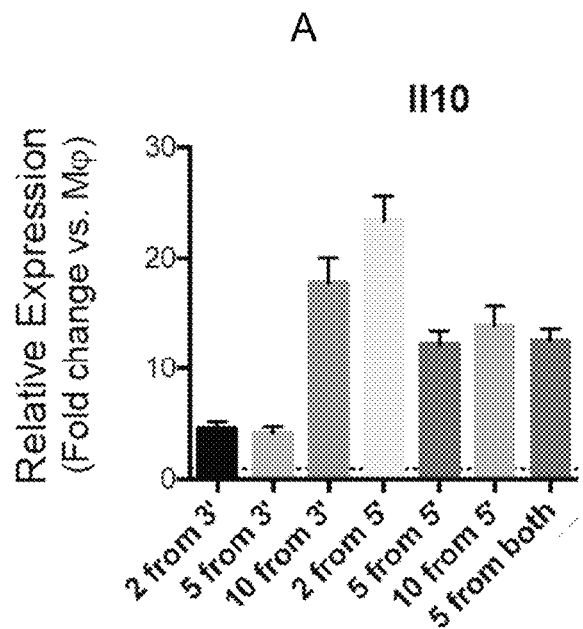
FIGS. 33A-33C show that distinct truncated forms of EV-YF1 according to the present invention elicit distinct gene expression changes in macrophages. Synthetic RNAs were transfected (DHARMAFECT, GE) into mouse bone marrow-derived macrophages. Gene expression changes of Il10 and Il1b were assessed by qPCR and expressed relative to untreated macrophages.
Figure 33B:
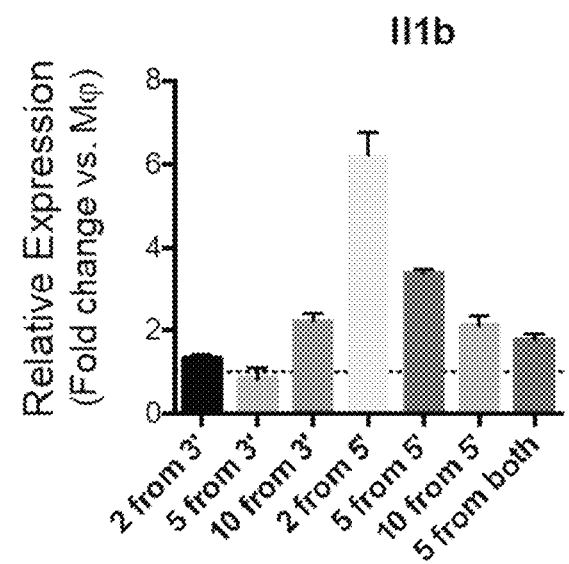
Figure 33C:
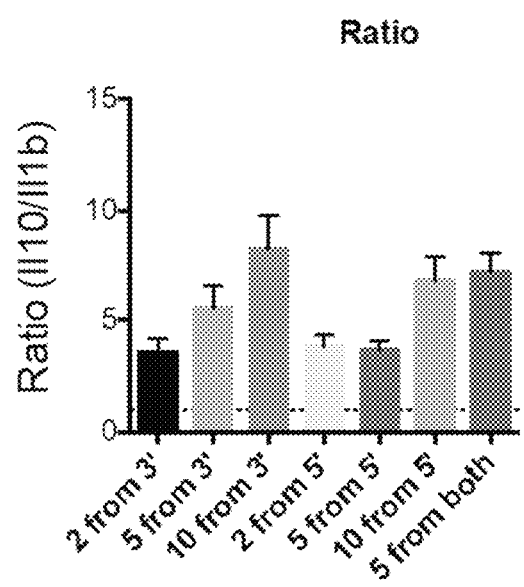
Figure 35A:
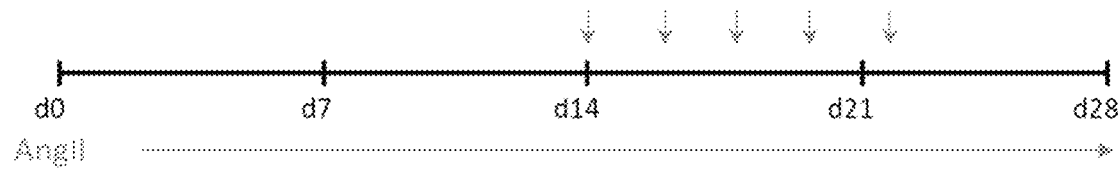
FIGS. 35A-35B shows that distinct truncated EV-YF1 fragments according to the present invention prevent cardiomyocyte hypertrophy.
Figure 35B:
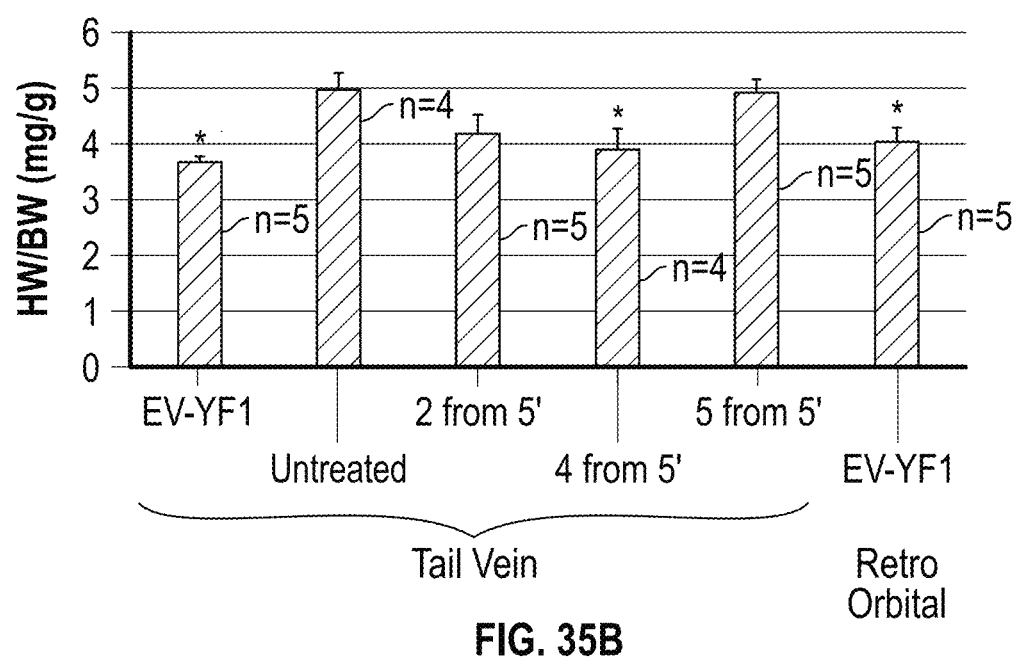
Figure 36:
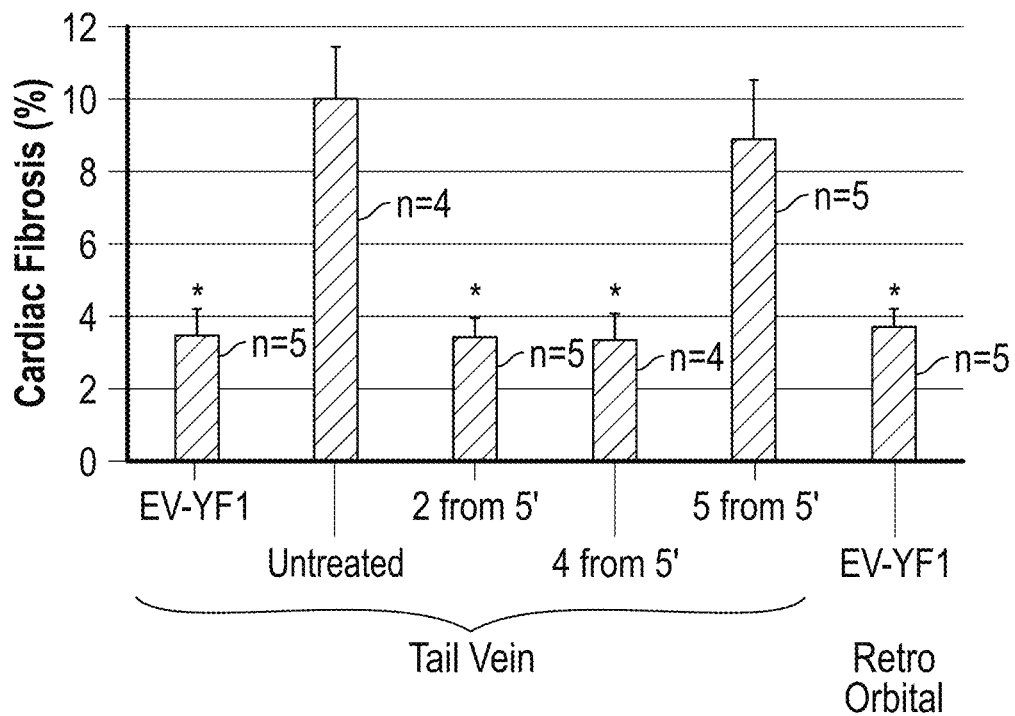
FIG. 36 shows that distinct truncated EV-YF1 fragments according to the present invention prevent cardiac fibrosis. Percentage of cardiac fibrosis in each treatment group following 4 weeks of continuous AngII infusion. Hearts were excised and stained with Masson's Trichrome to determine the percent of fibrosis per heart (n=4-5/group). Data presented as mean+/−SD. Statistical significance was determined using 1-way ANOVA followed by Tukey's multiple comparisons test. *p<0.05, relative to untreated.
Figure 37A:
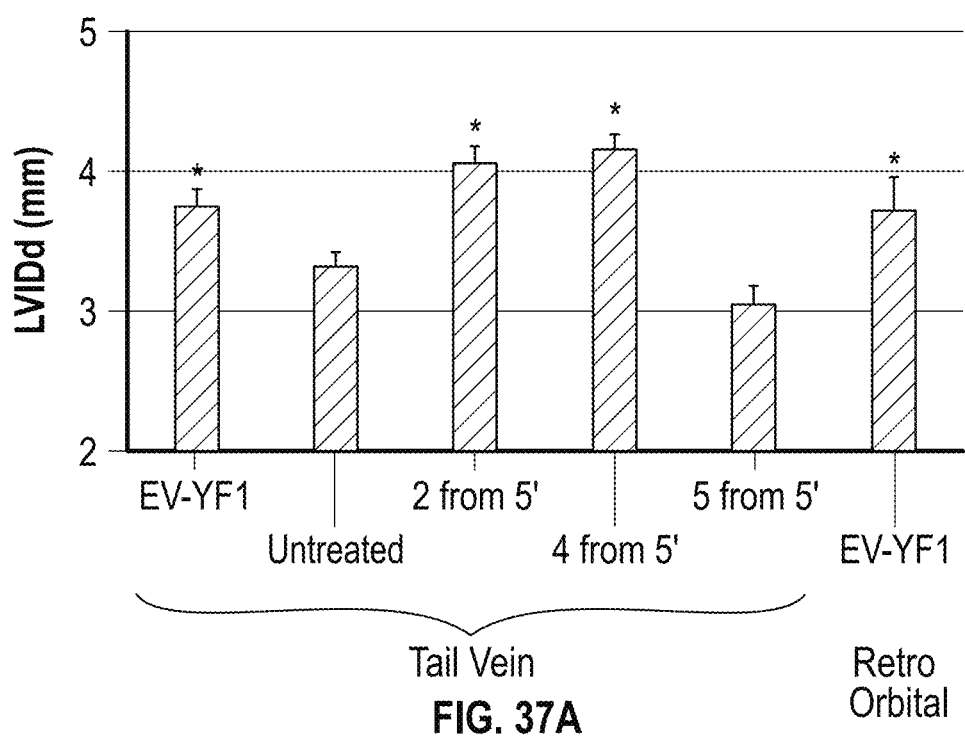
FIGS. 37A-37B show that distinct truncated EV-YF1 fragments according to the present invention preserve cardiac morphology. Cardiac morphology (LVIDd and LVPWd.
Figure 37B:
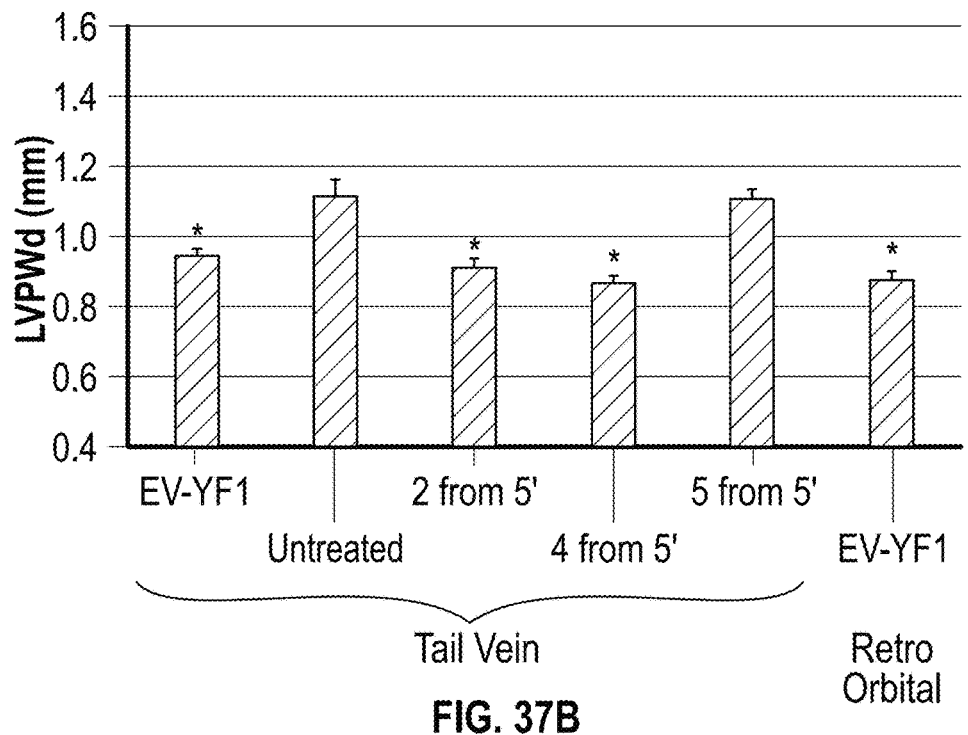
Figure 38A:
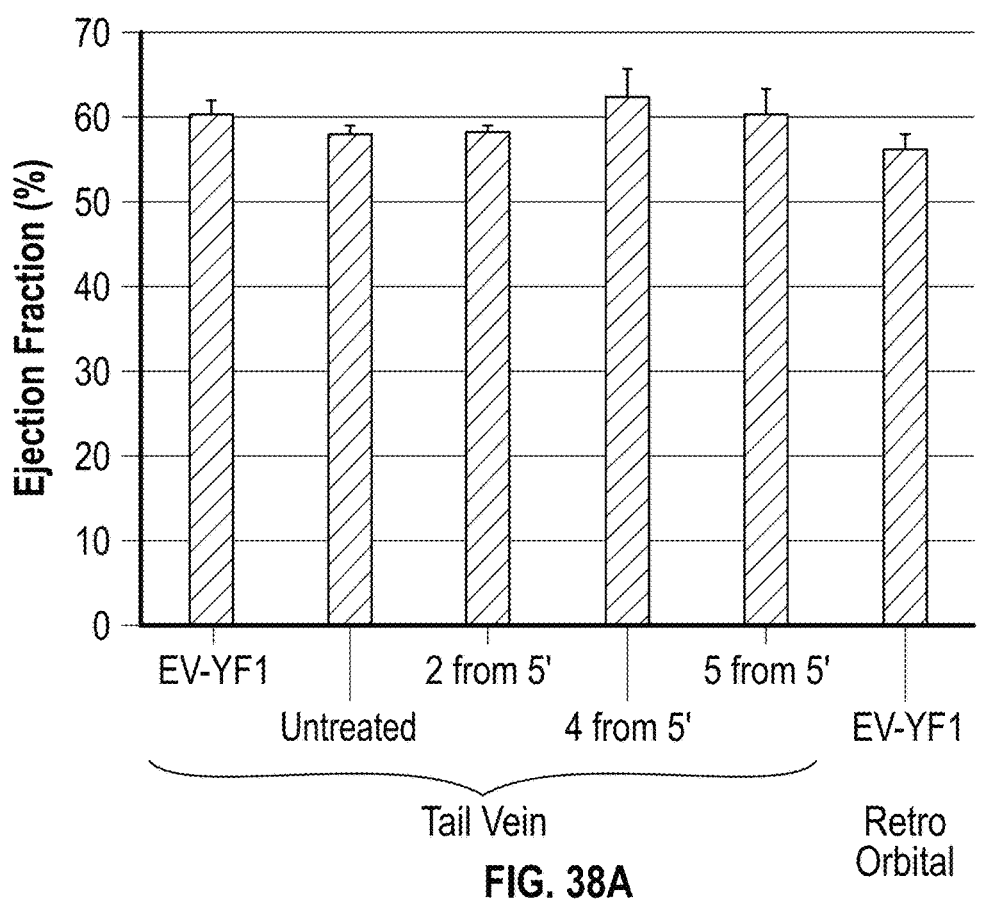
FIGS. 38A-38C show that distinct truncated EV-YF1 fragments according to the present invention prevent diastolic dysfunction. Echocardiographic measurements reveal no change in ejection fraction between groups (FIG. 38A), but distinct Y RNA fragments (2 from 5' and 5 from 5') preserve E/A (FIG. 38B) and E/e' (FIG. 38C) ratios after 28 days of AngII infusion. Data presented as mean+/−SD. Statistical significance was determined using 1-way ANOVA followed by Tukey's multiple comparisons test.*p<0.05, relative to untreated.
Figure 38B:
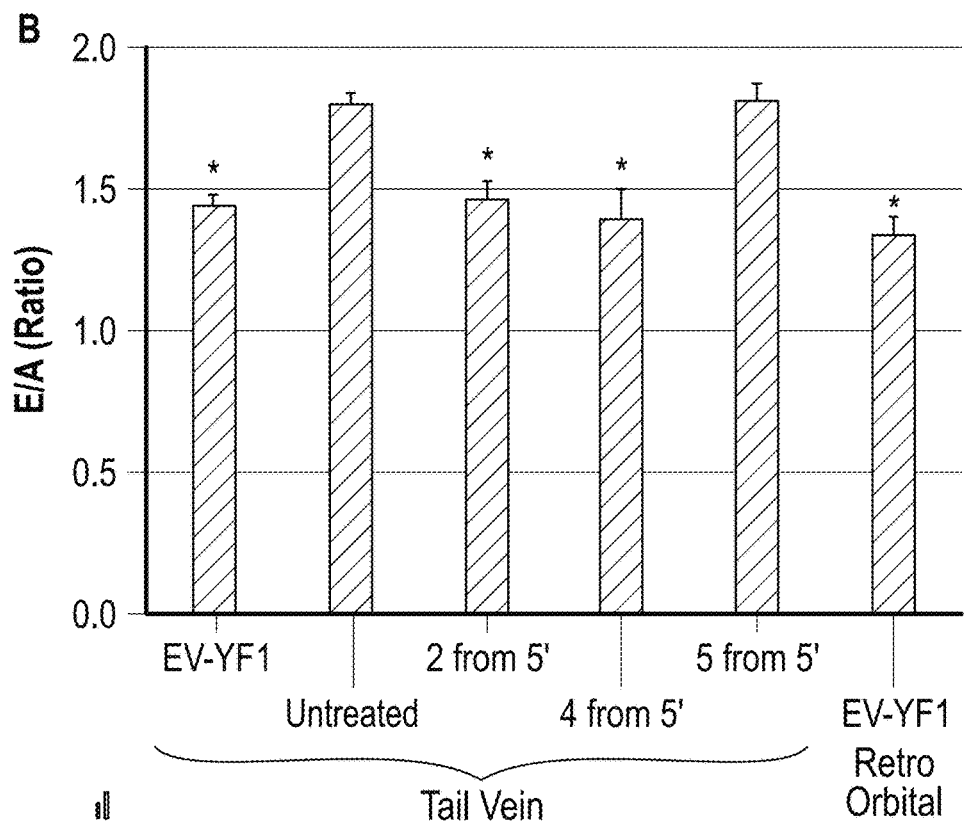
Figure 38C:
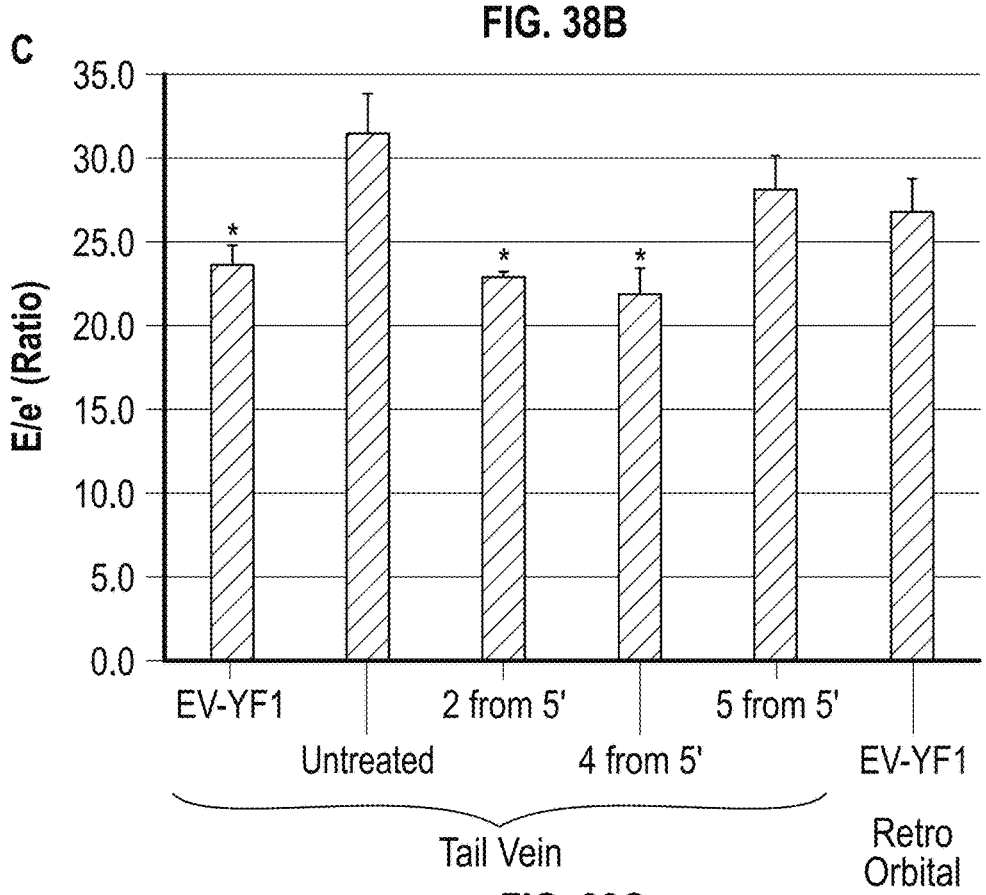

EV-YF1 and CDC-exo re-established normal levels of IL-10 in heart, kidney and spleen after Ang II infusion. Some of the benefits were associated with expected changes in IL-10. High levels of plasma IL-10, observed after the first injections of EV-YF1, likely arose from splenic macrophages homing to sites of injuries in heart and kidney, and counterbalanced the progression of the inflammatory state in these and other organs (FIG. 30). In contrast, during Ang II infusion, the persistent cardiac inflammation likely requires a permanent production of IL-10 as a compensatory effect that explains the high levels of IL-10 in heart and splenic tissues in Ang II-infused animals.

Overall, EV-YF1 and CDC-exo each attenuated LV remodeling and improved kidney function in a murine hypertensive model. EV-YF1 and CDC-exo are therefore, each likely to attenuate LV remodeling and improve kidney function in humans or other animals with hypertension, according to several embodiments disclosed herein. Because of the similar effects on IL-10 mRNA expression induced by EV-YF1 and EV-YF1-U16 (see FIG. 9), according to several embodiments, the same beneficial cardiorenal protective effects as seen herein with EV-YF1 are seen with EV-YF1-U16.

Example 3

Figure 25A:
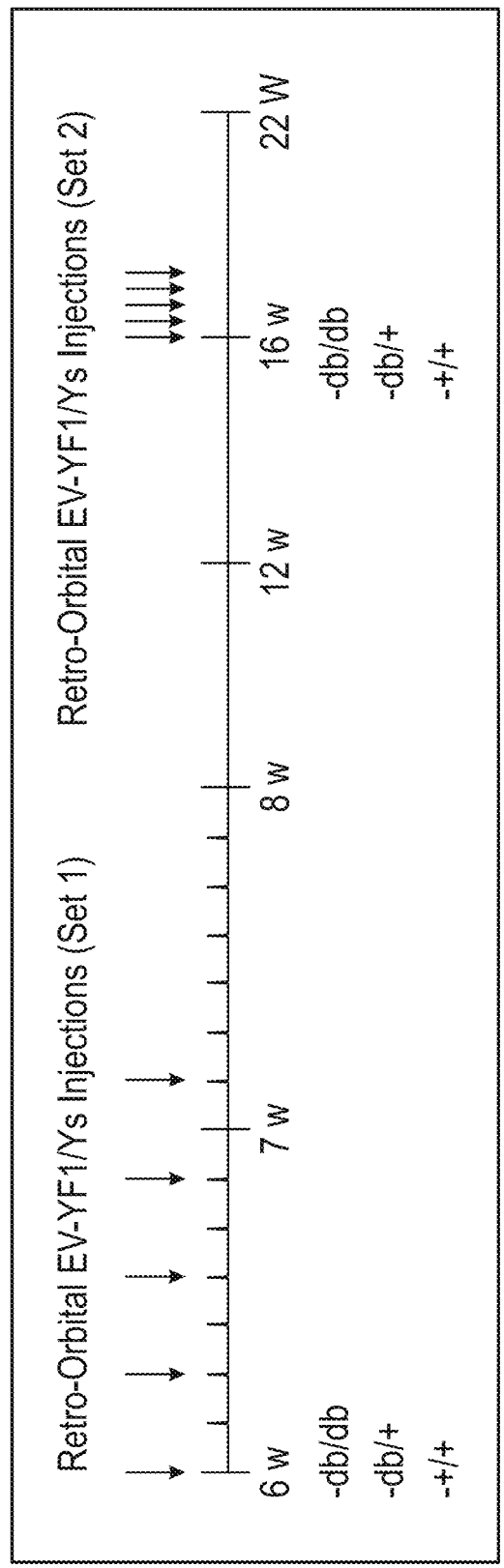
FIGS. 25A-25C. EV-YF1 ameliorates glucose tolerance and modulates IL-10 expression.
Figure 25B:
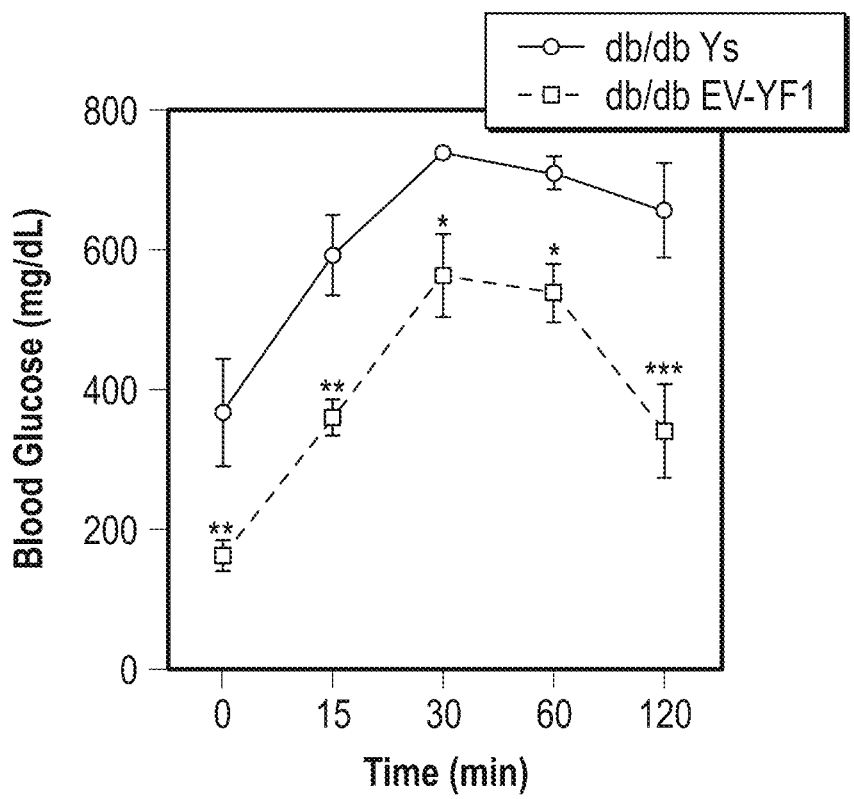
Figure 25C:
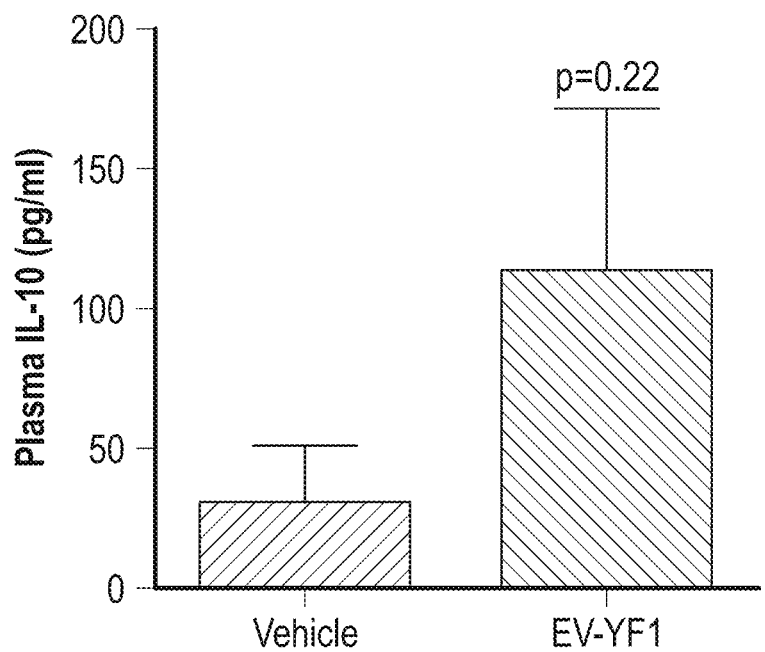

A test was performed to see whether EV-YF1 could exert beneficial effects on metabolic syndrome associated with obesity. Db/db mice (a strain of obese mice with diabetes) were given retro-orbital injections of EV-YF1 or a scramble control oligonucleotide (Ys) starting at six weeks of age (FIG. 25A). At eight weeks of age, glucose tolerance tests were performed, and plasma levels of IL-10 were measured. EV-YF1 significantly decreased blood glucose levels before and in response to glucose challenge (FIG. 25B). These data indicate that administering EV-YF1 to obese, diabetic subjects results in improved metabolic function and decreased metabolic dysfunction in the subjects. These benefits are associated with a trend for enhanced IL-10 secretion (FIG. 25C). Because of the similar effects on IL10 mRNA expression induced by EV-YF1 and EV-YF1-U16 (see FIG. 9), according to several embodiments, the same beneficial metabolic effects as seen herein with EV-YF1 are seen with EV-YF1-U16.

The compositions and related methods set forth in further detail elsewhere herein describe certain actions taken by a practitioner; however, it should be understood that they can also include the instruction of those actions by another party. Thus, actions such as "administering an oligonucleotide to a subject" include "instructing the administration of an oligonucleotide to a subject."

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede or take precedence over any such contradictory material. U.S. Application Publication No. 2015/0203844 A1 and International Publication No. WO2018/195210 disclose EVs and are incorporated by reference herein in their entireties.

What is claimed is:

1. A method for treating a subject suffering from hypertension, comprising:
   administering an exosome-free composition comprising an oligonucleotide to a subject with hypertension;
   wherein the oligonucleotide comprises SEQ ID NO: 5 or a truncated form thereof having a truncation of up to 10 nucleotides from the 3' end of SEQ ID NO: 5 and/or up to 5 nucleotides from the 5' end of SEQ ID NO: 5;
   wherein the oligonucleotide increases the amount of plasma IL-10 protein, induces macrophage IL-10 gene expression, attenuates one or more of cardiac CD68 and IL1b gene expression, and/or attenuates one or more of renal CD68, Il6 and Il1b gene expression; and
   wherein the increase in the amount of plasma IL-10 protein, induction of macrophage IL-10 gene expression, attenuation of one or more of cardiac CD68 and IL1b gene expression, and/or attenuation of one or more of renal CD68, Il6 and Il1b gene expression, induces a therapeutic effect on the subject's heart and/or kidneys.

2. The method of claim 1, wherein the subject's heart is hypertrophic prior to treating the subject.

3. The method of claim 1, wherein administration of the oligonucleotide decreases cardiac hypertrophy in the subject.

4. The method of claim 1, wherein the subject's heart is fibrotic prior to treating the subject.

5. The method of claim 1, wherein administration of the oligonucleotide decreases cardiac fibrosis in the subject.

6. The method of claim 1, wherein the subject's heart is inflamed prior to treating the subject.

7. The method of claim 1, wherein administration of the oligonucleotide decreases inflammation in the subject's heart.

8. The method of claim 1, wherein at least one of the subject's kidneys is injured or dysfunctional prior to treating the subject.

9. The method of claim 1, wherein administration of the oligonucleotide improves the subject's kidney function.

10. The method of claim 1, wherein at least one of the subject's kidneys is fibrotic prior to treating the subject.

11. The method of claim 1, wherein administration of the oligonucleotide decreases fibrosis in at least one of the subject's kidneys.

12. The method of claim 1, wherein at least one of the subject's kidneys is inflamed prior to treating the subject.

13. The method of claim 1, wherein administration of the oligonucleotide decreases inflammation is in at least one of the subject's kidneys.

14. The method of claim 1, wherein the therapeutic effect does not affect the subject's blood pressure.

15. The method of claim 1, wherein the truncated form comprises at least a portion of SEQ ID NO:5 that starts at any one of residues 1-6 of SEQ ID NO: 5.

16. The method of claim 1, wherein the oligonucleotide comprises at least 50 contiguous nucleotide residues from SEQ ID NO: 5.

17. The method of claim 1, wherein the oligonucleotide comprises at least residues 6-46 of SEQ ID NO:5.

18. The method of claim 1, wherein the hypertension is associated with activation of the renin-angiotensin system (RAS) of the subject.

19. The method of claim 1, comprising:
   (i) administering the exosome-free composition systemically, or
   (ii) administering the exosome-free composition intracardially, wherein the increase in the amount of plasma IL-10 protein, induction of macrophage IL-10 gene expression, attenuation of one or more of cardiac CD68 and IL1b gene expression, and/or attenuation of one or more of renal CD68, Il6 and Il1b gene expression, induces the therapeutic effect on the subject's heart.

20. A method for treating a subject suffering from hypertension, comprising:
   administering a cardiosphere-derived cell (CDC)-exosome to a subject with hypertension, wherein at least one of the subject's kidneys before treating the subject is (i) injured or dysfunctional, (ii) fibrotic, or (iii) inflamed;
   wherein the CDC-exosome comprises EV-YF1 (SEQ ID NO: 5) or a truncated form thereof having a truncation of up to 10 nucleotides from the 3' end and/or up to 5 nucleotides from the 5' end;
   wherein the CDC-exosome increases the amount of plasma IL-10 protein and/or attenuates one or more of renal CD68, Il6 and Il1b gene expression; and
   wherein the increase in the amount of plasma IL-10 protein, induction of macrophage IL-10 gene expression and/or attenuation of one or more of renal CD68, Il6 and Il1b gene expression, induces a therapeutic effect on the at least one of the subject's kidneys.

21. The method of claim 20, wherein the subject's heart is hypertrophic prior to treating the subject.

22. The method of claim 21, wherein administration of the CDC-exosome decreases cardiac hypertrophy in the subject.

23. The method of claim 20, wherein the subject's heart is fibrotic prior to treating the subject.

24. The method of claim 23, wherein administration of the CDC-exosome decreases cardiac fibrosis in the subject.

25. A method for treating a subject, comprising:
   administering an exosome-free composition comprising an oligonucleotide to a subject;
   wherein the oligonucleotide comprises SEQ ID NO: 5 or a truncated form thereof having a truncation of up to 10 nucleotides from the 3' end and/or up to 5 nucleotides from the 3' end, or SEQ ID NO: 30 or a truncated form thereof having a truncation of up to 10 nucleotides from the 3' end and/or up to 5 nucleotides from the 5' end;
   wherein the subject's heart is hypertrophic, fibrotic, or inflamed, and/or the subject's kidney is fibrotic or inflamed, due to hypertension;
   wherein the oligonucleotide increases the amount of plasma IL-10 protein, induces macrophage IL-10 gene expression, attenuates one or more of cardiac CD68 and IL1b gene expression, and/or attenuates one or more of renal CD68, Il6 and Il1b gene expression; and wherein the increase in the amount of plasma IL-10 protein, induction of macrophage IL-10 gene expression, attenuation of one or more of cardiac CD68 and IL1b gene expression, and/or attenuation of one or more of renal CD68, Il6 and Il1b gene expression, induces a therapeutic effect on the subject's heart and/or kidney, thereby treating the subject's hypertrophic, fibrotic, or inflamed heart and/or the subject's fibrotic or inflamed kidney.

* * * * *